United States Patent
Huang et al.

(10) Patent No.: US 11,845,984 B2
(45) Date of Patent: Dec. 19, 2023

(54) METHODS FOR OBTAINING AND CORRECTING BIOLOGICAL SEQUENCE INFORMATION

(71) Applicant: CYGNUS BIOSCIENCES (BEIJING) CO., LTD., Beijing (CN)

(72) Inventors: Yanyi Huang, Beijing (CN); Zitian Chen, Beijing (CN); Wenxiong Zhou, Beijing (CN); Haifeng Duan, Beijing (CN); Li Kang, Beijing (CN); Shuo Qiao, Beijing (CN)

(73) Assignee: CYGNUS BIOSCIENCES (BEIJING) CO., LTD., Beijing (CN)

( * ) Notice: Subject to any disclaimer, the term of this patent is extended or adjusted under 35 U.S.C. 154(b) by 527 days.

(21) Appl. No.: 16/927,970

(22) Filed: Jul. 13, 2020

(65) Prior Publication Data

US 2020/0407787 A1 Dec. 31, 2020

Related U.S. Application Data

(60) Division of application No. 15/879,388, filed on Jan. 24, 2018, now Pat. No. 10,738,356, which is a continuation of application No. PCT/CN2016/106117, filed on Nov. 16, 2016.

(30) Foreign Application Priority Data

| Nov. 19, 2015 | (CN) | 201510815685.X |
| Nov. 19, 2015 | (CN) | 201510822361.9 |
| Dec. 12, 2015 | (CN) | 201510944878.5 |
| Oct. 14, 2016 | (CN) | 201610899880.X |

(51) Int. Cl.
| C12Q 1/6869 | (2018.01) |
| G16B 30/00 | (2019.01) |
| G16B 30/10 | (2019.01) |
| G06F 17/10 | (2006.01) |

(52) U.S. Cl.
CPC ........... C12Q 1/6869 (2013.01); G06F 17/10 (2013.01); G16B 30/00 (2019.02); G16B 30/10 (2019.02)

(58) Field of Classification Search
CPC ........... C12Q 1/6869; C12Q 2535/122; C12Q 2537/165; G16B 30/00; G16B 30/10
See application file for complete search history.

(56) References Cited

U.S. PATENT DOCUMENTS

| 7,057,026 | B2 | 6/2006 | Barnes et al. |
| 7,223,541 | B2 | 5/2007 | Fuller et al. |
| 7,566,537 | B2 | 7/2009 | Balasubramanlan et al. |
| 8,236,532 | B2 | 8/2012 | Ronaghi et al. |
| 8,247,177 | B2 | 8/2012 | Smith |
| 8,364,417 | B2 | 1/2013 | Chen et al. |
| 9,005,929 | B2 | 4/2015 | Ronaghi et al. |
| 9,416,413 | B2 | 8/2016 | Schultz et al. |
| 10,738,356 | B2 | 8/2020 | Huang et al. |
| 2003/0194740 | A1 | 10/2003 | Williams |
| 2004/0152119 | A1 | 8/2004 | Sood et al. |
| 2006/0147935 | A1 | 7/2006 | Linnarsson |
| 2007/0117190 | A1 | 5/2007 | Damude et al. |
| 2010/0173303 | A1 | 7/2010 | Ronaghi et al. |
| 2011/0213563 | A1 | 9/2011 | Chen et al. |
| 2013/0053252 | A1* | 2/2013 | Xie .................. C12Q 1/6874 506/26 |
| 2014/0031238 | A1 | 1/2014 | Schultz et al. |
| 2014/0329699 | A1 | 11/2014 | Esfandyarpour |
| 2015/0111759 | A1 | 4/2015 | Ju et al. |

FOREIGN PATENT DOCUMENTS

| CN | 1446228 | A1 | 10/2003 |
| CN | 1973048 | A | 5/2007 |
| CN | 101384729 | A | 3/2009 |
| CN | 101390101 | A | 3/2009 |
| CN | 101948519 | A | 1/2011 |
| CN | 102329884 | A | 1/2012 |
| CN | 102622534 | A | 8/2012 |
| CN | 102834828 | A | 12/2012 |
| CN | 104105797 | A | 10/2014 |
| CN | 104379761 | A | 2/2015 |
| CN | 104711340 | A | 6/2015 |
| CN | 104844674 | A | 8/2015 |
| CN | 104910229 | A | 9/2015 |
| CN | 106874709 | B | 3/2019 |
| CN | 106755292 | B | 6/2019 |
| CN | 107958138 | B | 6/2019 |
| GB | 2398383 | A | 8/2004 |
| WO | 9423064 | A1 | 10/1994 |
| WO | 2004071155 | A2 | 8/2004 |
| WO | 2004072294 | A2 | 8/2004 |
| WO | 2004072297 | A2 | 8/2004 |
| WO | 2008051530 | A2 | 5/2008 |

(Continued)

OTHER PUBLICATIONS

Pu et al., A real-time decoding sequencing based on dual mononucleotide addition for cyclic synthesis, 2014, Analytica Chimica Acta 852, 274-283. (Year: 2014).*
Statement of Proposed Amendments from Australian Divisional Patent Application No. 2021201594, dated Jun. 19, 2023 (1 page).
Amended Marked-Up Claims from Australian Divisional Patent Application No. 2021201594, dated Jun. 19, 2023 (2 pages).
Exhibit A: Ledergerber, et al. "Base-Calling for Next-Generation Sequencing Platforms". Briefings in Bioinformatics, vol. 12(5): 489-497 (Jan. 18, 2011).
Exhibit B: Chen, et al. "Highly Accurate Fluorogenic DNA Sequencing with Information Theory-Based Error Correction". Nature Biotechnology, vol. 35(12): 1170-1178 (Dec. 2017). Submitted with Nature Research Life Sciences Reporting Summary (2 pages).
Exhibit C: Balzer, et al. "Characteristics of 454 Pyrosequencing Data-Enabling Realistic Simulation with Flowsim". Bioinformatics, vol. 26: 1420-1425 (2010).

(Continued)

*Primary Examiner* — Narayan K Bhat

(57) ABSTRACT

A method for sequencing a biological molecule, such as a nucleic acid molecule, and a method for detecting and/or correcting sequencing error(s) in the sequencing results are provided. Kits and systems based on the above methods are also provided.

12 Claims, 60 Drawing Sheets

Specification includes a Sequence Listing.

(56) References Cited

FOREIGN PATENT DOCUMENTS

| WO | 2010/075188 A2 | 7/2010 |
|---|---|---|
| WO | 2013082619 A1 | 6/2013 |
| WO | 2013154999 A2 | 10/2013 |

OTHER PUBLICATIONS

Exhibit D: Golan, et al. "Using State Machines to Model the Ion Torrent Sequencing Process and to Improve Read Error Rates". Bioinformatics, vol. 29: i344-i351 (2013).
Response to Examination Report for Australian Divisional Patent Application No. 2021201594, dated Jun. 19, 2023 (7 pages).
Restriction Requirement for U.S. Appl. No. 15/879,388, dated May 22, 2019 (7 pages).
Response to Restriction Requirement for U.S. Appl. No. 15/879,388, filed Jul. 22, 2019 (12 pages).
Non-Final Office Action for U.S. Appl. No. 15/879,388, dated Sep. 16, 2019 (17 pages).
Response to Non-Final Office Action for U.S. Appl. No. 15/879,388, filed Mar. 12, 2020 (25 pages).
Notice of Allowance for U.S. Appl. No. 15/879,388, dated Apr. 30, 2020 (22 pages).
Amendment Under 37 CFR 1.312 for U.S. Appl. No. 15/879,388, filed Jun. 18, 2020 (3 pages).
Examiner-Initiated Interview Summary for U.S. Appl. No. 15/879,388, dated Jun. 16, 2020 (3 pages).
Response to Rule 312 Communication for U.S. Appl. No. 15/879,388, dated Jun. 25, 2020 (2 pages).
Voluntary Amendment for Australian Application No. 2016356395, dated Oct. 20, 2020 (30 pages).
First Examination Report for Australian Application No. 2016356395, dated Oct. 21, 2020 (3 pages).
Response to First Examination Report for Australian Application No. 2016356395, dated Nov. 4, 2020 (1 page).
Clean Claims for Australian Application No. 2016356395, dated Oct. 20, 2020 (7 pages).
Claims as accepted for Australian Application No. 2016356395, dated Oct. 20, 2020 (7 pages).
Notice of Acceptance for Patent Application and Bibliographic Attachment for Australian Application No. 2016356395, dated Dec. 2, 2020 (3 pages).
Published Specification for Australian Application No. 2016356395, published May 26, 2017 (217 pages).
Voluntary Amendment for Australian Application No. 2021201594, dated May 13, 2021 (31 pages).
First Examination Report for Australian Application No. 2021201594, dated Jan. 23, 2023 (4 pages).
Response to First Examination Report for Australian Application No. 2021201594, dated Feb. 28, 2023 (2 pages).
Second Examination Report for Australian Application No. 2021201594, dated Mar. 8, 2023 (3 pages).
Submission of Request for Examination for Canadian Patent Application No. 3,005,671, dated Oct. 19, 2021 (6 pages).
Acknowledgement of Request for Examination for Canadian Patent Application No. 3,005,671, dated Oct. 27, 2021 (1 page).
Examiner's Report or Canadian Patent Application No. 3,005,671, dated Jan. 27, 2023 (4 pages).
Submission of Response to Examiner's Report for Canadian Patent Application No. 3,005,671, dated Apr. 5, 2023 (47 pages).
Amended Claims filed with Response for Canadian Patent Application No. 3,005,671, dated Apr. 5, 2023 (14 pages).
Reply to Examination Report for European Patent Application 16 865 757.5, dated Oct. 10, 2020 (4 pages).
Marked-Up Claims for European Patent Application 16 865 757.5, dated Oct. 10, 2020 (5 pages).
Office Action Pursuant to Article 94(3) EPC for European Patent Application 16 865 757.5, dated Feb. 24, 2021 (4 pages).
Reply to Examination Report for European Patent Application 16 865 757.5, dated Sep. 6, 2021 (7 pages).
Amended Claims, Clean Version for European Patent Application 16 865 757.5, dated Oct. 10, 2020 (4 pages).
Office Action Pursuant to Article 94(3) EPC for European Patent Application 16 865 757.5, dated Aug. 24, 2022 (4 pages).
Reply to Examination Report for European Patent Application 16 865 757.5, dated Mar. 2, 2023 (6 pages).
Marked-Up Claims for European Patent Application 16 865 757.5, dated Mar. 2, 2023 (5 pages).
Sebra. "DNA Sequencing at Ultra-High Fidelity". Nature Biotechnology, 2017, 35: 1143-1144.
Extended European Search Report for European patent application EP16865757.5, dated Mar. 18, 2019, 7 pages.
Response to the Communication pursuant to Rules 70(2) and 70a(2)EPC for European patent application EP16865757.5, dated Oct. 11, 2019, 18 pages.
Communication pursuant to Article 94(3) EPC for European patent application EP16865757.5, dated Jan. 4, 2020, 6 pages.
Balzer et al., "Characteristics of 454 pyrosequencing data—enabling realistic simulation with flowsim," Bioinformatics, vol. 26 ECCB 2010, pp. i420-i425 doi:10.1093/bioinformatics/btq365.
Chen Wei et al., "Simulation algorithm for 454 pyrosequencing sequencers", Computer Science, vol. 41, No. 2, Feb. 28, 2014 (Feb. 28, 2014), p. 261-263 and p. 284.
Chen Zitian et al., "Highly accurate fluorogenic DNA sequencing with information theory-based error correction," Nature Biotechnology, Dec. 2017, vol. 35, No. 12, p. 1170-1178 doi:10.1038/nbt.3982.
Golan and Medvedev, "Using state machines to model the Ion Torrent sequencing process and to improve read error rates," Bioinformatics, vol. 29 ISMB/ECCB 2013, pp. i344-i351 doi:10.1093/bioinformatics/btt212.
Ledergerber and Dessimoz, "Base-calling for next-generation sequencing platforms," Briefings in Bioinformatics, Jan. 18, 2011, vol. 12, No. 5, p. 489-497 doi:10.1093/bib/bbq077.
Ye Binggang et al., "Phase emendation of high-throughput genome sequencing", Journal of Computer Applications, vol. 30, No. 4, Apr. 30, 2010 (Apr. 30, 2010), p. 1114-1116.
Pu, et al. "A Real-Time Decoding Sequencing Based on Dual Mononucleotide Addition for Cyclic Synthesis". 2014, Analytica Chimica Acta, 852: 274-283.
Pu, et al. "A Real-Time Decoding Sequencing Based on Dual Mononucleotide Addition for Cyclic Synthesis". 2014, Analytica Chimica Acta, 852: 274-283—Supplemental Information 1-5.
Sims, et al. "Fluorogenic DNA Sequencing in PDMS Microreactors". Nature Methods, 2011, 575-580.
Sims, et al. "Fluorogenic DNA Sequencing in PDMS Microreactors". Nature Methods, 2011, 575-580—Supplemental Information 1-12.
International Search Report in PCT/CN2016/106117, dated Feb. 8, 2017, 7 pages.
Written Opinion of the International Searching Authority in PCT/CN2016/106117, dated Feb. 8, 2017, 6 pages.
State Intellectual Property Office of the P.R. China, Office Action for Application No. CN201510815685.X, dated Jul. 16, 2018, 9 pages.
State Intellectual Property Office of the P.R. China, Office Action for Application No. CN201510822361.9, dated Jul. 5, 2018, 9 pages.
State Intellectual Property Office of the P.R. China, Office Action for Application No. CN201610899880.X, dated Jul. 4, 2018, 6 pages.
State Intellectual Property Office of the P.R. China, Office Action for Application No. CN201510944878.5, dated Jul. 3, 2018, 6 pages.
Shendure, et al. "Next-Generation DNA Sequencing". Oct. 9, 2008. Nature Biotechnology, vol. 26, 10th, p. 1135-1145.
Sood, et al. "Terminal Phosphate-Labeled Nucleotides with Improved Substrate Properties for Homogeneous Nucleic Acid Assays". Mar. 2, 2005. J. Am. Chem. Soc., vol. 127, 8th, p. 2394-2395.
Response to 1st Office Action (Arguments) for Chinese patent application 201510815685, dated Aug. 10, 2018, 4 pages.
Response to 1st Office Action (Claims) for Chinese patent application 201510815685, dated Aug. 10, 2018, 3 pages.
2nd Office Action for Chinese patent application 201510815685.X, dated Sep. 12, 2018, 9 pages.
Response to 2nd Office Action (Arguments) for Chinese patent application 201510815685, dated Nov. 26, 2018, 7 pages.

(56) References Cited

OTHER PUBLICATIONS

Response to 2nd Office Action (Claims) for Chinese patent application 201510815685, dated Nov. 26, 2018, 3 pages.
Response to 2nd Office Action (Specification) for Chinese patent application 201510815685, dated Nov. 26, 2018, 14 pages.
3rd Office Action for Chinese patent application 201510815685.X, dated Dec. 27, 2018, 9 pages.
Response to 3rd Office Action (Arguments) for Chinese patent application 201510815685, dated May 10, 2019, 4 pages.
Response to 3rd Office Action (Claims) for Chinese patent application 201510815685, dated May 10, 2019, 2 pages.
Response to 1st Office Action (Arguments) for Chinese patent application 201510822361.9, dated Aug. 10, 2018, 4 pages.
Response to 1st Office Action (Claims) for Chinese patent application 201510822361.9, dated Aug. 10, 2018, 3 pages.
2nd Office Action for Chinese patent application 201510822361.9, dated Sep. 11, 2018, 7 pages.
Response to 2nd Office Action (Arguments) for Chinese patent application 201510822361.9, dated Nov. 26, 2018, 8 pages.
Response to 2nd Office Action (claims) for Chinese patent application 201510822361.9, dated Nov. 26, 2018, 14 pages.
3rd Office Action for Chinese patent application 201510822361.9, dated Dec. 27, 2018, 6 pages.
Response to 3rd Office Action (Arguments) for Chinese patent application 201510822361.9, dated Apr. 25, 2019, 5 pages.
Response to 3rd Office Action (Claims) for Chinese patent application 201510822361.9, dated Apr. 25, 2019, 5 pages.
Response to 1st Office Action (Arguments) for Chinese patent application 201510944878.5, dated Aug. 10, 2018, 3 pages.
Response to 1st Office Action (Claims) for Chinese patent application 201510944878.5, dated Aug. 10, 2018, 1 pages.
2nd Office Action for Chinese patent application 201510944878.5, dated Sep. 11, 2018, 3 pages.
Response to 2nd Office Action (Arguments) for Chinese patent application 201510944878.5, dated Nov. 20, 2018, 1 pages.
Response to 2nd Office Action (Claims) for Chinese patent application 201510944878.5, dated Nov. 20, 2018, 3 pages.
Response to 1st Office Action (Arguments) for Chinese patent application 201610899880.X, dated Aug. 10, 2018, 1 pages.
2nd Office Action for Chinese patent application 201610899880.X, dated Sep. 20, 2018, 5 pages.
Response to 2nd Office Action (Arguments) for Chinese patent application 201610899880.X, dated Nov. 30, 2018, 2 pages.
3rd Office Action for Chinese patent application 201610899880.X, dated Jan. 25, 2019, 4 pages.
Response to 3rd Office Action (Arguments) for Chinese patent application 201610899880.X, dated May 25, 2019, 2 pages.
Response to 3rd Office Action (Claims) for Chinese patent application 201610899880.X, dated May 25, 2019, 4 pages.
Third Examination Report issued in Australian Patent Application No. 2021201594 dated Aug. 4, 2023, 3 pages.
AU Application No. 2021201594, Response to Examination Report filed Oct. 5, 2023.
AU Application No. 2021201594, Clean amended claims filed Oct. 5, 2023.
AU Application No. 2021201594, Marked-up claims filed Oct. 5, 2023.
AU Application No. 2021201594, Statement of Proposed Amendments filed Oct. 5, 2023.

* cited by examiner

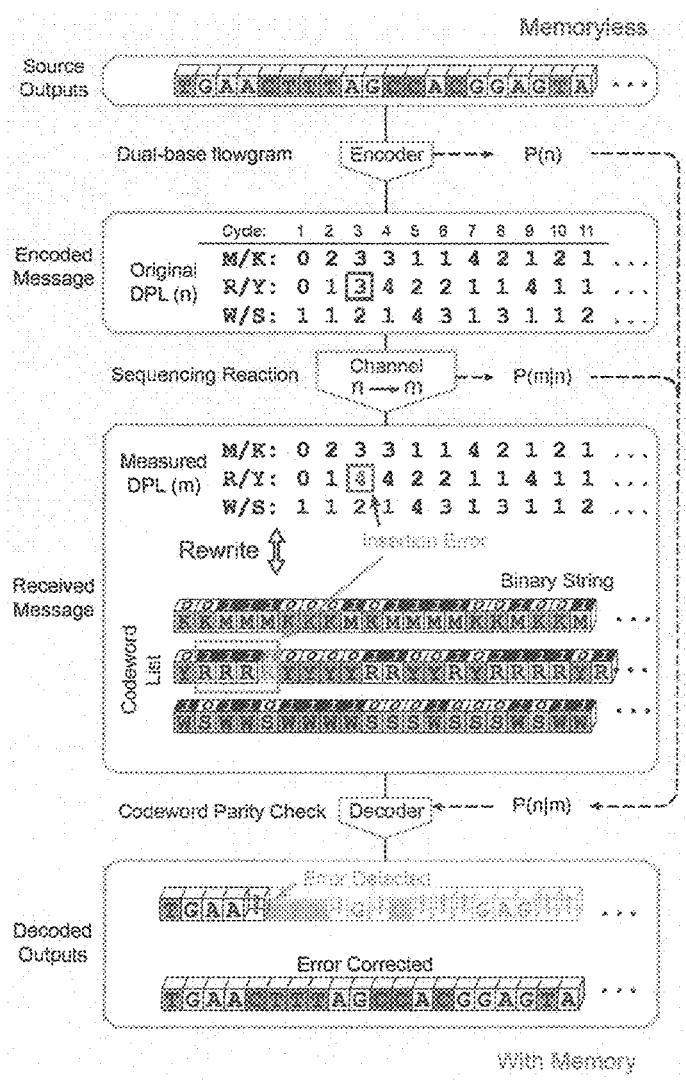
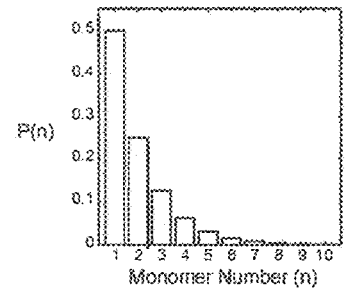
FIG.54B
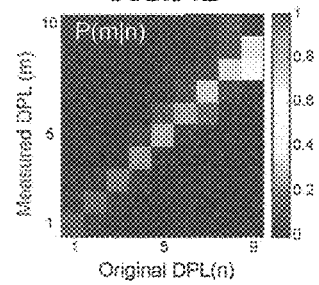
FIG.54C
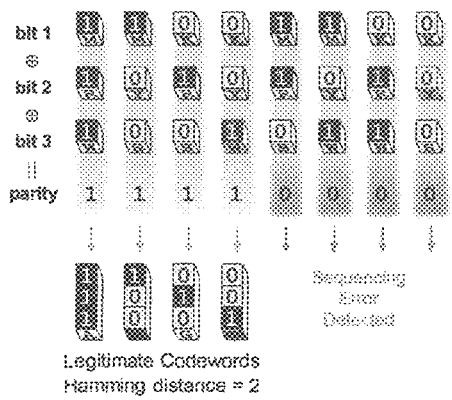
FIG.54A
FIG.54D

METHODS FOR OBTAINING AND CORRECTING BIOLOGICAL SEQUENCE INFORMATION

CROSS-REFERENCE TO RELATED APPLICATIONS

This application is a divisional of U.S. patent application Ser. No. 15/879,388, filed Jan. 24, 2018, now allowed, which is a continuation of PCT Application PCT/CN2016/106117 having an international filing date of Nov. 16, 2016, entitled "Methods for Obtaining and Correcting Biological Sequence Information," which claims priority to Chinese Patent Application No. CN201510822361.9, filed on Nov. 19, 2015, entitled "Sequencing Method Using Nucleotide Molecules Having Phosphate Modified Fluorophores," Chinese Patent Application No. CN201510815685.X, filed on Nov. 19, 2015, entitled "Sequencing Method Using Nucleotide Molecules Having Fluorescence Switching Fluorophores," Chinese Patent Application No. CN201510944878.5, filed on Dec. 12, 2015, entitled "Method for Detecting and/or Correcting Sequence Data Errors in Sequencing Results," and Chinese Patent Application No. CN201610899880.X, filed on Oct. 14, 2016, entitled "A Method for Reading Sequence Information from the Original Signal of High-throughput DNA Sequencing." The contents and disclosures of the above applications are incorporated herein by reference in their entireties for all purposes.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 4551-2000110_SeqList_ST25.txt, date recorded: Jul. 13, 2020, size: 14,466 bytes).

FIELD

The present disclosure in some aspects relates to a high-throughput sequencing method, belonging to the gene sequencing field.

BACKGROUND

The high-throughput sequencer represents a technology rapidly developing in recent years. Compared with the conventional Sanger sequencing, the high-throughput sequencing technology has the advantage that a large amount of sequence information may be read out. Its accuracy is not as high as the former, but the information exceeding the data sequence itself may be obtained, such as gene expression level or copy number variation, through the analysis on a large amount of data.

Today's mainstream sequencers all adopt SBS (sequencing by synthesis) methods, like Solexa/Illumina, 454, Ion Torrent, etc. These sequencers have a similar structure, and each of them consists of a fluid system, an optical system and a chip system. The sequencing reaction occurs in the chip. Their sequencing process is very similar as well, including: let the reaction solution flow into the chip for SBS reaction, and then, conduct signal acquisition and washing. Next, proceed with a new round of sequencing. This is a cyclical process. With the increase of cycles, the continuous single-base non-merged sequence information (e.g., ACTGACTG) may be tested. However, the high-throughput sequencer cannot completely eliminate sequencing errors. Sequencing errors may be caused by: occasional error or cumulative error in reaction, signal acquisition error, signal correction error, and so on. In existing sequencers, these chemical or optical or software errors may become noise, and cannot be identified at a single readout site, but can be eliminated through deep sequencing by multiple readout at different sites in the same sequence. The more accurate readout is an important development direction of high-throughput sequencing. However, the optimization on the accuracy by existing technologies is mostly concentrated on the optimization of the chemical reaction itself and subsequent image signal processing, and there is no innovation in the sequencing logic. There is a need for an improved sequencing method.

SUMMARY

The summary is not intended to be used to limit the scope of the claimed subject matter. Other features, details, utilities, and advantages of the claimed subject matter will be apparent from the detailed description including those aspects disclosed in the accompanying drawings and in the appended claims.

In one aspect, provided herein is a method for obtaining sequence information of a target polynucleotide, the method comprising: a) providing a first sequencing reagent to a target polynucleotide in the presence of a first polynucleotide replicating catalyst, wherein the first sequencing reagent comprises at least two different nucleotide monomers each of which is conjugated to a first label, and the nucleotide monomer/first label conjugates are substantially non-fluorescent until after incorporation of the nucleotide monomer into the target polynucleotide based on complementarity to the target polynucleotide, wherein the first labels for the at least two different nucleotide monomers are the same or different; and b) providing a second sequencing reagent to the target polynucleotide in the presence of a second polynucleotide replicating catalyst, wherein the second sequencing reagent comprises one or more nucleotide monomers each of which is conjugated to a second label, and the nucleotide monomer/second label conjugate(s) is or are substantially non-fluorescent until after incorporation of the nucleotide monomer(s) into the target polynucleotide based on complementarity to the target polynucleotide, at least one of the one or more nucleotide monomers being different from the nucleotide monomers present in the first sequencing reagent, and wherein the second sequencing reagent is provided subsequent to providing the first sequencing reagent, and c) obtaining sequence information for at least a portion of the target polynucleotide by detecting fluorescence emission resulting from the first label and second label after incorporation of the nucleotide monomers into the polynucleotide in the steps a) and b).

In one embodiment, the method is used to obtain sequence information for at least a portion of a single target polynucleotide. In another embodiment, the method is used to obtain sequence information for at least a portion of a plurality of target polynucleotides simultaneously.

In any of the preceding embodiments, the first polynucleotide replicating catalyst and the second polynucleotide replicating catalyst can be the same polynucleotide replicating catalyst, or different polynucleotide replicating catalysts.

In any of the preceding embodiments, said sequence information can be obtained from one or more sequencing reactions, wherein optionally the one or more sequencing reactions are performed in one or more reaction volumes (such as reaction chambers), such as about 1×10⁶ to about 5×10⁸ reaction volumes, about 1×10⁶ to about 1×10⁸ reaction volumes, or about 1×10⁶ to about 5×10⁷ reaction volumes, wherein optionally the reaction volumes are physically separated from each other and/or there is no or substantially no material exchange between the reaction volumes, wherein optionally the reaction volumes are located in a array such as a chip, are wherein optionally the reaction volumes are closed and/or insulated from each other by a liquid that is immiscible with the liquid in the reaction volumes, such as an oil. When there is no substantially no material exchange between the reaction volumes, some material exchange is allowed but it will not affect the sequencing result in any of the reaction volumes so as to cause cross-contamination.

In any of the preceding embodiments, the reaction volumes can be provided in reaction chambers, and the target polynucleotide in each reaction chamber is immobilized on a solid support in the reaction chamber, wherein optionally the sequence information is obtained by high-throughput sequencing, for example, wherein at least about $10^3$, $10^4$, $10^5$, $10^6$, $10^7$, $10^8$, or $10^9$ sequences are read in parallel. In any of the preceding embodiments, the first polynucleotide replicating catalyst and/or the second polynucleotide replicating catalyst can be a polymerase, such as a DNA polymerase, a RNA polymerase, or a RNA-dependent RNA polymerase, a ligase, a reverse transcriptase, or a terminal deoxynucleotidyl transferase.

In any of the preceding embodiments, the nucleotide monomers in the first and/or second sequencing reagent can be selected from the group consisting of deoxyribonucleotides, modified deoxyribonucleotides, ribonucleotides, modified ribonucleotides, peptide nucleotides, modified peptide nucleotides, modified phosphate sugar backbone nucleotides and mixtures thereof. In one embodiment, the nucleotide monomers in both the first and the second sequencing reagents are deoxyribonucleotides. In some embodiments, the nucleotide monomers are selected from the group consisting of A, T/U, C and G deoxyribonucleotides, and an analog thereof. In another embodiment, the nucleotide monomers in both the first and the second sequencing reagents are ribonucleotides. In specific embodiments, the nucleotide monomers are selected from the group consisting of A, U/T, C and G ribonucleotides, and an analog thereof.

In any of the preceding embodiments, the first and/or second label can be releasably conjugated to the nucleotide monomer. In one embodiment, the first and/or second label is conjugated to a terminal phosphate group of the nucleotide monomer. In specific embodiments, the nucleotide monomer/first label conjugates in the first sequencing reagent and/or the one or more nucleotide monomers/second label conjugate(s) in the second sequencing reagent have the structure of the following formulae I:

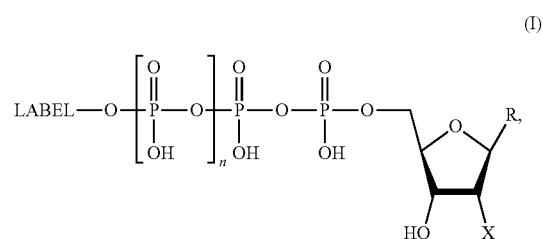

wherein n is 0 to 6, R is a nucleoside base, X is H, OH, or OMe, or a salt thereof. In some embodiments, the first and/or second label is substantially non-fluorescent until its release from the terminal phosphate group of the nucleotide monomer. In one other embodiment, the method further comprises releasing the first and/or second label(s) from the terminal phosphate group of the nucleotide monomer using an activating enzyme. In one embodiment, the activating enzyme is an exonuclease, a phosphate transferase, or a phosphatase.

In any of the preceding embodiments, the nucleotide monomer/first label conjugates in the first sequencing reagent and/or the one or more nucleotide monomers/second label conjugate(s) in the second sequencing reagent can have the structure of the following formulae II:

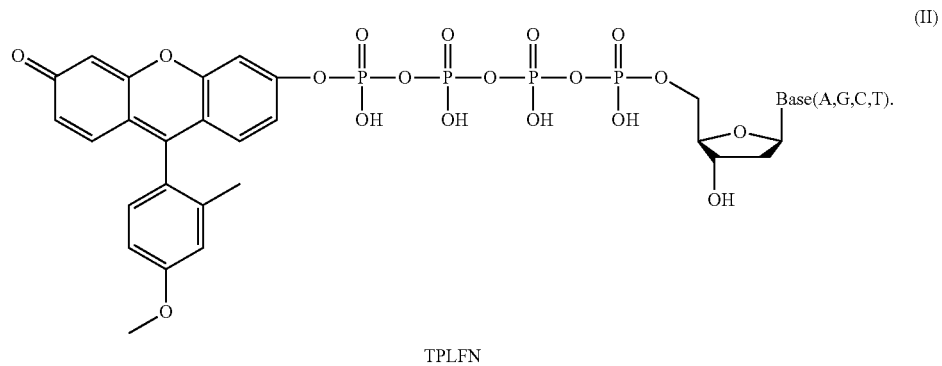

TPLFN

In any of the preceding embodiments, the first labels for the at least two different nucleotide monomers can be the same or different from each other. In any of the preceding embodiments, the method can further comprise a washing step between steps a) and b).

In any of the preceding embodiments, the target polynucleotide can be immobilized on a surface, such as a solid surface, a soft surface, a hydrogel surface, a microparticle surface, or a combination thereof. In one embodiment, the solid surface is a part of a microreactor, and steps a) and b) are conducted in the microreactor. In any of the preceding embodiments, the method can be conducted at a temperature ranging from about 20° C. to about 70° C.

In any of the preceding embodiments, multiple rounds of steps a) and b) using different combinations of the first sequencing reagent and the second sequencing reagent can be conducted.

In any of the preceding embodiments, the sequence information obtained in step c) can be a degenerate sequence. In one embodiment, at least one additional round of steps a) and b) using a combination of the first sequencing reagent and the second sequencing reagent different from the combination of the first sequencing reagent and the second sequencing reagent in the previous round(s) of steps a) and b) is conducted to obtain at least one additional sequence, and the additional sequence is compared with the degenerate sequence to obtain a non-degenerate sequence.

In any of the preceding embodiments, the initial sequence information obtained in step c) can contain no error, or contain one or more errors. In one embodiment, at least one additional round of steps a) and b) using a combination of the first sequencing reagent and the second sequencing reagent different from the combination of the first sequencing reagent and the second sequencing reagent in the previous round(s) of steps a) and b) is conducted to obtain at least one additional sequence, and the additional sequence is compared with the initial sequence to reduce or eliminate the sequence error(s).

In any of the preceding embodiments, the sequence comparison can be conducted using a mathematical analysis, algorithm, or method. In one embodiment, the mathematical analysis, algorithm, or method comprises a Markov model, or the maximum likelihood method based on Bayesian Scheme.

In any of the preceding embodiments, the first sequencing reagent can comprise two different nucleotide monomer/first label conjugates, each nucleotide monomer/first label conjugate comprising a different nucleotide monomer. In any of the preceding embodiments, the second sequencing reagent can comprise two different nucleotide monomer/second label conjugates, each nucleotide monomer/second label conjugate comprising a different nucleotide monomer. In any of the preceding embodiments, the two nucleotide monomers in the first sequencing reagent can be different from the two nucleotide monomers in the second sequencing reagent.

In any of the preceding embodiments, the two nucleotide monomers in the first sequencing reagent and the two nucleotide monomers in the second sequencing reagent can be selected from the group consisting of A, T/U, C and G deoxyribonucleotides, and an analog thereof. In one embodiment, the two nucleotide monomers in the first sequencing reagent and the two nucleotide monomers in the second sequencing reagent are selected from the group consisting of the following combinations: 1) A and T/U deoxyribonucleotides in one sequencing reagent and C and G deoxyribonucleotides in the other sequencing reagent; 2) A and G deoxyribonucleotides in one sequencing reagent and C and T/U deoxyribonucleotides in the other sequencing reagent; and 3) A and C deoxyribonucleotides in one sequencing reagent and G and T/U deoxyribonucleotides in the other sequencing reagent. In another embodiment, one round of steps a) and b) or at least two rounds of steps a) and b) are conducted, one of the combinations 1)-3) is used in one round of steps a) and b), and another combination from the combinations 1)-3) but different from the combination used in the previous round of steps a) and b) is used in another round of steps a) and b). In one aspect, three rounds of steps a) and b) are conducted, each of the rounds uses a different combination selected from the combinations 1)-3). In any of the preceding embodiments, the sequences obtained from the multiple rounds of steps a) and b) can be compared to obtain a non-degenerate sequence and/or to reduce or eliminate sequence error(s) in the non-degenerate sequence.

In any of the preceding embodiments, the two nucleotide monomers in the first sequencing reagent and the two nucleotide monomers in the second sequencing reagent can be selected from the group consisting of A, T/U, C and G ribonucleotides, and an analog thereof. In one embodiment, the two nucleotide monomers in the first sequencing reagent and the two nucleotide monomers in the second sequencing reagent are selected from the group consisting of the following combinations: 1) A and T/U ribonucleotides in one sequencing reagent and C and G ribonucleotides in the other sequencing reagent; 2) A and G ribonucleotides in one sequencing reagent and C and T/U ribonucleotides in the other sequencing reagent; and 3) A and C ribonucleotides in one sequencing reagent and G and T/U ribonucleotides in the other sequencing reagent. In one aspect, one round of steps a) and b) or at least two rounds of steps a) and b) are conducted, one of the combinations 1)-3) is used in one round of steps a) and b), and another combination from the combinations 1)-3) but different from the combination used in the previous round of steps a) and b) is used in another round of steps a) and b). In another aspect, at least three rounds of steps a) and b) are conducted, each of the rounds uses a different combination from the combinations 1)-3). In any of the preceding embodiments, the sequences obtained from the multiple rounds of steps a) and b) can be compared to obtain a non-degenerate sequence and/or to reduce or eliminate sequence error(s) in the non-degenerate sequence.

In any of the preceding embodiments, the first labels for the two different nucleotide monomers can be the same, and the second labels can be the same as the first labels.

In any of the preceding embodiments, the first labels for the two different nucleotide monomers can be different, while the second labels can be the same as the first labels.

In any of the preceding embodiments, one of the first and second sequencing reagents can comprise three different nucleotide monomer/first label conjugates, each nucleotide monomer/first label conjugate comprising a different nucleotide monomer, while the other sequencing reagent can comprise one nucleotide monomer/second label conjugate, and the three nucleotide monomers in one sequencing reagent can be different from the nucleotide monomer in the other sequencing reagent.

In any of the preceding embodiments, the nucleotide monomers in the first sequencing and the second sequencing reagents can be selected from the group consisting of A, T/U, C and G deoxyribonucleotides, and an analog thereof. In a specific embodiment, the nucleotide monomers in the first and second sequencing reagents are selected from the group consisting of the following combinations: 1) C, G, and T/U deoxyribonucleotides in one sequencing reagent and A deoxyribonucleotide in the other sequencing reagent; 2) A, G and T/U deoxyribonucleotides in one sequencing reagent and C deoxyribonucleotide in the other sequencing reagent; 3) A, C and T/U deoxyribonucleotides in one sequencing reagent and G deoxyribonucleotide in the other sequencing reagent; and 4) A, C and G deoxyribonucleotides in one sequencing reagent and T/U deoxyribonucleotide in the other sequencing reagent. In one embodiment, one round of steps a) and b) or at least two rounds of steps a) and b) are conducted, one of the combinations 1)-4) is used in one round of steps a) and b), and another combination from the combinations 1)-4) but different from the combination used in the previous round of steps a) and b) is used in another round of steps a) and b). In another embodiment, three rounds of steps a) and b) are conducted, each of the rounds uses a different combination selected from the combinations 1)-4). In yet another embodiment, four rounds of steps a) and b) are conducted, each of the rounds uses a different combination selected from the combinations 1)-4). In any of the preceding embodiments, the sequences obtained from the multiple rounds of steps a) and b) can be compared to obtain a non-degenerate sequence and/or to reduce or eliminate sequence error(s) in the non-degenerate sequence.

In any of the preceding embodiments, the nucleotide monomers in the first sequencing and the second sequencing reagents can be selected from the group consisting of A, T/U, C and G ribonucleotides, and an analog thereof. In one embodiment, the nucleotide monomers in the first and second sequencing reagents are selected from the group consisting of the following combinations: 1) C, G and T/U ribonucleotides in one sequencing reagent and A ribonucleotide in the other sequencing reagent; 2) A, G and T/U ribonucleotides in one sequencing reagent and C ribonucleotide in the other sequencing reagent; 3) A, C and T/U ribonucleotides in one sequencing reagent and G ribonucleotide in the other sequencing reagent; and 4) A, C and G ribonucleotides in one sequencing reagent and T/U ribonucleotide in the other sequencing reagent. In one embodiment, one round of steps a) and b) or at least two rounds of steps a) and b) are conducted, one of the combinations 1)-4) is used in one round of steps a) and b), and another combination from the combinations 1)-4) but different from the combination used in the previous round of steps a) and b) is used in another round of steps a) and b). In one specific embodiment, at least three rounds of steps a) and b) are conducted, each of the rounds uses a different combination from the combinations 1)-4). In another embodiment, at least four rounds of steps a) and b) are conducted, each of the rounds uses a different combination from the combinations 1)-4). In any of the preceding embodiments, the sequences obtained from the multiple rounds of steps a) and b) can be compared to obtain a non-degenerate sequence and/or to reduce or eliminate sequence error(s) in the non-degenerate sequence.

In any of the preceding embodiments, a read length of about 250 bp, about 350 bp, about 400 bp, about 450 bp, about 500 bp, about 550 bp, about 600 bp, about 650 bp, about 700 bp, about 750 bp, about 800 bp, about 850 bp, about 900 bp, about 950 bp, about 1000 bp, about 1050 bp, about 1100 bp, about 1150 bp, about 1200 bp, about 1250 bp, about 1300 bp, about 1350 bp, about 1400 bp, about 1450 bp, about 1500 bp, about 1550 bp, about 1600 bp, about 1650 bp, about 1700 bp, about 1750 bp, about 1800 bp, about 1850 bp, about 1900 bp, about 1950 bp, about 2000 bp, about 2050 bp, about 2100 bp, about 2150 bp, about 2200 bp, about 2250 bp, about 2300 bp, about 2350 bp, or about 2400 base pairs can be obtained.

In any of the preceding embodiments, a code accuracy rate of at least about 95% can be obtained. In any of the preceding embodiments, the target polynucleotide can be a single-stranded polynucleotide.

In another aspect, disclosed herein is a method for obtaining sequence information of a target polynucleotide, the method comprising: a) providing a first sequencing reagent to a target polynucleotide in the presence of a first polynucleotide replicating catalyst, wherein the first sequencing reagent comprises two different nucleotide monomers each of which is conjugated to a first label, and the nucleotide monomer/first label conjugates are substantially non-fluorescent until after incorporation of the nucleotide monomer into the target polynucleotide based on complementarity to the target polynucleotide; and b) providing a second sequencing reagent to the target polynucleotide in the presence of a second polynucleotide replicating catalyst, wherein the second sequencing reagent comprises two different nucleotide monomers each of which is conjugated to a second label, and the nucleotide monomer/second label conjugates are substantially non-fluorescent until after incorporation of the nucleotide monomers into the target polynucleotide based on complementarity to the target polynucleotide, and wherein the second sequencing reagent is provided subsequent to providing the first sequencing reagent, and c) obtaining sequence information for at least a portion of the target polynucleotide by detecting fluorescence emission resulting from the first label and second label after incorporation of the nucleotide monomers into the polynucleotide in the steps a) and b), wherein the nucleotide monomers in the first sequencing reagent and the second sequencing reagent are selected from the group consisting of the following combinations: 1) an adenine (A) nucleotide monomer and a thymine (T)/uracil (U) nucleotide monomer in one sequencing reagent and a cytosine (C) nucleotide monomer and a guanine (G) nucleotide monomer in the other sequencing reagent; 2) an adenine (A) nucleotide monomer and a guanine (G) nucleotide monomer in one sequencing reagent and a cytosine (C) nucleotide monomer and a thymine (T)/uracil (U) nucleotide monomer in the other sequencing reagent; and 3) an adenine (A) nucleotide monomer and a cytosine (C) nucleotide monomer in one sequencing reagent and a guanine (G) nucleotide monomer and a thymine (T)/uracil (U) nucleotide monomer in the other sequencing reagent. In one embodiment, the first labels for the two different nucleotide monomers in step a) and the second labels for the two different nucleotide monomers in step b) are the same label. In another embodiment, the first labels are different labels, and one of the first labels is the same as one of the second labels, while the other one of the first labels is the same as the other one of the second labels. In any of the preceding embodiments, multiple rounds of steps a) and b) can be conducted, each round using a combination selected from the combinations 1)-3). In another embodiment, at least two or three sets of sequence information are obtained in step c), the method comprising: conducting multiple rounds of steps a) and b) using combination 1) in a first sequencing reaction volume to obtain a first set of sequence information, conducting multiple rounds of steps a) and b) using combination 2) in a second sequencing reaction volume to obtain a second set of sequence information, and/or conducting multiple rounds of steps a) and b) using combination 3) in a third sequencing reaction volume to obtain a third set of sequence information. In one embodiment, the first, second, and third sets of sequence information are obtained in parallel from separate sequencing reaction volumes. In another embodiment, the first, second, third sets of sequence information are obtained sequentially from the same sequencing reaction volume, and the products of an earlier sequencing reaction are removed before the next sequencing reaction starts. In any of the preceding embodiments, the method can further comprise comparing the at least two or three sets of sequence information to reduce or eliminate the sequence error(s). In one embodiment, the comparison indicates no error in the obtained target polynucleotide sequence when the at least two or three sets of sequence information are consistent with each other. In another embodiment, the comparison indicates error in the obtained target polynucleotide sequence when the at least two or three sets of sequence information comprise a discrepancy in at least one nucleotide residue of the target polynucleotide sequence. In one embodiment, the method further comprises correcting at least one nucleotide residue in the obtained target polynucleotide sequence such that after the correction, the at least two or three sets of sequence information are consistent with each other.

In yet another aspect, disclosed herein is a method for obtaining sequence information of a target polynucleotide, the method comprising: a) providing a first sequencing reagent to a target polynucleotide in the presence of a first polynucleotide replicating catalyst, wherein the first sequencing reagent comprises three different nucleotide monomers each of which is conjugated to a first label, and the nucleotide monomer/first label conjugates are substantially non-fluorescent until after incorporation of the nucleotide monomer into the target polynucleotide based on complementarity to the target polynucleotide; and b) providing a second sequencing reagent to the target polynucleotide in the presence of a second polynucleotide replicating catalyst, wherein the second sequencing reagent comprises one nucleotide monomer conjugated to a second label, and the nucleotide monomer/second label conjugate is substantially non-fluorescent until after incorporation of the nucleotide monomer into the target polynucleotide based on complementarity to the target polynucleotide, and wherein the second sequencing reagent is provided prior to or subsequent to providing the first sequencing reagent, and c) obtaining sequence information for at least a portion of the target polynucleotide by detecting fluorescence emission resulting from the first label and second label after incorporation of the nucleotide monomers into the polynucleotide in the steps a) and b), wherein the nucleotide monomers in the first sequencing reagent and the second sequencing reagent are selected from the group consisting of the following combinations: 1) a cytosine (C) nucleotide monomer, a guanine (G) nucleotide monomer, and a thymine (T)/uracil (U) nucleotide monomer in one sequencing reagent, and an adenine (A) nucleotide monomer in the other sequencing reagent; 2) an adenine (A) nucleotide monomer, a guanine (G) nucleotide monomer, and a thymine (T)/uracil (U) nucleotide monomer in one sequencing reagent, and a cytosine (C) nucleotide monomer in the other sequencing reagent; and 3) an adenine (A) nucleotide monomer, a cytosine (C) nucleotide monomer, and a thymine (T)/uracil (U) nucleotide monomer in one sequencing reagent, and a guanine (G) nucleotide monomer in the other sequencing reagent; and 4) an adenine (A) nucleotide monomer, a cytosine (C) nucleotide monomer, and a guanine (G) nucleotide monomer in one sequencing reagent, and a thymine (T)/uracil (U) nucleotide monomer in the other sequencing reagent. In one embodiment, the first labels for the three different nucleotide monomers in step a) and the second label for the one nucleotide monomer in step b) are the same label. In any of the preceding embodiments, multiple rounds of steps a) and b) can be conducted, each round using a combination selected from the combinations 1)-4). In one embodiment, at least two, three, or four sets of sequence information are obtained in step c), the method comprising: conducting multiple rounds of steps a) and b) using combination 1) in a first sequencing reaction volume to obtain a first set of sequence information, conducting multiple rounds of steps a) and b) using combination 2) in a second sequencing reaction volume to obtain a second set of sequence information, conducting multiple rounds of steps a) and b) using combination 3) in a third sequencing reaction volume to obtain a third set of sequence information, and/or conducting multiple rounds of steps a) and b) using combination 4) in a fourth sequencing reaction volume to obtain a fourth set of sequence information. In one embodiment, the first, second, third, and fourth sets of sequence information are obtained in parallel from separate sequencing reaction volumes. In another embodiment, the first, second, third, and fourth sets of sequence information are obtained sequentially from the same sequencing reaction volume, and the products of an earlier sequencing reaction are removed before the next sequencing reaction starts. In any of the preceding embodiments, the method can further comprise comparing the at least two, three, or four sets of sequence information to reduce or eliminate the sequence error(s). In one embodiment, the comparison indicates no error in the obtained target polynucleotide sequence when the at least two, three, or four sets of sequence information are consistent with each other. In one aspect, when the monochrome sequencing method is used, at least three sets of sequence information are needed to detect the sequencing error(s). In another aspect, when the two-color sequencing method is used, only two sets of sequence information are needed to detect the sequencing error(s), because the information from the two fluorescence labels provide an extra piece of information for comparing the sequences.

In another embodiment, the comparison indicates error in the obtained target polynucleotide sequence when the at least two, three, or four sets of sequence information comprise a discrepancy in at least one nucleotide residue of the target polynucleotide sequence. In one embodiment, the method further comprises correcting at least one nucleotide residue in the obtained target polynucleotide sequence such that after the correction, the at least two, three, or four sets of sequence information are consistent with each other. In one aspect, the at least one nucleotide residue is corrected by a deletion or insertion at the position where the error occurs, in order to arrive at the correct sequence. In one aspect, each insertion at the position where the error occurs extends the sequence by at least one nucleotide, and sequence information from one or more other rounds of sequencing is compared with the extended sequence in order to arrive at the corrected sequence. In another aspect, each deletion at the position where the error occurs shortens the sequence by at least one nucleotide, and sequence information from one or more other rounds of sequencing is compared with the shortened sequence in order to arrive at the corrected sequence.

In still another aspect, disclosed herein is a kit or system for obtaining sequence information of a polynucleotide, the kit or system comprising: a) a first sequencing reagent comprising at least two different nucleotide monomer/first label conjugates that are substantially non-fluorescent until after incorporation of the nucleotide monomer into a polynucleotide based on complementarity to a target polynucleotide; and b) a second sequencing reagent comprising one or more nucleotide monomers/second label conjugate(s) that is or are substantially non-fluorescent until after incorporation of the nucleotide monomer(s) into a polynucleotide based on complementarity to the target polynucleotide, at least one of the one or more nucleotide monomers being different from the nucleotide monomers present in the first sequencing reagent, and c) a detector for detecting fluorescence emission resulting from the first label and second label after incorporation of the nucleotide monomers into the polynucleotide. In one embodiment, the kit or system further comprises a first polynucleotide replicating catalyst and/or a second polynucleotide replicating catalyst. In any of the preceding embodiment, the first and/or second label can be conjugated to a terminal phosphate group of the nucleotide monomer. In one embodiment, the kit or system further comprises an activating enzyme for releasing the first and/or second label(s) from the terminal phosphate group of the nucleotide monomer. In any of the preceding embodiments, the kit or system can further comprise a solid surface upon which a target polynucleotide is configured to be immobilized. In one embodiment, the solid surface is a part of a microreactor.

In any of the preceding embodiments, the kit or system can further comprise means for obtaining sequence information for at least a portion of a target polynucleotide based on the fluorescence emission resulting from the first label and second label after incorporation of the nucleotide monomers into the polynucleotide. In one embodiment, the means comprises a computer readable medium containing executable instructions that when executed obtaining sequence information for at least a portion of a target polynucleotide based on the fluorescence emission resulting from the first label and second label after incorporation of the nucleotide monomers into the polynucleotide.

In any of the preceding embodiments, the kit or system can further comprise means for comparing multiple sequences to obtain a non-degenerate sequence and/or to reduce or eliminate sequence error(s) in the non-degenerate sequence. In one embodiment, the means comprises a computer readable medium containing executable instructions that when executed comparing multiple sequences to obtain a non-degenerate sequence and/or to reduce or eliminate sequence error(s) in the non-degenerate sequence.

In one aspect, provided herein is a method of correcting an error of sequencing information, comprising: (a) obtaining information of the leading and/or lagging dephasing phenomenon of a sequencing reaction, using parameter estimation based on a sequencing signal from one or more reference polynucleotides during the sequencing reaction and the known nucleic acid sequence(s) of the reference polynucleotide(s); (b) obtaining a sequencing signal from a target polynucleotide during the sequencing reaction; (c) calculating a secondary lead amount of the target polynucleotide based on the information obtained in step (a) and the sequencing signal obtained from step (b); (d) calculating the dephasing amount of the target polynucleotide based on the sequencing signal obtained from step (b) and the secondary lead amount of step (c); (e) correcting the sequencing signal obtained from step (b) using the dephasing amount in order to generate a predicted sequencing signal of the target polynucleotide; (f) repeating steps (c) to (e) one or more rounds, wherein the predicted sequencing signal from round i is used to calculate the secondary lead amount of the target polynucleotide in round 1+1, until the predicted sequencing signal of the target polynucleotide from round j is mathematically convergent, wherein i and j are integers and $1<i<1+1<j$. In one embodiment, the secondary lead phenomenon refers to that during sequencing, an unexpected nucleotide extension occurs at a residue of the target polynucleotide, and the unexpected extension is further extended by a nucleotide expected for the next residue. In one other embodiment, the dephasing amount comprises a change in the sequencing result due to the leading and/or lagging dephasing phenomenon during sequencing.

In any of the preceding embodiments, the parameter estimation in step (a) can comprise obtaining an attenuation coefficient. In any of the preceding embodiments, the parameter estimation in step (a) can further comprise obtaining an offset amount. In any of the preceding embodiments, the parameter estimation in step (a) can comprise obtaining a unit signal information. In any of the preceding embodiments, the parameter estimation in step (a) can comprise obtaining the lead coefficient and/or lag coefficient with respect to each nucleotide or nucleotide combination.

In any of the preceding embodiments, the method can comprise obtaining the information of the leading and/or lagging dephasing phenomenon of each round of sequencing reaction when multiple rounds of sequencing reactions are performed.

In another aspect, provided herein is a method of correcting an error of sequencing information, comprising: (a) performing parameter estimation based on a sequencing signal from one or more reference polynucleotides during the sequencing reaction and the known nucleic acid sequence(s) of the reference polynucleotide(s); (b) obtaining a sequencing signal from a target polynucleotide during the sequencing reaction; (c) calculating the secondary lead amount of the target polynucleotide based on the information of leading or lagging dephasing obtained by the parameter estimation in step (a) and the sequencing signal obtained from step (b); (d) calculating the dephasing amount of the target polynucleotide based on the sequencing signal obtained from step (b) and the secondary lead amount of step (c); (e) correcting the sequencing signal obtained from step (b) using the dephasing amount in order to generate a predicted sequencing signal of the target polynucleotide; (f) repeating steps (c) to (e) one or more rounds, wherein the predicted sequencing signal from round i is used to calculate the secondary lead amount of the target polynucleotide in round 1+1, until the predicted sequencing signal of the target polynucleotide from round j is mathematically convergent, wherein i and j are integers and $1 \le i < i+1 \le j$. In one aspect, the parameter estimation comprises obtaining the lead amount, the lag amount, the attenuation coefficient, and/or the offset amount, based on the sequencing signal from the reference polynucleotide(s) and the known nucleic acid sequence(s) of the reference polynucleotide(s). In another aspect, the secondary lead phenomenon refers to that during sequencing, an unexpected nucleotide extension occurs at a residue of the target polynucleotide, and the unexpected extension is further extended by a nucleotide expected for the next residue. In yet another aspect, the dephasing amount comprises a change in the sequencing result due to the leading and/or lagging dephasing phenomenon during sequencing.

In yet another aspect, disclosed herein is a method of correcting a lead amount during sequencing, comprising: obtaining a sequencing signal from a target polynucleotide during a sequencing reaction that corresponds to the sequence of the target polynucleotide; and correcting the sequencing signal from the target polynucleotide with a secondary lead amount due to the secondary lead phenomenon, optionally using parameter estimation. In one embodiment, the secondary lead phenomenon refers to that during sequencing, an unexpected nucleotide extension occurs at a residue of the target polynucleotide, and the unexpected extension is further extended by a nucleotide expected for the next residue.

In one aspect, the sequencing signal from a target polynucleotide comprises a primary lead amount due to the primary lead phenomenon, wherein the primary lead phenomenon refers to that during sequencing, an unexpected nucleotide extension occurs at a residue of the target polynucleotide.

In any of the preceding embodiments, if the sequencing signal from a particular nucleotide residue of the target polynucleotide is close to a unit signal, then the sequencing signal can be corrected using the secondary lead amount. In any of the preceding embodiments, the deviation of the sequencing signal intensity from the unit signal intensity is within about 60%, within about 50%, within about 40%, within about 30%, within about 20%, within about 10%, or within about 5%.

In any of the preceding embodiments, when the $n^{th}$ sequencing signal is obtained, the method can comprise: comparing the sequencing signal of a reference polynucleotide with the known sequence of the reference polynucleotide in order to identify an error during sequencing and a method of correcting the error; using the sequencing signal of the target polynucleotide prior to n and the method of correcting error to obtain a corrected sequencing signal, e.g., by feeding back the sequencing signal of the target polynucleotide prior to n into the method of correcting error; and determining if a secondary lead amount exists at residue n by comparing the sequencing signal of the target polynucleotide at residue n with the corrected sequencing signal.

In any of the preceding embodiments, the sequencing can comprise adding one or more sequencing regents into the reaction solution, wherein the one or more sequencing regents optionally comprise a nucleotide and/or an enzyme. In any of the preceding embodiments, in the sequencing, one, two, or three, types of nucleotides can be added in each sequencing reaction. In any of the preceding embodiments, the sequencing reaction can involve an open or unblocked 3' end of a polynucleotide. In any of the preceding embodiments, in the sequencing, the added nucleotide(s) can comprise one or more of A, G, C, and T, or one or more of A, G, C, and U. In any of the preceding embodiments, the detected sequencing signal can comprise an electrical signal, a bioluminescent signal, a chemiluminescent signal, or any combination thereof.

In any of the preceding embodiments, the parameter estimation can comprise: deducing the ideal signal h according to the reference polynucleotide, calculating the dephasing signal (or the phase mismatch) s and the predicted original sequencing signal p based on the preset parameters, and calculating the correlation coefficient c between p and the actual original sequencing signal f. In one aspect, the method further comprises using an optimization method to find a set of parameters so that the correlation coefficient c reaches the optimal value. In another aspect, the set of parameters comprises a lead coefficient or amount, a lag coefficient or amount, an attenuation coefficient, an offset amount, a unit signal, or any combination thereof.

In any of the preceding embodiments, during the sequencing, two groups of reaction solutions can be provided, each group containing one or more nucleotides different from the other group, and one reaction solution is provided in each sequencing reaction. In one aspect, the two groups of reaction solutions are used in an alternating manner to perform the sequencing reactions. In any of the preceding embodiments, the sequencing of the target polynucleotide and the reference polynucleotide can be performed simultaneously.

In any of the preceding embodiments, the reference polynucleotide can be used for parameter estimation in order to obtain one or more of the following parameters of the sequencing reaction: a lead coefficient or amount, a lag coefficient or amount, an attenuation coefficient, an offset amount, and a unit signal. In any of the preceding embodiments, the signal of the target polynucleotide can be corrected using one or more parameters of the sequencing reaction obtained by parameter estimation. In any of the preceding embodiments, the target polynucleotide can comprise a tag comprising a known sequence and/or known amount of nucleotides, and the nucleotides of known sequence and/or known amount are used to generate a unit signal of the sequencing reaction. In any of the preceding embodiments, the unit signal at each sampling point, for example, at each nucleotide residue of the target polynucleotide, can be different.

In still another aspect, disclosed herein is a computer readable medium that comprises an instruction for correcting an error of sequencing information. In one aspect, the instruction comprises: a) receiving sequencing information of a target polynucleotide and a reference polynucleotide; and b) correcting the sequencing information of the target polynucleotide using any of the method for correcting sequencing information disclosed herein.

In another aspect, a computer system for sequencing is provided and the system comprises the computer readable medium disclosed herein.

BRIEF DESCRIPTION OF THE DRAWINGS

FIG. 5A shows previously developed Me-FAM-labeled nucleotides.

FIG. 20A shows the complete sequencing template. FIG. 20B shows the P7 (5') end of the template drafted on solid surface. FIG. 20C shows PCR amplification.

FIGS. 27A & 27B show the responses with impurity at 0 and reaction time at 300. FIGS. 27C & 27D show the responses with impurity at 0.003 and reaction time at 300. FIGS. 27E & 27F show the responses with impurity at 0 and reaction time at 100.

FIG. 33A shows the impact using dephasing coefficient of 0.001. FIG. 33B shows the impact using dephasing coefficient of 0.005. FIG. 33C shows the impact using dephasing coefficient of 0.010.

FIG. 34A shows signal with σ=0 (the standard variation of the white noise). FIG. 34B shows signal with σ=0.01. FIG. 34C shows signal with σ=0.02.

FIG. 36A shows the signal disturbance using dephasing coefficient 0.01 and spike 0.5. FIG. 36B is a heat map of the maximum of $|h_v - h|$ in each tested condition.

FIG. 52A shows a family of fluorogenic sequencing substrates using Tokyo Green as the fluorophore. FIG. 52B shows the first two cycles of the sequencing using K(dG & dT) and K(dA & dC) reaction mixes sequentially. FIG. 52C shows the degenerated polymer length (DPL) array and its associated dual-base flowgrams.

FIG. 53A shows the change in fluorescence intensity and the error associated with the reaction cycle. FIG. 53B correlates the number of bases extended, corrected for decay effect only, and the reaction cycle. FIG. 53C correlates the number of bases extended in the MK round, corrected for dephasing and decay effects, and the reaction cycle. FIG. 53D correlates the number of bases extended in the RY round, corrected for dephasing and decay effects, and the reaction cycle. FIG. 53E correlates the number of bases extended in the WS round, corrected for dephasing and decay effects, and the reaction cycle.

FIGS. 54A-D show an information communication model for ECC sequencing, according to one aspect of the present disclosure. FIG. 54A shows an information communication model depicting the dual-base sequencing with intrinsic characteristic of error detection and correction. FIG. 54B shows the DPL distribution in human, yeast and E. coli genomes, where $P(n)=\frac{1}{2}^n$. FIG. 54C shows the concordance of original and measured DPLs that in 42 rounds of dual-base sequencing data. FIG. 54D shows degenerate sequence coded in bit string format providing information for error detection.

FIG. 55A shows an example of dynamic programing. FIG. 55B shows a codeword space constructed as a 3-dimensional matrix with the three BSs as its axis. FIG. 55C shows the process of dynamic programming approach to obtain the optimal path.

FIG. 56A shows that minor scattered sequencing error in Lambda phage sequences can be corrected by ECC decoding. These errors were completely eliminated before 200 bp and significantly reduced in 200-250 bp. FIG. 56B shows that complex neighboring sequencing errors can be corrected by ECC decoding. FIG. 56C shows the error frequencies of different DPLs along the sequencing read analyzed every 50 nt without ECC correction.

DETAILED DESCRIPTION

Figure 1:
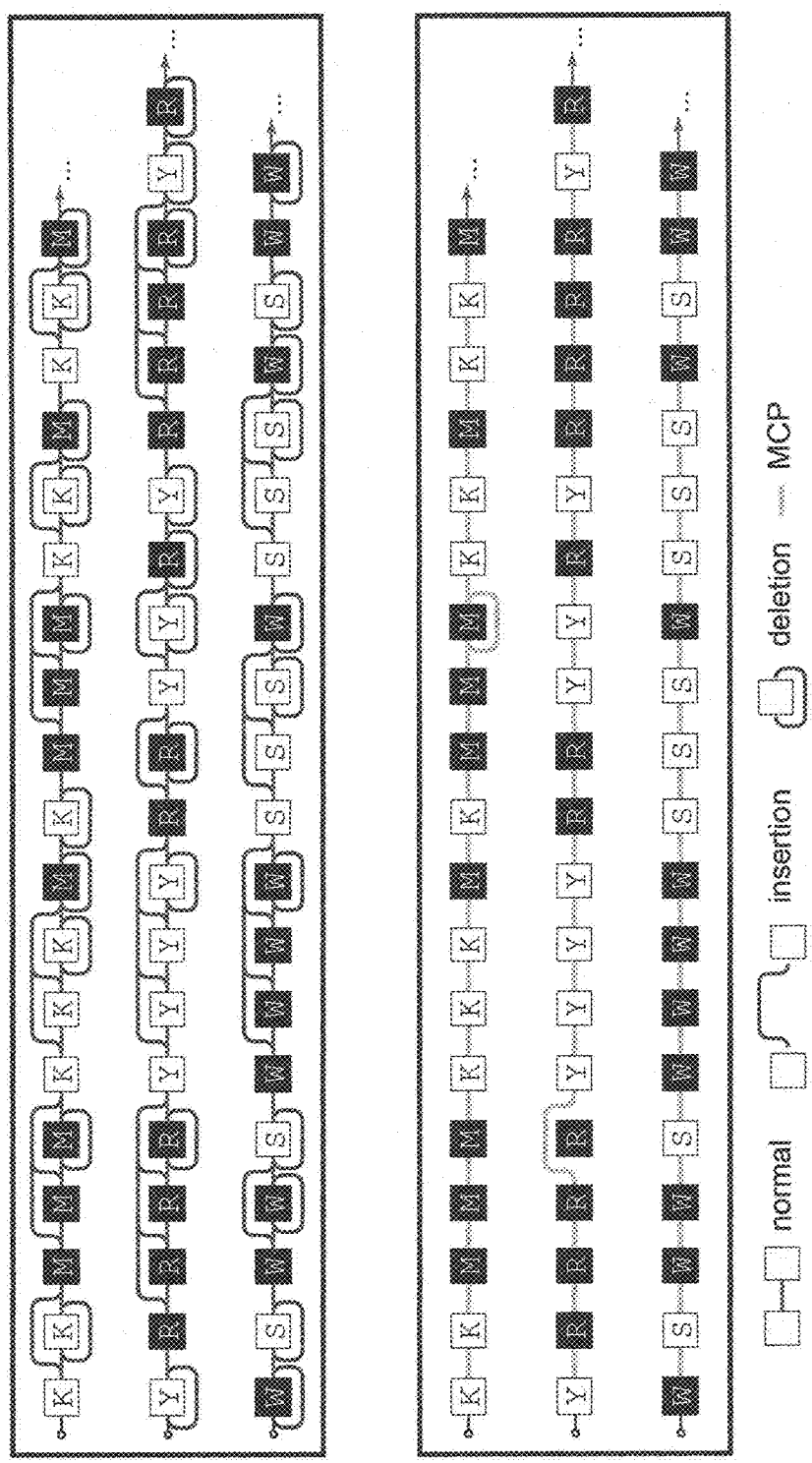
FIG. 1 shows a method for correction of a sequence data error.

A detailed description of one or more embodiments of the claimed subject matter is provided below along with accompanying figures that illustrate the principles of the claimed subject matter. The claimed subject matter is described in connection with such embodiments, but is not limited to any particular embodiment. It is to be understood that the claimed subject matter may be embodied in various forms, and encompasses numerous alternatives, modifications and equivalents. Therefore, specific details disclosed herein are not to be interpreted as limiting, but rather as a basis for the claims and as a representative basis for teaching one skilled in the art to employ the claimed subject matter in virtually any appropriately detailed system, structure, or manner. Numerous specific details are set forth in the following description in order to provide a thorough understanding of the present disclosure. These details are provided for the purpose of example and the claimed subject matter may be practiced according to the claims without some or all of these specific details. It is to be understood that other embodiments can be used and structural changes can be made without departing from the scope of the claimed subject matter. It should be understood that the various features and functionality described in one or more of the individual embodiments are not limited in their applicability to the particular embodiment with which they are described. They instead can, be applied, alone or in some combination, to one or more of the other embodiments of the disclosure, whether or not such embodiments are described, and whether or not such features are presented as being a part of a described embodiment. For the purpose of clarity, technical material that is known in the technical fields related to the claimed subject matter has not been described in detail so that the claimed subject matter is not unnecessarily obscured.

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art.

All publications, including patent documents, scientific articles and databases, referred to in this application are incorporated by reference in their entireties for all purposes to the same extent as if each individual publication were individually incorporated by reference. If a definition set forth herein is contrary to or otherwise inconsistent with a definition set forth in the patents, patent applications, published applications or other publications that are herein incorporated by reference, the definition set forth herein prevails over the definition that is incorporated herein by reference. Citation of the publications or documents is not intended as an admission that any of them is pertinent prior art, nor does it constitute any admission as to the contents or date of these publications or documents.

All headings are for the convenience of the reader and should not be used to limit the meaning of the text that follows the heading, unless so specified.

The practice of the provided embodiments will employ, unless otherwise indicated, conventional techniques and descriptions of organic chemistry, polymer technology, molecular biology (including recombinant techniques), cell biology, biochemistry, and sequencing technology, which are within the skill of those who practice in the art. Such conventional techniques include polypeptide and protein synthesis and modification, polynucleotide synthesis and modification, polymer array synthesis, hybridization and ligation of polynucleotides, and detection of hybridization using a label. Specific illustrations of suitable techniques can be had by reference to the examples herein. However, other equivalent conventional procedures can, of course, also be used. Such conventional techniques and descriptions can be found in standard laboratory manuals such as Green, et al., Eds., Genome Analysis: A Laboratory Manual Series (Vols. I-IV) (1999); Weiner, Gabriel, Stephens, Eds., Genetic Variation: A Laboratory Manual (2007); Dieffenbach, Dveksler, Eds., PCR Primer: A Laboratory Manual (2003); Bowtell and Sambrook, DNA Microarrays: A Molecular Cloning Manual (2003); Mount, Bioinformatics: Sequence and Genome Analysis (2004); Sambrook and Russell, Condensed Protocols from Molecular Cloning: A Laboratory Manual (2006); and Sambrook and Russell, Molecular Cloning: A Laboratory Manual (2002) (all from Cold Spring Harbor Laboratory Press); Ausubel et al. eds., Current Protocols in Molecular Biology (1987); T. Brown ed., Essential Molecular Biology (1991), IRL Press; Goeddel ed., Gene Expression Technology (1991), Academic Press; A. Bothwell et al. eds., Methods for Cloning and Analysis of Eukaryotic Genes (1990), Bartlett Publ.; M. Kriegler, Gene Transfer and Expression (1990), Stockton Press; R. Wu et al.

eds., Recombinant DNA Methodology (1989), Academic Press; M. McPherson et al., PCR: A Practical Approach (1991), IRL Press at Oxford University Press; Stryer, Biochemistry (4th Ed.) (1995), W. H. Freeman, New York N.Y.; Gait, Oligonucleotide Synthesis: A Practical Approach (2002), IRL Press, London; Nelson and Cox, Lehninger, Principles of Biochemistry (2000) 3rd Ed., W. H. Freeman Pub., New York, N.Y.; Berg, et al., Biochemistry (2002) 5th Ed., W. H. Freeman Pub., New York, N.Y.; D. Weir & C. Blackwell, eds., Handbook of Experimental Immunology (1996), Wiley-Blackwell; Cellular and Molecular Immunology (A. Abbas et al., W.B. Saunders Co. 1991, 1994); Current Protocols in Immunology (J. Coligan et al. eds. 1991), all of which are herein incorporated in their entireties by reference for all purposes.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6.

I. Definitions

As used herein, the singular forms "a," "an," and "the" include plural referents unless the context clearly dictates otherwise. For example, "a" or "an" means "at least one" or "one or more." It is understood that aspects and variations described herein include "consisting" and/or "consisting essentially of" aspects and variations.

The term "about" as used herein refers to the usual error range for the respective value readily known to the skilled person in this technical field. Reference to "about" a value or parameter herein includes (and describes) embodiments that are directed to that value or parameter per se. For example, description referring to "about X" includes description of "X".

The terms "polynucleotide," "oligonucleotide," "nucleic acid" and "nucleic acid molecule" are used interchangeably herein to refer to a polymeric form of nucleotides of any length, and comprise ribonucleotides, deoxyribonucleotides, and analogs or mixtures thereof. The terms include triple-, double- and single-stranded deoxyribonucleic acid ("DNA"), as well as triple-, double- and single-stranded ribonucleic acid ("RNA"). It also includes modified, for example by alkylation, and/or by capping, and unmodified forms of the polynucleotide. More particularly, the terms "polynucleotide," "oligonucleotide," "nucleic acid," and "nucleic acid molecule" include polydeoxyribonucleotides (containing 2-deoxy-D-ribose), polyribonucleotides (containing D-ribose), including tRNA, rRNA, hRNA, and mRNA, whether spliced or unspliced, any other type of polynucleotide which is an N- or C-glycoside of a purine or pyrimidine base, and other polymers containing nonnucleotidic backbones, for example, polyamide (e.g., peptide nucleic acids ("PNAs")) and polymorpholino (commercially available from the Anti-Virals, Inc., Corvallis, OR, as Neugene) polymers, and other synthetic sequence-specific nucleic acid polymers providing that the polymers contain nucleobases in a configuration which allows for base pairing and base stacking, such as is found in DNA and RNA. Thus, these terms include, for example, 3'-deoxy-2',5'-DNA, oligodeoxyribonucleotide N3' to P5' phosphoramidates, 2'-O-alkyl-substituted RNA, hybrids between DNA and RNA or between PNAs and DNA or RNA, and also include known types of modifications, for example, labels, alkylation, "caps," substitution of one or more of the nucleotides with an analog, inter-nucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalkylphosphoramidates, aminoalkylphosphotriesters), those containing pendant moieties, such as, for example, proteins (including enzymes (e.g. nucleases), toxins, antibodies, signal peptides, poly-L-lysine, etc.), those with intercalators (e.g., acridine, psoralen, etc.), those containing chelates (of, e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide. A nucleic acid generally will contain phosphodiester bonds, although in some cases nucleic acid analogs may be included that have alternative backbones such as phosphoramidite, phosphorodithioate, or methylphophoroamidite linkages; or peptide nucleic acid backbones and linkages. Other analog nucleic acids include those with bicyclic structures including locked nucleic acids, positive backbones, non-ionic backbones and non-ribose backbones. Modifications of the ribose-phosphate backbone may be done to increase the stability of the molecules; for example, PNA:DNA hybrids can exhibit higher stability in some environments. The terms "polynucleotide," "oligonucleotide," "nucleic acid" and "nucleic acid molecule" can comprise any suitable length, such as at least 5, 6, 7, 8, 9, 10, 20, 30, 40, 50, 100, 200, 300, 400, 500, 1,000 or more nucleotides.

It will be appreciated that, as used herein, the terms "nucleoside" and "nucleotide" include those moieties which contain not only the known purine and pyrimidine bases, but also other heterocyclic bases which have been modified. Such modifications include methylated purines or pyrimidines, acylated purines or pyrimidines, or other heterocycles. Modified nucleosides or nucleotides can also include modifications on the sugar moiety, e.g., wherein one or more of the hydroxyl groups are replaced with halogen, aliphatic groups, or are functionalized as ethers, amines, or the like. The term "nucleotidic unit" is intended to encompass nucleosides and nucleotides.

The terms "complementary" and "substantially complementary" include the hybridization or base pairing or the formation of a duplex between nucleotides or nucleic acids, for instance, between the two strands of a double-stranded DNA molecule or between an oligonucleotide primer and a primer binding site on a single-stranded nucleic acid.

Complementary nucleotides are, generally, A and T (or A and U), or C and G. Two single-stranded RNA or DNA molecules are said to be substantially complementary when the nucleotides of one strand, optimally aligned and compared and with appropriate nucleotide insertions or deletions, pair with at least about 80% of the other strand, usually at least about 90% to about 95%, and even about 98% to about 100%. In one aspect, two complementary sequences of nucleotides are capable of hybridizing, preferably with less than 25%, more preferably with less than 15%, even more preferably with less than 5%, most preferably with no mismatches between opposed nucleotides. Preferably the two molecules will hybridize under conditions of high stringency.

"Hybridization" as used herein may refer to the process in which two single-stranded polynucleotides bind non-covalently to form a stable double-stranded polynucleotide. In one aspect, the resulting double-stranded polynucleotide can be a "hybrid" or "duplex." "Hybridization conditions" typically include salt concentrations of approximately less than 1 M, often less than about 500 mM and may be less than about 200 mM. A "hybridization buffer" includes a buffered salt solution such as 5% SSPE, or other such buffers known in the art. Hybridization temperatures can be as low as 5° C., but are typically greater than 22° C., and more typically greater than about 30° C., and typically in excess of 37° C. Hybridizations are often performed under stringent conditions, i.e., conditions under which a sequence will hybridize to its target sequence but will not hybridize to other, non-complementary sequences. Stringent conditions are sequence-dependent and are different in different circumstances. For example, longer fragments may require higher hybridization temperatures for specific hybridization than short fragments. As other factors may affect the stringency of hybridization, including base composition and length of the complementary strands, presence of organic solvents, and the extent of base mismatching, the combination of parameters is more important than the absolute measure of any one parameter alone. Generally stringent conditions are selected to be about 5° C. lower than the Tm for the specific sequence at a defined ionic strength and pH. The melting temperature Tm can be the temperature at which a population of double-stranded nucleic acid molecules becomes half dissociated into single strands. Several equations for calculating the Tm of nucleic acids are well known in the art. As indicated by standard references, a simple estimate of the Tm value may be calculated by the equation, $Tm=81.5+0.41$ (% G+C), when a nucleic acid is in aqueous solution at 1 M NaCl (see e.g., Anderson and Young, Quantitative Filter Hybridization, in Nucleic Acid Hybridization (1985)). Other references (e.g., Allawi and SantaLucia, Jr., Biochemistry, 36:10581-94 (1997)) include alternative methods of computation which take structural and environmental, as well as sequence characteristics into account for the calculation of Tm.

In general, the stability of a hybrid is a function of the ion concentration and temperature. Typically, a hybridization reaction is performed under conditions of lower stringency, followed by washes of varying, but higher, stringency. Exemplary stringent conditions include a salt concentration of at least 0.01 M to no more than 1 M sodium ion concentration (or other salt) at a pH of about 7.0 to about 8.3 and a temperature of at least 25° C. For example, conditions of 5×SSPE (750 mM NaCl, 50 mM sodium phosphate, 5 mM EDTA at pH 7.4) and a temperature of approximately 30° C. are suitable for allele-specific hybridizations, though a suitable temperature depends on the length and/or GC content of the region hybridized. In one aspect, "stringency of hybridization" in determining percentage mismatch can be as follows: 1) high stringency: 0.1×SSPE, 0.1% SDS, 65° C.; 2) medium stringency: 0.2×SSPE, 0.1% SDS, 50° C. (also referred to as moderate stringency); and 3) low stringency: 1.0×SSPE, 0.1% SDS, 50° C. It is understood that equivalent stringencies may be achieved using alternative buffers, salts and temperatures. For example, moderately stringent hybridization can refer to conditions that permit a nucleic acid molecule such as a probe to bind a complementary nucleic acid molecule. The hybridized nucleic acid molecules generally have at least 60% identity, including for example at least any of 70%, 75%, 80%, 85%, 90%, or 95% identity. Moderately stringent conditions can be conditions equivalent to hybridization in 50% formamide, 5×Denhardt's solution, 5×SSPE, 0.2% SDS at 42° C., followed by washing in 0.2×SSPE, 0.2% SDS, at 42° C. High stringency conditions can be provided, for example, by hybridization in 50% formamide, 5×Denhardt's solution, 5×SSPE, 0.2% SDS at 42° C., followed by washing in 0.1×SSPE, and 0.1% SDS at 65° C. Low stringency hybridization can refer to conditions equivalent to hybridization in 10% formamide, 5×Denhardt's solution, 6×SSPE, 0.2% SDS at 22° C., followed by washing in 1×SSPE, 0.2% SDS, at 37° C. Denhardt's solution contains 1% Ficoll, 1% polyvinylpyrolidone, and 1% bovine serum albumin (BSA). 20×SSPE (sodium chloride, sodium phosphate, EDTA) contains 3 M sodium chloride, 0.2 M sodium phosphate, and 0.025 M EDTA. Other suitable moderate stringency and high stringency hybridization buffers and conditions are well known to those of skill in the art and are described, for example, in Sambrook et al., Molecular Cloning: A Laboratory Manual, 2nd ed., Cold Spring Harbor Press, Plainview, N.Y. (1989); and Ausubel et al., Short Protocols in Molecular Biology, 4th ed., John Wiley & Sons (1999).

Alternatively, substantial complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See M. Kanehisa, Nucleic Acids Res. 12:203 (1984).

A "primer" used herein can be an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process is determined by the sequence of the template polynucleotide. Primers usually are extended by a polymerase, for example, a DNA polymerase.

A "substantially non-fluorescent" moiety refers a moiety that is approximately or essentially without emitting detectable fluorescence. For example, a ratio of a detectable absolute fluorescent emission from a fluorescent moiety to a detectable absolute fluorescent emission from a substantially non-fluorescent moiety at approximately the same concentrations of the fluorescent moiety and the substantially non-fluorescent moiety is typically about 500:1 or more, more typically about 1000:1 or more, and even more typically about 1500:1 or more (e.g., about 2000:1, about 2500:1, about 3000:1, about 3500:1, about 4000:1, about 4500:1, about 5000:1, about $10^4$:1, about $10^5$:1, about $10^6$:1, about $10^7$:1, or about $10^8$:1).

"Sequence determination" and the like, such as a nucleotide sequencing method, include determination of information relating to the nucleotide base sequence of a nucleic acid. Such information may include the identification or determination of partial as well as full sequence information of the nucleic acid. Sequence information may be determined with varying degrees of statistical reliability or confidence. In one aspect, the term includes the determination of the identity and ordering of a plurality of contiguous nucleotides in a nucleic acid. "High throughput sequencing" or "next generation sequencing" includes sequence determination using methods that determine many (typically thousands to billions) of nucleic acid sequences in an intrinsically parallel manner, i.e. where DNA templates are prepared for sequencing not one at a time, but in a bulk process, and where many sequences are read out preferably in parallel, or alternatively using an ultra-high throughput serial process that itself may be parallelized. Such methods include but are not limited to pyrosequencing (for example, as commercialized by 454 Life Sciences, Inc., Branford, CT); sequencing by ligation (for example, as commercialized in the SOLiD™ technology, Life Technologies, Inc., Carlsbad, CA); sequencing by synthesis using modified nucleotides (such as commercialized in TruSeq™ and HiSeg™ technology by Illumina, Inc., San Diego, CA; HeliScope™ by Helicos Biosciences Corporation, Cambridge, MA; and PacBio RS by Pacific Biosciences of California, Inc., Menlo Park, CA), sequencing by ion detection technologies (such as Ion Torrent™ technology, Life Technologies, Carlsbad, CA); sequencing of DNA nanoballs (Complete Genomics, Inc., Mountain View, CA); nanopore-based sequencing technologies (for example, as developed by Oxford Nanopore Technologies, LTD, Oxford, UK), and like highly parallelized sequencing methods.

In any of the embodiments disclosed herein, the method for obtaining sequence information of a target polynucleotide can be performed in a multiplex assay. "Multiplexing" or "multiplex assay" herein may refer to an assay or other analytical method in which the presence and/or amount of multiple targets, e.g., multiple nucleic acid sequences, can be assayed simultaneously, each of which has at least one different detection characteristic, e.g., fluorescence characteristic (for example excitation wavelength, emission wavelength, emission intensity, FWHM (full width at half maximum peak height), or fluorescence lifetime) or a unique nucleic acid or protein sequence characteristic.

In any of the embodiments disclosed herein, the sequencing reactions of the target polynucleotides may be performed on an array, such as a microchip. The array may comprise a plurality of reaction volumes, for example, created by a plurality of reaction chambers disposed on the array. The target nucleotide sequences or fragments thereof can be fixed or otherwise immobilized in the reaction volumes, such as by adsorption or specific binding to a capture molecule on a solid support in each reaction volume. After the reaction solution is provided in the reaction mix and delivered to each reaction volume, each reaction volume can be closed and/or separated from other reaction volumes on the array. Then, a signal such as fluorescence information can be detected and/or recorded from each reaction volume.

In any of the embodiments disclosed herein, the array can be addressable. In one aspect, addressability comprises the capacity of a microchip to direct materials such as nucleic acids and enzymes and other amplification components from one position to another on the microchip the capture sites of the chip. In another aspect, addressability comprises the capacity of spatially encoding the sequencing reaction and/or sequencing product thereof on each array spot, such that after sequence readout, a sequencing reaction and/or sequencing product thereof can be mapped back to a specific spot on the array and associated with other identifying information from that specific spot. For example, space encoding tags may be conjugated to the target polynucleotides such that when the conjugated target polynucleotide are sequenced, the tag sequence reveals where on the array the target is located.

II. Sequencing Methods

In one aspect, disclosed herein is a sequencing method for nucleotide molecules by modifying a fluorophore using phosphate. In another aspect, disclosed herein is a sequencing method using a nucleotide molecule that is modified with a fluorescence switching fluorophore.

In one aspect, disclosed herein is a sequencing method of mixed nucleotide. In a specific embodiment, disclosed herein is a sequencing method by using phosphate to modify mixed nucleotide molecules with fluorophores. In addition, the present disclosure also relates to a sequencing method based on fluorophores having fluorescence switching property.

In one aspect, disclosed herein is a sequencing method using mixed nucleotide molecules. In a specific embodiment, disclosed herein is a sequencing method by using modified mixed nucleotide molecules with fluorophores. In addition, the present disclosure also relates to a sequencing method based on fluorophores having fluorescence switching property. The present disclosure combines the fluorescence switching sequencing and the mixed nucleotide molecules sequencing, achieving unexpected technical results. The special signal acquisition method and efficiency enable it has a great prospect in gene sequencing.

In one aspect, disclosed herein is a sequencing method using nucleotide substrate molecules, wherein the sequencing is achieved by modifying the 5' end or an intermediate phosphate of a nucleotide substrate molecule with a fluorophore; each round of sequencing uses one reaction solution group, each reaction solution group comprises two reaction solutions, and each reaction solution comprises two nucleotides with different bases. In one embodiment, the nucleotides in one reaction solution are complementary with two bases on the nucleotide sequence to be determined, and the nucleotides in the other reaction solution are complementary with the other two bases on the nucleotide sequence to be determined. In one embodiment, the method comprises first providing the nucleotide sequence fragment to be determined (for example, by fixing the nucleotide sequence on a solid support), and then providing the first reaction solution in one reaction solution group to start the first round of sequencing. In one embodiment, the method comprises detecting and recording the fluorescent signals from the first round of sequencing. In one embodiment, the method then comprises providing the second reaction solution of the same reaction solution group, to continue the first round of sequencing. Fluorescent signals are again detected and recorded. In one aspect, the above steps are repeated, and the first and second reaction solutions can be provided sequentially in any suitable order, in order to obtain the coded information of the nucleotide sequence to be determined through analysis of the fluorescent signals.

In one embodiment, each of the reaction solution includes two nucleotides with different bases, which may be labeled with different or the same fluorophores.

In any of the preceding embodiments, the sequencing can be achieved by modifying 5' end or intermediate phosphate of the nucleotide substrate molecules with fluorophores having fluorescence switching property. In one aspect, the fluorescence switching property refers to that the fluorescence signal after sequencing is significantly changed compared to the condition before the sequencing reaction.

In any of the preceding embodiments, the fluorescence switching property can refer to that the fluorescence signal after sequencing is significantly enhanced (or increased) compared to the condition before the sequencing reaction.

Also disclosed herein in one aspect is a sequencing method, using nucleotide substrate molecules with fluorophores having fluorescence switching property. In one aspect, the sequencing is achieved by modifying 5' end or intermediate phosphate of the nucleotide substrate molecules with fluorophores having fluorescence switching property. In one aspect, the fluorescence switching property refers to that the intensity of fluorescence signal after sequencing is significantly enhanced compared to the condition before the sequencing reaction. Each round of sequencing uses one reaction solution group, each reaction solution group includes two reaction solutions, and each reaction solution includes two nucleotide substrate molecules with different bases. In one aspect, the nucleotide substrate molecules in one reaction solution are complementary with two bases on the nucleotide sequence to be tested, and the nucleotide substrate molecules in the other reaction solution are complementary with the other two bases on the nucleotide sequence to be tested. In one aspect, the method comprises fixing the nucleotide sequence fragment to be tested in the reaction chamber, and letting in the first reaction solution in one reaction solution group. In one aspect, the method comprises releasing the fluorophores on the nucleotide substrate using enzymes to cause fluorescence switching. In one aspect, the method comprises letting in the second reaction solution of the same reaction solution group. In one aspect, the method comprises releasing the fluorophores on the nucleotide substrate using enzymes to cause fluorescence switching. In one aspect, the method comprises adding the two reaction solutions in an alternating manner, and obtaining the coded information of the nucleotide substrate to be tested through the fluorescent information.

In another aspect, disclosed herein is a sequencing method using nucleotide substrate molecules with fluorophores having a fluorescence switching property. In one aspect, the sequencing is achieved by modifying the 5' end or an intermediate phosphate of a nucleotide substrate molecule with a fluorophore having a fluorescence switching property. In one aspect, the fluorescence switching property refers to that the intensity of fluorescence signal after sequencing is significantly enhanced compared to the intensity of fluorescence signal before the sequencing reaction. In one aspect, each sequencing run uses one reaction solution group, each reaction solution group comprising at least two reaction solutions, and each reaction solution comprising at least one of the A, G, C, or T nucleotide substrate molecules, or one of the A, G, C, or U nucleotide substrate molecules. In one aspect, a nucleotide sequence fragment to be tested is first fixed in a reaction chamber, and a reaction solution from one reaction solution group is provided in the reaction chamber. The sequencing reaction can be started under a suitable condition, and a fluorescent signal is recorded. Then, additional reaction solutions are provided one at a time, so that the other reaction solutions in the same reaction solution group are provided sequentially in the sequencing reaction. At the same time, one or more fluorescent signals from each reaction solution are recorded. In one aspect, there is at least one reaction solution in a reaction solution group that comprises two or three nucleotide molecules.

In one other aspect, disclosed herein is a sequencing method using nucleotide substrate molecules with fluorophores having fluorescence switching property, achieved by modifying 5'end or intermediate phosphate of the nucleotide substrate molecules with fluorophores having fluorescence switching property. In one aspect, the fluorescence switching property refers to that the intensity of fluorescence signal after sequencing is significantly enhanced compared to the condition before the sequencing reaction. In one aspect, each sequencing run uses one reaction solution group, each reaction solution group includes two reaction solutions, and each reaction solution includes any of A, G, C or T nucleotide substrate molecule, or any of A, G, C or U nucleotide substrate molecule. In one aspect, the method comprises first fixing the nucleotide sequence fragment to be tested in the reaction chamber, and letting in one reaction solution in one reaction solution group. In one aspect, the method comprises testing and recording the fluorescent information. In one aspect, the method comprises adding one reaction solution at a time, and then the other reaction solutions in the same reaction solution group sequentially. Fluorescent information from each sequencing reaction is recorded.

In another aspect, disclosed herein is a sequencing method using nucleotide substrate molecules with fluorophores having fluorescence switching property, and the sequencing is achieved by modifying 5'end or intermediate phosphate of the nucleotide substrate molecules with fluorophores having fluorescence switching property, and the fluorescence switching property refers to that the intensity of fluorescence signal after sequencing is significantly enhanced compared to the condition before the sequencing reaction. In one aspect, each round of sequencing uses one reaction solution group, and the reaction solution includes A, G, C and T nucleotide substrate molecules, or A, G, C and U nucleotide substrate molecules. In one aspect, the method comprises fixing the nucleotide sequence fragment to be tested in the reaction chamber, and letting in the reaction solution, and recording the fluorescent information.

In any of the preceding embodiments, the method can further comprise removing the residual reaction solution and fluorescence molecules with cleaning solution, and then proceeding with the next round of sequencing reaction. In any of the preceding embodiments, the reaction solution can be provided at a low temperature, and then heated to an enzyme reaction temperature, wherein a fluorescence signal is detected. In any of the preceding embodiments, after the reaction solution is provided in the reaction mix, the reaction chamber can be closed and fluorescence information can be detected and/or recorded.

In any of the preceding embodiments, after the reaction solution is provided, the space outside the reaction chamber can be filled with oil to insulate and close the reaction chamber. In any of the preceding embodiments, the nucleotide substrate molecules of poly-phosphoric acid can refer to the nucleotide with 4 to 8 phosphoric acid molecules. In any of the preceding embodiments, the modified nucleotide substrate molecules with fluorophores can be labeled with one fluorescence group for single-color sequencing; or with different fluorescence groups for multiple-color sequencing.

In any of the preceding embodiments, the method can comprise releasing the fluorophores on the nucleotide substrate with fluorophores having fluorescence switching property using enzymes, wherein the enzymes can optionally comprise DNA polymerase and/or alkaline phosphatase.

In any of the preceding embodiments, wherein the two bases on the nucleotide sequence to be tested can comprise any two of A, G, C and T bases or of A, G, C and U bases; wherein Base C is methylated C or non-methylated C.

In any of the preceding embodiments, the reaction solution can comprise the enzymes, namely, when the reaction solution is let into the reaction area where the gene segment to be tested is located, the included enzyme can release the fluorophores on the nucleotide substrate with fluorophores having fluorescence switching property.

In any of the preceding embodiments, the reaction solution and the enzyme can be added at different times, namely, first letting in the first reaction solution of one reaction solution group, and then letting in the enzyme solution; next, let in the second reaction solution in the same reaction solution group, and then the enzyme solution.

In any of the preceding embodiments, one reaction solution group can be used to conduct one round of sequencing, or two reaction solution groups can be used to conduct two rounds of sequencing, or three reaction solution groups can be used for three rounds of sequencing.

In any of the preceding embodiments, the method can comprise conducting one round of sequencing using one reaction solution group and obtaining a degenerate code result.

In any of the preceding embodiments, the method can comprise conducting two rounds of sequencing using two reaction solution groups and obtain a base sequence information.

In any of the preceding embodiments, the method can comprise conducting three reaction solutions to conduct three rounds of sequencing, and performing error checking and correction using the mutual information among the three rounds of sequencing based on the results of two rounds of sequencing.

In any of the preceding embodiments, the fluorophores having fluorescence switching property can comprise the fluorophores with structures like methyl fluorescein, halogenated methyl fluorescein, DDAO, or resorufin.

In any of the preceding embodiments, the method can comprise releasing the fluorophores on the nucleotide substrate with fluorophores having fluorescence switching property using enzymes, wherein the optimization optionally comprises releasing the fluorophores substituted by the polyphosphoric acid using DNA polymerase first, and then excising the substituting polyphosphoric acid using the phosphatase to release the fluorophores.

In any of the preceding embodiments, the reaction solution can comprise two or more nucleotides with different bases, the reaction solution may be simply decomposed into two or more reaction solutions, so that each of the reaction solution includes one or more nucleotides; and at least one reaction solution can comprise two or three nucleotides with different bases.

Also disclosed herein is a high-throughput sequencing method according to any of foregoing embodiments, wherein the sequencing reaction is conducted on a chip which has several reaction chambers. The method can optionally comprise fixing the nucleotide sequence fragment to be tested in the reaction chamber.

In another aspect, disclosed herein is a sequencing method using nucleotide substrate molecules with fluorophores having fluorescence switching property, and the sequencing is achieved by using 5'end polyphosphoric acid to modify nucleotide substrate molecules with fluorophores having fluorescence switching property. In one aspect, provided herein is a method comprising first immobilizing the nucleotide sequence fragment to be tested, and adding in the reaction solution which contains nucleotide substrate molecules. Then, fluorophores on the nucleotide substrate can be released using enzymes to cause fluorescence switching.

In one embodiment, the sequencing method further comprises removing the residual reaction solution and fluorescence molecules with a cleaning solution, and then proceeding with the next round of sequencing reaction. In any of the preceding embodiments, the sequencing method can comprise a reaction solution at a low temperature, which is then heated to an enzyme reaction temperature. A fluorescence signal may then be detected and/or recorded.

In any of the preceding embodiments, the nucleotide substrate molecules can comprise the nucleotide molecules containing A, G, C and T bases, or those that contain A, G, C and U bases; wherein the C is the methylated C or non-methylated C. In any of the preceding embodiments, the nucleotide substrate molecules can comprise fluorophores having fluorescence switching property, modified by 5' end polyphosphoric acid. In any of the preceding embodiments, the nucleotide substrate molecules can comprise fluorophores having fluorescence switching property, modified by 5' end phosphoric acid.

Also disclosed herein is a method according to any of the foregoing embodiments, wherein different nucleotide substrate molecules may be connected with one fluorophore for single-color sequencing or connected with multiple fluorophores for multiple-color sequencing, depending on the base.

Disclosed herein is a method according to any of the foregoing embodiments, wherein the fluorescence switching property refers to that the fluorescence signal after each step of sequencing reaction is significantly enhanced or weakened, or the frequency of the emission light is significantly changed compared to the conditions before the sequencing reaction;

Disclosed herein is a method according to any of the foregoing embodiments, wherein the fluorescence switching property refers to that the fluorescence signal after each step of sequencing reaction is significantly enhanced compared to the condition before the sequencing reaction;

Disclosed herein is a method according to any of the foregoing embodiments, wherein the reaction solution containing nucleotide substrate molecules is used for sequencing. The nucleotide substrate molecules refer to the mixture of any two or three of A, G, C and T nucleotide substrate molecules; or the mixture of any two or three of A, G, C and U nucleotide substrate molecules.

Disclosed herein is a method according to any of the foregoing embodiments, wherein the reaction solution containing nucleotide substrate molecules is used for sequencing. The nucleotide substrate molecules refer to any of A, G, C and T nucleotide substrate molecules; or any of A, G, C and U nucleotide substrate molecules.

Disclosed herein is a sequencing method using nucleotide substrate molecules with fluorophores having fluorescence switching property according to any of the preceding embodiments, wherein each round of sequencing uses one reaction solution group, each reaction solution group includes at least two reaction solutions, and each reaction solution includes at least one of A, G, C or T nucleotide substrate molecule, or one of A, G, C or U nucleotide substrate molecule. The method in one aspect comprises fixing the nucleotide sequence fragment to be tested, and letting in one reaction solution in one reaction solution group, and recording the fluorescent information. The method in one aspect comprises letting in one reaction solution each time, and letting in the other reaction solutions in the same reaction solution group sequentially. In one aspect, there is at least one reaction solution that contains two or three nucleotide molecules in the reaction solution group.

Disclosed herein is a sequencing method using nucleotide substrate molecules with fluorophores having fluorescence switching property according to any of the preceding embodiments, wherein each round of sequencing uses one reaction solution group, each reaction solution group includes two reaction solutions, and each reaction solution includes two nucleotides with different bases. In one aspect, the nucleotide in one reaction solution is complementary with two bases on the nucleotide sequence to be tested, and the nucleotide in the other reaction solution is complementary with the other two bases on the nucleotide sequence to be tested. In one aspect, the method comprises fixing the nucleotide sequence fragment to be tested, and letting in the first reaction solution in one reaction solution group. Then, the second reaction solution of the same reaction solution group is provided. The two reaction solutions can be added sequentially in an alternating fashion, in order to obtain the coded information of the nucleotide substrate to be tested through the fluorescent information.

In any of the foregoing embodiments, after the reaction solution is added in sequencing the reaction, the reaction chamber is closed, and then the fluorescent signal is record.

In any of the foregoing embodiments, after the reaction solution is added in sequencing the reaction, the space outside the reaction chamber is filled with oil or an oil-like substance that is capable of insulating and closing the reaction chamber.

In any of the foregoing embodiments, the polyphosphoric acid nucleotide substrate can be a nucleotide with about 4 to about 8 phosphoric acid molecules.

In any of the foregoing embodiments, one reaction solution group can be used to conduct one round of sequencing, or two reaction solution groups can be used to conduct two rounds of sequencing, or three reaction solution groups can be used for three rounds of sequencing.

In any of the foregoing embodiments, the method can comprise releasing the fluorophores on the nucleotide substrate with fluorophores having fluorescence switching property using an enzyme. The enzyme may comprise a DNA polymerase and/or an alkaline phosphatase.

In any of the foregoing embodiments, the method can comprise conducting one round of sequencing using one reaction solution group, and obtaining degenerate code results.

In any of the foregoing embodiments, the method can comprise conducting two rounds of sequencing using two reaction solution groups, and obtaining base sequence information.

In any of the foregoing embodiments, the method can comprise using three reaction solutions to conduct three rounds of sequencing, and performing the error checking and correction using the mutual information based on the results of any two rounds of sequencing among the three rounds of sequencing.

In any of the foregoing embodiments, the reaction solution can comprise an enzyme. When the reaction solution is let into the reaction area where the gene segment to be tested is located, the included enzyme can release the fluorophores on the nucleotide substrate with fluorophores having fluorescence switching property.

In any of the foregoing embodiments, the reaction solution and the enzyme may be added at different times. In one aspect, the first reaction solution of one reaction solution group is added in the reaction first, and then the enzyme solution is added. Next, the second reaction solution in the same reaction solution group is added, and then the enzyme solution is added.

In any of the foregoing embodiments, the fluorophores having fluorescence switching property can comprise a fluorophore comprising a group such as methyl fluorescein, halogenated methyl fluorescein, DDAO (7-hydroxy-9H-(1, 3-dichloro-9,9-dimethylacridin-2-one)) and/or resorufin.

In any of the foregoing embodiments, the releasing the fluorophores on the nucleotide substrate with fluorophores having fluorescence switching property can be optimized, for example, using an enzyme. In one aspect, the optimization comprises releasing the fluorophores substituted by a polyphosphoric acid using DNA polymerase first, and then excising the substituting polyphosphoric acid using the phosphatase, to release the fluorophores.

In any of the foregoing embodiments, the reaction solution can comprise two or more nucleotides with different bases. In one aspect, two or more reaction solutions may be used, so that each of the reaction solutions comprises one or more nucleotides. The order in which the reaction solutions are added in the reaction may be adjusted appropriately, and in one aspect, at least one reaction solution comprises two or three nucleotides with different bases.

Also provided herein is a high-throughput sequencing method according to any of foregoing embodiments, wherein the sequencing reaction is conducted on a chip which has several reaction chambers. In one aspect, the method comprises immobilizing a nucleotide sequence fragment to be tested in each reaction chamber.

In one aspect, the present disclosure relates to a sequencing method, e.g., using mixed nucleotide molecules. More specifically, it is a sequencing method by using modified (e.g., modified by phosphate) mixed nucleotide molecules with fluorophores. In addition, the present disclosure also relates to a sequencing method based on fluorophores having fluorescence switching property. The sequencing of the fluorophores having fluorescence switching property is achieved by using the nucleotide substrate labeled with the terminal phosphate. The substrate with fluorophores having fluorescence switching property are the fluorophores having fluorescence switching property modified by 5' end polyphosphate or intermediate phosphate, characterized by modifying the fluorophores having fluorescence switching property on the terminal phosphate or intermediate phosphate of 4, 5, 6 or more phosphate deoxyribonucleotides (including A, C, G, T, U and other nucleotides), and there is no label on the base and 3'-hydroxyl. The absorption spectra and/or emission spectra of this fluorophore modified by phosphate are different from those disengaged from the phosphate. The sequencing reaction typically comprises continuous and similar cycles. Each cycle may comprise such steps like sample injection/application, reaction, signal acquisition, and cleaning unreacted reactant molecules. In the method reported previously, when one substrate molecule with base enters, no reaction will occur if it is not correctly paired; and the polymerase will connect the substrate molecule to the 3' end, and release the fluorescence molecules modified by polyphosphoric acid, and the fluorescent spectra will change. If paired with homopolymer continuously, the spectra will change in multiple. In practice, fluorophores having fluorescence switching property are often used, without absorption in the terminal phosphate and whose releasing state is high quantum yield, as the modification label of the substrate molecules, such as methyl fluorescein, halogenated methyl fluorescein, DDAO, resorufin, and fluorescent molecules involved in CN104844674 and so on. Four kinds of substrate molecules may be labeled with different fluorescence molecules. The sequencing process is performed by sample injection through ACGTACGT . . . or any cycling or non-cycling injection process, using the reaction solution containing substrate molecules in a limited period, to obtain the extended information of each cycle and then obtain the DNA sequence.

In one aspect, the present disclosure relates to a sequencing method of multiple nucleotides. More specifically, it is a sequencing method by using phosphate to modify mixed nucleotide molecules with fluorophores. The sequencing is achieved by modifying 5' end or intermediate phosphate of the nucleotide substrate molecules with fluorophores; each round of sequencing uses one reaction solution group, each reaction solution group includes two reaction solutions, and each reaction solution includes two nucleotides with different bases; wherein the nucleotide in one reaction solution is complementary with two bases on the nucleotide sequence to be tested, and the nucleotide in the other reaction solution is complementary with the other two bases on the nucleotide sequence to be tested; first, fix the nucleotide sequence fragment to be tested, and let in the first reaction solution in one reaction solution group; test and record the fluorescent information; and then, let in the second reaction solution of the same reaction solution group; test and record the fluorescent information as well; and add the two reaction solutions circularly, and obtain the coded information of the nucleotide substrate to be tested through the fluorescent information.

In some embodiments, the reaction solution in the present disclosure refers to the sequencing reaction solution in general sense. The auxiliary solution like other cleaning or washing solutions is allowed to enter the clearance between reaction solutions. In one aspect, each of the reaction solution includes two nucleotides with different bases, which may be labeled with different or the same fluorophores. In one aspect, the sequencing is achieved by modifying 5' end or an intermediate phosphate of the nucleotide substrate molecules with fluorophores having fluorescence switching property; the fluorescence switching property refers to that the fluorescence signal after sequencing is significantly changed compared to the condition before the sequencing reaction.

In one aspect, the fluorescence switching property refers to that the fluorescence signal after sequencing is significantly enhanced (or increased) compared to the condition before the sequencing reaction. The frequency of its emission lights will probably change, but the overall intensity of emission lights or the intensity of emission lights in a certain frequency band will be significantly enhanced.

In one aspect, the present disclosure relates to a sequencing method using nucleotide molecules with fluorophores having fluorescence switching property, wherein the sequencing is achieved by modifying 5' end or intermediate phosphate of the nucleotide substrate molecules with fluorophores having fluorescence switching property; the fluorescence switching property refers to that the intensity of fluorescence signal after sequencing is significantly enhanced compared to the condition before the sequencing reaction; each round of sequencing uses one reaction solution group, each reaction solution group includes two reaction solutions, and each reaction solution includes two nucleotide substrate molecules with different bases; wherein the nucleotide in one reaction solution is complementary with two bases on the nucleotide sequence to be tested, and the nucleotide in the other reaction solution is complementary with the other two bases on the nucleotide sequence to be tested. First, one can fix the nucleotide sequence fragment to be tested in the reaction chamber, and let in the first reaction solution in one reaction solution group; then release the fluorophores on the nucleotide substrate using enzymes to cause fluorescence switching; and then, let in the second reaction solution of the same reaction solution group; release the fluorophores on the nucleotide substrate using enzymes to cause fluorescence switching; add the two reaction solutions circularly, and obtain the coded information of the nucleotide substrate to be tested through the fluorescent information.

In one aspect, the present disclosure relates to a sequencing method using nucleotide molecules with fluorophores having fluorescence switching property, wherein the sequencing is achieved by modifying 5' end or intermediate phosphate of the nucleotide substrate molecules with fluorophores having fluorescence switching property; the fluorescence switching property refers to that the intensity of fluorescence signal after sequencing is significantly enhanced compared to the condition before the sequencing reaction; each round of sequencing uses one reaction solution group, each reaction solution group includes at least two reaction solutions, and each reaction solution includes at least one of A, G, C or T nucleotide substrate molecule, or one of A, G, C or U nucleotide substrate molecule. In one aspect, one can first fix the nucleotide sequence fragment to be tested in the reaction chamber, and let in one reaction solution in one reaction solution group; test and record the fluorescent information; let in one reaction solution each time, and let in the other reaction solutions in the same reaction solution group in sequence. At the same time, one can test and record the fluorescent information after each reaction solution is let in, wherein there is at least one reaction solution including two or three nucleotide molecules in the reaction solution group.

In one aspect, the present disclosure relates to a sequencing method using nucleotide molecules with fluorophores having fluorescence switching property, wherein the sequencing is achieved by modifying 5' end or intermediate phosphate of the nucleotide substrate molecules with fluorophores having fluorescence switching property; the fluorescence switching property refers to that the intensity of fluorescence signal after sequencing is significantly enhanced compared to the condition before the sequencing reaction; each round of sequencing uses one reaction solution group, each reaction solution group includes at least two reaction solutions, and each reaction solution includes any of A, G, C or T nucleotide substrate molecule, or any of A, G, C or U nucleotide substrate molecule. In one aspect, one can first fix the nucleotide sequence fragment to be tested in the reaction chamber, and let in one reaction solution in one reaction solution group; test and record the fluorescent information; let in one reaction solution each time, and let in the other reaction solutions in the same reaction solution group in sequence. At the same time, one can test and record the fluorescent information after each reaction solution is let in.

In one aspect, the present disclosure relates to a sequencing method using nucleotide molecules with fluorophores having fluorescence switching property, wherein the sequencing is achieved by modifying 5' end or intermediate phosphate of the nucleotide substrate molecules with fluorophores having fluorescence switching property; the fluorescence switching property refers to that the intensity of fluorescence signal after sequencing is significantly enhanced compared to the condition before the sequencing reaction; each round of sequencing uses one reaction solution group, and the reaction solution includes A, G, C and T nucleotide substrate molecules, or A, G, C and U nucleotide substrate molecules. In one aspect, one can fix the nucleotide sequence fragment to be tested in the reaction chamber, and let in the reaction solution, and then test and record the fluorescent information.

In one aspect, the method comprises removing the residual reaction solution and fluorescence molecules with a cleaning solution, and then proceeding with the next round of sequencing reaction. In one aspect, the method comprises delivering the reaction solution at a low temperature, and then heating it to the enzyme reaction temperature, and testing the fluorescence signal. In one aspect, after the reaction solution is let in, the method comprises closing the reaction chamber, and then testing and recording the fluorescent information.

In one aspect, after the reaction solution is let in, the method comprises filling the space outside the reaction chamber with oil to insulate and close the reaction chamber. In one aspect, the nucleotide substrate molecules of polyphosphoric acid refer to a nucleotide with 4 to 8 phosphoric acid molecules. In one aspect, the modified nucleotide substrate molecules with fluorophores may be labeled with one fluorescence group for monochrome sequencing, or with different fluorescence groups for multiple-color sequencing.

In one aspect, the method comprises the following steps: releasing the fluorophores on the nucleotide substrate with fluorophores having fluorescence switching property using an enzyme, such as a DNA polymerase and/or alkaline phosphatase. In one aspect, the two bases on the nucleotide sequence to be tested refer to any two of A, G, C and T bases or of A, G, C and U bases, wherein base C is methylated C or non-methylated C. In one aspect, when the reaction solution is let into the reaction area where the gene segment to be tested is located, an enzyme in the reaction solution can release the fluorophores on the nucleotide substrate with fluorophores having fluorescence switching property. In one aspect, the method comprises conducting one round of sequencing using one reaction solution group, and obtaining degenerate code results. In one aspect, the method comprises conducting two rounds of sequencing using two reaction solution groups, and obtaining base sequence information. In one aspect, the method comprises using three reaction solutions to conduct three rounds of sequencing, and performing the error checking and correction using the mutual information among the three rounds of sequencing based on the results of the two rounds of sequencing.

In one aspect, the present disclosure relates to a sequencing method of mixed nucleotide molecules. More specifically, it is a sequencing method by using phosphate to modify mixed nucleotide molecules with fluorophores. Compared to the sequencing method of the mixed nucleotide not modified by phosphate, this method is easy for hydrolysis, and no other groups are introduced after completion of the reaction, which is conducive to extend the sequencing reaction, and the sequencing reaction is simple.

In one aspect, the present disclosure relates to a sequencing method of mixed nucleotide molecules, by using 5' end polyphosphoric acid to modify nucleotide substrate molecules with fluorophores having fluorescence switching property. In one aspect, the method comprises first fixing the nucleotide sequence fragment to be tested, and letting in the reaction solution containing nucleotide substrate molecules. In one aspect, the method comprises releasing fluorophores on the nucleotide substrate using enzymes to cause fluorescence switching. In one aspect, the method comprises removing the residual reaction solution and fluorescence molecules with a cleaning solution, and then proceeding with the next round of sequencing reaction.

In a further embodiment, the present disclosure combines the fluorescence switching sequencing and the mixed nucleotide molecules sequencing, achieving unexpected effects. For example, providing characteristics of data redundancy and checking to the mixed nucleotide molecules sequencing with fluorescence switching improves the accuracy of the sequencing data. Besides, the 3' end-closure sequencing enables that no real-time information acquisition is required in the sequence reaction, enhancing the accuracy of signals. Independent of the sequencing chemistry itself, it may be matched with different sequencing chemistries. Further, the 2+2 mode (the sequencing mode with two bases entering each time) with the fluorescence switching property has obvious advantages compared to other mixed nucleotide molecules sequencing. For example, the data analysis is relatively easy, and the characteristics of data redundancy and checking are provided as well. The special signal acquisition method and efficiency enable it has a great prospect in gene sequencing direction. The multiple-base sequencing with fluorescence switching has a reduced error rate compared to the mixed nucleotide molecules sequencing without fluorescence switching, and simplifies the reaction. The mixed nucleotide molecules sequencing method with fluorescence switching method of the present disclosure has the sequencing accuracy up to 99.99 percent, exceeding the read of Illumina sequencing by reaching 300 nt or more, and the cost of raw materials are very low. It adopts the method of first reaction and then scanning, without no-flux limit. It requires a short time for single round of reaction, and can achieve the quick test. The use of the fluorescence switching and multiple nucleotide molecules mixed sequencing strategy can extend the sequence read and information amount of each reaction cycle. For example, the Illumina sequencing has the read of 1 nt (1 base), and information amount of 2 bit in each reaction cycle. The 2+2 (two nucleotide molecules with different bases enter each time, and a total of two reaction solutions are used) monochrome sequencing had the read of 2 nt and the information amount of 2 bit in each reaction cycle. In one aspect, the 2+2 double-color sequencing has the read of 2 nt and the information amount of 3.4 bit in each reaction cycle.

In some aspects, provided herein are fluorescence generation and fluorescence generation fluorophores. Some fluorophores have characteristic of fluorescence spectroscopy (absorption and reflection spectra) changing when any change occurs in the substituent group, which is called fluorescence switching. In one aspect, if the intensity of acquired signals rises under specific excitation and acquisition (emission) conditions it is called fluorescence generation.

In some aspects, provided herein are nucleotide and nucleotide labels. In one aspect, the nucleotide molecule consists of ribose backbone, base molecule in glucoside position, and polyphosphate strand connected to 5-hydroxy of ribose backbone. 2C of ribose may connected with hydroxyl (becoming ribonucleotide), or only connected with H (called as deoxyribonucleotide). Nucleotide molecules may be the main bases in 4: ACGT, uracil, and modified base such as methylated base, hydroxymethylated base, etc. The number of phosphate backbones may be 1 to 8. It may modify molecular group in multiple locations. On the base, there may be one or more modification positions on 3C hydroxyl of the ribose backbone. For example, fluorophore is modified on the phosphate, and the ethynyl is modified on 3C.

In one aspect, the polyphosphate nucleotide substrate not modified on 3C (more than 3 phosphates) has 3 active hydroxyls when the strand reaction of polymerase occurs. In one aspect, as long as the subsequent bases can still be paired, the polymerase reaction will continue until there is lack of paired bases or 3C non-hydroxyl nucleotide molecules are combined. In some aspects, provided herein are fluorescence-generating nucleotides. In one aspect, the nucleotide molecules are on the phosphate terminal and labeled with fluorescence generation fluorophores that may be switched by the phosphate hydrolytic process, referred to as fluorescence generation (or fluorescence-generating) nucleotide. The length of phosphate strand may be 4 to 8.

In one aspect, the phosphate may be on the terminal or the side strand. The number of labels may be one or more. When there are multiple labels, they may be the same or different. More precisely, in one aspect, it is called polymerase fluorescence generation nucleotides. In another aspect, a fluorescence generation nucleotide which is not labeled in a phosphate position and does not need the fluorescence generation of polymerase may also be used. Nucleotide molecules may be ribonucleotide, deoxyribonucleotide, or (deoxy) ribonucleotide modified on 3'C.

In some aspects, provided herein are fluorescence generation nucleotide polymerase reactions. In one aspect, the reaction uses fluorescence generation nucleotide, nucleic acid polymerase (DNA polymerase), phosphatase, together with nucleic acid substrate. In some embodiments, first, the DNA polymerase polymerizes the fluorescence generation nucleotide into the nucleic acid substrate to release the phosphorylated fluorescence generation fluorophores, and then, it will further be hydrolyzed to remove the phosphatase and release the fluorescence generation fluorophores with the fluorescence state changed.

In some aspects, provided herein is fluorescence generation sequencing method. In one aspect, the method is to obtain the information about the polymerase reaction by fluorescence generation nucleotide polymerase reaction to test the fluorescence change of the fluorescence generation fluorophores (light intensity and spectrum). In some aspects, provided herein are sequencing reaction solutions for fluorescence generation, which may include fluorescence generation nucleotide, nucleic acid polymerase (DNA polymerase) and phosphatase.

As used herein, a "fluorescence generation nucleotide" may comprise one or more fluorescence generation nucleotides. As used herein, a "nucleotide" may comprise one or more nucleotides. In some embodiments, multiple nucleotides can be labeled with the same or different fluorescence generation substrates. In some aspects, provided herein is a set of fluorescence generation sequencing reaction solutions, which may comprise two or more fluorescence generation sequencing reaction solutions, for example, including A, C, G and T reaction solution with specific concentrations, or including AC and GT reaction solutions with specific concentrations.

In some aspects, provided herein is a fluorescent sequencing reaction cycle, which may comprise using one sequencing reaction solution to perform one fluorescence generation polymerase reaction and test the fluorescence signal. In some aspects, provided herein is a round of fluorescence generation sequencing reaction, which may comprise using the members of a fluorescence generation sequencing reaction solution group in determined sequence to perform sequencing reactions of a cycle. In some aspects, provided herein is a group of fluorescence generation sequencing reactions, which may comprise one or more rounds of fluorescence generation sequencing.

In some aspects, provided herein is a single-base resolution sequencing reaction. In one aspect, one way is (2+2 monochrome two sets), the first reaction solution is made by mixing two bases (e.g., AC), and the second reaction solution is made by mixing the other two bases (GT), and the two reaction solutions are alternately used for sequencing. Then, the number of extended bases in every cycle will be increased. After N cycles of sequencing, the number of extended bases will be 2N nt. The carried information is 2N bit. There will be three combinations completing the sequencing above, namely, AC/GT, AG/CT, and AT/CG; or write them as M/K, R/Y, and W/S as per the standard degenerate bases (degenerate nucleotide) identification. The three combinations can be sequenced separately, or re-sequenced after one set of sequencing is completed. The $i^{th}$ base determined on the DNA sequence must be subject to the pairing reaction in some unique cycle of two sets of sequencing, and release signals. In each set of sequencing, the determined sampling injection cycles of bases includes two types, so there will be a total of 2×2=4 possible situations, which just correspond to four bases. The sequence of sequencing combinations cannot affect the deduction of bases.

TABLE 1

| | Possible conditions | | | |
|---|---|---|---|---|
| Sampling cycle of bases | 1 | 2 | 3 | 4 |
| Sequencing with MK combination | M (AC) | M (AC) | K (GT) | K (GT) |
| Sequencing with RY combination | R (AG) | Y (CT) | R (AG) | Y (CT) |
| Inferred bases | A | C | G | T |

TABLE 2

| | Possible conditions | | | |
|---|---|---|---|---|
| Sampling cycle of bases | 1 | 2 | 3 | 4 |
| Sequencing with MK combination | M (AC) | M (AC) | K (GT) | K (GT) |
| Sequencing with WS combination | W (AT) | S (CG) | S (CG) | W (AT) |
| Inferred bases | A | C | G | T |

TABLE 3

| | Possible conditions | | | |
|---|---|---|---|---|
| Sampling cycle of bases | 1 | 2 | 3 | 4 |
| Sequencing with RY combination | R (AG) | Y (CT) | R (AG) | Y (CT) |
| Sequencing with WS combination | W (AT) | S (CG) | S (CG) | W (AT) |
| Inferred bases | A | C | G | T |

In further implementation, the method further comprises conducting the sequencing using the third set of different reaction solution combinations after two sets of different sequencing are completed. The $i^{th}$ base determined on the DNA sequence must be subject to the pairing reaction in the unique cycle of three sets of sequencing, and release signals. In each set of sequencing, the determined sampling injection cycles of bases includes two types, so there will be a total of 2×2×2=8 possible situations, of which, four are reasonable and the other four are non-reasonable. In a fluorescence switching sequencing, insertion or loss errors are likely to occur. For one base, if any sequencing error occurs in one of the three sets of sequencing, then the sequence cannot be deducted correctly, and it can be concluded that one or more of the three sets of sequencing must have error at this point.

TABLE 4

| Cycles of bases | Possible conditions | | | | | | | |
|---|---|---|---|---|---|---|---|---|
| | 1 | 2 | 3 | 4 | 5 | 6 | 7 | 8 |
| Sequencing with MK combination | M (AC) | M (AC) | K (GT) | K (GT) | M (AC) | M (AC) | K (GT) | K (GT) |
| Sequencing with RY combination | R (AG) | Y (CT) | R (AG) | Y (CT) | R (AG) | Y (CT) | R (AG) | Y (CT) |
| Sequencing with WS combination | W (AT) | S (CG) | S (CG) | W (AT) | S (CG) | W (AT) | W (AT) | S (CG) |
| Inferred bases | A | C | G | T | Error | Error | Error | Error |

This kind of error may be corrected since when the sequencing error in a single set of data is corrected, a large number of subsequent errors will be corrected as the same time.

Another specific implementation ways is 2+2 double-color and double round mode. The first reaction solution is made by mixture of two bases, carrying different fluorescent labels (e.g. AX/CY), and the second reaction solution is made by the mixture of the other two bases (GX/TY). In this case, the extended bases in every cycle will become more, with the average of 2 nt. And the carried information is 2N bit.

III. Methods of Detecting and/or Correcting Sequencing Errors

In one aspect, the present disclosure relates to a method to detect and/or correct one or more sequence data errors in a sequencing result, and belongs to the nucleic acid sequencing field.

In one aspect, the present disclosure provides a method to detect and/or correct the sequence data error in the sequencing results. In one aspect, the sequencing reaction solution comprises at least two types of nucleotide substrate molecules with different bases. In one aspect, a degenerate gene encoding information may be obtained. By comparing two or more degenerate coding information, a determination can be made as to whether conflicting sequence information appears in one or more nucleotide residues. Using the present method to correct the sequence information, any minor improvement that can decrease the sequencing error rate in the raw sequencing data can lead to a more remarkable decrease in the error rate of the corrected sequence information.

In one aspect, disclosed herein is a method to detect and/or correct a sequence data error in a sequencing result. In one aspect, the method comprises conducting sequencing on a nucleic acid sequence to obtain the sequence data of three or more orthogonal nucleotide degenerate sequences. In another aspect, the method further comprises detecting an error in the sequence by comparing the three or more orthogonal nucleotide degenerate sequences. In one aspect, a corrected sequence is obtained by modifying at least one sequence at a position where the error is found during comparison.

Also disclosed herein is a method to detect and/or correct a sequence data error in a sequencing result, wherein the method comprises conducting a sequencing reaction on a nucleotide sequence to obtain three or more degenerate sequences expressed with the letters of M, K, R, Y, W, S, B, D, H, and V. In one aspect, according to the nucleic acid notation of IUPAC, the letters in Table 5 are used to express the degenerate bases in the present disclosure. For example, M represents A and/or C bases.

TABLE 5

| Letters representing degenerate bases. | |
|---|---|
| Letter | Represented Bases |
| M | AC |
| K | GT |
| R | AG |
| Y | CT |
| W | AT |
| S | CG |
| B | CGT |
| D | AGT |
| H | ACT |
| V | ACG |

In any of the preceding embodiments, the sequence error may be detected by comparing the three or more degenerate sequences. In any of the preceding embodiments, the corrected sequence may be obtained by modifying at least one sequence at a nucleotide position where the error is identified during comparison. In any of the preceding embodiments, where the error is identified during comparison can be where a sequencing error actually occurs.

In one other aspect, disclosed herein is a method to detect and/or correct a sequence data error in a sequencing result, wherein the method comprises conducting sequencing on the same nucleic acid sequence to obtain two or more degenerate sequences expressed with the letters M, K, R, Y, W, S, B, D, H, and V, in order to obtain sequence information expressed in nucleic acid residues A, G, T, and C, or sequence information expressed in nucleic acid residues A, G, U, and C. In another aspect, the method further comprises detecting the sequence error by using a light or electric signal resulted from one or more functional groups coupled to different bases in the sequencing reaction. For example, the light or electric signal from different fluorescent groups coupled to different bases in the sequencing reaction may be used as the "redundant" information that distinguishes one base from another at a particular position in the sequence. In any of the preceding embodiments, a corrected sequence may be obtained by modifying at least one sequence at a nucleotide position where the error is found during comparison. In any of the preceding embodiments, where the error is identified during comparison can be where a sequencing error actually occurs.

In a further aspect, disclosed herein is a method for detecting and/or correcting a sequencing error in a sequencing result, using the memorability of a nucleic acid sequence. In one aspect, the method comprises conducting sequencing on the same nucleic acid sequence to obtain the data of three or more orthogonal nucleic acid degenerate sequences. In another aspect, the method further comprises comparing the degenerate sequences comprehensively, and detecting the sequence error using the memorability of the nucleic acid sequences. In one aspect, a corrected sequence may be obtained by modifying at least one sequence in a position where the error is found during comparison. In some embodiments, each of the degenerate sequences only represents part of sequence information of the actual polynucleotide template, and the nucleotide identity at a position of one degenerate sequence cannot or do not necessarily indicate the nucleotide identity at the same position of another degenerate sequence.

In one aspect, disclosed herein is a method to detect and/or correct a sequence data error in a sequencing result, wherein the method comprises fixing a nucleic acid fragment whose sequence is to be determined onto a support, and providing a reaction solution to cause a sequencing reaction from which a degenerate nucleic acid sequence is obtained. The sequencing reaction can be repeated multiple rounds so that a degenerate nucleic acid sequence is obtained from each round of sequencing. After N rounds of sequencing, N degenerate nucleic acid sequences may be obtained. In one aspect, the position where the sequence error occurs may be detected by comparing the N degenerate sequences comprehensively. In one aspect, the method may further comprise obtaining a corrected sequence by modifying at least one sequence in a position where an error is found during comparison. In any of the preceding embodiments, the reaction solution may comprise two or more types of nucleotide substrate molecules with different bases. In any of the preceding embodiments, N can be a positive integer equal to or greater than 2.

In any of the preceding embodiments, the method can comprise comparing (N−1) of the N degenerate nucleic acid sequences to obtain a nucleic acid sequence information coded with A, G, T, and C, or a nucleic acid sequence information coded with A, G, U, and C. In one aspect, the method further comprises comparing the N degenerate nucleic acid sequences. In any of the preceding embodiments, N can be a positive integer equal to or greater than 3.

In any of the preceding embodiments, the method can comprise comparing the N degenerate nucleic acid sequences to obtain a nucleic acid sequence information coded with A, G, T, and C, or a nucleic acid sequence information coded with A, G, U, and C. In one aspect, the method further comprises detecting the position where the error occurs by using a light and/or electromagnetic information provided by two or more functional groups coupled to the nucleotide residues. In any of the preceding embodiments, N can be a positive integer equal to or greater than 2.

In another aspect, disclosed herein is a method to detect and/or correct a sequence data error in a sequencing result, wherein the method comprises fixing a nucleic acid fragment to be tested on a support. In one aspect, the method further comprises providing a reaction solution to cause a sequencing reaction, wherein the reaction solution comprises nucleotide substrate molecules used for sequencing and is divided into three groups according to different bases, each group comprising two different reaction solutions, and each reaction solution comprising nucleotide substrate molecules with different bases. In one aspect, there is no intersection between the bases of the nucleotides in the two reaction solutions within the same group of reaction solution. In one aspect, each round of sequencing uses one reaction solution group, and the two reaction solutions of each group is provided to react with the nucleic acid template sequentially in any suitable order. In one aspect, three rounds of sequencing are conducted using the three groups of reaction solutions to obtain three degenerate sequences. In a further aspect, the position where the sequence error occurs may be detected by comparing the three degenerate sequences comprehensively. In one embodiment, the corrected sequence may be obtained by modifying at least one sequence in a position where the error is found during comparison.

In any of the foregoing embodiments, the sequencing reaction can be achieved by using a nucleotide substrate molecule (such as a dNTP or ddNTP) modified with a fluorophore having a fluorescence switching property, wherein the modification is at a 5'-end polyphosphoric acid group of the nucleotide substrate molecule. In one aspect, the fluorescence switching property can refer to that the fluorescence signal after sequencing is significantly changed compared to the condition before the sequencing reaction. In another aspect, the fluorescence switching occurs after the polymerase-catalyzed incorporation of the nucleotide substrate into the extending primer. In one aspect, the nucleotide sequence fragment to be determined is fixed on a support, and then a reaction solution comprising a nucleotide substrate molecule is provided to react to react with the template nucleotide sequence fragment. In one aspect, an enzyme is then used to release a fluorescence group from the nucleotide substrate incorporated into the extending primer (and the duplex polymerase extension product), to cause fluorescence switching.

In one aspect, the fluorescence signals can be significantly enhanced or weakened after each step of a sequencing reaction, or the frequency of the emission light is significantly can be changed compared to the conditions before the sequencing reaction.

In any of the preceding embodiments, the sequence error may comprise an insertion and/or a deletion. In any of the preceding embodiments, the sequence data error may be considered to have occurred at a particular position when at least two degenerate nucleic acid sequences do not have a common base at that position.

In any of the preceding embodiments, correcting a sequence error may comprise correcting a nucleotide residue of at least one sequence, so that the corrected sequence has the correct nucleotide residue(s) in at least one position following the corrected nucleotide residue. In one aspect, a nucleotide residue is correct if the nucleic acid sequence information of any two rounds of sequences determined in the same nucleotide residue position is not inconsistent with the nucleic acid sequence information of another round of sequencing.

In any of the preceding embodiments, correcting a sequence error may comprise correcting an error of at least one sequence, so that a common nucleotide residue in at least one position of the sequence may be obtained through a comparison of the sequence information from the multiple rounds of sequencing.

In any of the preceding embodiments, correcting a sequence error may comprise extending (e.g., by inserting a nucleic acid residue at a position where an error is believed to have occurred) and/or shortening (e.g., by deleting a nucleic acid residue at a position where an error is believed to have occurred) the sequence representing the nucleic acid sequence information from the multiple rounds of sequencing. In one aspect, by extending and/or shortening at least one sequence from the multiple rounds of sequencing, the corrected sequence will be consistent with sequence(s) from the other rounds in at least one nucleotide residue position.

In any of the preceding embodiments, the memorability of a nucleic acid sequence can refer to that in the sequencing results, the nucleic acid sequence information at a particular position not only relates to the nucleotide residue in its corresponding nucleic acid in the template, but also relates to the sequence information before it.

In any of the preceding embodiments, a sequence in the sequencing signals can be extended (e.g., by inserting a nucleic acid residue at a position where an error is believed to have occurred) by a certain length to obtain a corrected nucleic acid sequence using sequencing signals from the other two rounds of sequencing. In any of the preceding embodiments, a sequence in the sequencing signals can be shortened (e.g., by deleting a nucleic acid residue at a position where an error is believed to have occurred) by a certain length to obtain a corrected nucleic acid sequence using sequencing signals from the other two rounds of sequencing.

In any of the preceding embodiments, the reaction solution can be divided into three groups according to different bases, wherein the base comprises A, G, C, and T bases, or A, G, C, and U bases. In any of the preceding embodiments, the bases may be methylated, hydroxymethylated, or modified with an aldehyde group or a carboxylic group, or non-methylated, non-hydroxymethylated, or not modified with an aldehyde group or a carboxylic group.

In any of the preceding embodiments, the nucleotide substrate reaction solution can comprise different bases, which may be divided into two reaction solutions according to different bases, for example, A+G in one reaction solution and C+T in the other reaction solution; A+C in one reaction solution and G+T in the other reaction solution; or A+T in one reaction solution and C+G in the other reaction solution.

In any of the preceding embodiments, the reaction solutions can comprise multiple reaction solutions, and one reaction solution can be used for a sequencing reaction. In one aspect, each round of sequencing uses one or more reaction solutions. In another aspect, at least one reaction solution comprises two or more types of nucleotide substrate molecules with different bases. In any of the preceding embodiments, the reaction solutions used in different rounds of sequencing comprise different combinations of nucleotide substrate molecules.

In any of the preceding embodiments, the nucleotide substrate molecules may be labeled by fluorescence. In one aspect, a fluorescent group (or a functional group which will have fluorescence alternation through a chemical reaction) is coupled to a base of the nucleotide residue. In one aspect, the nucleotide substrate molecules may be modified using one of the fluorophores or functional groups, or the nucleotide substrate molecules may be modified with different bases using multiple fluorophores or functional groups.

As people have more in-depth understanding on genes in recent years, gene sequencing has brought tremendous changes in medicine and biology. Conventional sequencing methods include Sanger DNA, restriction fragment length polymorphism, single-strand conformation polymorphism and gene chip-based allele-specific oligonucleotide hybridization sequencing methods. It is inevitable that an error occurs in the sequencing results due to various affecting factors in the sequencing process, such as inaccurate CD lighting, fluid movement, ambient light, miscellaneous DNA, error in the signal correction system or impure sequencing reaction solution. As a genetic material, DNA stores the organism genetic information and this feature also enables DNA to be used as a storage medium of general information. When DNA is used to store information, it is required to encode the information into a DNA sequence, and then read the information with the gene sequencing method. To avoid coding and/or reading errors, the redundant information is often introduced in the encoding process, and it will be used to perform signal correction in reading. For example, George Church et al., "Next-Generation Digital Information Storage in DNA," Science, 2012, coded the information into DNA sequences using Reed Solomon codes and read the information in the DNA sequences using the Illumina sequencing platform. The DNA coding-reading technology is also used in the combinatorial chemistry and other fields. In the previous DNA encoding technology, the type of each base is usually not associated with the bases in other positions (memoryless coding), or only associated with the bases within its vicinity. The present disclosure provides a memory-based, distributed, orthogonal DNA coding method, and the type of each base is associated with all the bases in the position in front of it. Besides, the method can effectively improve the accuracy of the coding-reading process through decoding based on the comprehensive comparison of multiple groups of orthogonal codes.

In one aspect, the present disclosure provides a method to detect and/or correct the coding error in the sequencing results, wherein the method comprises conducting sequencing on the same nucleic acid sequence to obtain three or more orthogonal nucleotide degenerate sequences, wherein the error in the sequence may be detected by comparing the three or more orthogonal nucleotide degenerate sequences, and wherein the corrected sequence may be obtained by modifying at least one sequence in the position where the error is found during comparison.

In one aspect, the present disclosure provides a method to detect and/or correct the code error in the sequencing results, wherein the method comprises conducting sequencing on the same nucleic acid sequence to obtain three or more degenerate sequences expressed with the letters of M, K, R, Y, W, S, B, D, H and V, wherein the error in the sequence may be detected by comparing the three or more degenerate sequences, and wherein the corrected sequence may be obtained by modifying at least one sequence in the position where the error is found during comparison. In one aspect, the method applies to normal sequencing. In another aspect, as long as the sequencing substrate is designed reasonably, three or more coding results may be obtained through several rounds of sequencing, the redundancy of information therein may be used to detect and/or correct the wrong codes.

In one aspect, the present disclosure provides a method to detect and/or correct the code error using the memorability of gene codes, wherein the method comprises conducting sequencing on the same nucleic acid sequence to obtain two or more degenerate sequences expressed with the letters of M, K, R, Y, W, S, B, D, H and V, or obtaining the nucleic acid sequence information coded with A, G, T and C, or the nucleic acid sequence information coded with A, G, U and C, wherein the sequence error may be detected by taking the light or electrical signals caused by different functional groups which are connected with different bases in the sequencing reaction as the redundant information, and wherein the corrected sequence may be obtained by modifying at least one sequence in the position where the error is found during comparison.

In one aspect, the present disclosure provides a method to detect and/or correct the code error using the memorability of gene codes, wherein the method comprises conducting sequencing on the same nucleic acid sequence to obtain three or more orthogonal nucleotide degenerate sequences, and comparing the degenerate sequences comprehensively and detect the sequence error using the memorability of the nucleic acid sequence, wherein the corrected sequence may be obtained by modifying at least one sequence in the position where the error is found during comparison, wherein in the degenerate sequences, each of the sequence signals represents part of gene sequence information, and wherein the signals in the same position in another degenerate sequence cannot be presumed through the signals in one of such degenerate sequences.

In any of the preceding embodiments, the method can comprise fixing a nucleic acid fragment to be tested onto a support, providing a reaction solution to cause a sequencing reaction so that a degenerate nucleic acid sequence is obtained from each round of sequencing, wherein N degenerate nucleic acid sequences may be obtained at least after N rounds of sequencing, wherein the position where the sequence error occurs may be detected by comparing the N degenerate sequences comprehensively, wherein the corrected sequence may be obtained by modifying at least one sequence in the position where the error is found during comparison, wherein the reaction solution can contain two or more types of nucleotide substrate molecules with different bases, and wherein the N is a positive integer equal to or greater than 2.

In one aspect, the nucleic acid sequence information coded with A, G, T and C, or the nucleic acid sequence information coded with A, G, U and C may be obtained by comparing N-1 degenerate nucleic acid sequences, and the position where the sequence error occurs may be detected by comparing N degenerate nucleic acid sequences. The N can be a positive integer equal to or greater than 3.

In one aspect, the nucleic acid sequence information coded with A, G, T and C, or the nucleic acid sequence information coded with A, G, U and C may be obtained by comparing N degenerate nucleic acid sequences, and the position where the sequence error occurs may be detected by comparing N degenerate nucleic acid sequences. In one aspect, the position where the error occurs may be detected using the lighting information provided by two or more functional groups connected to the base, and the N is a positive integer equal to or greater than 2. In another aspect, the method comprises conducting the correction by taking the information change of the base itself in the sequencing reaction of the information of the molecules like phosphate and hydrogen ions released in the reaction process as the redundant information.

In one aspect, the present disclosure provides a method to detect and/or correct the code error in the sequencing results, wherein the method comprises fixing the nucleic acid fragment to be tested, providing the reaction solution to cause the sequencing reaction, wherein the reaction solution of nucleotide substrate molecules used for sequencing is divided into three groups according to different bases, each group comprising two different reaction solutions, and each reaction solution comprising nucleotide substrate molecules with different bases. In one aspect, there is no intersection between the bases of nucleotides in the two reaction solutions. In another aspect, each round of sequencing uses one reaction solution group, and the two reaction solutions of each group is provided in alternation. In one aspect, the method comprises conducting three rounds of sequencing using the three groups of reaction solutions to obtain three degenerate sequences, and the position where the error occurs may be detected through the comprehensive comparison of the three degenerate sequences, and the corrected sequence may be obtained by modifying at least one sequence in the position where the error is found during comparison.

In one aspect, the reaction solution containing two different bases may be divided into two reaction solutions; and the other steps of the method may be adjusted accordingly.

In one aspect, the reaction solutions may comprise multiple reaction solutions, and one is used for each sequencing, wherein each round of sequencing uses one or more reaction solutions, wherein at least one reaction solution contains two or more types of nucleotide substrate molecules with different bases, and wherein the reaction solutions used in different rounds of sequencing comprise different combinations of nucleotide substrate molecules.

In one aspect, the sequencing of the present disclosure comprises sequencing by using 5'-end polyphosphoric acid to modify nucleotide substrate molecules with fluorophores having a fluorescence switching property, wherein the fluorescence switching property refers to that the fluorescence signal after sequencing is significantly changed compared to the condition before the sequencing reaction, wherein the nucleotide sequence fragment to be tested is first fixed on a support, a reaction solution containing nucleotide substrate molecules is then provided, and the fluorophores on the nucleotide substrate are then released using an enzyme to cause the fluorescence switching.

In one aspect, when reference is made to that "the fluorescence signals will be changed significantly after sequencing than the condition before sequencing," the fluorescence signals will be significantly enhanced or weakened after each step of sequencing reaction, or the frequency of the emission light is significantly changed compared to the condition before the sequencing reaction.

In one aspect, the sequence error refers to an insertion error or deletion error. In another aspect, the sequence data error refers to that it will be considered as an error occurs when at least two pieces of nucleic acid sequences do not represents the same base although they are in the same position. In yet another aspect, the method comprises correcting the error of at least one sequence, so that the subsequent sequences are correct at least in one position, wherein the correctness of sequence refers to that the nucleic acid sequence information of any two rounds of sequences determined in the same position is not inconsistent with the nucleic acid sequence information of another round of sequence, or alternatively, the nucleic acid sequence information of any two rounds of sequences expressed in the same position is not inconsistent with the lighting information provided by the functional groups connected to the bases or the information in another sequencing process.

In one aspect, the method comprises correcting sequence by correcting the error of at least one sequence, so that the common base may be obtained through the comprehensive comparison of the sequences in at least one position.

In one aspect, by modifying at least one sequence, a corrected sequence may be obtained by extending or shortening the sequence representing the nucleic acid sequence information in the position where the error occurs, wherein the extending or shortening refers to the increase or decrease of the length of the same detected sequence, wherein when the coding result in this position is shortened or extended, the sequence information expressed by the code has no change and the result is the same code. For example, when the signal intensity of the degenerate code M is 2, i.e., MM, it may be extended to 3, i.e., MMM.

In one aspect, the memorability of nucleic acid sequence refers to that in the sequencing results, the nucleic acid sequence information in some position not only relates to the sequence in its corresponding nucleic acid to be tested, but also relates to the sequence information before it.

In one aspect, by extending or shortening some sequencing signal at a position, the gene sequence represented by this position is extended or shortened, in order to obtain the corrected nucleic acid sequence using other two rounds of sequencing signals, wherein extending a sequencing signal comprises adding or inserting into the gene sequence represented by this position by a certain length, wherein shortening some sequencing signal comprises shortening or deleting the gene sequence represented by this position by a certain length, and obtaining the corrected nucleic acid sequence using other two rounds of sequencing signals.

In one aspect, the reaction solutions are divided into three groups according to different bases, wherein the base refers to A, G, C and T bases, or A, G, C and U bases, and wherein the bases may be methylated, hydroxymethylated, having an aldehyde or carboxylic base, or non-methylated, non-hydroxymethylated, or having a non-aldehyde or non-carboxylic base.

In one aspect, the nucleotide substrate reaction solutions containing different bases may be divided into two reaction solutions according to different bases.

In one aspect, the nucleotide substrate molecules may be labeled by fluorescence. In one aspect, the method comprises modifying the fluorophores or the functional groups which will have fluorescence alternation through chemical reaction on the bases of nucleotide substrate molecules. In another aspect, the nucleotide substrate molecules may be modified using one of the fluorophores or functional groups, or the nucleotide substrate molecules may be modified with different bases using multiple fluorophores or functional groups.

In one aspect, a group of degenerate gene sequence information may be obtained through each round of sequencing. In one aspect, the degenerate gene sequence information refers to containing possible gene sequence information. For example, when the reaction solution contains nucleotide substrate molecules with A and G bases, the degenerate gene sequence information obtained from sequencing contains the gene sequence information of C and/or T base in the nucleotide sequence to be tested. When the reaction solution contains nucleotide substrate molecules with A and T bases, the degenerate gene sequence information obtained from sequencing contains the gene sequence information of C and/or G base in the nucleotide sequence to be tested. When the reaction solution contains nucleotide substrate molecules with A and C bases, the degenerate gene sequence information obtained from sequencing contains the gene sequence information of C and/or T base in the nucleotide sequence to be tested. When the reaction solution contains nucleotide substrate molecules with C and G bases, the gene sequence information obtained from sequencing contains the gene sequence information of A and/or T base in the nucleotide sequence to be tested. When the reaction solution contains nucleotide substrate molecules with C and T bases, the gene sequence information obtained from sequencing contains the gene sequence information of A and/or C base in the nucleotide sequence to be tested. And when the reaction solution contains nucleotide substrate molecules with T and G bases, the gene sequence information obtained from sequencing contains the gene sequence information of C and/or A base in the nucleotide sequence to be tested.

In one aspect, in the comprehensive comparison of the information of three rounds of sequencing, if the gene sequence information represented by the signal of one round of sequencing is a big error sequence signal, then the gene sequence information represented by this sequence signal may be shortened, so that the comparison result of at least one sequencing signal thereafter is correct.

In one aspect, in the comprehensive comparison of the information of three rounds of sequencing, if the gene sequence information represented by the signal of one round of sequencing is a small error sequence signal, then a vacancy may be added in the gene sequence information represented by this position, or extend the same so that the comparison result of at least one sequencing signal thereafter is correct. For example, when the signal intensive of the degenerate code M is 2, i.e., MM, it may be extended to 3, i.e., MMM.

In one aspect, provided herein is a method to detect and/or correct the error in a gene sequencing coding result, and in particular for sequencing methods using one or more reaction solutions comprising nucleotide substrate molecules with two or more bases. In a particular aspect, the present method is applicable to SBS (sequencing by synthesis) methods for sequencing.

In one aspect, the degenerate gene sequence information herein comprises possible gene sequence information for a given target (or template) sequence. For example, when the reaction solution comprises nucleotide substrate molecules with A and G bases, the degenerate gene sequence information obtained from sequencing comprises the gene sequence information of C and/or T base in the nucleotide sequence to be tested. Suppose the intensity information obtained from the sequencing reaction is 3, then it means the gene to be tested may contain three Cs and/or Ts, such as three Cs, or three Ts, or one C and two Ts, or one T two Cs, and the exact relative positions of the T(s) and/or C(s) cannot be distinguished based on the degenerate sequence. The degenerate gene sequence information and the degenerate code are commonly used term of art.

In one aspect, the method described herein can detect and/or correct the error in sequencing, but it cannot completely eliminate the sequence errors. It is possible that a particular position being modified in a sequence signal is not the actual position where a sequencing error has occurred, but the probability is extremely low. The final accuracy may be further improved. For example, if putting the modified signals of MK, RY, and WS together, and the signals are modified for two times out of N consecutive times, it will be considered that an error is most likely to have occurred, and the corresponding sequence should be discarded. The N herein is a positive integer equal to or greater than 2. The larger the N value is, the higher the probability that the sequence should be discarded will be, and so is the final decoding rate. In one aspect, an optimized value of N in the present disclosure is 3.

A DNA sequence is a co-polymer, for example, a DNA region comprising two different deoxyribonucleotides, such as AAC and GGTG.

In one aspect, the method to detect and/or correct the sequence data error can detect the position where the error occurs, and/or correct the sequence error.

In one aspect, in an actual sequencing process, the method comprises obtaining the relative intensity value of an optical or other signal first through cycling sequencing reaction, and such intensity value may be expressed in a certain form. For example, M represents the information of the position and quantity of the bases in this position (multiple bases are acceptable), and can also express the degenerate gene coding results. Through decoding the relative intensity value of enough amount of information, the gene sequence information to be tested may be obtained.

In one aspect, delivering or providing a reagent or a reaction solution means adding the reagent or reaction solution to a volume, such as a reaction mix for a sequencing reaction. In one aspect, three or more rounds of sequencing can be used. Alternatively, two or more rounds of sequencing can be used. In one aspect, the sequencing signals are counted by times. The intensity information of signals in each time of sequencing can be recorded, and in some embodiments, the intensity information is ideally the same as the length of the corresponding copolymer.

The sequencing signals can be counted by level, or by times a certain nucleotide is detected. For example, if the signal intensity is n, and the nucleotide added into the reaction solution is X, then the sequencing result is expressed as XXX . . . X, wherein the length of the sequence is n nucleotides. For example, the sequencing signal in FIG. 1 when counted by times can be converted into the sequencing signal counted by level as MMMKKKKKMKKKMMK, or written as (A/C, A/C, A/C, G/T, G/T, G/T, G/T, G/T, A/C, G/T, G/T, G/T, A/C, A/C and G/T).

For example, the sequencing reaction solution containing dA4P and dC4P (nucleotide with 4 phosphate groups and the end phosphate labeled with fluorescence groups) can be used at odd number times, and the sequencing reaction solution containing dG4P and dT4P can be used at even number times. Refer to Table 6 below for a group of fluorescence signal values obtained after several times of reactions.

The fluorescence signal values related to the target DNA sequence may be obtained using combination of nucleotide with other fluorescence labels. Possible combination examples are as below:

M/K mode: dA4P and dC4P delivered for the odd-number times, and dG4P and dT4P delivered for even-number times; or in reverse;

R/Y mode: dA4P and dG4P delivered for the odd-number times, and dC4P and dT4P delivered for even-number times; or in reverse; and W/S mode: dA4P and dT4P delivered for the odd-number times, and dC4P and dT4P delivered for even-number times; or in reverse.

TABLE 6

| Sequence | A | A | C | T | T | T | G | G | A | T | T | G | C | C | T | Monochrome signal intensity 6 |
|---|---|---|---|---|---|---|---|---|---|---|---|---|---|---|---|---|
| Round 1: A + C | A | A | C | | | | | | | | | | | | | 3 |
| Round 2: G + T | A | A | C | T | T | T | G | G | | | | | | | | 5 |
| Round 3: A + C | A | A | C | T | T | T | G | G | A | | | | | | | 1 |
| Round 4: G + T | A | A | C | T | T | T | G | G | A | T | T | G | | | | 3 |
| Round 5: A + C | A | A | C | T | T | T | G | G | A | T | T | G | C | C | | 2 |
| Round 6: G + T | A | A | C | T | T | T | G | G | A | T | T | G | C | C | T | 1 |

The sequencing data obtained under three different nucleotide combinations as the signals counted by level can be combined. For each position, the next step is to solve the intersection of nucleotide types expressed by the three sequencing signals counted by level in this position, to obtain the target DNA sequence. In one aspect, this is the basic principle for decoding signals. For example, if the sequencing signals counted by times corresponding the combinations of M/K, R/Y, and W/S are respectively (3, 5, 1, 3, 2, 1), (2, 4, 3, 2, 1, 3) and (2, 1, 3, 2, 3, 3, 1), then the sequence may be concluded as AACTTTGGATTGCCT (SEQ ID NO: 1).

In one aspect, the comprehensive comparison of the results of three rounds of sequencing reactions comprises converting the chemiluminescence signals or other forms of intensity signals into gene sequence information, and then, comparing the three rounds of sequencing results in the same base position. If the expressions of results obtained from the three rounds of sequencing are consistent, it will be considered that the sequencing in this position is correct; if the gene sequence information expressed by the results obtained from the three rounds of sequence is inconsistent, it will be considered the sequencing result in the base position is wrong.

In one aspect, if the sequence signal of a certain time counted by times is bigger or smaller due to factors like inaccurate CCD lighting, fluid movement, ambient light, miscellaneous DNA, error in the signal correction system or impure sequencing reaction solution, it will result in that the sequencing signal counted by level has empty intersection of the nucleotide type expressed in the corresponding position or the subsequent positions, then the nucleotide type cannot be solved. Obviously, the error in the sequencing signal counted by times may cause the overall shift of the sequencing signal counted by level, from the position where the error occurs. Therefore, the sequencing signal counted by level is a kind of signal with memory. The error in the sequencing signal may be corrected based on the feature of that the sequencing signal counted by level has memory.

In one aspect, the present disclosure provides a method to detect and/or correct the sequence data error in the sequencing results. The sequencing reaction solution contains at least two types of nucleotide substrate molecules with different bases; the degenerate gene encoding information may be obtained. Technical personnel in this field can judge whether the conflicting situation appears in the code of this position by comparing two or more degenerate coding information. Compared to the same substrate to be tested, the method using different primers or testing for several rounds directly is easier, and the testing may be completed via one test design. In one aspect, the method provided herein is completely different from the method testing for several rounds for the same gene to be tested. In some aspects, the method provided herein has no correction basis if there are only two mutually orthogonal degenerate gene encoding results (excluding the conditions in which redundant information like color is added). In one aspect, the present disclosure first proposes the detection and correction of the error in three or more mutually orthogonal degenerate coding results in this type of sequencing.

In one aspect, the present disclosure provides a method to detect and/or correct the sequence data error in the sequencing results. Especially conduct sequencing by using 5' end polyphosphoric acid to modify nucleotide substrate molecules with fluorophores having fluorescence switching property; the method is also called the fluorescence switching sequencing method. When using the fluorescence switching sequencing method combined with the 2+2 sequencing method, the sequencing method itself can bring many advantages, such as long read of 300 bp and sequencing accuracy up to 99.99%; all of these cannot be achieved by simply using the 2+2 sequencing method or the fluorescence switching sequencing method; besides, there are some other advantages using the combined method, like higher allowable flux, simple reaction, low error rate, and no need to acquire the information in real time. Similarly, the sequencing on other nucleotide substrate molecules with fluorescence switching also has the same properties. For example, the fluorescence switching sequencing method and the 2+2 sequencing method, provide the redundant information other than the color information (lighting information or other detectable information) during three rounds of sequencing, which may be used for correction; and it can also extend the effective read without the accuracy changed; the correction result depends on the accuracy of the sequencing method, and it can greatly improve the overall accuracy of the effective read under the condition that the sequencer accuracy is fixed; for example, the correctness of sequencing on the nucleic acid fragment with the length of 400 bp is up to 97.36%. The correctness after correction is up to 99.17%. Therefore, the effective read may be extended accordingly if the sequencer for this error detection and correction method is applied. Obvious rules can be found when conducting correction using the method provided herein: any minor improvement in the sequencing method that can reduce the error rate can significantly reduce the error rate of the modified coding data.

IV. A Method to Read Sequence Information from the Original Signal of High-throughput DNA Sequencing In one aspect, the present disclosure relates to a method of reading nucleic acid sequence information from the raw or original signals of a sequencing reaction, such as a high-throughput DNA sequencing reaction. In particular aspects, the present disclosure relates to a method of reading and/or correcting sequence information from the raw or original signals of a second-generation sequencing technology, for example, for use in gene or genome sequencing. In one aspect, the present disclosure considers many reasons for causing the deviation in the original signal from the actual sequence information during nucleic acid sequencing, in order to achieve a comprehensive correction of the detected sequence information, thereby reading an accurate DNA sequence from the original sequencing signal. In one aspect, the presently disclosed method does not affect the normal process of the sequencing reaction. In one aspect, the present disclosure involves processing of both monochromatic sequencing signals and polychromatic sequencing signals. In one aspect, the processing of each kind of signals comprises parameter estimation and signal correction.

In high-throughput DNA sequencing, under ideal conditions, the intensity of the original signal released by each sequencing reaction is proportional to the number of bases incorporated into a nascent DNA strand. In the actual situation, however, the proportional relation is not always true due to several reasons. For example, first, the intensity of the original signal is generally attenuated as a result of fluid erosion, hydrolysis of DNA template, and/or base mismatch. Second, the lengths of nascent DNA strands gradually become desynchronized (e.g., there are inconsistencies among the lengths of nascent DNA strands, due to the dephasing phenomenon) as the sequencing reactions progress, due to incomplete sequencing reactions, side (e.g., unwanted) reactions, and/or base mismatch. The desynchronized nascent DNA strand lengths in turn contribute to the deviation of the intensity of the original signal from the actual target DNA sequence. Third, the overall intensity of the original signals will be high due to spontaneous hydrolysis of nucleotides and/or background fluorescence from the sequencing chip or substrate. All these factors make it difficult and sometimes impossible to directly read the sequence of the target DNA from the intensities of original sequencing signals, based on their proportional relationship under ideal conditions.

Existing methods to read sequence information from the original sequencing signal only take part of the reasons mentioned above into account. For example, the 454 sequencing technology only considers the dephasing phenomenon, and corrects the signal deviation caused by dephasing through matrix transformation. In fact, because the above reasons exist simultaneously, if only the dephasing phenomenon is considered or if dephasing is simply isolated from other factors such as attenuation and the overall high value, the accuracy of reading DNA sequence information will be affected. In addition, the 454 sequencing technology only considers the primary lead of the dephasing phenomenon, and ignores the secondary lead, which also affects the accuracy of the final results. Furthermore, the effectiveness of the 454 sequencing technology is also affected by many artificially-set parameters, and the technology is not convenient to use.

The Ion Torrent sequencing technology is trying to alleviate the signal deviation caused by the above reasons through change of the order in which nucleotides are added in the sequencing reaction. However, on one hand, this method can only alleviate, but not really correct the signal deviation. On the other hand, changing the order in which nucleotides are added in the sequencing reaction will reduce the average sequencing read length of each sequencing reaction.

In another aspect, disclosed herein is a sequencing method using nucleotide substrate molecules with fluorophores having a fluorescence switching property. In one aspect, the sequencing is achieved by modifying the 5' end or an intermediate phosphate of a nucleotide substrate molecule with a fluorophore having a fluorescence switching property. In one aspect, the fluorescence switching property refers to that the intensity of fluorescence signal after sequencing is significantly enhanced compared to the intensity of fluorescence signal before the sequencing reaction. In one aspect, each sequencing run uses one reaction solution group, each reaction solution group comprising at least two reaction solutions, and each reaction solution comprising at least one of the A, G, C, or T nucleotide substrate molecules, or one of the A, G, C, or U nucleotide substrate molecules. In one aspect, a nucleotide sequence fragment to be tested is first fixed in a reaction chamber, and a reaction solution from one reaction solution group is provided in the reaction chamber. The sequencing reaction can be started under a suitable condition, and a fluorescent signal is recorded. Then, additional reaction solutions are provided one at a time, so that the other reaction solutions in the same reaction solution group are provided sequentially in the sequencing reaction. At the same time, one or more fluorescent signals from each reaction solution are recorded. In one aspect, there is at least one reaction solution in a reaction solution group that comprises two or three nucleotide molecules.

In one aspect, the high-throughput sequencing is to obtain the sequence information of a DNA to be tested, by performing a series of enzymatic reactions and detecting the signals released in the reactions. If a certain nascent DNA strand has been extended to the $n^{th}$ base, and the nucleotides added into the current enzymatic reaction are exactly pairing with and are complementary to the $(n+1)^{th}$ and $(n+m)^{th}$ bases of the DNA template to be tested, then ideally the nascent DNA strand in the enzymatic reaction will extend to the $(n+m)^{th}$ base. If the nascent DNA strand in the enzymatic reaction has actually been extended to exceed the $(n+m)^{th}$ base, then a "lead" has occurred in the nascent DNA strand of this enzymatic reaction. If the nascent DNA strand in the enzymatic reaction actually has not been extended to the $(n+m)^{th}$ base, then a "lag" has occurred in the nascent DNA strand of this enzymatic reaction. The "lead" and "lag" phenomena are collectively known as the dephasing phenomenon. Note that, when the nascent DNA strand extends to the $n^{th}$ base, a plurality of "leads" and "lags," in any possible order, may have occurred.

Figure 38:
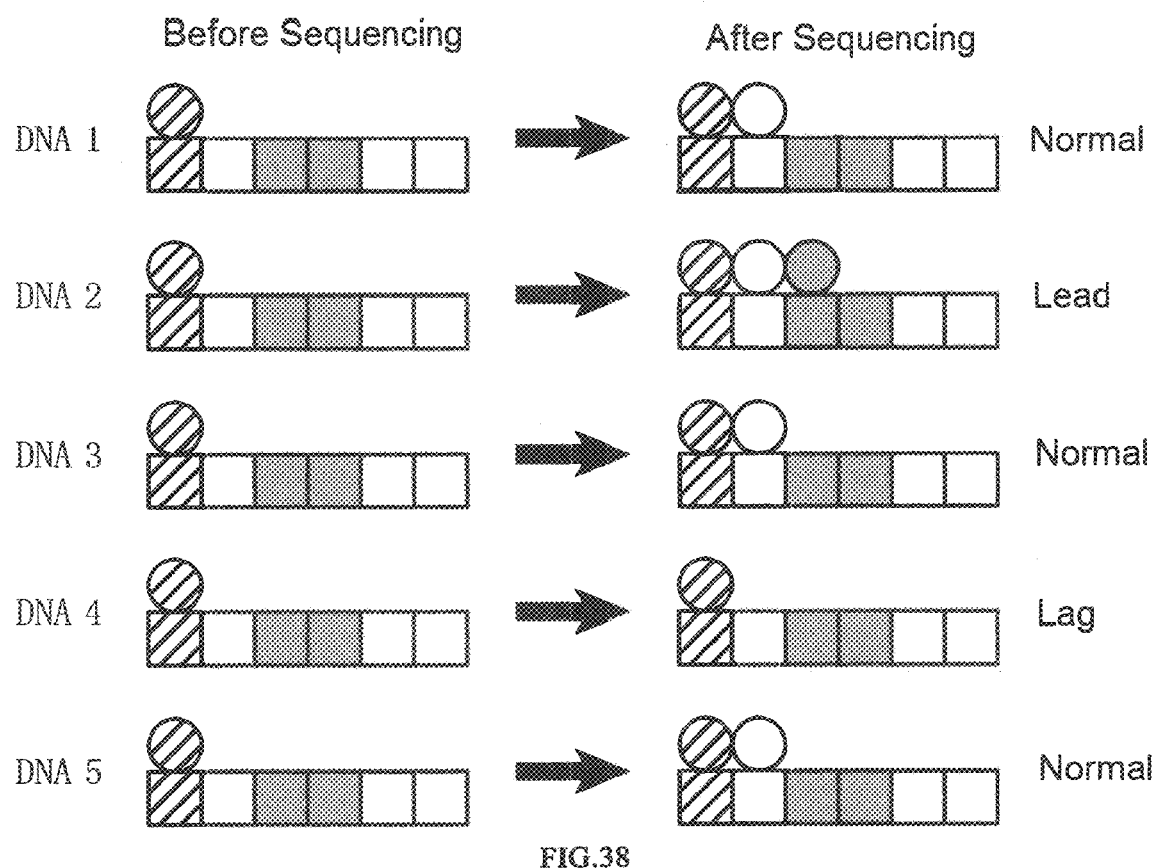
FIG. 38 shows a dephasing phenomenon in the sequencing of high-throughput DNA. The squares represent the nucleotides of the template DNA, and the circles represent the nucleotides composing nascent DNA strands. The patterns with oblique lines stand for sequencing primer areas, and the patterns full of white or gray refer to different types of nucleotides.

As shown in FIG. 38, all of the nascent DNA strands have the same length 1 prior to the sequencing reaction. Each of the hashed, white, or grey boxes represents a nucleotide in the sequence to be determined. For example, if the hashed box represents A, the white box represents T, and the grey box represents C, then the template sequence shown in FIG. 38 is ATCCTT. After the sequencing reaction, DNA molecules 1, 3 and 5 are extended and the extensions are normal, and their length is 2. In DNA molecule 2, the "leading" phenomenon has occurred, e.g., due to side (e.g., unwanted) reactions, and its length is 3 because the extension has exceeded the expected length of 2 nucleotides. In DNA molecule 4, the "lagging" phenomenon has occurred, e.g., due to an incomplete reaction, and its length is 1. In one aspect, after the sequencing reaction, the lengths of nascent DNA strands are different. The five DNA molecules shown in FIG. 38 are only of schematic representation, it does not mean that there are five DNA molecules in the actual sequencing, and in fact there may be multiple DNA molecules in the actual sequencing.

Figure 39:
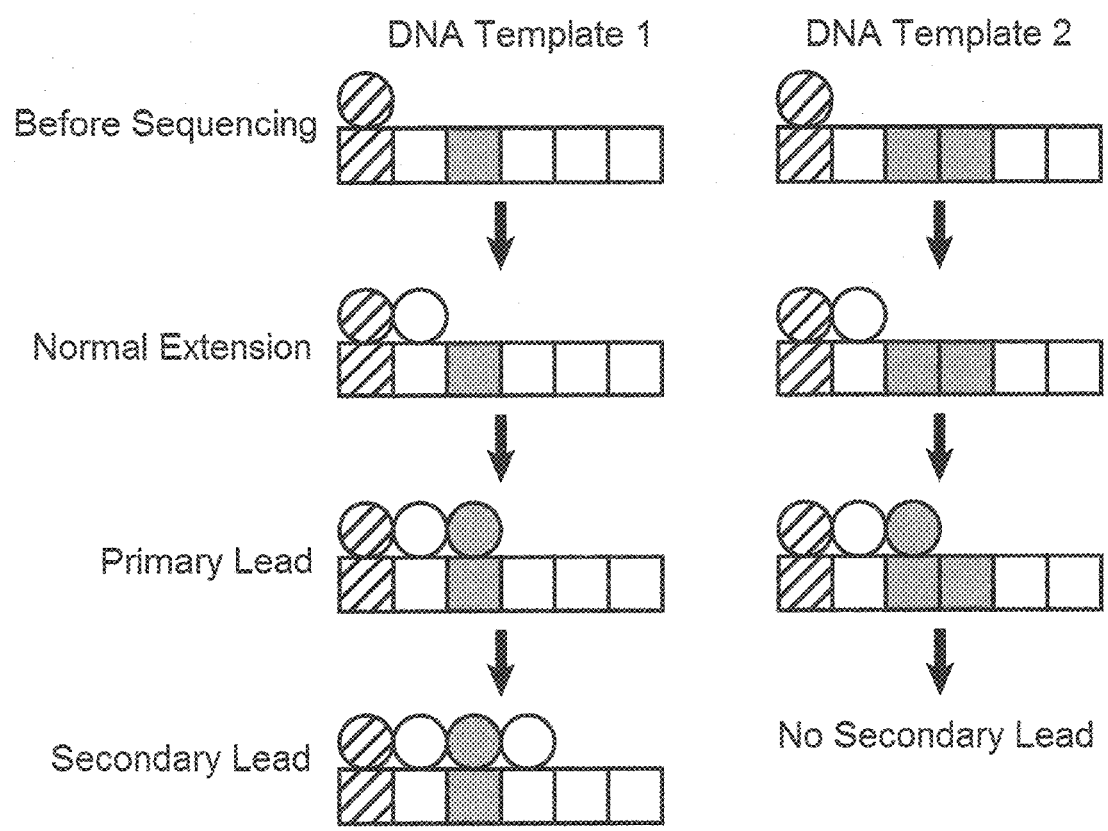
FIG. 39 illustrates the primary lead phenomenon and secondary lead phenomenon.

As shown in FIG. 39, DNA Template 1 can have a sequence of ATCTTT, and DNA Template 2 can have a sequence of ATCCTT. After a polymer A is extended normally (DNA Template 1, Normal Extension, showing the polymer A has a sequence of AT), in the same sequencing reaction, polymer A (i.e., AT) can be further extended by a side reaction to generate polymer B (DNA Template 1, Primary Lead, showing the polymer B has a sequence of ATC). Since in this sequencing reaction only nucleotide T is provided and the polymer is only expected to extend to position 2 (i.e., to have a T at position 2), polymer B presents a "primary lead" which already extends to position 3 and has a sequence of ATC. Note in this sequencing reaction, only nucleotide T is provided and no nucleotide C is provided, meaning that the C at position 3 may be a result of contamination (e.g., from previous sequencing reactions), a side reaction, or polymerase error. In this example, polymer B may be further extended to position 4 to generate polymer C (having a sequence of ATCT) because nucleotide T is provided in the sequence reaction, and this phenomenon is termed "secondary lead." Compare this with DNA Template 2, which has a C rather than a T at position 4. When DNA Template 2 is subject to sequencing, since nucleotide T is provided, a primary lead may occur to extend the polymer to position 3 (C) due to a side reaction. However, in one aspect, the chance that another side reaction occurs to add another C at position 4 is negligible. As a result, DNA Template 2 will not be extended to position 4 and the secondary lead phenomenon will not occur in DNA Template 2.

Sequencing Method

In some aspects, methods for DNA sequencing are employed in the present disclosure. In some embodiments, the method comprises fixing the DNA to be tested on a solid surface, hybridizing it with one or more sequencing primers, and/or conducting the sequencing reaction continuously and detecting the released signals. In one aspect, each reaction comprises the following steps: adding the reaction liquids containing the reagents that are required for the reaction, such as nucleotide, enzymes, etc., into the reactor (e.g., chip), to cause specific biochemical reactions; detecting the released signals from the reaction; and/or cleaning the reactor. The added nucleotides may be natural deoxynucleotide, or the nucleotide with chemically-modified groups, but in one aspect, there should be a hydroxyl group on its 3' end. The number of types of the nucleotides added in each reaction may be 1, 2, or 3, but it should not be 4 (referring to ACGT or ACGU). In one aspect, the union of types of the nucleotides added into two adjacent reactions includes all four nucleotides. For example, if A and G are added in the first reaction, then C and T will be added in the second reaction. In another example, if ACG are added in the first reaction, then T will be added in the second reaction.

If two types of nucleotides are added in a certain reaction, then the two types of nucleotides can release the same or different types of signals in the reaction. If three types of nucleotides are added into a certain reaction, then the three types of nucleotides can release the same or different types of signals. Alternatively, two of them can release the same signal, and the other one releases a different signal. The type of signals herein refers to the form of signals (such as electrical signals, bioluminescent signals, chemiluminescent signals, etc.), or the color of optical signals (such as green fluorescent signals, red fluorescent signals, etc.), or a combination thereof. Here, for simplicity, in one aspect, the signals released by all nucleotides in a certain reaction that are of the same type are referred to as monochrome signals; and those released by all nucleotides in a certain reaction that are of different types are referred to as polychrome signals. The "color" here is just used for the sake of simplicity, and the type of signals is not limited to optical signals of different colors (e.g., wavelengths).

In certain embodiments, the present disclosure relates to three types of signals with different meanings, and they are:
1. Ideal Signal h, which refers to the sequencing signal directly deduced in the ideal circumstance according to the sequence of the DNA to be tested and the sequence of added nucleotides, which directly reflects the DNA sequence information;
2. Dephasing Signal s, which refers to the signal formed by the ideal signal h after it is subject to the dephasing phenomenon and a bias is generated;
3. Predicted Original Sequencing Signal p, which refers to the signal formed by the dephasing signal (or the phase mismatch) s after a number of factors are taken into account: the number of extended bases, the multiplication relationship of the sequencing signal intensity, the signal attenuation, and the overall offset. The Predicted Original Sequencing Signal p is the prediction of the actual original signal according to the preset parameters;
4. Actual Original Sequencing Signal f, which refers to the signal obtained by direct measurement of the instrument in the high-throughput DNA sequencing.

Parameter Estimation

Figure 41:
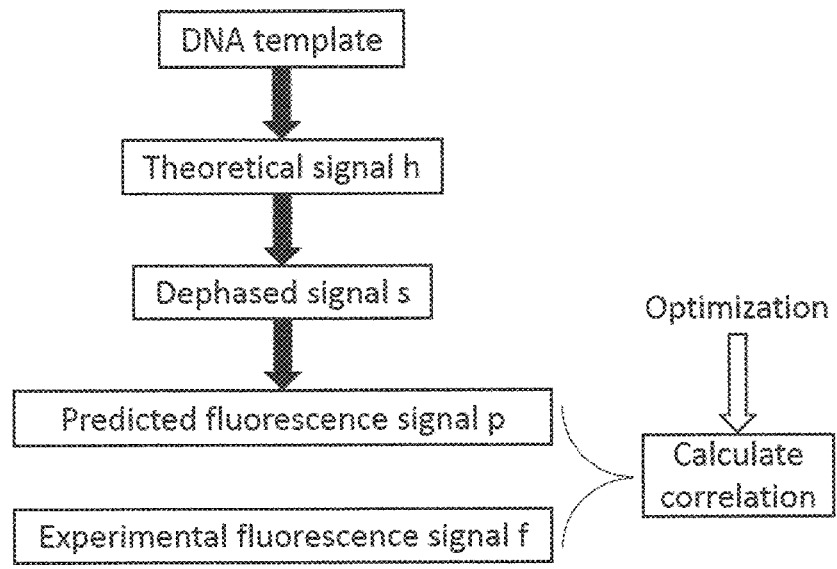
FIG. 41 shows the basic process of the parameter estimation.

The process of deducing relevant parameters of a sequencing reaction based on one or more reference DNA molecules and the actual original sequencing signal(s) of known sequence(s) is called parameter estimation. The basic process of parameter estimation is as shown in FIG. 41. The parameter estimation relates to a set of parameters describing relevant properties in a sequencing reaction, such as the dephasing coefficient, the intensity of unit signal strength, the attenuation coefficient, and the overall offset coefficient.

First, the method comprises deducing the ideal signal h according to the reference DNA molecule, and then calculating the dephasing signal (or the phase mismatch) s and the predicted original sequencing signal p based on the preset parameters. In one aspect, the method comprises calculating the correlation coefficient c between p and the actual original sequencing signal f. In one aspect, the method comprises using an optimization method to find a set of parameters, so that the correlation coefficient c reaches the optimal value. The correlation coefficient c herein includes but is not limited to Pearson correlation coefficient, Spearman correlation coefficient, average mutual information, Euclidean distance, Hamming distance, Chebyshev distance, Chebyshev distance, Mahalanobis distance, Manhattan distance, Minkowski distance, maximum or minimum value of the absolute value of the corresponding signal difference. Here, the optimization methods include, but are not limited to grid search method, brute-force method, gradient descent method, Newton method, Hessian matrix method, heuristic search, etc. In some aspects, the heuristic search includes but is not limited to genetic algorithm, simulated annealing algorithm, ant colony algorithm, harmonic algorithm, spark algorithm, Particle swarm optimization algorithm, and immune algorithm. The correlation coefficient and optimization methods mentioned here belong to general knowledge in mathematics.

In one aspect, based on the influence of the lead, lag, and/or offset on the sequencing signals, a conversion (or transformation) between the ideal signal h and the actual original sequencing signal f can be performed. In another aspect, in the processing of deducing the relationship between the ideal signal h and the actual original sequencing signal f (e.g., based on the signals measured from reference sequences of known nucleotide sequence), these parameters (e.g., lead, lag, and/or offset) can also be obtained, in the parameter estimation process. In some aspects, the estimation process comprises using a matrix (e.g., a transformation matrix T) and/or a function (e.g., a transformation function $\varphi$).

If the monochrome signal is acquired from the sequencing, then the calculation can be done directly as described above. If the polychrome signal is acquired from the sequencing, then each type of signal can be isolated from the polychrome signal and calculated separately using the method described above.

In one aspect, the calculation of the implementation method of s using h comprises constructing the transformation matrix T according to the characteristics of h and relevant parameters, and using T to transform h into s. In one aspect, the calculation of the implementation method of p using s comprises constructing the transformation function $\varphi$ according to relevant parameters, and using d to transform s into p. The specific implementation methods are detailed below.

Signal Correction

Figure 42:
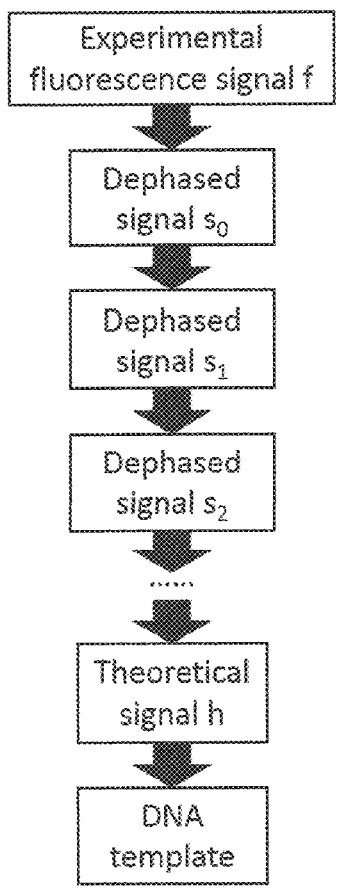
FIG. 42 shows the basic process of signal correction.

In one aspect, signal correction comprises a process of deducing the sequence information of the DNA to be tested according to (1) the parameters obtained through the parameter estimation, and (2) the actual original sequencing signal of the DNA to be tested, which is of unknown sequence. In one aspect, the basic process of signal correction is shown in FIG. 42, which may be substantially regarded as the reverse process of the parameter estimation process.

In a first aspect, the process comprises transforming the actual original sequencing signal f into the dephasing signal (or the phase mismatch) s using the inverse function of the transformation function $\varphi$ according to the parameters obtained from the parameter estimation. In one aspect, the process comprises regarding s as the zero-order dephasing signal $s_0$, constructing the transformation matrix $T_1$ based on so and relevant parameters, and using the generalized inverse matrix of $T_1$ to transform so into the first-order dephasing signal $s_1$. In another aspect, the process further comprises constructing the transformation matrix $T_2$ based on $s_1$ and relevant parameters, and using the generalized inverse matrix of $T_2$ to transform $s_1$ into the second-order dephasing signal $s_2$. In yet another aspect, the process further comprises constructing the transformation matrix $T_{i+1}$ based on $s_i$ and relevant parameters, and using the generalized inverse matrix of $T_{i+1}$ to transform $s_i$ into the (i+1)-order dephasing signal wherein i is an integer of 2 or greater. In one aspect, the process comprises calculating a series of dephasing signal $s_0, s_1, s_2, \ldots, s_{i+1}, \ldots, s_j$. In one aspect, if it is found that two adjacent dephasing signals $s_i$ and $s_{i+1}$ are equal to each other in the calculation, then the calculation may be stopped, leaving $s_i$ as the result of signal correction.

In one aspect, the above generalized inverse matrix can be substituted with a Tikhonov regularization method.

If the monochrome signal is acquired from the sequencing, then the calculation can be done directly as described above. If the polychrome signal is acquired from the sequencing, then each type of signal can be isolated from the polychrome signal and calculated separately using the method described above.

The above process of transforming f into s using the inverse function of the transformation function $\varphi$ and the process of transforming $s_i$ into $s_{i+1}$ using the generalized inverse matrix of T are detailed below.

Construction Method of Transformation Matrix T

In one aspect, the construction of the transformation matrix T is dependent on a sequencing-related signal x and sequencing and dephasing parameters. During parameter estimation, the signal x is the ideal signal h; during signal correction, the signal x is any-order dephasing signal $s_1$. In order to improve the accuracy of correction, the signal x may be extended by adding several is after it. In preferred embodiments, one to one hundred is can be added. In particular embodiments, five to ten is are added. In one aspect, the dephasing parameters comprise the lead coefficient c and the lag coefficient $\lambda$.

In one aspect, the construction of the transformation matrix T also comprises constructing a secondary matrix D. In one aspect, suppose the signal x has m values, and the sequencing reaction has actually been carried out for n times, then the transformation matrix T and the auxiliary matrix D both have n rows and m columns. For example, in the first row of the auxiliary matrix D, only the elements of the first column is 1 and the other elements are all zeros.

In one aspect, the method comprises calculating the $k^{th}$ row of the transformation matrix T using the $k^{th}$ row of auxiliary matrix D. For the first element in the $k^{th}$ row of the transformation matrix T:

1. If k is an odd number, the lagging phenomenon should be considered, and the element is designated as $(1-\lambda)D_{li}$;
2. If k is an even number, the element is designated as 0.

For the $i^{th}$ element in the $k^{th}$ row of the transformation matrix T (excluding the first element):

1. If k and i have the same parity, then the lagging phenomenon should be considered, and the element is set as $(1-\lambda)D_{ki}$;

2. If k and i have different parities, the primary leading phenomenon should be considered, and the element is set as $\varepsilon(1-\lambda)D_{k,i-1}$;

3. If the $(i-1)^{st}$ element of the signal x is less than 2, then the secondary leading phenomenon should be considered, and on the basis of calculation results from steps 1 and 2 above, the $(i-1)^{st}$ element $T_{k,i-1}$ in the same row of the transformation matrix T should be added to this element.

In one aspect, the method comprises calculating the $(k+1)^{st}$ row of the auxiliary matrix using the $k^{th}$ row of the transformation matrix T. In the first row of the auxiliary matrix D, only the elements of the first column is 1, and the other elements are all zeros. For the $k^{th}$ row of the auxiliary matrix (excluding the first row):

1. The first element is the difference between the element $D_{k-k1,i}$ in the previous row and the same column of the auxiliary matrix and the $T_{k-l,i}$ in the previous row and the same column of the corresponding element of the transformation matrix T.

2. The $i^{th}$ element is the sum of the difference between the element $D_{k-1,i}$ in the previous row and the same column of the auxiliary matrix and the $T_{k-1,i}$ in the previous row and the same column of the corresponding element of the transformation matrix T, plus the element $T_{k-1,i-1}$ in the previous row and previous column of the corresponding element of the transformation matrix T.

Therefore, in one aspect, the present disclosure firstly specifies the value of the first row of the auxiliary matrix D, and then uses the first row of the auxiliary matrix D to calculate the first row of the transformation matrix. In one aspect, the method further comprises using the first row of the transformation matrix T to calculate the second row of the auxiliary matrix, and using the second row of the auxiliary matrix D to calculate the second row of the transformation matrix T. The values of all the elements in the auxiliary matrix and the transformation matrix can be obtained in the same manner.

In one aspect, the auxiliary matrix D is only introduced for easy calculation, and it may be removed through a normal mathematics deformation method, so that the transformation matrix T may be directly calculated.

In the above calculation, the dephasing parameter is related to the type of nucleotide, as well as the row number k and the column number i where the calculated element is located. In the actual calculation, for the sake of simplicity, it is possible to either keep the dephasing coefficients $\varepsilon$ and/or $\lambda$ constant, or make the dephasing coefficients $\varepsilon$ and $\lambda$ change with the type of nucleotide, row number k, and/or column number i of the nucleotide.

In one aspect, during parameter estimation, the transformation matrix T may be obtained according to the above calculation method, based on the preset dephasing coefficient and the ideal signal h. In one aspect, the dephasing signal (or the phase mismatch) s is the product between the transformation matrix T and the ideal signal h. If the ideal signal h is expressed as a column vector, then s is namely T multiplied by h; if the ideal signal is expressed as a row vector, then s is a transposed matrix of h multiplied by T.

During parameter correction, the transformation matrix T may be obtained according to the above calculation method, based on the preset dephasing coefficient and the i-order dephasing signal $s_i$. In one aspect, the $(i+1)$-order dephasing signal s is the product between the generalized inverse matrix $T^+$ of the transformation matrix T and the i-order dephasing signal. If $s_i$ is expressed as a column vector, then $s_{i+1}$ is the $T^+$ multiplied by $s_i$; if $s_i$ is expressed as a row vector, then $s_i+1$ is a transposed matrix of $s_i$ multiplied by $T^+$. After the $(i+1)$-order dephasing signal $s_{i-1}$ is calculated with the above method, it may be further rounded. The rounding methods include but not limited to:

1. Rounding off by taking the most proximate integer;
2. Rounding up to an integer by taking the smallest integer larger than $s_{i+1}$;
3. Rounding down to an integer by taking the biggest integer larger than $s_{i+1}$;
4. Rounding toward zero: if $s_{i+1}$ is larger than 0, rounding down to an integer; if $s_{i+1}$ is less than 0, round up to an integer.
5. Positive rounding: rounding in any of the above ways, and then changing all the non-positive numbers to 1.

Construction Method of Transformation Function

In one aspect, the transformation function $\varphi$ is dependent on several parameters including unit signal a (the number of extended bases has a multiplication relationship with the intensity of sequencing signal), the attenuation coefficient b, and the overall offset c, etc. The parameters a, b and c herein may be a single factor, or a set of coefficients. For example, the unit signal a is related to the type of nucleotide and the times of sequencing reactions. In the calculation, it is possible to use single values of these parameters for the sake of simplicity, or to make them change with relevant factors for the sake of precision, or use single values for some parameters and make the other ones change with the relevant factors.

The forms of the transformation function $\varphi$ (s) include but not limited to the following:

1. $\varphi(s)=\varphi_a\varphi_b\varphi_s+\varphi_c$
2. $\varphi(s)=\varphi_a\varphi_b\varphi_s+\varphi_c)$
3. $\varphi(s)=\varphi_b\varphi_a\varphi_s+(Pc)$
4. $\varphi(s)=\varphi_a\varphi_b\varphi_s+\varphi_c)$.

In the above functions, $\varphi_a$, $\varphi_b$, $\varphi_c$ and $\varphi_s$ are mathematical functions associated with a, b and c, including but not limited to constant function, power function, exponential function, logarithmic function, trigonometric function, inverse trigonometric function, rounding function and special function, as well as the functions generated by mutual operation, composition, iteration or segment of the above-mentioned functions. In some embodiments, the special functions include but are not limited to elliptic function, gamma function, Bessel function, beta function and so on.

In one aspect, the transformation function $\varphi(x)$ can change the dephasing signal (or the phase mismatch) s into the predicted original sequencing signal p, namely $p=\varphi(s)$. In one aspect, the inverse function $\varphi^{-1}(x)$ of the transformation function $\varphi(x)$ can change the actual original sequencing signal f into the dephasing signal (or the phase mismatch) s, namely $s=\varphi^{-1}(f)$. The inverse function herein shall take the conventional meaning in mathematics.

Compared to existing methods (e.g., the 454 patent method, for examples, as disclosed in US 2011/0213563 A1, System and method to correct out of phase errors in DNA sequencing data by use of a recursive algorithm, issued as U.S. Pat. No. 8,364,417), the present disclosure has major improvements on the following three aspects. Firstly, the present method comprises constructing the transformation matrix by considering the primary lead, the secondary lead, and the lag in the dephasing phenomenon simultaneously, and using the transformation matrix to correct the sequencing errors caused by dephasing. Secondly, the present method comprises solving the signal deviation due to attenuation, dephasing, or overall offset as a whole. The present method neither only corrects the signal deviation caused by a single problem, nor simply solves the problems one by one. Thirdly, the signal correction method is improved, avoiding the introduction of parameter settings which need judgment by subjective factors, and enhancing the robustness and reproducibility of the method. Fourthly, both monochrome signal and bi-color signal may be corrected using a method disclosed herein.

Figure 40:
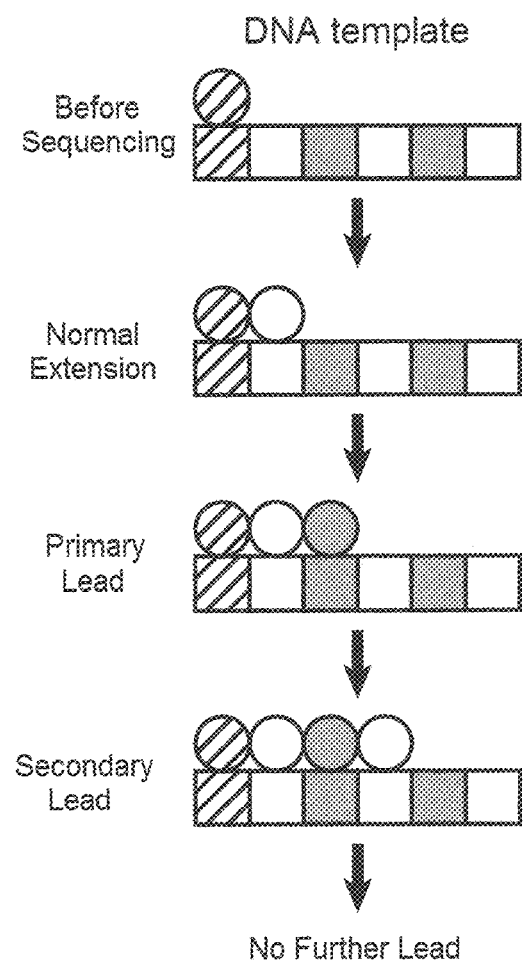
FIG. 40 shows that tertiary lead not occurring any longer.

In one aspect, the tertiary lead is not considered herein (FIG. 40).

In one aspect, the method in the present disclosure has following effects and advantages detailed below, as compared to the method mentioned in the background technology:

1. In the 2+2 sequencing method, the secondary lead phenomenon is very significant, and the resulted deviation cannot be corrected by the 454 patent method in which the secondary lead phenomenon is not taken into account. In the present disclosure, in one aspect, the secondary lead phenomenon is taken into account, depending on which, the signal deviation caused by this phenomenon may be well corrected.
2. In practice, if reading out the sequence information from the original sequencing signal only with the simple linear fitting method, the accuracy of the reading typically will reach about 100 bp at the most. If reading out the same data with the method described in the present disclosure, the accuracy of the reading may reach about 350 bp, which greatly improves the sequencing read length and the sequencing accuracy. In some embodiments, the accuracy of the reading may reach about 400 bp, about 450 bp, about 500 bp, about 550 bp, about 600 bp, about 650 bp, about 700 bp, about 750 bp, about 800 bp, about 850 bp, about 900 bp, about 950 bp, about 1000 bp, about 1050 bp, about 1100 bp, about 1150 bp, about 1200 bp, about 1250 bp, about 1300 bp, about 1350 bp, about 1400 bp, about 1450 bp, about 1500 bp, about 1550 bp, about 1600 bp, about 1650 bp, about 1700 bp, about 1750 bp, about 1800 bp, about 1850 bp, about 1900 bp, about 1950 bp, about 2000 bp, about 2050 bp, about 2100 bp, about 2150 bp, about 2200 bp, about 2250 bp, about 2300 bp, about 2350 bp, or about 2400 bp.
3. In one aspect, the present disclosure can correct both monochrome signal and bi-color signal.
4. In another aspect, the present disclosure does not affect the normal order in which samples and/or reagents (e.g., dNTPs or ddNTPs) are added for sequencing, compared to certain art methods, for example, the Ion Torrent sequencing method as disclosed in US 2014/0031238 A1 and U.S. Pat. No. 9,416,413 (Alternative nucleotide flows in sequencing-by-synthesis methods).

In one aspect, disclosed herein is a method to feed back the error generated by iteration in the template molecule sequence data, comprising: a) detecting multiple signals corresponding to the nucleic acid sequence, which are generated due to multiple nucleotides being introduced into the sequencing reaction; b) producing quantitative (normalized or digitalized) information using the detecting signal; c) obtaining a series of lead amount and/or lag amount information using the parameter estimation; d) obtaining a phase mismatch using the amount of generated new nucleotides and the accumulation of the secondary lead amount; e) calculating the amount of new nucleotides generated in each reaction using the phase mismatch; and f) repeating Steps d) and e) until the amount of the new nucleotides generated in each reaction becomes convergent, wherein said parameter estimation refers to deduce the lead amount and/or lag amount according to the reference sequence and its sequencing signals; wherein the secondary lead amount refer to that the extension not matching with the nucleotide substrate of this sequencing reaction occurs in the sequencing reaction, on that basis, the extension matching with the nucleotide substrate of this sequencing reaction occurs; wherein the phase mismatch is the change in the sequencing results due to lead amount and/or lag, and wherein the amount of new nucleotides is the extension length of the sequence after added with the sequencing reaction solution.

In one aspect, in the parameter estimation, the method further comprises obtaining the attenuation coefficient. In another aspect, in the parameter estimation, the method further comprises obtaining the offset amount. In another aspect, in the parameter estimation, the method further comprises obtaining the unit signal information.

In another aspect, disclosed herein is a method to feed back the error generated by iteration in the template molecule sequence data, comprising: a) detecting multiple signals corresponding to the nucleic acid sequence, which are generated due to multiple nucleotides being introduced into the sequencing reaction; b) producing quantitative (normalized or digitalized) information using the detecting signal; c) obtaining a series of lead amount and/or lag amount, attenuation coefficient and offset amount using the parameter estimation; d) obtaining the phase mismatch using the amount of generated new nucleotides and the accumulation of the secondary lead amount; e) calculating the amount of new nucleotides generated in each reaction using the phase mismatch; and f) repeating Steps d) and e) until the amount of the new nucleotides generated in each reaction becomes convergent; wherein the parameter estimation refers to deduce lead amount and/or lag amount, attenuation coefficient and offset amount according to the reference sequence and its sequencing signals; wherein the secondary lead amount refer to that the extension not matching with the nucleotide substrate of this sequencing reaction occurs in the sequencing reaction, on that basis, the extension matching with the nucleotide substrate of this sequencing reaction occurs; wherein the phase mismatch is the change in the sequencing results due to lead amount and/or lag; and wherein the amount of new nucleotides refers to the extension length of the sequence after added with the sequencing reaction solution.

In one aspect, disclosed herein is a method to correct the lead amount in the sequencing results using the secondary lead amount, wherein in the sequencing results, if the signal obtained from a certain reaction is similar to the unit signal, the method comprises correcting the signal using the secondary lead amount; and wherein the secondary lead amount refer to that the extension not matching with the nucleotide substrate of the sequencing reaction occurs in the sequencing reaction, and then, the extension matching with the nucleotide substrate of this sequencing reaction occurs.

In one aspect, in the sequencing results, the primary lead amount is included, wherein the primary lead amount refers to the extension not matching with the nucleotide substrate in the sequencing reaction.

In one aspect, the influence of the subsequent lead amount includes the secondary lead amount effect and the primary lead amount, except for the first secondary lead amount, will be accumulated into the subsequent sequencing reaction.

In any of the preceding embodiments, the signal obtained from the reaction can be similar to the unit signal, referring to that the signal obtained from the reaction is similar to the unit signal; a deviation of less than about 60% between the intensity information for the signal obtained from the optional reaction and the unit information may be obtained through the optimization reaction, a deviation of less than about 50% between the same two obtained through further optimization reaction, a deviation of less than about 40% between the same two obtained through further optimization reaction, a deviation of less than about 30% between the same two obtained through further optimization reaction, a deviation of less than about 20% between the same two obtained through further optimization reaction, a deviation of less than about 10% between the same two obtained through further optimization reaction and a deviation of less than about 5% between the same two obtained through further optimization reaction.

In one aspect, in the sequencing reaction, the method comprises when the $n^{th}$ sequencing signal is obtained, obtaining the corrected sequencing signal by feeding back the error generated by iteration in the template molecule sequence data, using the sequencing signal prior to n; and then, judging if the secondary lead amount exists in this position according to the judging rules described above.

In any of the preceding embodiments, the sequencing can be the process of adding the reaction solution of sequencing regents like nucleotide and enzymes into the nucleic acid sequence to be tested.

In any of the preceding embodiments, in the sequencing, one type or two types or three type or four types of nucleotide may be added in each reaction.

In any of the preceding embodiments, the sequencing can be the sequencing process with three ends open. In the sequencing reaction, one type or two types or three type of nucleotide may be added. In any of the preceding embodiments, in the sequencing, the added nucleotide may be one or more of A, G, C and T, or one or more of A, G, C and U.

In any of the preceding embodiments, in the sequencing, the detected signal may be electrical signal, bioluminescent signal, chemiluminescent signal, or combination of thereof.

In any of the preceding embodiments, in the parameter estimation, the method can comprise first deducing the ideal signal h according to the reference DNA molecule, and then calculating the dephasing signal (or the phase mismatch) s and the predicted original sequencing signal p based on the preset parameters, and calculating the correlation coefficient c between p and the actual original sequencing signal f.

In any of the preceding embodiments, the method can comprise using the optimization method to find a set of parameters, so that the correlation coefficient c reaches the optimal value. The found parameters may include lead amount and/or lag amount, or also include one or more of attenuation coefficient, offset amount and unit signal.

In any of the preceding embodiments, the lead amount and/or lag amount can refer to the degree of dephasing due to lead amount and/or lag in the sequencing reaction.

In any of the preceding embodiments, in the sequencing, the nucleotides can be divided into two groups, and the method can comprise adding the sequencing reaction solution containing one group of nucleotide molecule in each sequencing reaction.

EXAMPLES

Example 1: Sequencing by the "2+2, Monochrome" Method

In order to further describe the present disclosure, specific examples are provided below. The specific parameters, steps, etc. are conventional in the field unless otherwise specified. The specific examples are not to limit the scope of the present disclosure.

For sequencing by the "2+2, monochrome" method, three sets of reaction solutions are prepared. Each set comprises two vials, and each vial comprises two kinds of bases labeled with the same fluorescence group, X. For each set, the two vials together contain all four bases for the sequencing reaction. The six vials (two in each set) are different from each other.

TABLE 7

Reaction Solutions in the "2 + 2, monochrome" Method

|  | First Vial | Second Vial |
| --- | --- | --- |
| First Set | AX + CX | GX + TX |
| Second Set | AX + GX | CX + TX |
| Third Set | AX + TX | CX + GX |

A complete sequencing process comprises three rounds of sequencing, and the three rounds of sequencing are conducted sequentially in any suitable order. Each round of sequencing uses one of the three sets of reaction solutions listed in Table 7. For example, the order of the three rounds can be First Set 4 Second Set 4 Third Set, or Second Set 4 Third Set 4 First Set, etc. Except for the different set of reaction solutions used in each round, all the other conditions are the same (for example, the same sequencing primers and reaction conditions are used for all three rounds). The two vials in the same set of reaction solutions can also be used in any suitable order, for example, the first vial can be used before or after the second vial.

Each round of sequencing comprises:
1. Hybridizing the sequencing primers onto a prepared DNA array.
2. Starting the sequencing reactions. The steps from 2.1 to 2.4 can be repeated multiple times.
   2.1. Providing a first vial of reaction solution (e.g., the first vial or the second vial of the first set) to the sequencing reaction mix (for example, in a flowcell), letting the reaction proceed and acquiring fluorescence signals from the fluorescence group X.
   2.2. Washing off all residual reaction solution and fluorescence molecules in the flowcell.
   2.3. Providing a second vial of reaction solution (e.g., the second vial or the first vial of the first set) to the sequencing reaction mix, letting the reaction proceed and acquiring fluorescence signals.
   2.4. Washing off all residual reaction solution and fluorescence molecules in the flowcell.
3. Unwinding the extended sequencing primers.

At this point, a new round of sequencing reaction can be started.

Solutions used in this example can be prepared as follows. The washing solution for the sequencing reaction solution comprises: 20 mM Tris-HCl pH 8.8; 10 mM $(NH_4)_2SO_4$; 50 mM KCl; 2 mM $MgSO_4$; and 0.1% Tween® 20. The master solution for the sequencing reaction comprises: 20 mM Tris-HCl pH 8.8; 10 mM $(NH_4)_2SO_4$; 50 mM KCl; 2 mM $MgSO_4$; 0.1% Tween® 20; 8000 unit/mL Bst polymerase; and 100 unit/mL CIP (Alkaline Phosphatase, Calf Intestinal)

Three groups of sequencing reaction solutions are prepared as follows: Set 1 (Vials 1A and 1B):
   Vial 1A: Master solution+20 μM dA4P-TG+20 μM dC4P-TG
   Vial 1B: Master solution+20 μM dG4P-TG+20 μM dT4P-TG Set 2 (Vials 2A and 2B):
   Vial 2A: Master solution+20 μM dA4P-TG+20 μM dG4P-TG Vial 2B: Master solution+20 μM dC4P-TG+20 μM dT4P-TG Set 3 (Vials 3A and 3B):
Vial 3A: Master solution+20 μM dA4P-TG+20 μM dT4P-TG
Vial 3B: Master solution+20 μM dC4P-TG+20 μM dG4P-TG The prepared reaction solutions and master solutions are placed in a 4° C. refrigerator or on ice for future use.

In order to hybridize the sequencing primers, a sequencing primer solution (10 μM of primers in 1×SSC buffer) is injected the into the sequencing chip, which is then heated to 90° C., and then cooled to 40° C. at the rate of 5° C./min. The sequencing primer solution is then washed off with the washing solution.

In order to conduct the sequencing reactions, the sequencing chip is placed onto the sequencer. To perform the sequencing using the first group of reaction solutions, the steps below are followed:
1. Providing 10 mL washing solution to wash the chip.
2. Cool the chip to 4° C.
3. Providing 100 μL reaction solution 1A.
4. Heating the chip to 65° C.
5. Waiting for 1 min.
6. Taking fluorescence images under the excitation laser wavelength of 473 nm.
7. Providing 10 mL washing solution to wash the chip.
8. Cooling the chip to 4° C.
9. Providing 100 μL reaction solution 1B.
10. Heating the chip to 65° C.
11. Waiting for 1 min.
12. Taking fluorescence images under the excitation laser wavelength of 473 nm.
13. Repeating steps 1 to 12 for 50 times in order to obtain 100 fluorescence signals.

The second round of sequencing can be conducted as follows. First, the chip is cooled to room temperature. 200 μL 0.1 M NaOH solution is then provided to denature the DNA double strands extended in the first round of sequencing. 10 ml washing solution is the provided to wash off the residual NaOH and denatured DNA single strands.

The sequencing primers are then re-hybridized to the DNA array as described above. The sequencing reaction using the second set of reaction solutions is conducted as follows:
1. Providing 10 mL washing solution to wash the chip.
2. Cool the chip to 4° C.
3. Providing 100 μL reaction solution 2A.
4. Heating the chip to 65° C.
5. Waiting for 1 min.
6. Taking fluorescence images under the excitation laser wavelength of 473 nm.
7. Providing 10 mL washing solution to wash the chip.
8. Cooling the chip to 4° C.
9. Providing 100 μL reaction solution 2B.
10. Heating the chip to 65° C.
11. Waiting for 1 min.
12. Taking fluorescence images under the excitation laser wavelength of 473 nm.
13. Repeating steps 1 to 12 for 50 times in order to obtain 100 fluorescence signals.

The third round of sequencing can be conducted as follows. First, the chip is cooled to room temperature. 200 μL 0.1 M NaOH solution is then provided to denature the DNA double strands extended in the second round of sequencing. 10 ml washing solution is the provided to wash off the residual NaOH and denatured DNA single strands.

The sequencing primers are then re-hybridized to the DNA array as described above. The sequencing reaction using the third set of reaction solutions is conducted as follows:
1. Providing 10 mL washing solution to wash the chip.
2. Cool the chip to 4° C.
3. Providing 100 μL reaction solution 3A.
4. Heating the chip to 65° C.
5. Waiting for 1 min.
6. Taking fluorescence images under the excitation laser wavelength of 473 nm.
7. Providing 10 mL washing solution to wash the chip.
8. Cooling the chip to 4° C.
9. Providing 100 μL reaction solution 3B.
10. Heating the chip to 65° C.
11. Waiting for 1 min.
12. Taking fluorescence images under the excitation laser wavelength of 473 nm.
13. Repeating steps 1 to 12 for 50 times in order to obtain 100 fluorescence signals.

The three rounds of sequencing are completed at this point.

Example 2: Sequencing by the "2+2, Two Colors" Method

In this example, three sets of reaction solutions are prepared. There are two vials for each set, each vial comprising two kinds of nucleotide bases. The two kinds of nucleotide bases in each vial are labeled with two different fluorophores (such that their emission wavelengths are different) for distinguishing signals from the two kinds of nucleotide bases.

In this example, the two types of fluorophores are X and Y. For each set, the two vials together contain all four bases for the sequencing reaction. The six vials (two in each set) are different from each other.

TABLE 8

Reaction Solutions in the "2 + 2, two colors" Method

| | First Vial | Second Vial |
| --- | --- | --- |
| First Set | AX + CY | GX + TY |
| Second Set | AX + GY | CX + TY |
| Third Set | AX + TY | CX + GY |

A complete sequencing process comprises three rounds of sequencing, and the three rounds of sequencing are conducted sequentially in any suitable order. Each round of sequencing uses one of the three sets of reaction solutions listed in Table 8. For example, the order of the three rounds can be First Set→Second Set→Third Set, or Second Set→Third Set→First Set, etc. Except for the different set of reaction solutions used in each round, all the other conditions are the same (for example, the same sequencing primers and reaction conditions are used for all three rounds). The two vials in the same set of reaction solutions can also be used in any suitable order, for example, the first vial can be used before or after the second vial.

Each round of sequencing comprises:
1. Hybridizing the sequencing primers onto a prepared DNA array.
2. Starting the sequencing reactions. The steps from 2.1 to 2.4 can be repeated multiple times.
 2.1. Providing a first vial of reaction solution (e.g., the first vial or the second vial of the first set) to the sequencing reaction mix (for example, in a flowcell), letting the reaction proceed and acquiring fluorescence signals from the fluorescence group X and fluorescence signals from the fluorescence group Y.
2.2. Washing off all residual reaction solution and fluorescence molecules in the flowcell.
2.3. Providing a second vial of reaction solution (e.g., the second vial or the first vial of the first set) to the sequencing reaction mix, letting the reaction proceed and acquiring fluorescence signals from the fluorescence group X and fluorescence signals from the fluorescence group Y.
2.4. Washing off all residual reaction solution and fluorescence molecules in the flowcell.
3. Unwinding the extended sequencing primers.

At this point, a new round of sequencing reaction can be started.

Example 3: Examples for Comparison

Example for Comparison No. 1

In this example offered as a comparison, four kinds of 3' end-blocked nucleotide molecules are used. The 3' blocking group may hinder polymerase molecules from continued extension using this nucleotide molecule as the substrate. The 3' blocking group can be removed under specific conditions in order to generate a terminal hydroxyl group. Each kind of nucleotide molecule is labeled with a different fluorescent molecule. The fluorescent molecules used herein are not fluorophores having fluorescence switching property, and may be removed under certain conditions. The fluorescence labels are W, X, Y, and Z, respectively. The labeled nucleotide monomers are W-A, X-C, Y-G, and Z-T, respectively.

Regent 1 is the main sequencing reaction solution, which comprises four kinds of 3' end-blocked nucleotide molecules labeled with fluorescence, and the polymerase that uses the labeled nucleotide molecules for the polymerase catalyzed extension. Regent 2 is the washing solution. Regent 3 is the de-blocking solution which comprises regents for removing the 3' end blocking groups and the fluorescent groups.

During sequencing, the sequencing primer is first hybridized onto the template strand. Reagent 1 and the hybridized template are then mixed in order to cause the polymerase reaction. After the reaction, reagent 2 is used to wash off the unreacted sequencing solution. Fluorescence signals are acquired in order to determine the nucleotide base added to the sequencing primer in the polymerase extension reaction. Then reagent 3 is used to remove the 3' end blocking group and the fluorescence groups. The template polynucleotide can then proceed to the next round of sequencing reaction after washing. This sequencing method does not have data redundancy and quality control characteristics.

Example for Comparison No. 2

In this example offered as a comparison, the sequencing reactions are conducted using nucleotides without the fluorescence switching property. This example is similar to Example 1, except that the fluorescent label is not in the phosphate group. This example relates to four kinds of nucleotide molecules, and all of them may be extended freely by the polymerase under the complementary pairing conditions. The bases of each kind of nucleotide molecules is labeled with the same fluorescence group, and the molecule group does not have the fluorescence switching property, and may be removed under certain conditions. Three sets of reaction solutions are provided, two vials for each set. For each set, the two vials together contain all four bases for the sequencing reaction. The six vials (two in each set) are different from each other.

TABLE 9

Reaction Solutions in Example for Comparison No. 2

| | First Vial | Second Vial |
|---|---|---|
| First Set | AX + CX | GX + TX |
| Second Set | AX + GX | CX + TX |
| Third Set | AX + TX | CX + GX |

A complete sequencing process comprises three rounds of sequencing, and the three rounds of sequencing are conducted sequentially in any suitable order. Except for the different set of reaction solutions used in each round, all the other conditions are the same (for example, the same sequencing primers and reaction conditions are used for all three rounds).

Each round of sequencing comprises:
1. Hybridizing the sequencing primers onto a prepared DNA array.
2. Starting the sequencing reactions. The steps from 2.1 to 2.8 can be repeated multiple times.
    2.1. Providing a first vial of reaction solution to the sequencing reaction mix, letting the reaction proceed.
    2.2. Washing off all residual reaction solution and fluorescence molecules in the flowcell.
    2.3. Acquiring fluorescence signals from the fluorescence group.
    2.4. Providing a reagent to remove the fluorescent labeling group.
    2.5. Providing a second vial of reaction solution to the sequencing reaction mix, letting the reaction proceed.
    2.6. Washing off all residual reaction solution and fluorescence molecules in the flowcell.
    2.7. Acquiring fluorescence signals from the fluorescence group.
    2.8. Providing a reagent to remove the fluorescent labeling group.
3. Unwinding the extended sequencing primers.

Then, a new round of sequencing can be started. The assay is completed after three rounds of sequencing.

In this example, because the substrates (nucleotide molecules) without fluorescence switching property are used, an excision reagent needs to be provided in the sequencing steps to remove the fluorescent labels, and the sequencing process takes longer. Besides, molecular scars are created and left on the generated double strand DNA molecules, preventing further extension.

Example 4: Detecting and/or Correcting Sequencing Errors

In this example, a single-stranded DNA molecule whose sequence is to be determined is fixed onto a solid surface. The fixing methods may be chemical crosslinking, molecular adsorption, etc. The 3' end or 5' end of the DNA may be fixed to the surface. The DNA to be determined comprises a fragment with known sequence, which is complementary and capable of hybridizing to a sequencing primer. The sequence from the 3' end of the segment with known sequence to the 3' end of the DNA to be tested is the fragment whose sequence is to be determined. In this example, the sequence to be determined is 5'-TGAACTT-TAGCCACGGAGTA-3' (SEQ ID NO: 2).

A sequencing primer is first hybridized onto the segment with known sequence of the target DNA. The base of each nucleotide substrate molecule is coupled to a functional group having a fluorescence switching property, and the number of phosphate modules is 4.

dG4P and dT4P, as well as corresponding reaction buffer solutions, enzymes and metal ions, are added to the reaction to cause the sequencing reaction which generates fluorescence signals. The signals are acquired by a CCD (charge coupled device). The values of these fluorescence signals are recorded. The reaction is recorded as the first reaction.

The residual dG4P and dT4P in the reaction are then washed off. Then, dA4P and dC4P are added into the reaction system to cause the same sequencing reaction as mentioned above, and the fluorescence signal values are recorded. The reaction should be recorded as the second reaction. This method is also called monochrome 2+2 sequencing method.

The above process is repeated. dG4P and dT4P are added for the odd-number reactions, and dA4P and dC4P are added for the even-number reactions, to obtain a group of sequencing signal values: x=(2, 3, 3, 1, 1, 3, 2, 1, 2, 1).

The DNA nascent strand synthetized in the above sequencing reaction is then unwound and washed off, for example, using high temperature or strong hydrophilic substances (such as urea and formamide). The sequencing primer is then re-hybridized onto the template DNA. dC4P and dT4P are added for the odd-number reactions, and dA4P and dG4P are added for the even-number reactions, to obtain a group of sequencing signal values: y=(1, 4, 4, 2, 2, 1, 1, 4, 1, 1).

The DNA nascent strand synthetized in the above sequencing reaction is then unwound and washed off, for example, using high temperature or strong hydrophilic substances (such as urea and formamide). The sequencing primer is then re-hybridized onto the template DNA. dA4P and dT4P are added for the odd-number reactions, and dC4P and dG4P are added for the even-number reactions, to obtain a group of sequencing signal values: z=(1, 1, 2, 1, 4, 3, 1, 3, 1, 1, 2).

The above sequencing signal values are then analyzed in view of the types of nucleotide bases represented by the signals to obtain the sequencing information. For each residue of the target DNA, the common base among the three signals are identified and listed in the table below, as the nucleotide residue in that position.

TABLE 10

Sequencing Results before Correction

| Signal x | K | K | M | M | M | K | K | K | M | K | M | M | M | K | K | M | K | K | M |   |
|---|---|---|---|---|---|---|---|---|---|---|---|---|---|---|---|---|---|---|---|---|
| Signal y | Y | R | R | R | R | Y | Y | Y | Y | R | R | Y | Y | R | Y | R | R | R | Y | R |
| Signal z | W | S | W | W | S | W | W | W | W | S | S | S | W | S | S | S | W | S | W | W |
| Common base | T | G | A | A | ? | T | T | T | ? | G | ? | C | ? | G | ? | ? | ? | G | A | ? | ? |

When solving the common base in each position for the three groups of signals, there is no common base at several positions. This indicates that error has occurred in the sequence. In this example, the second value of Signal Y is changed from 4 to 3, and the sixth value of Signal X is changed from 3 to 4, then the signal will be changed to be the condition as shown in the table below.

TABLE 11

Sequencing Results after Correction

| Signal x | K | K | M | M |   | M | K | K | M | K | M | M | *M* | M | K | K | M | K | K | M |
|---|---|---|---|---|---|---|---|---|---|---|---|---|---|---|---|---|---|---|---|---|
| Signal y | Y | R | R | R | ~~R~~ | Y | Y | Y | Y | R | R | Y | Y | R | Y | R | R | R | Y | R |
| Signal z | W | S | W | W |   | S | W | W | W | W | S | S | S | W | S | S | S | W | S | W | W |
| Common base | T | G | A | A |   | C | T | T | T | A | G | C | C | A | C | G | G | A | G | T | A |

In the above table, changing the second value of Signal Y from 4 to 3 is expressed as R with strikethrough, and changing the sixth value of Signal X from 3 to 4 is expressed as adding an M (in underline and with italics). After the two modifications, there are common bases in all positions of the three groups of signals, and the sequence consisting of these common bases is the DNA sequence to be determined. This result indicates that by "coding" the DNA with degenerate indicators (e.g., M, K, R, Y, W, S, B, and D), the method can effectively detect error(s) in the sequencing process, while the method of "decoding" the sequence can effectively correct the error(s). The short sequence in this example can effectively explain the error correction method provided by the present disclosure. The modification method used in this example is a method with the smallest change, and a method achieving the simplest matching of subsequent sequences. In the practical application, a mathematical model may be built to achieve this change. In a realistically practical algorithm, all the possible changes are counted based on probability. The above change subject to the probability parameter correction is the most possible correct change. In one aspect, this calculation is the simple application of the maximum likelihood method based on Bayesian Scheme. In another aspect, this calculation method is generally a conventional mathematical method.

By coding and decoding DNA sequences, the method can improve the sequencing accuracy effectively if applied to DNA sequencing signals. For decoding, the sequencing signals can be expressed as a weighted graph, for example, as shown in FIG. 1. A weighted graph is recorded as G (V, E, W), wherein V is the node of the graph, E is the edge of the graph, and W is the weight value of each edge (e.g., a real number). The coding and decoding process is explained below, supposing the sequencing signal counted by time i is $a_i$.

1) For each signal $a_i$ if the nucleotide provided in the sequencing reaction at the $i^{th}$ time is X, then node $a_i$ is drawn, and each node standing for one X base.
2) Nodes $a_i$ are connected sequentially, namely, the first point of the node points to the second point, and the second point points to the third point, and so on.
3) The last point of the node has a ring pointing to itself.
4) All the nodes of the $i^{th}$ time point to the first node of $(i+1)^{th}$ time.
5) According to the statistical results of a large amount of sequencing data, all the edges are assigned a weight.

If a DNA sequence is sequenced once using M/K, R/Y and W/S combinations, respectively, then three sequencing signals are obtained. The three sequencing signals are then expressed as a graph using the above method, as shown in FIG. 1.

The three groups of signals in sequence 5'-TGAACTT-TAGCCACGGAGTA-3' (SEQ ID NO: 2) are (including errors):

M/K: 2, 3, 3, 1, 1, 3, 2, 1, 2, 1
R/Y: 1, 4, 4, 2, 2, 1, 1, 4, 1, 1
W/S: 1, 1, 2, 1, 4, 3, 1, 3, 1, 1, 2

The path of the directed weighted graph is defined as one group of nodes of the directed weighted graph, i.e., $v_1 v_2 \ldots v_n$. This group of nodes may be completely different or some nodes are the same (for example, $v_1$ and $v_2$ may stand for the same node). In addition, there is one directed edge pointing from $v_i$ to $v_{i+1}$, wherein $v_i$ and $v_{i-1}$ are two adjacent nodes in this group of nodes. The weight value used for defining the path is the sum of all the weight values in the path. If each sequencing signal is expressed as a weighted graph, then each of the paths in the graph stands for one possible DNA sequence. The process of decoding signals is to find out the maximum common path of all the graphs. The specific methods used may include the exhaustion method, the greedy method, the dynamic programming method, and the heuristic search method.

Example 5: Detecting and/or Correcting Sequencing Errors

According to the sequencing method in Example 4, 5000 DNA sequences with the length of 400 bp were decoded, and all the DNAs were divided into 5 groups, with 1000 DNAs in each group. According to the sequencing correction method in Example 4, the coding accuracy and the accuracy after decoding are summarized in the table below.

TABLE 12

Sequencing Accuracy Rates

| Group | Code accuracy rate | Accuracy rate after decoding |
|---|---|---|
| 1 | 0.9736 | 0.9917 |
| 2 | 0.9813 | 0.9951 |
| 3 | 0.9878 | 0.9977 |
| 4 | 0.9953 | 0.9997 |
| 5 | 0.9973 | 0.9999 |

It is apparent that the coding-decoding method provided herein can effectively improve the accuracy for sequencing. For example, when the error rate is 0.0364 (in other words, the accuracy rate is 0.9736), it will become 0.0083 after correction (in other words, the accuracy rate becomes 0.9917). When the error rate is 0.0047, it will become 0.0003 after correction. Through comparison, when the error rate is reduced by 7.74 times (0.0364 divided by 0.0047) before correction, it will be reduced by 27.6 times (0.0083 divided by 0.0003) after correction. The apparent trend from the overall data is that by reducing the sequencing error rate, the deduction in error rate is further reduced after correction. In other words, by using the correction method disclosed herein, any minor improvement in the sequencing method that reduces the sequencing error rate can lead to a much more significant reduction of the error rate in the modified sequencing data.

Figure 2:
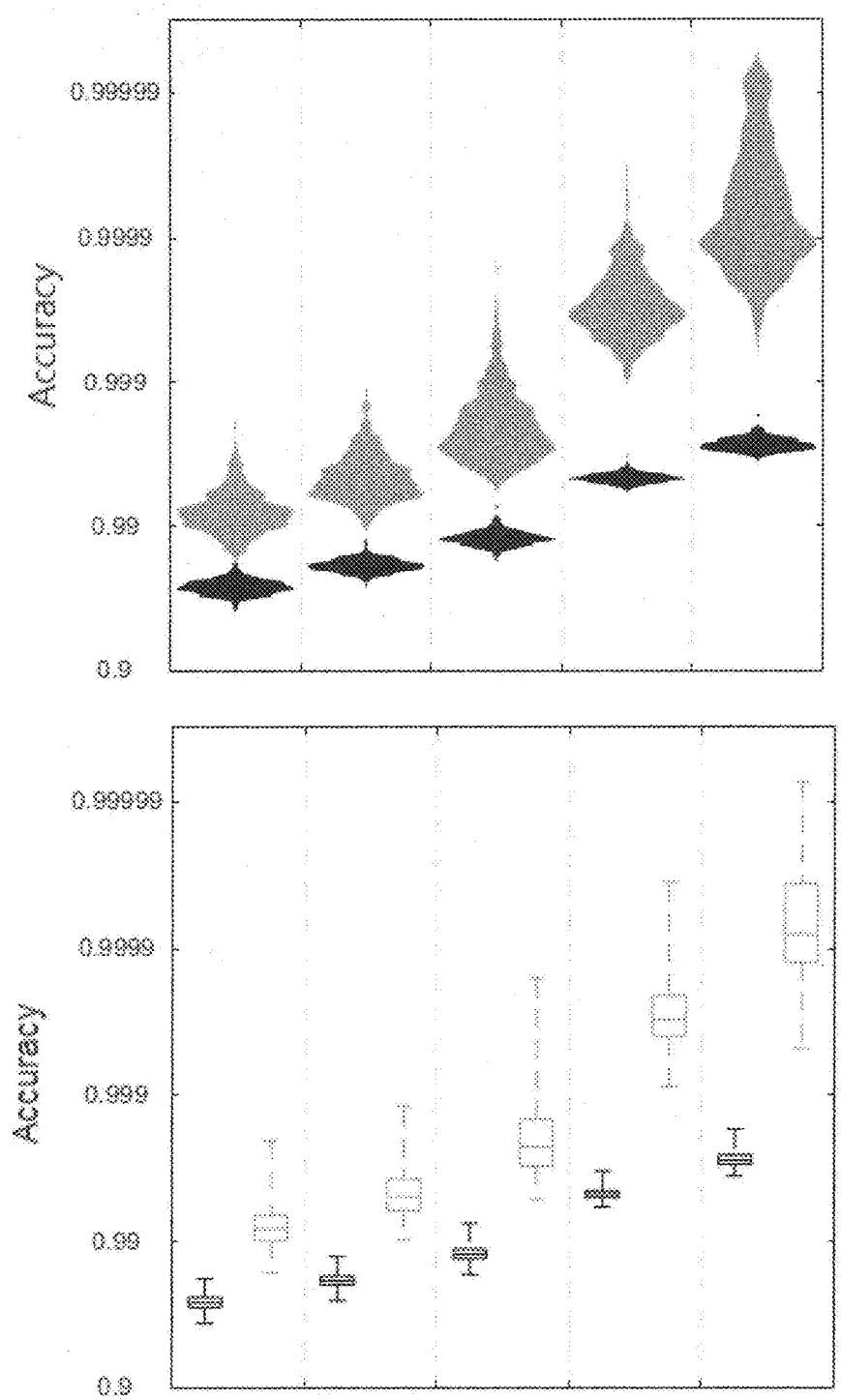
FIG. 2 shows data distribution of the data of Group 1 to Group 5 illustrated by the violin plot and the box plot. The coding accuracy is represented by black, and the decoding accuracy is represented by gray. The data of Group 1 to Group 5 is presented in sequence from left to right.

The coding accuracy and the accuracy after decoding of each group are expressed using the violin plot or the box plot, as shown in FIG. 2.

Figure 3:
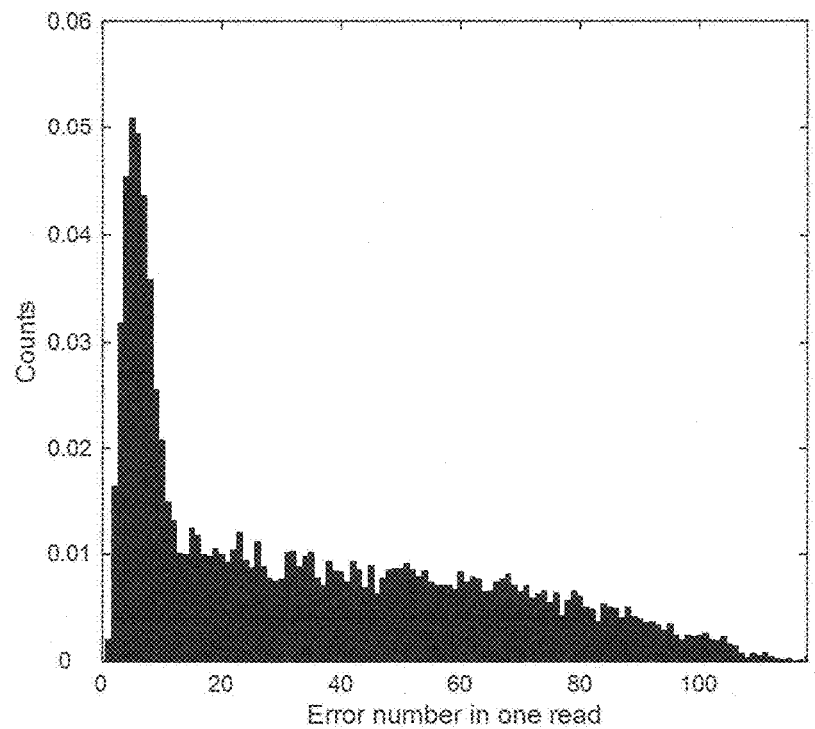
FIG. 3 shows a frequency distribution histogram illustrating the number of signals of each sequence of 5000 items of sequence data, which are modified during decoding.

According to the features of the modified signal during coding, the sequences with a higher possibility of being correctly decoded may be screened out, further improving the accuracy of decoding. The number of the modified signals during decoding in each of the sequences is counted based on the above data, and its frequency distribution histogram is shown in FIG. 3. The frequency distribution histogram has following features: there is a peak on the left of the histogram, and the frequency is distributed like a long tail on the right of the peak. If the sequences in the long tail area are discarded, and only the sequences in the peak area are included for analysis, then the accuracy after decoding is further improved by 2 to 10 times.

Figure 4:
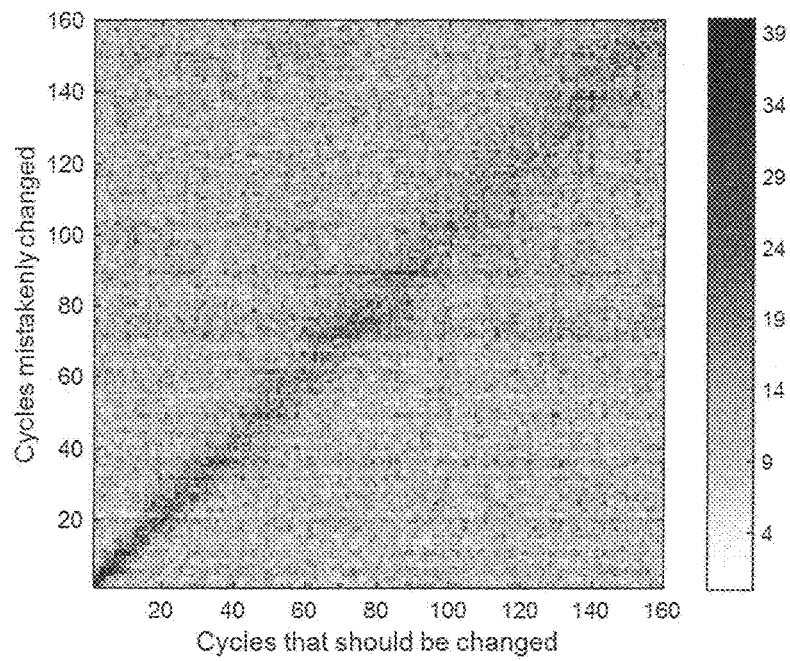
FIG. 4 shows the number of the signals with error during coding and the correlated relation between the numbers of the wrongly-modified signals during decoding, the horizontal ordinate stands for the number of signals with error during coding; and the vertical coordinate stands for the correlated relation between the numbers of wrongly-modified signals during decoding, the gray scale of colors stands for the proportion of the counted times of the point in all of the sequences.

FIG. 4 shows the relationship between the number of the signals with errors during coding and the number of the wrongly-modified signals during decoding. The horizontal coordinate stands for the number of the signals with errors during coding, and the vertical coordinate stands for the number of the wrongly-modified signals during decoding. The gray scale of colors stands for the proportion of the counted times of the point in all of the sequences. FIG. 3 shows that in most cases, the modified signals and the signals with actual errors are close to each other, even if an error occurs during decoding. Therefore, this feature may be used to judge the decoding quality. If a certain signal and its adjacent signals are not modified during decoding, then the base type represented by the signal has an extremely high confidence level.

Example 6: Detecting and/or Correcting Sequencing Errors

In this example, a single-stranded DNA molecule whose sequence is to be determined is fixed onto a solid surface. The fixing methods may be chemical crosslinking, molecular adsorption, etc. The 3' end or 5' end of the DNA may be fixed to the surface. The DNA to be determined comprises a fragment with known sequence, which is complementary and capable of hybridizing to a sequencing primer. The sequence from the 3' end of the segment with known sequence to the 3' end of the DNA to be tested is the fragment whose sequence is to be determined. In this example, the sequence to be determined is 5'-TGAACTT-TAGCCACGGAGTA-3' (SEQ ID NO: 2).

A sequencing primer is first hybridized onto the segment with known sequence of the target DNA. Four types of dNTP and corresponding reaction buffer solutions, enzymes and metal ions are added into the reaction system. The 3' end of each type of dNTP is blocked by a chemical group. Besides, dGTP and dTTP are each labeled with a fluorescence group in the same color, while dATP and dCTP are each labeled with another type of fluorescence group in the same color. In the reaction, the dNTP which is complementary to and capable of pairing with the base the template DNA is incorporated into the nascent DNA strand by a DNA polymerase. After the reaction, the residual dNTPs are washed off, and fluorescence signals are recorded using a CCD. The above reaction is repeated to obtain a group of sequencing signal values: x=KKMMMKKKMKMMMKKMKKM.

The DNA nascent strand synthetized in the above sequencing reaction is then unwound and washed off, for example, using high temperature or strong hydrophilic substances (such as urea and formamide). The sequencing primer is re-hybridized to the DNA template, and the above sequencing process is repeated, but dCTP and dTTP are labeled with fluorescence group in the same color, while dATP and dGTP are both labeled with a fluorescence group in another color. The value of this group of sequencing signals is obtained: y=YRRRRYYYYRRYYRYRRRRYR.

The DNA nascent strand synthetized in the above sequencing reaction is then unwound and washed off, for example, using high temperature or strong hydrophilic substances (such as urea and formamide). The sequencing primer is re-hybridized to the DNA template, and the above sequencing process is repeated, but dATP and dTTP are labeled with fluorescence group in the same color and dCTP and dGTP are both labeled with a fluorescence group in another color. The value of this group of sequencing signals is obtained: z=WSWWSWWWWSSSWSSSWSWW.

The above sequencing signal values are then analyzed in view of the types of nucleotide bases represented by the signals to obtain the sequencing information. For each residue of the target DNA, the common base among the three signals are identified and listed below in the table below, as the nucleotide residue in that position.

as adding an M (in underline and with italics). After the two modifications, there are common bases in all positions of the three groups of signals, and the sequence consisting of these common bases is the DNA sequence to be determined. This result indicates that by "coding" the DNA with degenerate indicators (e.g., M, K, R, Y, W, S, B, and D), the method can effectively detect error(s) in the sequencing process, while the method of "decoding" the sequence can effectively correct the error(s).

Example 7: Detecting and/or Correcting Sequencing Errors

In this example, the DNA to be determined comprises a fragment with known sequence, which is complementary and capable of hybridizing to a sequencing primer. The sequence from the 3' end of the segment with known sequence to the 3' end of the DNA to be tested is the fragment whose sequence is to be determined. In this example, the sequence to be determined is 5'-TGAACTT-TAGCCACGGAGTA-3' (SEQ ID NO: 2).

A sequencing primer is first hybridized onto the segment with known sequence of the target DNA. The reaction volume containing the template DNA molecule with the hybridized sequencing primer is divided into three portions, which can be assayed in parallel or sequentially. Four types of dNTP, certain types of ddNTP, as well as the enzyme and buffer solutions required for the synthetic reaction of DNA are added into each portion. In some aspects, the added dNTP is a natural dNTP, and the added ddNTP has a detectable label (such as one that can be detected by an instrument), including but not limited to a radio-isotopic label, a chemical fluorescence label, etc. In the first portion, ddGTP and ddTTP have the same label, while ddATP and ddCTP have another same label. In the second portion, ddATP and ddCTP have the same label, and ddATP and

TABLE 13

Sequencing Results before Correction

| Signal x | K | K | M | M | M | K | K | K | M | K | M | M | M | K | K | M | K | K | M |
|---|---|---|---|---|---|---|---|---|---|---|---|---|---|---|---|---|---|---|---|
| Signal y | Y | R | R | R | R | Y | Y | Y | Y | R | R | Y | Y | R | Y | R | R | R | R | Y | R |
| Signal z | W | S | W | W | S | W | W | W | W | S | S | S | W | S | S | S | W | S | W | W |
| Common base | T | G | A | A | ? | T | T | T | ? | G | ? | C | ? | G | ? | ? | ? | G | A | ? | ? |

When solving the common base in each position for the three groups of signals, there is no common base at several positions. This indicates that error has occurred in the sequence. In this example, the second value of Signal Y is changed from 4 to 3, and the sixth value of Signal X is changed from 3 to 4, then the signal will be changed to be the condition as shown in the table below.

ddGTP have another same label. In the third portion, ddATP and ddTTP have the same label, and ddCTP and ddGTP have another same label.

These three portions are all reacted for a suitable period of time under the appropriate conditions, during which the synthetic reaction of DNA occurs. After the reaction, the reaction products may optionally be cleaned or purified. And

TABLE 14

Sequencing Results after Correction

| Signal x | K | K | M | M |   | M | K | K | K | M | K | M | M | M | *M* | K | K | M | K | K | M |
|---|---|---|---|---|---|---|---|---|---|---|---|---|---|---|---|---|---|---|---|---|---|
| Signal y | Y | R | R | R | ~~R~~ | Y | Y | Y | Y | R | R | Y | Y | R | *Y* | R | R | R | R | Y | R |
| Signal z | W | S | W | W |   | S | W | W | W | W | S | S | S | W | S | S | S | W | S | W | W |
| Common base | T | G | A | A |   | C | T | T | T | A | G | C | C | A | C | G | G | A | G | T | A |

In the above table, changing the second value of Signal Y from 4 to 3 is expressed as R with strikethrough, and changing the sixth value of Signal X from 3 to 4 is expressed then, DNA electrophoresis on the three portions of reaction products may be performed. According to electrophoretic bands, three sequencing signals can be obtained:

x = KKMMMKKKMKMMMKKMKKM y = YRRRRYYYYRRYYRYRRRRYR z = WSWWSWWWWSSSWSSSWSWW

The above sequencing signal values are then analyzed in view of the types of nucleotide bases represented by the signals to obtain the sequencing information. For each residue of the target DNA, the common base among the three signals are identified and listed below in the table below, as the nucleotide residue in that position.

TABLE 15

Sequencing Results before Correction

| | | | | | | | | | | | | | | | | | | | | |
|---|---|---|---|---|---|---|---|---|---|---|---|---|---|---|---|---|---|---|---|---|
| Signal x | K | K | M | M | M | K | K | K | M | K | M | M | M | K | K | M | K | K | M | |
| Signal y | Y | R | R | R | R | Y | Y | Y | Y | R | R | Y | Y | R | Y | R | R | R | R | Y | R |
| Signal z | W | S | W | W | S | W | W | W | W | S | S | S | W | S | S | S | W | S | W | W | |
| Common base | T | G | A | A | ? | T | T | T | ? | G | ? | C | ? | G | ? | ? | ? | G | A | ? | ? |

When solving the common base in each position for the three groups of signals, there is no common base at several positions. This indicates that error has occurred in the sequence. In this example, the second value of Signal Y is changed from 4 to 3, and the sixth value of Signal X is changed from 3 to 4, then the signal will be changed to be the condition as shown in the table below.

TABLE 16

Sequencing Results after Correction

| | | | | | | | | | | | | | | | | | | | | |
|---|---|---|---|---|---|---|---|---|---|---|---|---|---|---|---|---|---|---|---|---|
| Signal x | K | K | M | M | | M | K | K | K | M | K | M | M | M | *M* | K | K | M | K | K | M |
| Signal y | Y | R | R | R | ~~R~~ | Y | Y | Y | Y | R | R | Y | Y | R | Y | R | R | R | R | Y | R |
| Signal z | W | S | W | W | | S | W | W | W | W | S | S | S | W | S | S | S | W | S | W | W |
| Common base | T | G | A | A | | C | T | T | T | A | G | C | C | A | C | G | G | A | G | T | A |

In the above table, changing the second value of Signal Y from 4 to 3 is expressed as R with strikethrough, and changing the sixth value of Signal X from 3 to 4 is expressed as adding an M (in underline and with italics). After the two modifications, there are common bases in all positions of the three groups of signals, and the sequence consisting of these common bases is the DNA sequence to be determined. This result indicates that by "coding" the DNA with degenerate indicators (e.g., M, K, R, Y, W, S, B, and D), the method can effectively detect error(s) in the sequencing process, while the method of "decoding" the sequence can effectively correct the error(s).

Example 8: Sequencing by the "2+2, Two Colors, Three Rounds" Method

In this example, a single-stranded DNA molecule whose sequence is to be determined is fixed onto a solid surface. The fixing methods may be chemical crosslinking, molecular adsorption, etc. The 3' end or 5' end of the DNA may be fixed to the surface. The DNA to be determined comprises a fragment with known sequence, which is complementary and capable of hybridizing to a sequencing primer. The sequence from the 3' end of the segment with known sequence to the 3' end of the DNA to be tested is the fragment whose sequence is to be determined. In this example, the sequence to be determined is 5'-TGAACTT-TAGCCACGGAGTA-3' (SEQ ID NO: 2).

A sequencing primer is first hybridized onto the segment with known sequence of the target DNA. dG4P and dT4P (each labeled with a fluorescent group emitting a different color, such as fluorescent group X and group Y), as well as corresponding reaction buffer solutions, enzymes and metal ions, are added to the reaction to cause the sequencing reaction which generates fluorescence signals. The signals are acquired by a CCD. The values of these fluorescence signals are recorded. The reaction is recorded as the first reaction.

The residual dG4P and dT4P in the reaction are then washed off. Then, dA4P and dC4P (each labeled with a fluorescent group emitting a different color, such as fluorescent group X and group Y) are added into the reaction system to cause the same sequencing reaction as mentioned above, and the fluorescence signal values are recorded. The reaction should be recorded as the second reaction.

The above process is repeated. dG4P and dT4P are added for the odd-number reactions, and dA4P and dC4P are added for the even-number reactions. The two types of dN4P added for each reaction are labeled with fluorescence groups in different colors. The value of a group of signals may be obtained: x=(1G+1T, 2A+1C, 0G+3T, 1A+0C, 1G+0T, 1A+2C, 2G+0T, 1A+0C, 1G+1T, 1A+0C).

The DNA nascent strand synthetized in the above sequencing reaction is then unwound and washed off, for example, using high temperature or strong hydrophilic substances (such as urea and formamide). The sequencing primer is then re-hybridized onto the template DNA. The two types of dN4P added for each reaction are labeled with fluorescence groups in different colors. The value of a group of signals may be obtained: y=(0C+1T, 3A+1G, 1C+3T, 1A+1G, 2C+0T, 1A+0G, 1C+0T, 1A+3G, 0C+1T, 1A+0G).

The DNA nascent strand synthetized in the above sequencing reaction is again unwound and washed off, for example, using high temperature or strong hydrophilic substances (such as urea and formamide). The sequencing primer is then re-hybridized onto the template DNA. dA4P and dT4P are added for the odd-number reactions, and dC4P and dG4P are added for the even-number reactions, and the two types of dN4P added for each reaction are labeled with fluorescence groups in different colors. A group of sequencing signals may be obtained: z=(0A+1T, 0C+1G, 2A+0T, 1C+0G, 1A+3T, 2C+1G, 1A+0T, 0C+1G, 1A+1T).

This method is called "2+2, double-color" sequencing method. The sequence information may be obtained from the sequencing data of any two rounds of sequencing. It may be considered as the orthogonal sequencing results.

The above sequencing signal values are then analyzed in view of the types of nucleotide bases represented by the signals to obtain the sequencing information. For each residue of the target DNA, the common base among the three signals are identified and listed below in the table below, as the nucleotide residue in that position.

TABLE 17

Sequencing Results before Correction

|   | 1 | 2 | 3 | 4 | 5 | 6 | 7 | 8 | 9 | 10 | 11 | 12 | 13 | 14 | 15 | 16 | 17 | 18 | 19 |
|---|---|---|---|---|---|---|---|---|---|----|----|----|----|----|----|----|----|----|----|
| x-A |   |   | A | A |   | A |   | A |   |    |    |    | A  |    | A  |    |    |    |    |
| x-C |   |   |   |   | C |   |   |   | C | C  |    |    |    |    |    |    |    |    |    |
| x-G |   | G |   |   |   |   | G |   |   |    | G  | G  |    | G  |    |    |    |    |    |
| x-T | T |   |   |   | T | T | T |   |   |    |    |    |    |    |    | T  |    |    |    |
| y-A |   |   | A | A A |   | A |   |   |   |    | A  |    |    |    | A  |    |    | A  |    |
| y-C |   |   |   |   | C |   |   |   | C | C  |    | C  |    |    |    |    |    |    |    |
| y-G |   | G |   |   |   |   | G |   |   |    | G  | G  |    | G  |    |    |    |    |    |
| y-T | T |   |   |   | T | T | T |   |   |    |    |    |    |    |    |    |    | T  |    |
| z-A |   |   | A | A |   | A |   |   |   |    | A  |    |    |    | A  |    |    | A  |    |
| z-C |   |   |   |   | C |   |   |   | C | C  |    | C  |    |    |    |    |    |    |    |
| z-G |   | G |   |   |   |   | G |   |   |    | G  | G  |    | G  |    |    |    |    |    |
| z-T | T |   |   |   | T | T | T |   |   |    |    |    |    |    |    |    |    | T  |    |
| Common base | T | G | A | A | ? | ? | T | T | ? | ?  | ?  | C  | ?  | ?  | ?  | ?  | ?  | ?  | ?  |

When solving the common base in each position for the three groups of signals, there is no common base at several positions, so it can be concluded that error occurs in the sequence. The second value (3A+1G) of Signal Y can be changed to (2A+1G), and the sixth value (1A+2C) of Signal X can be changed to (1A+3C), then the signals will be changed as shown in the table below.

TABLE 18

Sequencing Results after Correction

|   | 1 | 2 | 3 | 4 | 5 | 6 | 7 | 8 | 9 | 10 | 11 | 12 | 13 | 14 | 15 | 16 | 17 | 18 | 19 |
|---|---|---|---|---|---|---|---|---|---|----|----|----|----|----|----|----|----|----|----|
| x-A |   |   | A | A |   |   |   | A |   |    |    | A  |    |    |    | A  |    |    | A  |
| x-C |   |   |   |   | C |   |   |   |   | C  | C  |    | *C* |    |    |    |    |    |    |
| x-G |   | G |   |   |   |   |   |   | G |    |    |    |    | G  | G  |    | G  |    |    |
| x-T | T |   |   |   |   | T | T |   |   |    |    |    |    |    |    |    |    | T  |    |
| y-A |   |   | A | A ~~A~~ |   |   | A |   |    |    | A  |    |    |    | A  |    |    | A  |    |
| y-C |   |   |   |   | C |   |   |   |   | C  | C  |    | C  |    |    |    |    |    |    |
| y-G |   | G |   |   |   |   |   |   | G |    |    |    |    | G  | G  |    | G  |    |    |
| y-T | T |   |   |   |   | T | T |   |   |    |    |    |    |    |    |    |    | T  |    |
| z-A |   |   | A | A |   |   |   | A |   |    |    | A  |    |    |    | A  |    |    | A  |
| z-C |   |   |   |   | C |   |   |   |   | C  | C  |    | C  |    |    |    |    |    |    |
| z-G |   | G |   |   |   |   |   |   | G |    |    |    |    | G  | G  |    | G  |    |    |
| z-T | T |   |   |   |   | T | T |   |   |    |    |    |    |    |    |    |    | T  |    |
| Common base | T | G | A | A | C | T | T | A | G | C | C | A | C | G | G | A | G | T | A |

In the above table, "the second value (3A+1G) of signal y is changed to (2A+1G)" is expressed as A with strikeout, and "the sixth value (1A+2C) of signal x is changed to (1A+3C)" is expressed as adding a C (in underline and with italics). After the two modifications, there are common bases in all positions of the three groups of signals, and the sequence consisting of these common bases is the DNA sequence to be determined. This result indicates that by "coding" the DNA with degenerate indicators (e.g., M, K, R, Y, W, S, B, and D), the method can effectively detect error(s) in the sequencing process, while the method of "decoding" the sequence can effectively correct the error(s).

Example 9: Sequencing by the "2+2, Two Colors, Two Rounds" Method

In this example, a single-stranded DNA molecule whose sequence is to be determined is fixed onto a solid surface. The fixing methods may be chemical crosslinking, molecular adsorption, etc. The 3' end or 5' end of the DNA may be fixed to the surface. The DNA to be determined comprises a fragment with known sequence, which is complementary and capable of hybridizing to a sequencing primer. The sequence from the 3' end of the segment with known sequence to the 3' end of the DNA to be tested is the fragment whose sequence is to be determined. In this example, the sequence to be determined is 5'-TGAACTT-TAGCCACGGAGTA-3' (SEQ ID NO: 2).

A sequencing primer is first hybridized onto the segment with known sequence of the target DNA. dG4P and dT4P (each labeled with a fluorescent group emitting a different color, such as fluorescent group X and group Y), as well as corresponding reaction buffer solutions, enzymes and metal ions, are added to the reaction to cause the sequencing reaction which generates fluorescence signals. The signals are acquired by a CCD. The values of these fluorescence signals are recorded. The reaction is recorded as the first reaction.

The residual dG4P and dT4P in the reaction are then washed off. Then, dA4P and dC4P (each labeled with a fluorescent group emitting a different color, such as fluorescent group X and group Y) are added into the reaction system to cause the same sequencing reaction as mentioned above, and the fluorescence signal values are recorded. The reaction should be recorded as the second reaction.

The above process is repeated. dG4P and dT4P are added for the odd-number reactions, and dA4P and dC4P are added for the even-number reactions. The two types of dN4P added for each reaction are labeled with fluorescence groups in different colors. The value of a group of signals may be obtained: x=(1G+1T, 2A+1C, 0G+3T, 1A+0C, 1G+0T, 1A+2C, 2G+0T, 1A+0C, 1G+1T, 1A+0C).

The DNA nascent strand synthetized in the above sequencing reaction is then unwound and washed off, for example, using high temperature or strong hydrophilic substances (such as urea and formamide). The sequencing primer is then re-hybridized onto the template DNA. The two types of dN4P added for each reaction are labeled with fluorescence groups in different colors. The value of a group of signals may be obtained: y=(0C+1T, 3A+1G, 1C+3T, 1A+1G, 2C+0T, 1A+0G, 1C+0T, 1A+3G, 0C+1T, 1A+0G).

The above sequencing signal values are then analyzed in view of the types of nucleotide bases represented by the signals to obtain the sequencing information. For each residue of the target DNA, the common base among the three signals are identified and listed below in the table below, as the nucleotide residue in that position.

TABLE 19

Sequencing Results before Correction

| x-A |   |   | A | A |   |   |   | A |   |   | A |   |   | A |   | A |   |   |   |
|---|---|---|---|---|---|---|---|---|---|---|---|---|---|---|---|---|---|---|---|
| x-C |   |   |   |   | C |   |   |   | C | C |   |   |   |   |   |   |   |   |   |
| x-G |   | G |   |   |   |   |   | G |   |   |   | G | G |   | G |   |   |   |   |
| x-T | T |   |   |   |   | T | T | T |   |   |   |   |   |   |   |   | T |   |   |
| y-A |   |   | A | A | A |   |   | A |   |   | A |   | A |   |   | A |   |   | A |
| y-C |   |   |   |   | C |   |   |   | C | C | C |   |   |   |   |   |   |   |   |
| y-G |   | G |   |   |   |   |   | G |   |   |   | G | G |   | G |   |   |   |   |
| y-T | T |   |   |   |   | T | T | T |   |   |   |   |   |   |   |   | T |   |   |
| Common base | T | G | A | A | ? | ? | T | T | ? | ? | ? | C | ? | ? | ? | ? | ? | ? | ? | ? |

When solving the common base in each position for the two groups of signals, there is no common base in several positions, so it can be concluded that error occurs in the sequence. The second value (3A+1G) of Signal Y can be changed to (2A+1G), and the sixth value (1A+2C) of Signal X can be changed to (1A+3C), and then the signal will be changed as shown in the table below.

TABLE 20

Sequencing Results after Correction

| x-A |   |   | A | A |   |   |   | A |   |   | A |   |   | A |   | A |   |   |   |
|---|---|---|---|---|---|---|---|---|---|---|---|---|---|---|---|---|---|---|---|
| x-C |   |   |   |   | C |   |   |   | C | C | *C* |   |   |   |   |   |   |   |   |
| x-G |   | G |   |   |   |   |   | G |   |   |   | G | G |   | G |   |   |   |   |
| x-T | T |   |   |   |   | T | T | T |   |   |   |   |   |   |   |   | T |   |   |
| y-A |   |   | A | A̶ |   |   |   | A |   |   | A |   | A |   |   | A |   |   | A |
| y-C |   |   |   |   | C |   |   |   | C | C | C |   |   |   |   |   |   |   |   |
| y-G |   | G |   |   |   |   |   | G |   |   |   | G | G |   | G |   |   |   |   |
| y-T | T |   |   |   |   | T | T | T |   |   |   |   |   |   |   |   | T |   |   |
| Common base | T | G | A | A |   | C | T | T | T | A | G | C | C | A | C | G | G | A | G | T | A |

In the above table, "the second value (3A+1G) of signal Y is changed to (2A+1G)" is expressed as A with strikeout, and "the sixth value (1A+2C) of signal x is changed to (1A+3C)" is expressed as adding a C (in underline and with italics). After the two modifications, there are common bases in all positions of the three groups of signals, and the sequence consisting of these common bases is the DNA sequence to be determined. This result indicates that by "coding" the DNA with degenerate indicators (e.g., M, K, R, Y, W, S, B, and D), the method can effectively detect error(s) in the sequencing process, while the method of "decoding" the sequence can effectively correct the error(s).

Example 10: Sequencing by the "1+3, Monochrome" Method

In this example, a single-stranded DNA molecule whose sequence is to be determined is fixed onto a solid surface. The fixing methods may be chemical crosslinking, molecular adsorption, etc. The 3' end or 5' end of the DNA may be fixed to the surface. The DNA to be determined comprises a fragment with known sequence, which is complementary and capable of hybridizing to a sequencing primer. The sequence from the 3' end of the segment with known sequence to the 3' end of the DNA to be tested is the fragment whose sequence is to be determined. In this example, the sequence to be determined is 5'-TGAACTT-TAGCCACGGAGTA-3' (SEQ ID NO: 2).

A sequencing primer is first hybridized onto the segment with known sequence of the target DNA. dC4P, dG4P, and dT4P, as well as corresponding reaction buffer solutions, enzymes and metal ions, are added to the reaction to cause the sequencing reaction which generates fluorescence signals. The signals are acquired by a CCD. The values of these fluorescence signals are recorded. The reaction is recorded as the first reaction.

The residual dC4P, dG4P, and dT4P in the reaction are then washed off. Then, dA4P is added into the reaction system to cause the same sequencing reaction as mentioned above, and the fluorescence signal values are recorded. The reaction should be recorded as the second reaction.

The above process is repeated. dC4P, dG4P, and dT4P are added for the odd-number reactions, and dA4P is added for the even-number reactions. The value of a group of signals is obtained: x=(2, 2, 4, 1, 3, 1, 3, 1, 2, 1).

The DNA nascent strand synthetized in the above sequencing reaction is then unwound and washed off, for example, using high temperature or strong hydrophilic substances (such as urea and formamide). The sequencing primer is then re-hybridized onto the template DNA. dA4P, dG4P, and dT4P are added for the odd-number reactions, and dC4P is added for the even-number reactions. The value of a group of signals is obtained: y=(4, 1, 6, 2, 1, 1, 6).

The DNA nascent strand synthetized in the above sequencing reaction is then unwound and washed off, for example, using high temperature or strong hydrophilic substances (such as urea and formamide). The sequencing primer is then re-hybridized onto the template DNA. dA4P, dC4P, and dT4P are added for the odd-number reactions, and dC4P is added for the even-number reactions. The value of a group of signals is obtained: z=(1, 1, 7, 1, 4, 2, 1, 1, 2).

The DNA nascent strand synthetized in the above sequencing reaction is then unwound and washed off, for example, using high temperature or strong hydrophilic substances (such as urea and formamide). The sequencing primer is then re-hybridized onto the template DNA. dT4P is added for the odd-number reactions, and dA4P, dC4P, and dG4P are added for the even-number reactions. The value of a group of signals is obtained: w=(1, 4, 3, 9, 1, 1).

The above sequencing signal values are then analyzed in view of the types of nucleotide bases represented by the signals to obtain the sequencing information. For each residue of the target DNA, the common base among the three signals are identified and listed below in the table below, as the nucleotide residue in that position.

TABLE 21

Sequencing Results before Correction

| Signal x | B | B | A | A | B | B | B | B | A | B | B | B | A | B | B | B | A | B | B | A |
|---|---|---|---|---|---|---|---|---|---|---|---|---|---|---|---|---|---|---|---|---|
| Signal y | D | D | D | D | C | D | D | D | D | D | D | C | C | D | C | D | D | D | D | D |
| Signal z | H | G | H | H | H | H | H | H | H | G | H | H | H | G | G | H | G | H | H |   |
| Signal w | T | V | V | V | V | T | T | T | V | V | V | V | V | V | V | V | V | T | V |   |
| Common base | T | G | A | A | C | T | T | T | A | G | ? | C | ? | ? | ? | G | A | ? | ? | ? | ? |

When solving the common base in each position for the two groups of signals, there is no common base in several positions, so it can be concluded that error occurs in the sequence. The third value of Signal Y can be changed from 6 to 5, and the fourth value of Signal W can be changed from 9 to 10, and then the signal will be changed as shown in the table below.

TABLE 22

Sequencing Results after Correction

| Signal x | B | B | A | A | B | B | B | B | A | B |   | B | B | A | B | B | B | A | B | B | A |
|---|---|---|---|---|---|---|---|---|---|---|---|---|---|---|---|---|---|---|---|---|---|
| Signal y | D | D | D | D | C | D | D | D | D | D | ~~D~~ | C | C | D | C | D | D | D | D | D |
| Signal z | H | G | H | H | H | H | H | H | H | G |   | H | H | H | H | G | G | H | G | H | H |
| Signal w | T | V | V | V | V | T | T | T | V | V |   | V | V | V | V | V | V | V | *V̲* | T | V |
| Common base | T | G | A | A | C | T | T | T | A | G |   | C | C | A | C | G | G | A | G̅ | T | A |

In the above table, "the third value 6 of signal y is changed to 5" is expressed as D with strikeout; and "the fourth value 9 of signal w is changed to 10" is expressed as adding a V (in underline and with italics). After the two modifications, there are common bases in all positions of the four groups of signals, and the sequence consisting of these common bases is the target DNA sequence to be determined. This result indicates that by "coding" the DNA with degenerate indicators (e.g., M, K, R, Y, W, S, B, and D), the method can effectively detect error(s) in the sequencing process, while the method of "decoding" the sequence can effectively correct the error(s).

Example 11: A Method of Detecting and/or Correcting Sequencing Errors

Section 1: Substrate Synthesis and Spectral Properties.

General Aspects: All Anhydrous solvents were freshly distilled using general procedure (Na or $CaH_2$). Reagents were used as received from commercial suppliers unless otherwise stated. Air- and/or moisture-sensitive experiments were carried out under an atmosphere of Argon. Mass spectral analyses were carried out with Bruker APEX IV Mass Spectrometer and AB Sciex MALDI-TOF 5800 Spectrometer. Reverse phase HPLC was carried out on a Shimadzu LC-20A HPLC system. Samples were dissolved in water and analyzed by analytical Inertsil ODS-3 C18 column (250×4.6 mm, 5 μm) at 1 mL/min flow rate, with a gradient of B ($CH_3CN$) in A (50 mM TEAA pH 7.3) (0-20% of B over 15 min, 20-30% of B over 10 min).

1.1 Synthesis of Terminal Phosphate-Labeled Fluorogenic Nucleotides (TPLFNs)

Figure 5A:
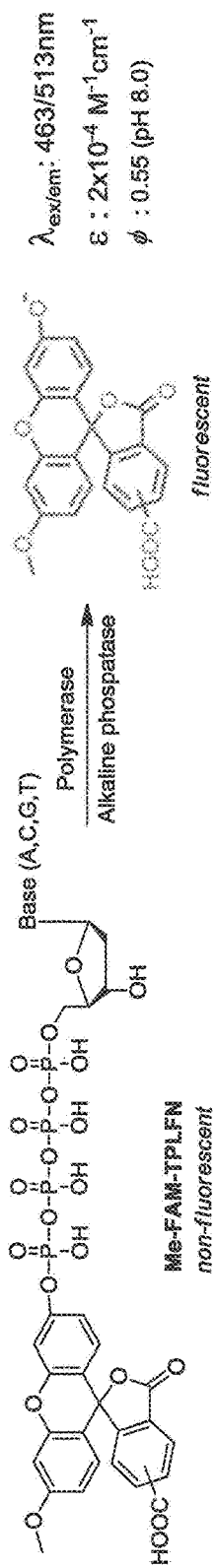
FIGS. 5A and B show improvement the fluorogenic performance of TPLFNs by changing the fluorophore structure.
Figure 5B:
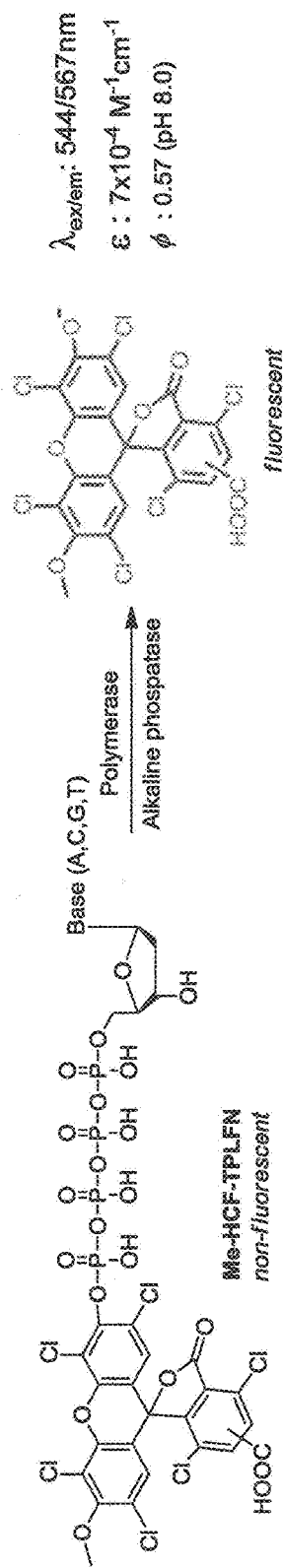
FIG. 5B shows previously developed Me-HCF-labeled nucleotides.
Figure 5C:
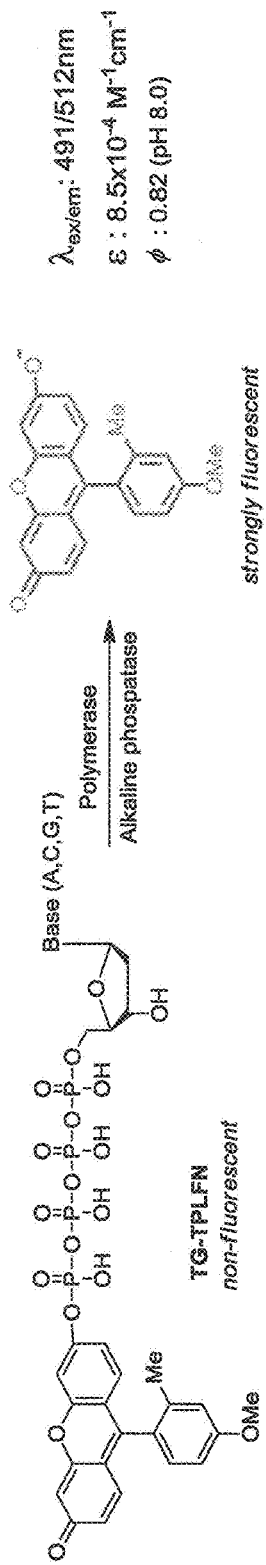
FIG. 5C shows TG-labeled nucleotides in this invention.

FIGS. 5A-C show improving the fluorogenic performance of TPLFNs by changing the fluorophore structure. FIG. 5A shows previously developed Me-FAM-labeled nucleotides. FIG. 5B shows previously developed Me-HCF-labeled nucleotides. FIG. 5C shows TG-labeled nucleotides in this example.

For fluorogenic sequencing purpose, fluorophores used for labeling the terminal phosphate of nucleotides are playing the key roles. In one aspect, the phosphorylated fluorophore must be quenched thoroughly, meaning no fluorescence emission is detected at certain excitation wavelength. Once the fluorophore is release, however, strong fluorescence emission intensity is required for sufficient signal detection. Following this principal, Me-FAM was selected as the labeling dye molecules in a previous report (FIG. 5A, see Sims, P. A.; Greenleaf, W. J.; Duan, H.; Xie, X. "Fluorogenic Pyrosequencing in PDMS Microreactors" Nature Method 2011, 8, 575-580). Later on, the chlorinated form of Me-FAM, named Me-HCF, was developed with a dramatic bathochromic shift of the excitation and emission wavelength, which is eligible for multi-color sequencing purpose (FIG. 5B, Chen, Z.; Duan, H.; Qiao, S.; Zhou, W.; Qiu, H.; Kang, L.; Xie, X.; Huang, Y. Fluorogenic Sequencing using Halogen-Fluorescein Labeled Nucleotides. Chembiochem, 2015, DOI: 10.1002/cbic.201500117). Despite the successful applications, the Me-FAM and Me-HCF (derived from FAM and HCF 3'-OH methylation) still have problems in their fluorescence properties, as seen from the parameters listed in FIGS. 5A-C. The 3'-OH methylation (or other protecting groups), which is prerequisite for generating fluorogenic substrate, not only broadened the absorption and emission spectrum, but also greatly decreased the extinction coefficient and quantum yield, especially for Me-FAM. Therefor developing fluorophores with better fluorogenic performance is still highly desirable.

TG (Tokyo Green) was developed by Nagano et al. Y. Urano, M. Kamiya, K. Kanda, T. Ueno, K. Hirose, T. Nagano, Evolution of fluorescein as a platform for finely tunable fluorescence probes, J. Am. Chem. Soc., 2005, 127, 4888-4894. TG has been shown to possess excellent fluorescence properties. The unique structure of TG comparing with 5(6)-FAM is that a methyl group was used instead of carboxyl group in the benzene moiety to keep the benzene ring and the fluorophore orthogonal to each other. Moreover, they also proved that the phosphorylated TG has outstanding fluorogenic properties. Another convenient aspect is that the only phenol group on TG structure will facilitate the TPLFNs synthesis, since no methylation is needed, comparing with the two phenol groups of 5(6)-FAM or HCF. The absence of this protective methyl group not only makes TPLFN's synthesis easier, but also keeps the original high extinction co-efficient and high quantum yield properties once the TG fluorophore was released by enzyme digestion, giving much higher fluorescence/background contrast. The detail synthesis procedure is described as below:

(I) Preparation of TG-monophosphate (S2)

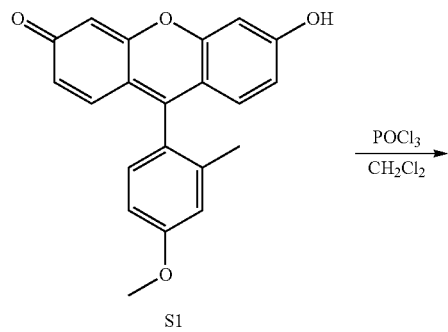

S1

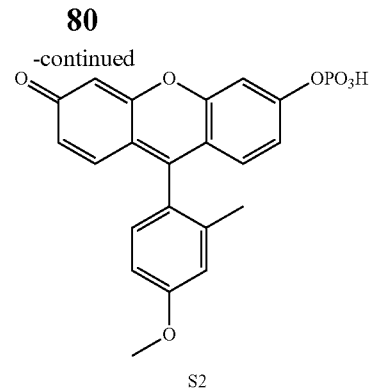

S2

Tokyo-green S1 was synthesized based on the reported procedure [Y. Urano, M. Kamiya, K. Kanda, T. Ueno, K. Hirose, T. Nagano, Evolution of fluorescein as a platform for finely tunable fluorescence probes, J. Am. Chem. Soc., 2005, 127, 4888-4894].

S1 (332 mg, 1.00 mmol) was suspended into 15 mL anhydrous $CH_2Cl_2$ in a flame-dried flask under Ar. To this solution Proton Sponge (759 mg, 3.50 mmol) was added with stirring. After 10 min the mixture was cooled to −10° C. and Phosphorous(V) Oxychloride (275 μL, 3.00 mmol) was added. The reaction was kept on at the same temperature for 30 min. Then TEAA buffer (20 mL of 1 M solution) was added to quench the reaction and to hydrolyze the phosphoryl chloride intermediate for 1h at 0° C. After that, the two phases were separated and the aqueous solution was filtered and concentrated in vacuum for further purification by reverse phase flash LC system. Conditions: AQ C-18 column (Agela 40 g) using 0-50% acetonitrile in 50 mM triethylammonium acetate buffer (PH 7.4), flow rate 20 ml/min. Fractions containing pure product were concentrated and coevaporated with anhydrous DMF (2 mL) twice and then dissolved in certain amount of anhydrous DMF, the resulting monophosphate S2 (100 mM DMF solution) was kept in a −20° C. freezer for further usage. MS (ESI): Calcd for $C_{21}H_{15}O_7P$ (M−H), 411.06. Found, m/z 411.21.

(II). Synthesis of dN4P-δ-TG (TPLFN)

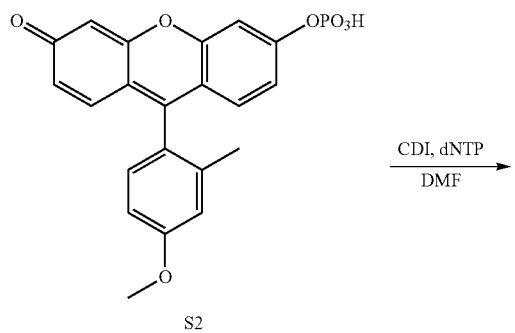

S2

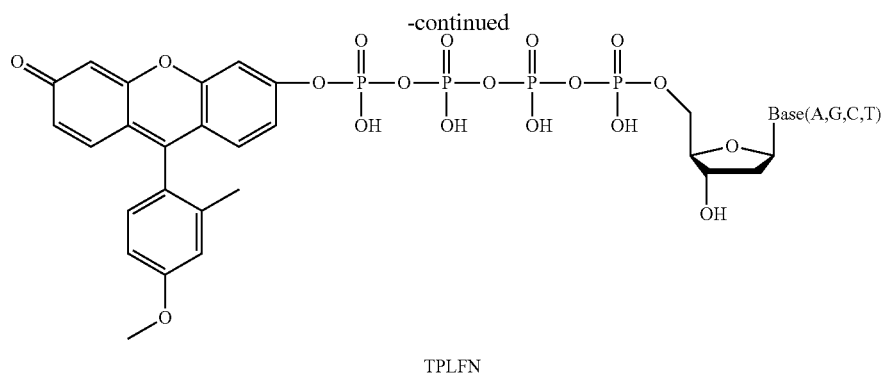

Figure 6:
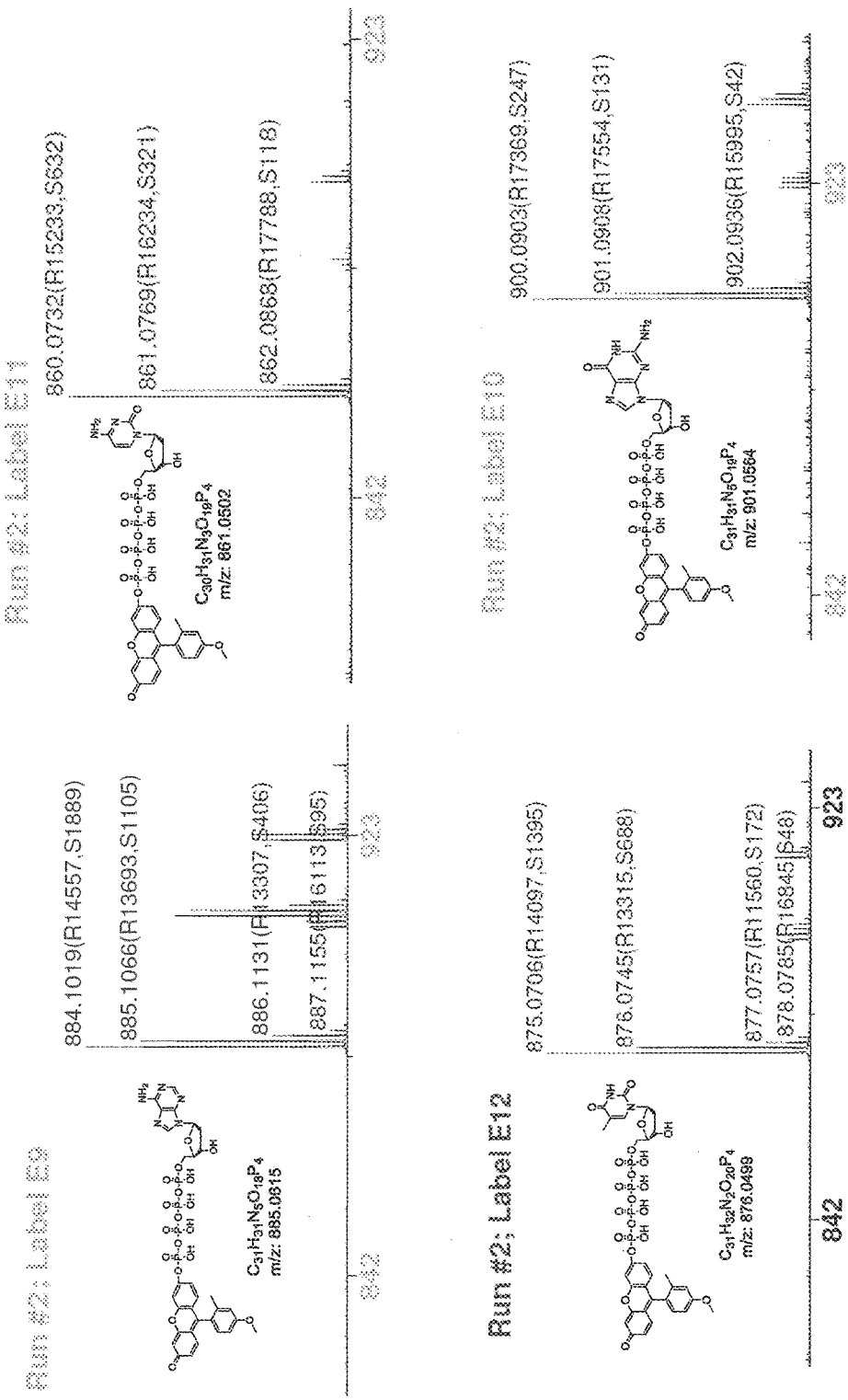
FIG. 6 shows MALDI-TOF mass spectrum of the purified TPLFNs.

TPLFN 1) dA4P-δ-TG: 2'-deoxyadenosine-5'-triphosphate (dATP) disodium salt (12.5 uL of 100 mM solution, 12.5 umol) was converted to the tributylammonium salt by treatment with ion-exchange resin (BioRad AG-50W-XB) and tributylamine. After removal of water on rotary evaporator by oil pump, the obtained tributylammonium salt was coevaporated with anhydrous DMF (1 mL) twice and then dissolved in 0.5 mL anhydrous DMF under Ar. To the solution, carbonyldiimidazole (CDI, 10.1 mg, 63 μmol) was added, and the mixture was stirred at room temperature for 12 h. After that, MeOH (3.2 μL) was added, and the solution was stirred for 0.5 h. Then TG-monophosphate tributylammonium salt S2 (25 μmol) DMF solution (0.25 ml) from the previous step was transferred into the reaction by syringe, and $MgBr_2$ (25 mg, 100 μmol) in DMF (0.5 mL) was added subsequently. The mixture was stirred for 30 h at room temperature. Then, the reaction mixture was concentrated by oil pump, diluted with water, and purified on C18 reverse-phase HPLC system (Shimadzu) using preparative sepax Amethyst C18-H (21.2×150 mm) at 5 mL/min flow rate, with a gradient of B ($CH_3CN$) in A (50 mM TEAA pH 7.3) (0-20% of B over 15 min, 20-30% of B over 10 min, 30-50% of B over 10 min). The desired fraction was collected and concentrated using a Hi-Trap Q-HP 5 mL anion exchange column (GE Healthcare). The collected solution containing the desired product can be purified again by HPLC using the same eluting conditions and concentrated by Hi-Trap Q-HP column. The product solution was stored at −20° C. for further usage. MS (MALDI-TOF): Calcd for $C_{31}H_{31}N_5O_{18}P_4$, 895.0615. Found, m/z 884.1019 (M−H). dC4P-δ-TG, dT4P-δ-TG, dG4P-δ-TG were synthesized following the same procedure as dA4P-δ-TG. dC4P-δ-TG: MS (MALDI-TOF): Calcd for $C_{30}H_{31}N_3O_{19}P4$, 861.0502. Found, m/z 860.0732 (M−H). dT4P-δ-TG: MS (MALDI-TOF): Calcd for $C_{31}H_{32}N_2O_{20}P4$, 876.0499. Found, m/z 875.0706 (M−H). dG4P-δ-TG: MS (MALDI-TOF): Calcd for $C_{31}H_{31}N_5O_{19}P4$, 901.0564. Found, m/z 900.0903 (M−H). FIG. 6 shows MALDI-TOF mass spectrum of the purified TPLFNs.

1.2. Spectral Properties of Fluorophores and TPLFNs.

Figure 7:
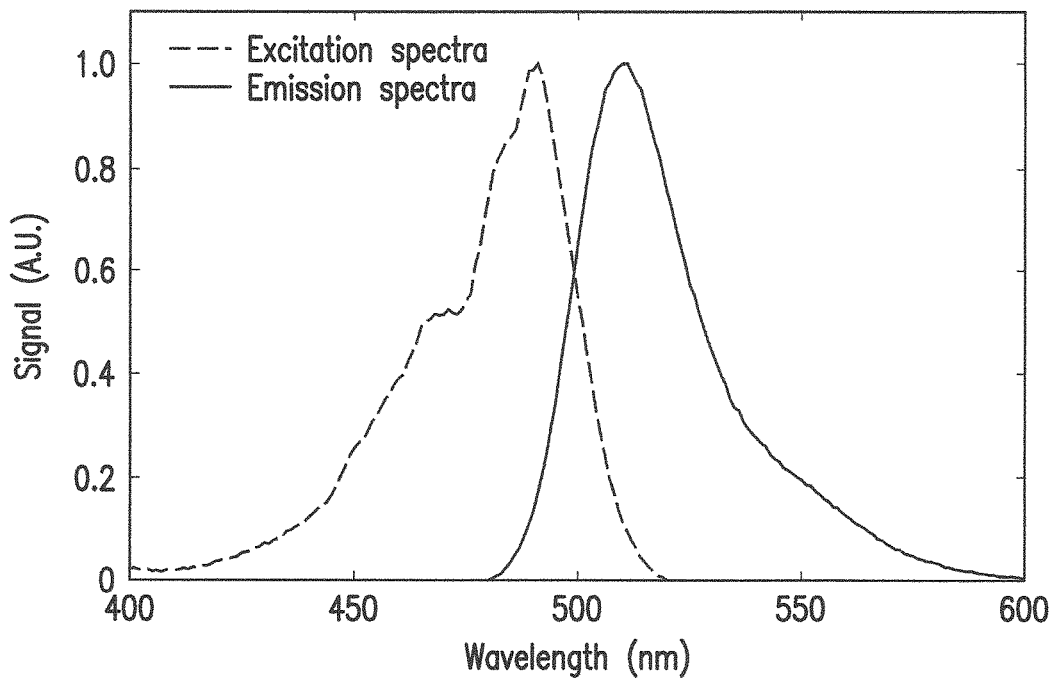
FIG. 7 shows the excitation and emission spectrum of TG (Tokyo Green).
Figure 8:
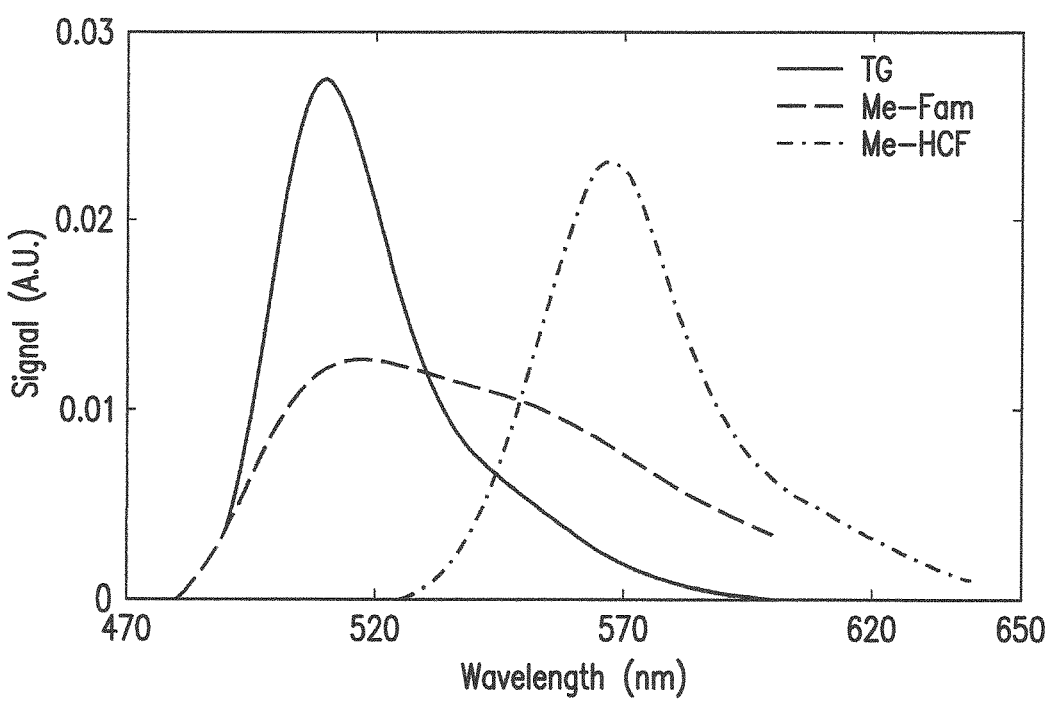
FIG. 8 shows the emission spectrum of TG (Tokyo Green), Me-FAM and Me-HCF at same condition (2 µM, pH 8.3, TE buffer, calculated with Area Normalization).

The excitation/emission spectrum of TG (51) is shown in FIG. 7. Although Me-FAM has similar maximum emission wavelength as TG, the extinction coefficient and quantum yield of Me-FAM are much lower (FIG. 8). At the same time, the broad emission spectrum of Me-FAM greatly overlapped with other fluorophores like Me-HCF, which makes it inapplicable for multi-color sequencing application in future. Instead, the strong fluorescence and narrower spectrum of TG will tackle the problem more easily. FIG. 7 shows the excitation and emission spectrum of TG (Tokyo Green). FIG. 8 shows emission spectrum of TG (Tokyo Green), Me-FAM and Me-HCF at same condition (2 μM, pH 8.3, TE buffer, calculated with Area Normalization). Optical Properties about TG, Me-FAM and Me-HCF are listed in the table below (also in FIG. 5).

TABLE 23

| | Excitation max(nm) | Emission max (nm) | Quantum Yield(%) | Extinction coefficient |
|---|---|---|---|---|
| TG | 490 | 513 | 82% | $8 \times 10^4$ |
| Me-FAM | 463 | 514 | 55% | $2 \times 10^4$ |
| Me-HCF | 544 | 567 | 0.57 | $7 \times 10^4$ |

Figure 9:
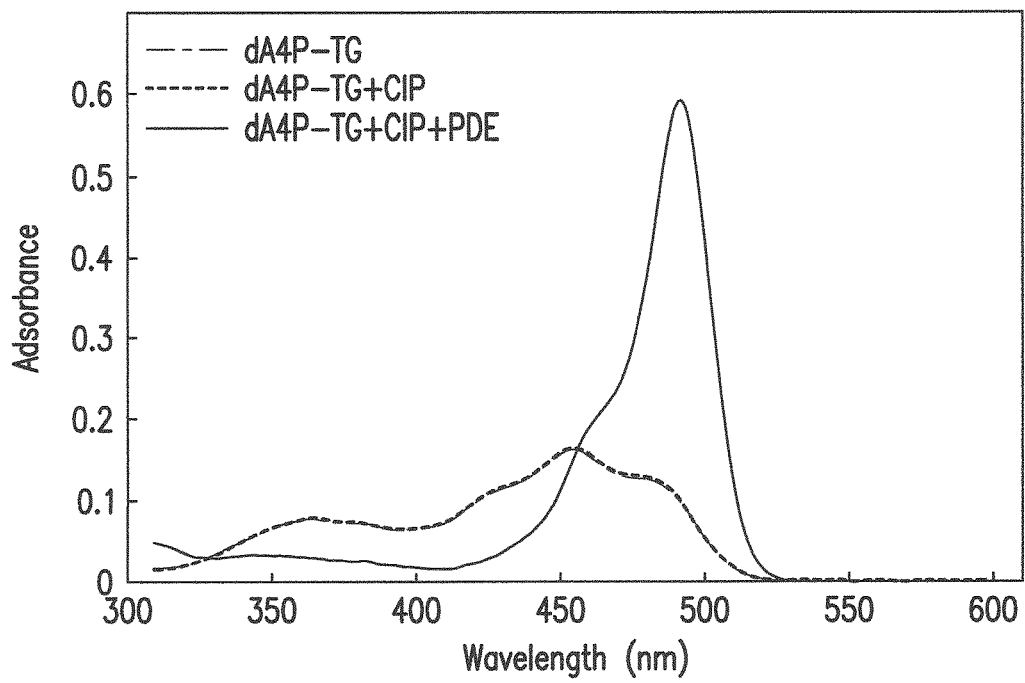
FIG. 9 shows the absorption spectrum of TPLFN (TG-dA4P) before and after enzyme digestion.
Figure 10:
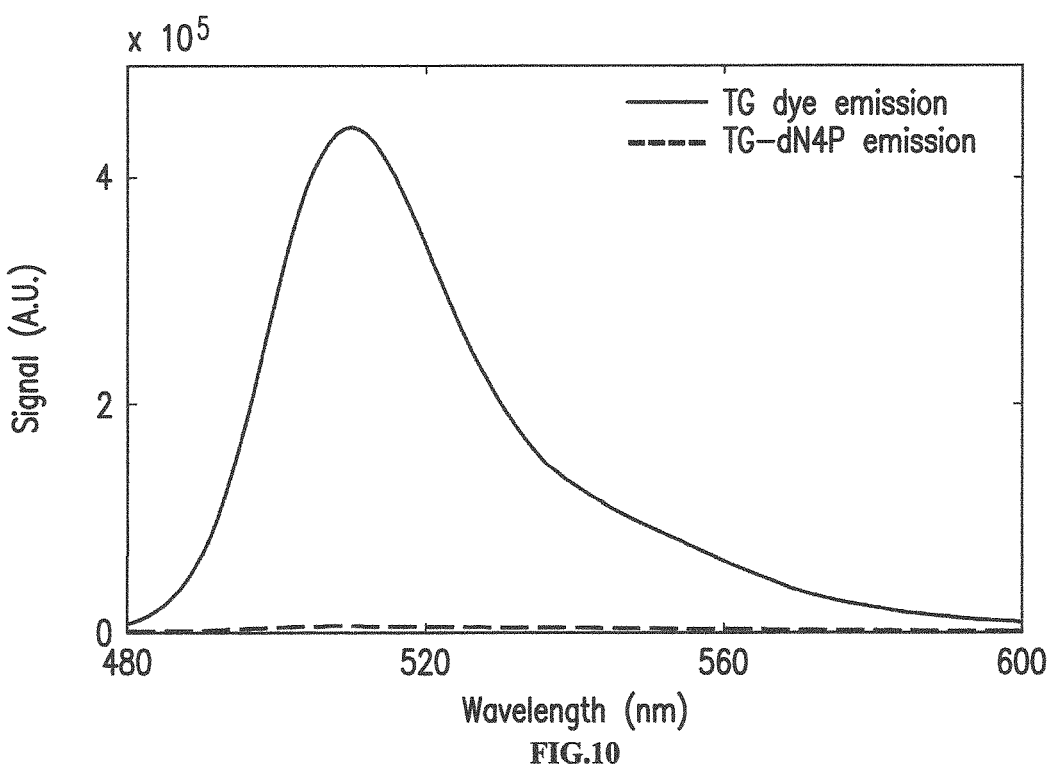
FIG. 10 shows the emission spectrum of TPLFN (TG-dA4P) before and after enzyme digestion.

In the sequencing method, the substrates (TPLFNs) are required to be non-fluorescent before incorporated by DNA polymerase. After primer extension by polymerase, the triphosphate with the dye label still attached on it was released, and the fluorescent products were generated subsequently through hydrolysis of triphosphate in the presence of phosphatase. FIG. 9 and FIG. 10 showed the difference of absorption and emission between TPLFN TG-dA4P and the released TG fluorophore. As shown in FIG. 9, TG-dA4P would not be digested by CIP (calf intestinal alkaline phosphatase) alone. However, once the polyphosphate chain of TG-dA4P was broken down by either polymerase or PDE (phosphodiesterase), the remaining triphosphate chain labeled with TG will be rapidly digested, giving free TG molecules with restored strong absorption and emission intensity.

The above spectrums were recorded in conditions as below:

First, the spectrums of TG-dA4P were measured at room temperature. For emission measurement: set excitation wavelength at 460 nm, scan 480 to 600 nm for emission; for absorption measurement: scan 310 to 550 nm. Then CIP and PDE were added and spectrum was recorded sequentially at the same condition.

The stability of TPLFNs substrates under certain aqueous conditions is also a concern, since spontaneous hydrolysis of TPLFNs will increase fluorescence background during sequencing reaction, which will interfere with the desired signal and decrease sequencing accuracy. Fortunately the hydrolyzing rate of the TPLFNs substrates is extremely low even measured at 65° C., about 2 ppm(substrate)/s, which is negligible comparing with the generated signal by polymerase incorporation. In spite of this, in some aspects, it is preferable to store the substrates solution in a 4° C. chilled holder during sequencing process and in −20° C. refrigerator for longtime storage.

Section 2: Polymerase Kinetic Studies.

Figure 11:
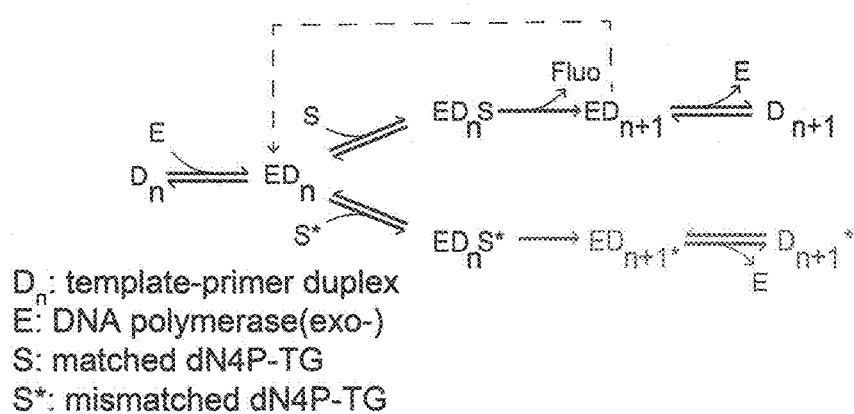
FIG. 11 shows a kinetic mode.

The polymerase kinetic assay was performed regarding to properties such as TPLFN incorporation/mis-incorporation rate, homopolymer linearity test and temperature dependence by using flourometer. FIG. 11 illustrated the proposed kinetic pathway of this sequencing-by-synthesis process, where S is the matched substrates (TPLFNs) and S' is mismatch substrates; E is Enzyme (polymerase) and DN is primer/template pair.

Although TPLFN and template are all involved as reaction substrates, the system can be simplified to a single-substrate reaction process, since the concentration of one of the substrates, TPLFNs, will stay nearly constant for its large excessive amount comparing to primer/template. Thus makes the analysis of the process much easier. As shown in FIG. 11, there are three steps in the polymerase catalyzed reactions, including: a) binding of DNA polymerase to the primer/template; b) incorporating the complementary nucleotide (TPLFN); c) elongation of the nucleotide along the template. By changing the reaction conditions such as primer/template concentration, matched or mismatched type of TPLFN and temperature, the kinetic properties of polymerase used for the sequencing process can be evaluated.

Figure 12:
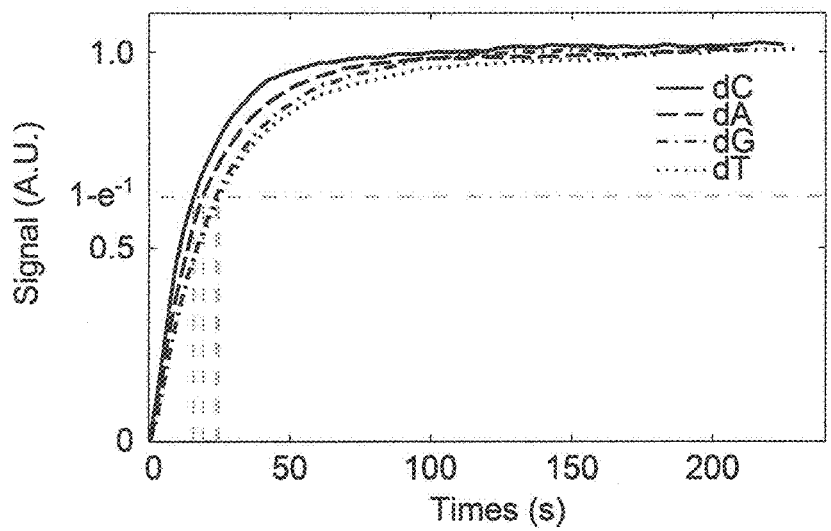
FIG. 12 shows reaction rate differences between four substrates.

FIG. 12 shows the polymerase (Bst) incorporation rate differences between TPLFNs. In order to test and compare the reaction rate, all the four TPLFNs (TG-dA4P, TG-dG4P, TG-dC4P, TG-dT4P) were adjusted into the same concentration (2.0 µM). Reactions were conducted at 65° C. with Bst (120 nM), single-base extension primer/template (T, C, G, A relative to the four TPLFNs), CIP (0.01 U) and pH 8.3 buffer, triggered by Mn(II) (1 mM). Typically, the labeled polyphosphate moiety, which was released by Bst mediated elongation, need to be hydrolyzed by CIP in order to generate fluorescent dye molecules. The excessive amount of CIP in the reaction was tested and verified that hydrolysis rate is ultrafast and will not become the rate-determining step to affect the Bst reaction rate observation. In FIG. 12, the observed Bst incorporation rates of the four labeled nucleotide were in the order of TG-dC4P>TG-dA4P>TG-dG4P>TG-dT4P.

The four curves in FIG. 12 can be fit into function in the table below. The fitting results indicated that the reaction system could be treated as first-order reaction regarding to primer/template concentration. However, other than running the reactions in cuvette on fluorometer, the actual sequencing reactions on chip will be slightly different, because all the primer/templates were grafted on the surface of the chip. In order to keep each reaction cycle with different TPLFNs being finished in same time scale, the reaction rate of the four TPLFNs can be adjusted into same level by increasing the concentration of slow-going TPLFNs.

TABLE 24

| Substrates | Fitting function | R² |
|---|---|---|
| dA4P | $9.319 \times 10^5(1-e^{-0.05242t})$ | 0.9976 |
| dT4P | $8.698 \times 10^5(1-e^{-0.02616t})$ | 0.9994 |
| dC4P | $8.977 \times 10^5(1-e^{-0.06189t})$ | 0.9959 |
| dG4P | $8.839 \times 10^5(1-e^{-0.0405t})$ | 0.9961 |

In 2+2 sequencing, two different nucleotides are together added into the reaction mixture, for example "M" means dA4P and dC4P are added in same cycle and "K" means dG4P and dT4P are added in same cycle. As mentioned above in FIG. 11, one of the nucleotides added in may serve as S*, which does not extend the current template nucleoside but competes to bind Bst with complement substrate S, so it is possible that S* may decelerate the extension rate of S. Therefore substrates competition was evaluated by competition experiment.

In this experiment, 100 nM template-primer consisting only one paired nucleoside to be sequenced at 3'-end of template, 2 µM complement and mismatch substrates each, and excessive Bst and CIP enzyme were mixed together. The reaction was done under 65° C., pH 8.3 and triggered by 1 mM Mn(II).

Figure 13:
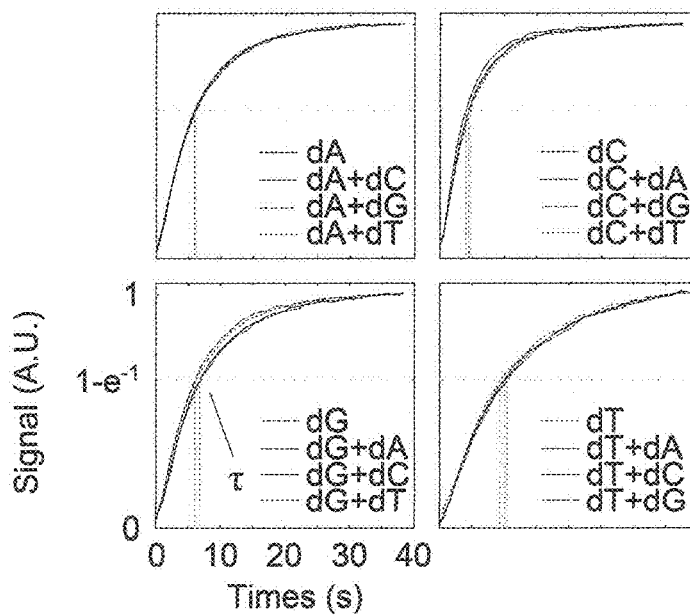
FIG. 13 shows substrates competition.

The results show that the reaction rate has no apparent decrease when substrates are added in with same concentration (see FIG. 13). This may be interpreted as below. Bst enzyme is a polymerase I from *Bacillus stearothermophilus*. When Bst binds primer-template with $K_d$ at 5 nM, and binds matched nucleotides with $K_d$ at 5 µM, while mismatched nucleotides with $K_d$ at 5 UM to 10 µM. See e.g., Kornberg and Baker, DNA replication, $2^{nd}$ edition, 2005, University Science Books, page 126. Considering 1) and 2) steps in FIG. 11 as two thermodynamic equilibriums with 5 nM and 30 µM (arithmetic mean) dissociation constant ($K_d$) respectively. if no substrate competition occurs, the two equilibriums can be added into one, and the new equilibrium's $K_d$ equals 150(nM)(µM).

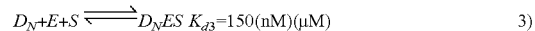

Thus, concentrations of $D_NES$ and $D_NE$ are 25.6 nm and 63.9 nm, respectively. If competition occurs, concentrations of $D_NES$ is 22.6 nM, $D_NES^*$ is 11.3 nM, and $D_NE$ is 56.5 nM. Calculation shows that with or without competition, concentration of $D_NES$ only changes slightly, therefore reaction rate too has slight differences.

In summary in 2+2 sequencing, reaction rates for four substrates are acceptably different but can be adjusted equal by changing substrates concentration. And competition between substrates doesn't decrease reaction rate apparently. Thus in the present methods reaction rate in each cycle can be set in a certain value and be adjusted to optimized lead and lag value.

The 100 nM single-base extension primer/template poly-G was equally divided into two PCR tubes, both of which were added mis-matched nucleotide TG-dG4P (2 µM), together with excessive Bst and CIP. After the two mixtures were bubbled with argon for 2 min, the caped tubes were incubated in different temperature, one in 4° C. and the other one in 65° C. After 1 hour, 2 µM matched nucleotide, TG-dC4P, was added into both tubes and the extension reactions were all measured by fluorometer at 65° C. If mis-incorporation occurred during the incubation process, one might expect to observe a different signal level from the two tubes, with the tube incubated in 65° C. lower than the one in 4° C. because mis-incorporation rate will be higher in 65° C. However, results in FIG. 13 showed that extension signals in both tubes were almost the same, suggesting that mis-incorporation rate of Bst over TPLFNs were in undetectable level in the sequencing conditions.

Figure 14:
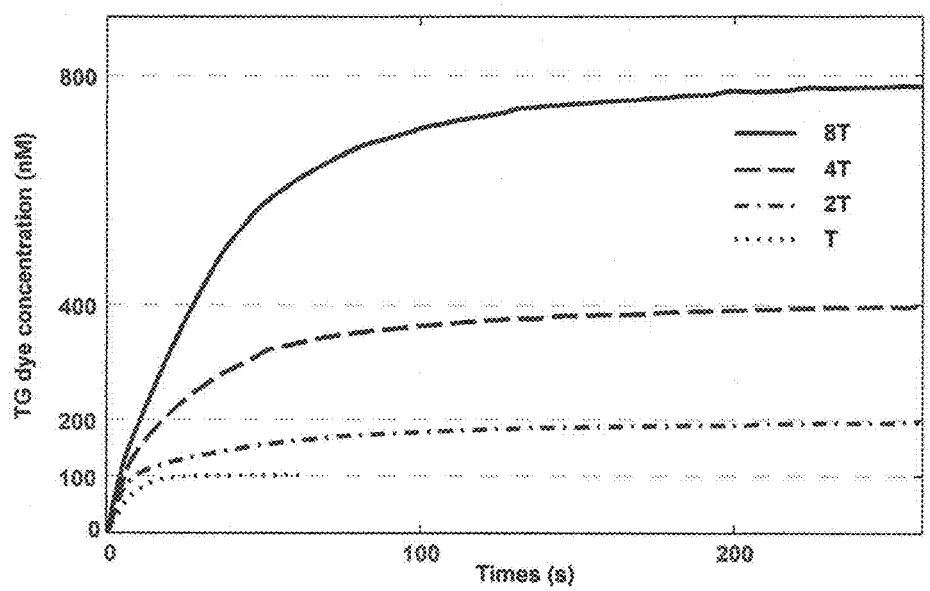
FIG. 14 shows homopolymer length versus signal linearity assay.
Figure 15:
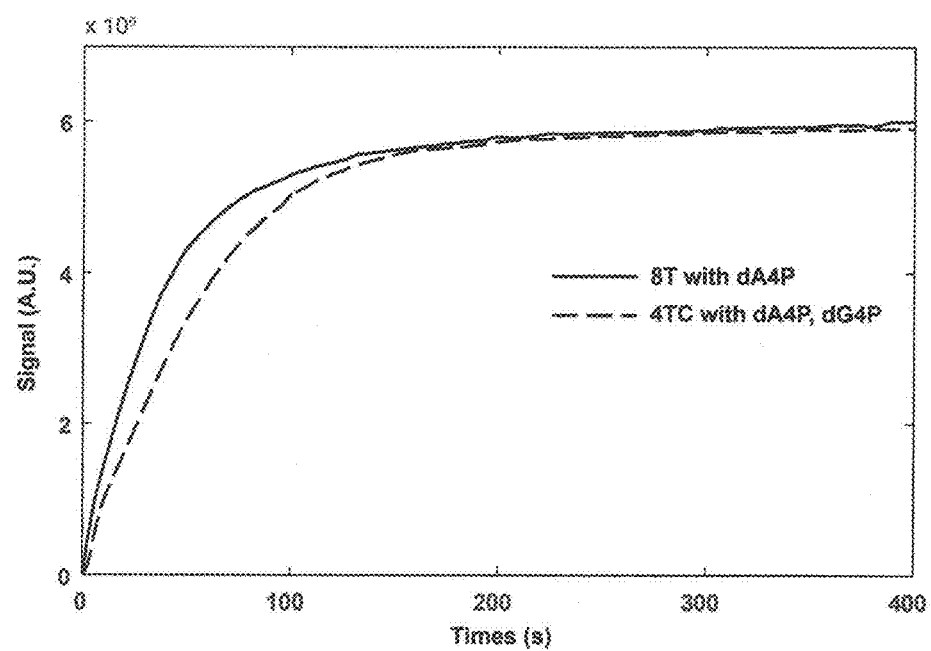
FIG. 15 shows homopolymer composes of only T and homopolymer composed of four repeated TC.

One of the challenges in the successive fluorogenic sequencing strategy is that the homopolymer or co-polymer regions on template need to be accurately measured through generated fluorescence signal. FIG. 14 demonstrated the primer elongation of different homopolymeric template by Bst polymerase. The reactions were conducted on flourometer using following conditions: 100 nM/each of template poly-T, poly-TT, poly-TTTT and poly-TTTTTTTT, excessive amount of Bst and CIP, 2 µM TG-dA4P, pH 8.3 buffer. 65° C., and triggered by Mn(II). The result in FIG. 14 showed that the generated fluorescent signals are proportional to the consecutively identical base numbers in a relatively broad range. Moreover, FIG. 15 showed that the hetero-polymeric (or co-polymeric) sequences, poly-TCTCTCTC, can give the same signal level as poly-TTTTTTTT by using dA-dG mixture instead of just dA in this linearity assay.

Except the reaction rate, the polymerase fidelity is also a crucial issue in the 2+2 sequencing strategy, especially considering the polymerase used herein in some aspects is proofreading deficient. The incorporation of mismatched nucleotide will not only decrease sequencing accuracy, but also cause the signal decay in each sequencing cycle. Although fidelity is mainly an inherent ability of polymerase, certain reaction conditions may still affect the performance of polymerase to discriminate against errors. To evaluate the fidelity of polymerase, a mis-incorporation experiment was designed, which is described below:

Excessive Bst and CIP, Mn(II), 100 nM primer-template with G unpaired nucleosides on template beside 3'-terminus of primer were mixed with 2 µM dC4P under 65° C., pH 8.3, the fluorescent signal generated was $4.5 \times 10^5$.

Then mixture with same concentrations of Bst, CIP, Mn(II) and primer-template was mixed with 2 µM dG4P, and bubbled in argon to prevent Mn(II) from oxidation. Next half of the mixture was incubated under 65° C. for 30 minutes and the other under 65° C. for 1 hour. After incubation, 2 µM dC4P was added in both mixture and fluorescent signals generated were $4.6 \times 10^5$ and $4.5 \times 10^5$. This suggests that mismatched extension is almost undetectable in the reaction system, using Bst polymerase. The trivial signal differences were mainly caused by inaccuracy in sample mixing. Extremely slow rate of mismatched extension is well preferred in the sequencing reaction, because once a primer-template is mismatched extended, a substitution mutation would be generated at current nucleoside site, changing the former duplex structure of the double strand, so that blocks the further extension of this primer-template. In this way, mismatched extension would gradually reduce the effective concentration of surface-grafted template array, and cause significant signal decay in each sequencing cycle. The study here has excluded the influence of mismatched extension in sequencing reaction, and confirmed the high accuracy of the reaction system.

Figure 16:
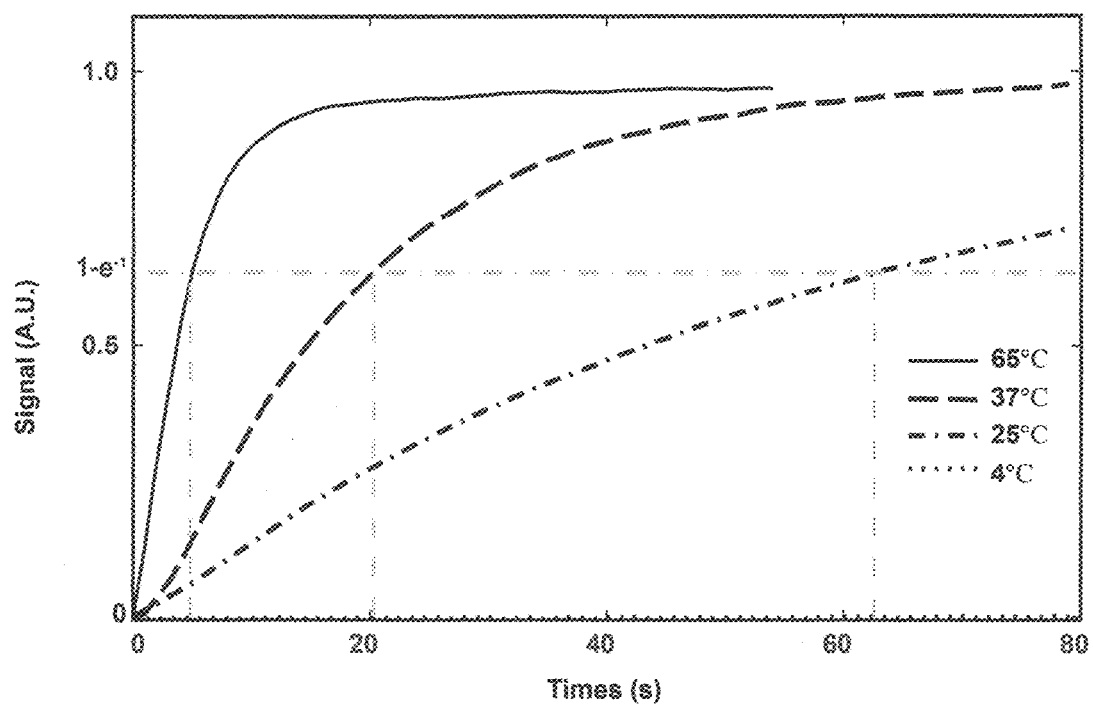
FIG. 16 shows temperature dependent activity of Bst.

FIG. 16 showed that the extension rate of Bst is temperature dependent, with optimal enzyme activity at 65° C. and totally inactive at 4° C. This temperature dependency could benefit the sequencing performance, since eventually all reactions for high-throughput sequencing will be separated and confined in micro-reactors on sequencing chips that was developed. Therefor no signal generation and diffusion is a crucial requirement when substrates and enzymes loaded at 4° C. Once the temperature is raised to 65° C., however, the polymerase will become fully active and generate signals instantly with high signal/noise ratio.

The stability of substrate TPLFNs were also measured at different temperature. The results have shown that the higher the temperature, the greater the hydrolysis rate. But it will not higher than 2 ppm/s, which means the background generated by auto-hydrolysis is still much lower than the polymerase extension signal. Even so, for better performance, the substrate will prefer to be stored in cold temperature to prevent auto-hydrolysis before extension started.

Section 3: Sequencing Chip Surface Grafting.

The glass chips that were used for the sequencing are all modified by hydrogel before oligonucleotides grafting. The modification method is based on the reported procedure and described as below. See e.g., U.S. Pat. No. 8,247,177.

3.1. Hydrogel Polymer Coating.

Figure 17:
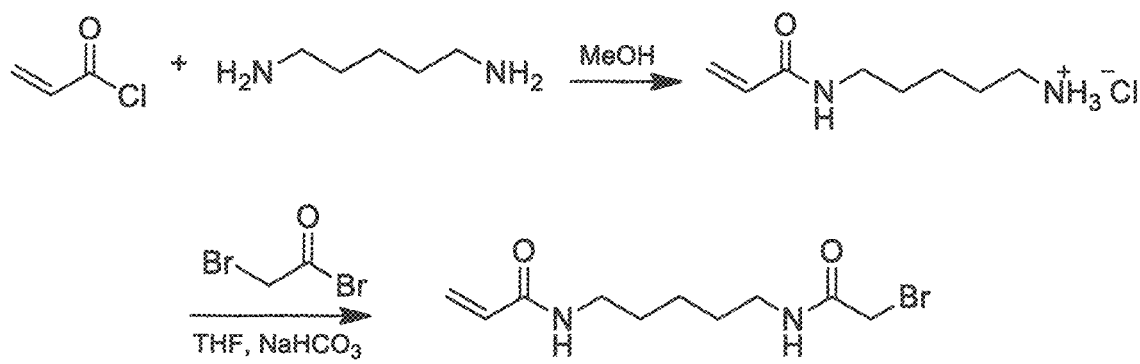
FIG. 17 shows synthesis of N-(5-(2-bromoacetamido)pentyl)acrylamide.

1) Brapa Synthesis:

The hydrogel monomer N-(5-(2-bromoacetamido)pentyl) acrylamide (BRAPA) was synthesized by the following method. (FIG. 17)

1,5-diaminopentane (10.2 g, 0.1 mole) was dissolved in 300 mL anhydrous methanol at 0° C., the solution of acryloyl chloride (0.9 g, 0.09 mol) in 15 ml anhydrous THF was dropwise added in with stirring. After the addition, the reaction mixture was stirred for 10h. 200 g silica gel and 1% benzoquinol was added into the reaction and all of the solvents were removed by vacuum evaporator. The silica gel powder with chemicals absorbed on it were loaded on the top of a prepared silica column and eluted with DCM/Methanol (10/1-1/1), the eluent containing the desired product was collected and concentrated to give 13 g faint white powder, which was used directly for next step without further purified or stored for longer time in case polymerization occurs.

The above product was suspended in 150 mL THF (20 mL Methanol could be added to increase solubility), then sodium hydrocarbonate solution in water (2 equiv.) was added at 0° C. To the mixture Bromoacetyl bromide (0.8 mole) was added dropwise at ° C. and the mixture was stirred for 10h before the reaction was stopped. Then 50 mL brine was added into the solution, the two phase was separated and the aqueous phase was extracted by 3×50 mL DCM. The combined organic phases were dried by $Na_2SO_4$ and concentrated, purified by silica gel column (eluted with EA/Methanol) to give 13.5 g BRAPA as white solid. The product can be further purified by recrystallization in Ethyl actate. Mp 102-104° C. HRMS Calcd for $C_{10}H_{18}BrN_2O_2$ (M+H), 277.0541. Found, m/z 277.0546. $^1H$ NMR (500 MHz, $d_6$-DMSO) δ 8.22 (s, 1H, NH), 8.02 (s, 1H, NH), 6.21 (dd, J=15 Hz, 10 Hz, 1H, CH), 6.07 (dd, J=15 Hz, 5 Hz, 1H, CH), 5.55 (dd, J=10 Hz, 5 Hz, 1H, CH), 3.82 (s, 2H, $CH_2$), 3.08 (ddd, J=10 Hz, 5 Hz, 4H, $CH_2$), 1.43 (m, 4H, $CH_2$), 1.27 (m, 2H, $CH_2$). $^{13}C$ NMR (126 MHz, $d_6$-DMSO) δ 166.29, 164.93, 132.40, 125.16, 39.40, 38.90, 30.05, 29.17, 28.95, 24.21.

2) Chip Surface Cleaning:

The glass chip with channels were cleaned using the following procedure: chromic acid cleaning solution for 5 min, then washed with milliQ $H_2O$ thoroughly; after dried in 120° C. oven, the chip surface was treated with oxygen-plasma for 3 min. Then immediately used for surface modification.

3) Hydrogel Preparation:

To 10 mL 2% acrylamide in milliQ $H_2O$, BRAPA (70 mg, in 700 µL DMF) was added and the solution was well mixed. The mixture was filtered by 0.22 µm filter, then bubbled with argon for 15 min. After that 11.5 µL TEMED was added, followed by addition of Potassium Persulfate in milliQ $H_2O$ (50 mg/mL, 100 µL). The well mixed solution was immediately loaded into the channels of the cleaned chip and stayed for 35 min under humid argon atmosphere. Then the hydrogel coated chip was washed thoroughly with 200 mL milliQ $H_2O$.

3.2. Primers Grafting and Template Amplification and Hybridization.

Figure 18:
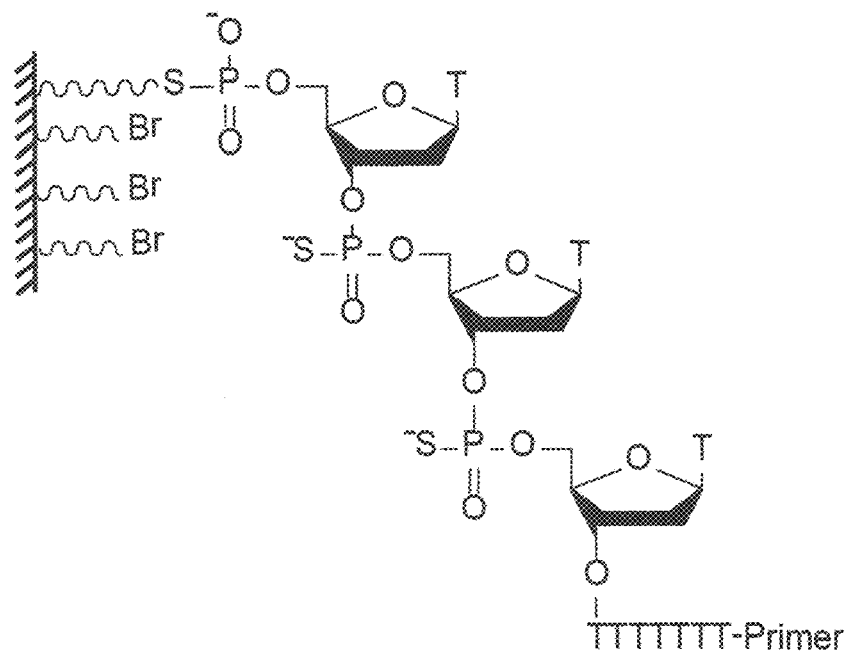
FIG. 18 illustrates primer grafting.
Figure 19:
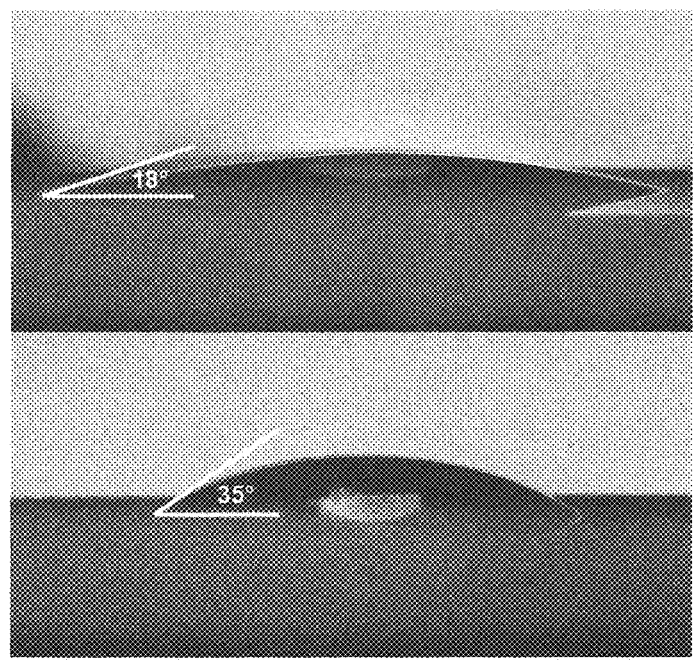
FIG. 19 shows contact angle difference between glass and BPAM coated-surface.
Figure 20A:
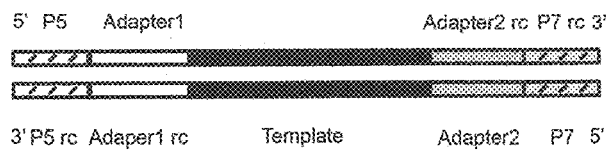
FIGS. 20A-C show ECCS library design.
Figure 20B:
Figure 20C:
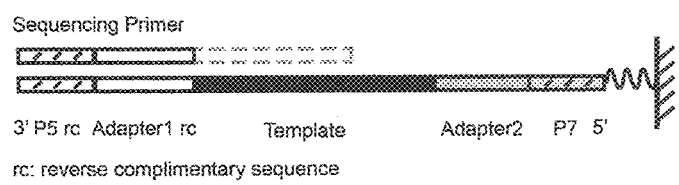
Figure 21:
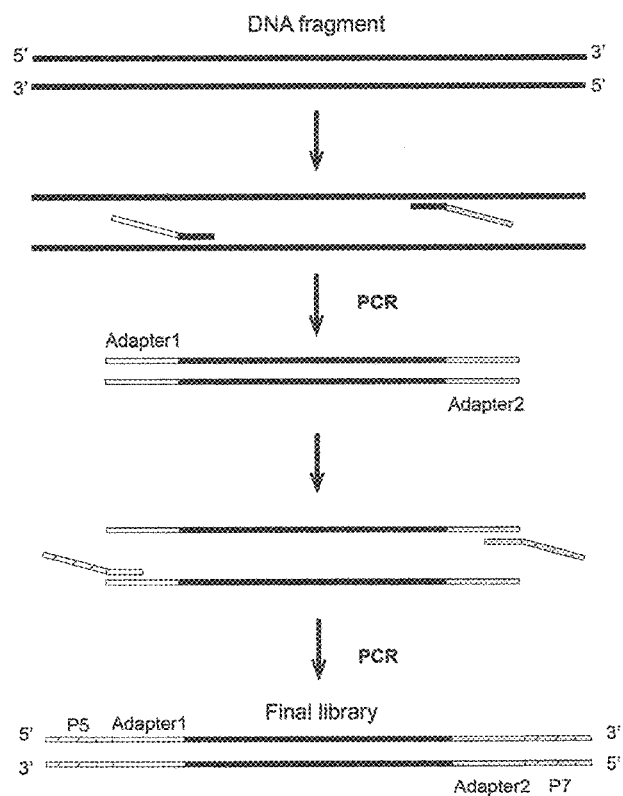
FIG. 21 shows a template preparation process.
Figure 22:
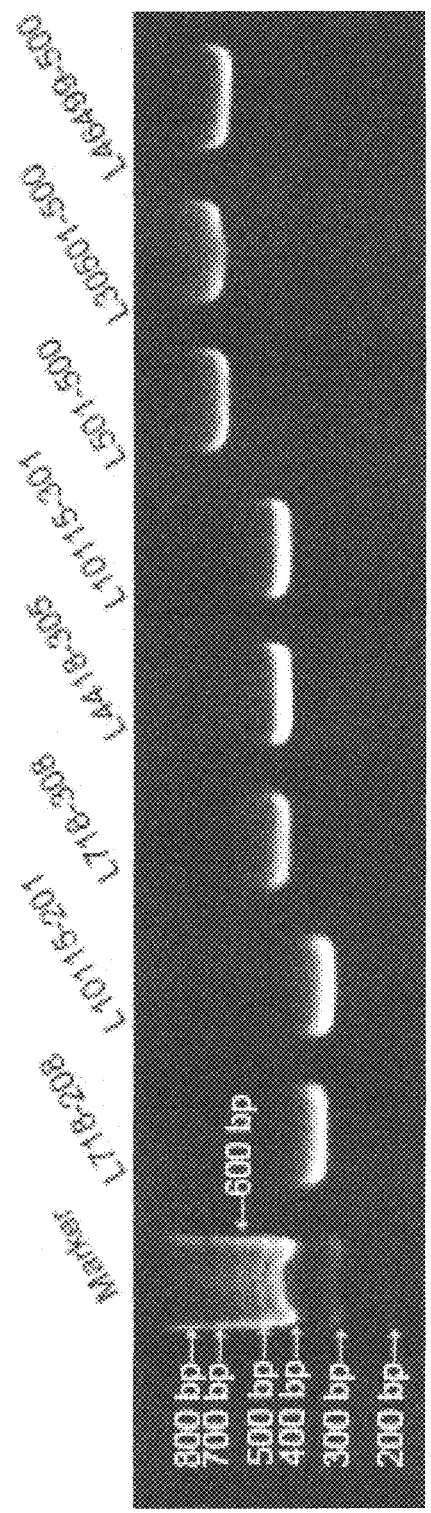
FIG. 22 shows gel-electrophoresis result of PCR products. Lane 1 is marker (Transgene, 100 bp Plus II DNA Ladder); lane 2, 3 are two 200 bp templates (L718-208 (330 bp), L10115-201 (323 bp), respectively); lane 4-6 are three 300 bp templates (L718-308 (430 bp), L4418-305 (427 bp), L10115-301 (423 bp), respectively); lane 7-9 are three 500 bp templates (L501-500 (622 bp), L30501-500 (622 bp), L46499-500 (622 bp), respectively).

5'-phosphorothioate oligonucleotides 10 µM PS-$T_{10}$-P7 (5'-T*T*T*TTTTTTTCAAGCAGAAGACGGCATACGA- 3', *=phosphorothioate) solution in pH 8.0 PBS buffer was load into the coated channels and stayed inside of the channels for 1 h at 50° C. After that, that grafted chip surface was blocked by 10 mM 2-mercaptoethanol solution in pH 8.0 PBS buffer for 40 min, then washed thoroughly with milliQ $H_2O$. The grafted surface is illustrated in FIG. 18.

3.3. Preparation of DNA Template.

ECCS Library Design:

Lambda phage genome DNA fragments (about 300 bp) were used as test DNA oligos for preparation of the sequencing template. Lambda DNA was obtained from New England Biolabs, USA. The complete sequencing template consisted of adapter2 (43 bp), P7 (21 bp), on the 5' termini of ssDNA templates, and reverse complimentary strands of adapter 1 (38 bp) and P5 (20 bp) on the 3' termini of lambda ssDNA. Sequences of P5, P7, adapter1 and adapter2 were exactly the same with Illumina's, except a few bases, in order to be compatible with it.

Single component library preparation (From bacteriophage lambda):

Two-step PCR amplification method was used to prepare sequencing template. In first step PCR, 50 μL mixture of Lambda genome DNA (500 ng, NEB), 1st-step PCR primers (200 nm, each) and 1× Q5 High-Fidelity 2× Master Mix (NEB) in H2O was treated with the following PCR thermal cycling profile: (i) hot start at 95° C. for 90 s; (ii) 30 cycles, each composed by 30s at 95° C., 30s at 65° C., 30s at 72° C. The amplified products were then purified by PCR purification kit (Zymo, D4061) and withdrawn into an Eppendorf tube for the second step PCR amplification. The conditions and thermal cycling profile for the second step PCR are similar to first step while the following primers used for the newly generated template were from above: P5-Adp1 (200 nM) and P7-Adp2 (200 nM).

The PCR products were gel-purified and verified by Sanger sequencing with primer P5, P7 and P5SeqP1. After measurement of its final concentration, the products containing identical DNA template were stored in −20° C. fridge for further usage.

3.4. Library immobilization: Solid phase PCR in flowcell.

The prepared identical DNA template from above were mixed together with PCR reagents and then loaded into flowcell, which was surface grafted with primer P7 as described above. The mixtures contains DNA template (1 nM), primer P5 (500 nM), primer P7 (62.5 nM), MgCl2 (6 mM), dNTP (0.5 mM), Platinum Taq polymerase (0.5 U/mL, Life Tech), BSA (0.2 mg/mL), PCR buffer (200 mM Tris HCl, 500 mM KCl). Solid phase amplification thermal cycles comprised two stages with different temperature profiles. The first stage was a process of asymmetric pre-amplification, following (i) hot start at 95° C. for 90 s; (ii) 15 cycles, each composed by 30 s at 95° C., 15 s at 65-60° C. gradually, 30 s at 72° C. After the asymmetric amplification, the primer P5 derived strands of templates were greatly dominated in the PCR solution. Then, the thermal cycles of second stage solid phase PCR were conducted to mainly hybridize and extend the flowcell surface grafted oligo P7, the thermal cycle profile is: 30 cycles, each composed by 30 s at 95° C., 300 s at 65° C. After that, the samples were denatured using formamide to remove the counterparts of the grafted oligos, leaving only P7 derived strand of template on the flowcell surface.

After solid-phase PCR, PCR solution was sucked out using pipette. Formamide was injected into flowcell to denature all remaining double strand DNA. Finally, chip was washed by wash buffer (20 mM Tris-HCl buffer, pH=8.0, 50 mM KCl) to exclude remaining formamide. Density measurement of solid-phase ssDNA template First, inject 5 μM oligonucleotide with fluorescent probe (FAM-T-SeqP1) into the flowcell and seal injection ports. The chip was then placed in a heat plate at 80° C. for 2 min, and then cooled to room temperature (or below 30° C.) in 30 minutes. Wash the flowcell thoroughly using wash buffer. Then fluorescence images of chip were taken by a fluorescence microscope with automatic stage. Images were taken at five different positions on each lane to examine evenness and minimize stochastic error.

Previous experiments proved that fluorescence value was positively linear correlated with the number of FAM modified primer. For this reason, while calculating PCR product concentration, a standard concentration curve was set firstly. By recording fluorescence values of lanes containing 0 nM (wash buffer without FAM modified primer) and 100 nM TG solution, a standard concentration curve was established. Average intensity of these images was fit into the standard concentration curve and then PCR product concentration came out.

Figure 24A:
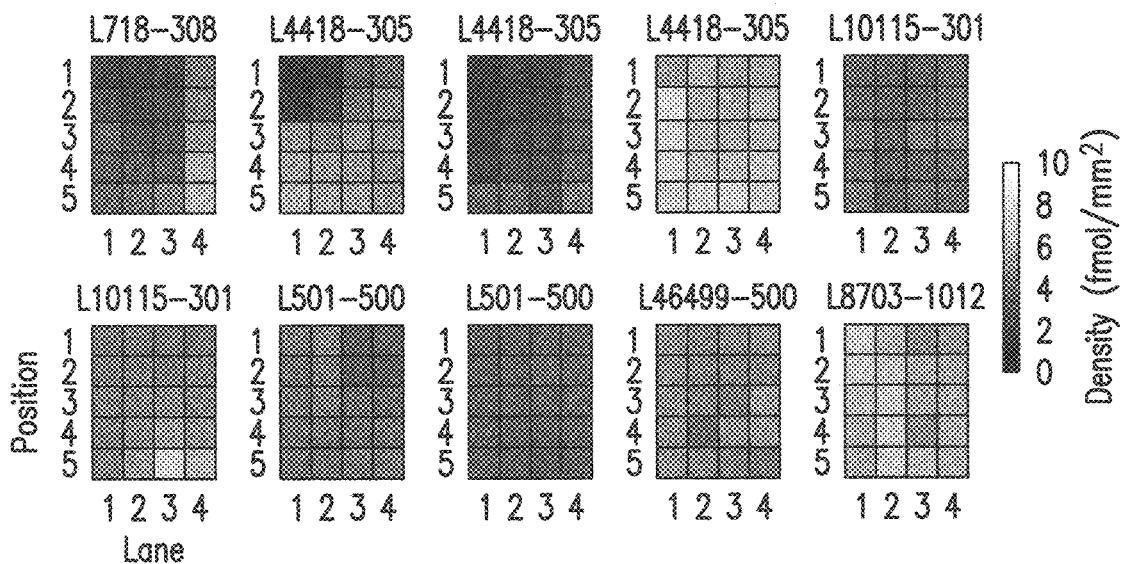
FIG. 24A shows a heatmap of PCR products density of different lanes and positions. X-axis labels of every panel mean four different lanes of a chip; Y-axis labels of every panel mean five different imaging positions on a lane. Color from black to green represents PCR products density from low to high.
Figure 24B:
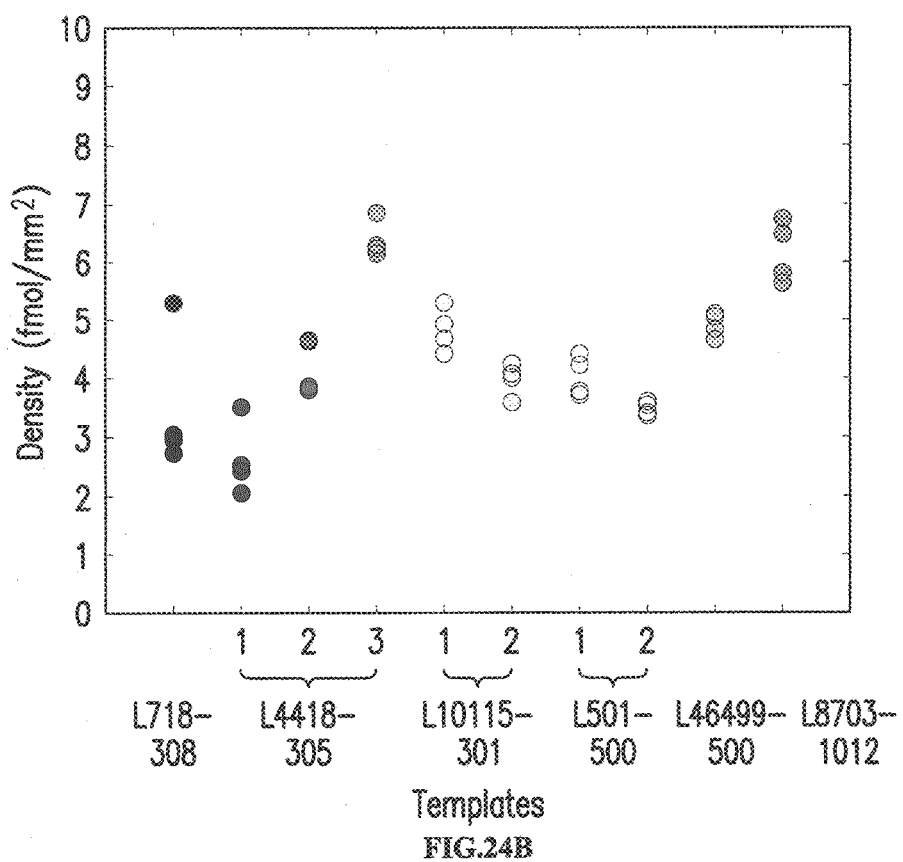
FIG. 24B shows PCR products density of different templates. X-axis labels are different experiment groups of solid phase PCR; Y-axis labels are mean density of every lane of a chip.

Characterization of solid-phase PCR product is shown in FIGS. 24A-B. FIG. 24A shows a heatmap of PCR products density of different lanes and positions. FIG. 24B shows PCR products density of different templates.

Normally, PCR product concentration of chips, which were used to sequence, was about 50~150 nM (2.5~7.5 fmol/mm$^2$). Mean densities of one chip's four lanes were roughly the same. Templates of different lengths were executed solid phase PCR and there was no obvious difference in density of different lengths templates. To evaluate evenness of PCR product density, coefficient of variation (CV) was measured by calculating density values of all the imaged positions of a chip. CV of all the chips was 0.15±0.13.

The characterized and qualified flowcell was denatured with formamide prior to hybridization of the sequencing primer (P5-SeqP1). Then this processed flowcell was transferred to microscope platform for sequencing.

3.5. Sequencing.

Figure 25A:
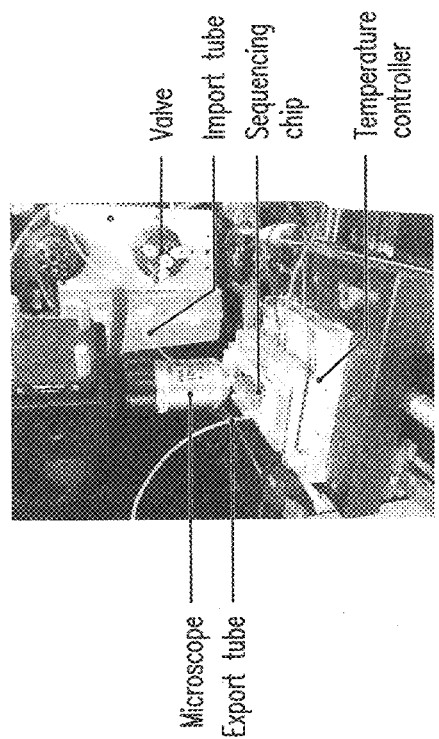
FIG. 25A shows a sequencing instrument.
Figure 25C:
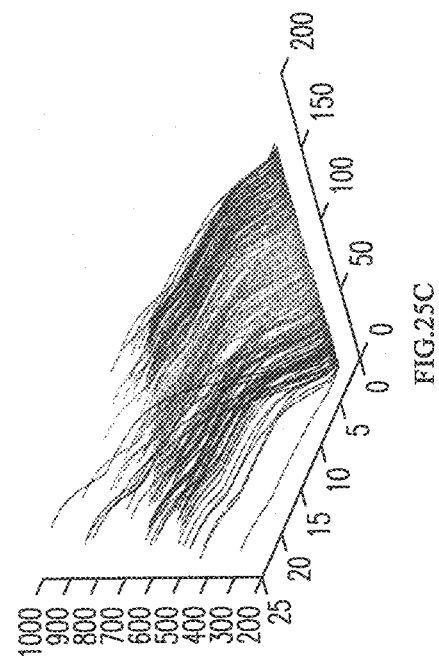
FIG. 25C shows kinetic curves of every reaction cycles along the whole sequencing, according to one embodiment.
Figure 25B:
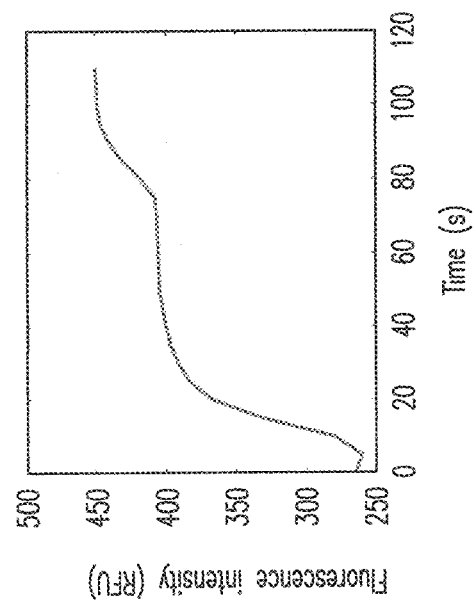
FIG. 25B shows a typical fluorogenic reaction kinetic curve.
Figure 26:
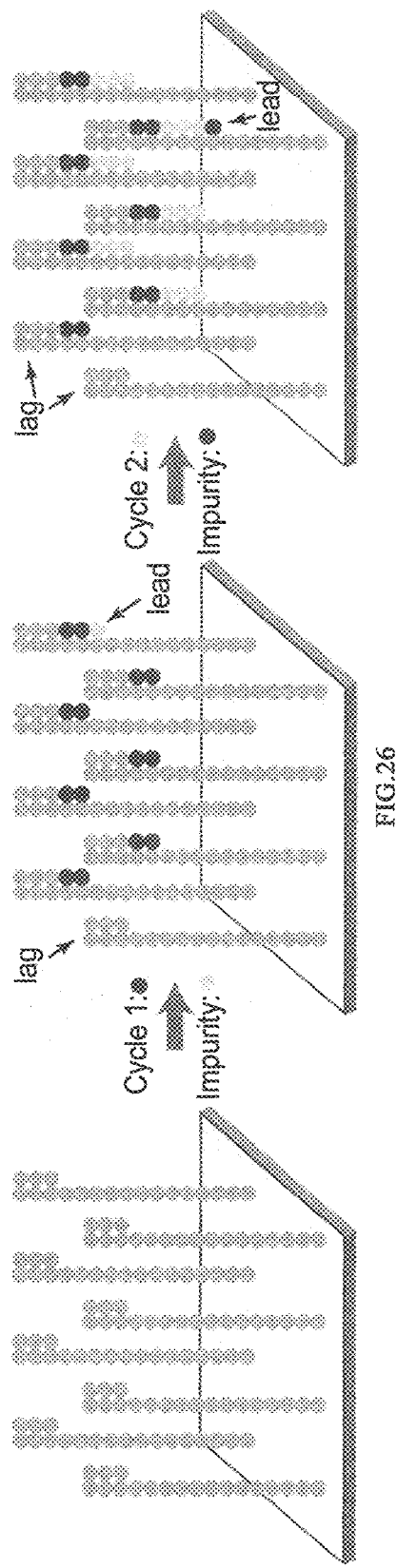
FIG. 26 shows a dephasing process.

To conduct the sequencing experiment, a simple sequencing instrument was developed, as shown in FIG. 25A-C. As shown in FIG. 25A, the sequencing chip (HiSeq 2000, research only) is put on a temperature controller, under which is a 3-D translation stage used to move sequencing chip in 3 dimensions. Above the chip is a highly sensitive CCD and 10× microscope. When the blue light irradiates on chip during reaction, the emitted green light is captured by CCD through microscope. On one end of the chip, there is a slim tube connected with valve and pump, to import reaction buffer and wash buffer, while on the other end, the chip is mounted to a tube to export waste liquid.

For the successive sequencing strategy, the mixture of two different nucleotides was added into the flowcell at each reaction cycle. Therefore, the paired combination of four nucleotides generates three groups, each of which has two pairs of nucleotides (AC/GT or AG/TC, or AT/GC). M/K, R/Y and W/S, were used to represent the six paired combinations, respectively.

Prior to each sequencing run, the reagents were pre-mixed and kept in two separate bottles in chilled holder. Both of the bottles contains Bst DNA Polymerase (100 U/μL, McLab), Calf Intestinal Alkaline Phosphatase (0.5 U/ml, NEB), MnCl$_2$ (1 mM), DTT (10 mM) in reaction buffer (40 mM Trisbase, 40 mM HN$_4$Cl, 100 mM KCl), and one the bottles was added TG-dA4P (3 μM)/TG-dG4P (3 μM) for R, the other bottle was added TG-dC4P (2.5 μM)/TG-dT4P (5 μM)

for Y. After one sequencing run, the reagent bottles were switched to W/S, then M/K, with the same recipe as R/Y. These nucleotides groups did not have to be added in a specific order, and any random sequence worked in the same manner.

With flowcell mounted on the microscope platform and reagents bottles placed in chilled holder, the automate sequencing process was performed by the following steps: (i) washed the flowcell and reagents input system (rotary valve, tubings between flowcell and reagent bottles) with wash buffer; (ii) wash the flowcell with wash buffer for 3 times; (iii) cooled the flowcell to 4° C., loaded one of the mixed nucleotides (for R, TG-dA4P/TG-dG4P) by syringe pump through rotary valve; (iv) warmed the flowcell to 15° C., took background fluorescent image by CCD camera (Hamamatsu); (v) Heated flowcell to 65° C. to trigger polymerase conducted nucleotide incorporation and primer elongation, kept 65° C. for 1 min; (vi) Cooled flowcell to 15° C., took image to record fluorescence signal, then back to step (ii). This process was automatically controlled until the whole template was sequenced or reached its sequencing limitation. Then the flowcell was denatured by formamide to regenerate the single strand template. After primer was annealed, the next round of sequencing with different group of reagent mix was performed by follow the same manner as above.

FIG. 25B is a typical fluorogenic reaction kinetic curve, which records fluorescent intensity in every 5 seconds. When chip heated in 65° C., the fluorescent intensity increases dramatically in about 20 seconds, reaching to a plateau, which means the reaction is about to complete. Then the temperature controller cools to 20° C. to take fluorescent intensity after reaction, so the fluorescent intensity rises because of temperature decline. However, the unit signal goes down along the whole sequencing process due to dephasing problem and templates loss. FIG. 25C depicts kinetic curves of every reaction cycles along the whole sequencing.

TABLE 25

Oligonucleotide sequences used in this section.

| SEQ ID NO | Name | Sequence (5'→3') |
|---|---|---|
| SEQ ID NO: 3 | PS3-T10-P7 | T*T*T*TTTTTTTCAAGCAGAAGACGGCATACGA |
| SEQ ID NO: 4 | P5 | AATGATACGGCGACCACCGA |
| SEQ ID NO: 5 | P7 | CAAGCAGAAGACGGCATACGA |
| SEQ ID NO: 6 | P5-SeqP1 | AATGATACGGCGACCACCGAGATCTACACTCTTTCCCTACACGACGCTCTTCCGATCT |
| SEQ ID NO: 7 | FAM-P7rc | FAM-TCGTATGCCGTCTTCTGCTTG |
| SEQ ID NO: 8 | FAM-T-SeqP1 | FAM-TTACACTCTTTCCCTACACGACGCTCTTCCGATCT |
| SEQ ID NO: 9 | Adp1-L10115-301-f | ACACTCTTTCCCTACACGACGCTCTTCCGATCTGTGTTCGACGGTGAGCTGAGTT |
| SEQ ID NO: 10 | Adp2-L10115-301-r | GTGACTGGAGTTCAGACGTGTGCTCTTCCGATCTCAAGCCCTGCCGCTTTCTGC |
| SEQ ID NO: 11 | Adp1-L4418-305-f | ACACTCTTTCCCTACACGACGCTCTTCCGATCTGTGACAGCAGAGCTGCGTAATC |
| SEQ ID NO: 12 | Adp2-L4418-305-r | GTGACTGGAGTTCAGACGTGTCATGCGATCATATGAGTACGGCTGCAGCGCCCG |
| SEQ ID NO: 13 | Adp1-L718-308-f | ACACTCTTTCCCTACACGACGCTCTTCCGATCTTATCGAACAGTCAGGTTAACAGGC |
| SEQ ID NO: 14 | Adp2-L718-308-r | GTGACTGGAGTTCAGACGTGTCATGCGATCATATCAACCAGATAAGGGTGTTGC |
| SEQ ID NO: 15 | Adp1-L501-500-f | ACACTCTTTCCCTACACGACGCTCTTCCGATCTACTCCGCTGAAGTGGTGGAA |
| SEQ ID NO: 16 | Adp2-L501-500-r | GTGACTGGAGTTCAGACGTGTCATGCGATCATATTTATGCTCTATAAAGTAGGC |
| SEQ ID NO: 17 | Adp1-L30501-500-f | ACACTCTTTCCCTACACGACGCTCTTCCGATCTCACTCACAACAATGAGTGGC |
| SEQ ID NO: 18 | Adp2-L30501-500-r | GTGACTGGAGTTCAGACGTGTCATGCGATCATATCACGGAATGCATTTTTCTGG |
| SEQ ID NO: 19 | Adp1-L46499-500-f | ACACTCTTTCCCTACACGACGCTCTTCCGATCTGCCTAAAGTAATAAAACCGA |
| SEQ ID NO: 20 | Adp2-L46499-500-r | GTGACTGGAGTTCAGACGTGTCATGCGATCATATGGCATAATGCAATACGTGTA |
| SEQ ID NO: 21 | Adp1-L8703-1012-f | ACACTCTTTCCCTACACGACGCTCTTCCGATCTAAGAGCTGGACAGCGATACC |
| SEQ ID NO: 22 | Adp2-L8703-1012-r | GTGACTGGAGTTCAGACGTGTGCTCTTCCGATCTCATCGCTGACTCTCCGGATT |
| SEQ ID NO: 23 | Adp1-L718-208-f | ACACTCTTTCCCTACACGACGCTCTTCCGATCTTATCGAACAGTCAGGTTAACAGGC |
| SEQ ID NO: 24 | Adp2-L718-208-r | GTGACTGGAGTTCAGACGTGTGCTCTTCCGATCTTCGCTGCCCATCGCATTCAT |
| SEQ ID NO: 25 | Adp1-L10115-201-f | ACACTCTTTCCCTACACGACGCTCTTCCGATCTGTGTTCGACGGTGAGCTGAGTT |
| SEQ ID NO: 26 | Adp2-L10115-201-r | GTGACTGGAGTTCAGACGTGTGCTCTTCCGATCTGCTGAAAAACAGGCTGAGCA |
| SEQ ID NO: 27 | P7-Adp2-r | CAAGCAGAAGACGGCATACGAGATACTGACGTGACTGGAGTTCAGACGTGT |
| SEQ ID NO: 28 | P5-Adp1-f | AATGATACGGCGACCACCGAGATCTACACTCTTTCCCTACACGAC |

Note:
"*" indicates phosphorothioate bond; FAM: 5, 6-fluorescein amidite

TABLE 26

Template sequences used in this section

| SEQ ID NO | Name | Sequence (5'→3') |
|---|---|---|
| SEQ ID NO: 29 | L10115-201 | GTGTTCGACGGTGAGCTGAGTTTTGCCCTGAAACTGGCGCGTGAGATGGGGCGACCCGACTGGCGTGCCATGCTTGCCGGGATGTCATCCACGGAGTATGCCGACTGGCACCGCTTTTACAGTACCCATTATTTTCATGATGTTCTGCTGGATATGCACTTTTCCGGGCTGACGTACACCGTGCTCAGCCTGTTTTTCAGC |
| SEQ ID NO: 30 | L718-208 | TATCGAACAGTCAGGTTAACAGGCTGCGGCATTTTGTCCGCGCCGGGCTTCGCTCACTGTTCAGGCCGGAGCCACAGACCGCCGTTGAATGGGCGGATGCTAATTACTATCTCCCGAAAGAATCCGCATACCAGGAAGGGCGCTGGGAAACACTGCCCTTTCAGCGGGCCATCATGAATGCGATGGGCAGCGA |
| SEQ ID NO: 31 | L10115-301 | TATCGAACAGTCAGGTTAACAGGCTGCGGCATTTTGTCCGCGCCGGGCTTCGCTCACTGTTCAGGCCGGAGCCACAGACCGCCGTTGAATGGGCGGATGCTAATTACTATCTCCCGAAAGAATCCGCATACCAGGAAGGGCGCTGGGAAACACTGCCCTTTCAGCGGGCCATCATGAATGCGATGGGCAGCGACTACATCCGTGAGGTGAATGTGGTGAAGTCTGCCCGTGTCGGTTATTCCAAATGCTGCTGGGTGTTTATGCCTACTTTATAGAGCATAAGCAGCGCAACACCCTTATCTGGTTG |
| SEQ ID NO: 32 | L4418-305 | GTGACAGCAGAGCTGCGTAATCTCCCGCATATTGCCAGCATGGCCTTTAATGAGCCGCTGATGCTTGAACCCGCCTATGCGCGGGTTTTCTTTTGTGCGCTTGCAGGCCAGCTTGGGATCAGCAGCCTGACGGATGCGGTGTCCGGCGACAGCCTGACTGCCCAGGAGGCACTCGCGACGCTGGCATTATCCGGTGATGATGACGGACCACGACAGGCCCGCAGTTATCAGGTCATGAACGGCATCGCCGTGCTGCCGGTGTCCGGCACGCTGGTCAGCCGGACGCGGGCGCTGCAGCCGTACTC |
| SEQ ID NO: 33 | L9730-303 | CATTTGAACATAACGGTGTGACCGTCACGCTTTCTGAACTGTCAGCCCTGCAGCGCATTGAGCATCTCGCCCTGATGAAACGGCAGGCAGAACAGGCGGAGTCAGACAGCAACCGGAAGTTTACTGTGGAAGACGCCATCAGAACCGGCGCGTTTCTGGTGGCGATGTCCCTGTGGCATAACCATCCGAGAAGACGCAGATGCCGTCCATGAATGAAGCCGTTAAACAGATTGAGCAGGAAGTGCTTACCACCTGGCCCACGGAGGCAATTTCTCATGCTGAAAACGTGGTGTACCGGCTGT |
| SEQ ID NO: 34 | L718-308 | GTGTTCGACGGTGAGCTGAGTTTTGCCCTGAAACTGGCGCGTGAGATGGGGCGACCCGACTGGCGTGCCATGCTTGCCGGGATGTCATCCACGGAGTATGCCGACTGGCACCGCTTTTACAGTACCCATTATTTTCATGATGTTCTGCTGGATATGCACTTTTCCGGGCTGACGTACACCGTGCTCAGCCTGTTTTTCAGCGATCCGGATATGCATCCGCTGGATTTCAGTCTGCTGAACCGGCGCGAGGCTGACGAAGAGCCTGAAGATGATGTGCTGATGCAGAAAGCGGCAGGGCTTG |
| SEQ ID NO: 35 | L29732-497 | TACTCAACCCGATGTTTGAGTACGGTCATCATCTGACACTACAGACTCTGGCATCGCTGTGAAGACGACGCGAAATTCAGCATTTTCACAAGCGTTATCTTTTACAAAACCGATCTCACTCTCCTTTGATGCGAATGCCAGCGTCAGACATCATATGCAGATACTCACCTGCATCCTGAACCCATTGACCTCCAACCCCGTAATAGCGATGCGTAATGATGTCGATAGTTACTAACGGGTCTTGTTCGATTAACTGCCGCAGAAACTCTTCCAGGTCACCAGTGCAGTGCTTGATAACAGGAGTCTTCCCAGGATGGCGAACAACAAGAAACTGGTTTCCGTCTTCACGGACTTCGTTGCTTTCCAGTTTAGCAATACGCTTACTCCCATCCGAGATAACACCTTCGTAATACTCACGCTGCTCGTTGAGTTTTGATTTTGCTGTTTCAAGCTCAACACGCAGTTTCCCTACTGTTAGCGCAATATCCTCGTTCTCC |
| SEQ ID NO: 36 | L501-500 | ACTCCGCTGAAGTGGTGAAACCGCATTCTGTACTTTCGTGCTGTCGCGGATCGCAGGTGAATTGCCAGTATTCTCGACGGGCTCCCCCTGTCGGTGCAGCGGCGTTTTCCGGAACTGGAAAACCGACATGTTGATTTCCTGAAACGGGATATCATCAAAGCCATGAACAAAGCAGCCGCGCTGGATGAACTGATACCGGGGTTGCTGAGTGAATATATCGAACAGTCAGGTTAACAGGCTGCGCATTTTGTCCGCGCCGGGCTTCGCTCACTGTTCAGGCCGGAGCCACAGACCGCGTTGAATGGGCGGATGCTAATTACTATCTCCCGAAAGAATCCGCATACCAGGAAGGGCGCTGGGAAACACTGCCCTTTCAGCGGGCCATCATGAATGCGATGGGCAGCGACTACATCCGTGAGGTGAATGTGGTGAAGTCTGCCCGTGTCGGTTATTCCAAATGCTGCTGGGTGTTTATGCCTACTTTATAGAGCATAA |
| SEQ ID NO: 37 | L30501-500 | CACTCACAACAATGAGTGGCAGATATAGCCTGGTGGTTCAGGCGGCGCATTTTTATTGCTGTGTTGCGCTGTAATTCTTCTATTTCTGATGCTGAATCAATGATGTCTGCCATCTTTCATTAATCCCTGAACTGTTGGTTAATACGCTTGAGGGTGAATGCGAATAATAAAAAAGGAGCCTGTAGCTCCCTGATGATTTGCTTTTCATGTTCATCGTTCCTTAAAGACGCCGTTTAACATGCCGATTGCCAGGCTTAAATGAGTCGGTGTGAATCCCATCAGCGTTACCGTTTCGCGGTGCTTCTTCAGTACGCTACGGCAAATGTCATCGACGT |

TABLE 26-continued

Template sequences used in this section

| SEQ ID NO | Name | Sequence (5'→3') |
|---|---|---|
| | | TTTTATCCGGAAACTGCTGTC<br>TGGCTTTTTTTGATTTCAGAA<br>TTAGCCTGACGGGCAATGCTG<br>CGAAGGGCGTTTTCCTGCTGA<br>GGTGTCATTGAACAAGTCCCA<br>TGTCGGCAAGCATAAGCACAC<br>AGAATATGAAGCCCGCTGCCA<br>GAAAAATGCATTCCGTG |
| SEQ ID NO: 38 | L46499-500 | GCCTAAAGTAATAAAACCGAG<br>CAATCCATTTACGAATGTTTG<br>CTGGGTTTCTGTTTTAACAAC<br>ATTTTCTGCGCCGCCACAAAT<br>TTTGGCTGCATCGACAGTTTT<br>CTTCTGCCCAATTCCAGAAAC<br>GAAGAAATGATGGGTGATGGT<br>TTCCTTTGGTGCTACTGCTGC<br>CGGTTTGTTTTGAACAGTAAA<br>CGTCTGTTGAGCACATCCTGT<br>AATAAGCAGGGCCAGCGCAGT<br>AGCGAGTAGCATTTTTTTCAT<br>GGTGTTATTCCCGATGCTTTT<br>TGAAGTTCGCAGAATCGTATG<br>TGTAGAAAATTAAACAAACCC<br>TAAACAATGAGTTGAAATTTC<br>ATATTGTTAATATTTATTAAT<br>GTATGTCAGGTGCGATGAATC<br>GTCATTGTATTCCCGGATTAA<br>CTATGTCCACAGCCCTGACGG<br>GGAACTTCTCTGCGGGAGTGT<br>CCGGGAATAATTAAAACGATG<br>CACACAGGGTTTAGCGCGTAC<br>ACGTATTGCATTATGCC |
| SEQ ID NO: 39 | L8703-1012 | AAGAGCTGGACAGCGATACCT<br>GGCAGGCGGAGCTGCATATCG<br>AAGTTTTCCTGCCTGCTCAGG<br>TGCCGGATTCAGAGCTGGATG<br>CGTGGATGGAGTCCCGGATTT<br>ATCCGGTGATGAGCGATATCC<br>CGGCACTGTCAGATTTGATCA<br>CCAGTATGGTGGCCAGCGGCT<br>ATGACTACCGGCGCGACGATG<br>ATGCGGGCTTGTGGAGTTCAG<br>CCGATCTGACTTATGTCATTA<br>CCTATGAAATGTGAGGACGCT<br>ATGCCTGTACCAAATCCTACA<br>ATGCCGGTGAAGGTGCCGGG<br>ACCACCCTGTGGGTTTATAAG<br>GGGAGCGGTGACCCTTACGCG<br>AATCCGCTTTCAGACGTTGAC<br>TGGTCGCGTCTGGCAAAAGTT<br>AAAGACCTGACGCCCGGCGAA<br>CTGACCGCTGAGTCCTATGAC<br>GACAGCTATCTCGATGATGAA<br>GATGCAGACTGGACTGCGACC<br>GGGCAGGGGCAGAAATCTGCC<br>GGAGATACCAGCTTCACGCTG<br>GCGTGGATGCCCGGAGAGCAG<br>GGGCAGCAGGCGCTGCTGGCG<br>TGGTTTAATGAAGGCGATACC<br>CGTGCCTATAAAATCCGCTTC<br>CCGAACGGCACGGTCGATGTG<br>TTCCGTGGCTGGGTCAGCAGT<br>ATCGGTAAGGCGGTGACGGCG<br>AAGGAAGTGATCACCCGCACG<br>GTGAAAGTCACCAATGTGGGA<br>CGTCCGTCGATGGCAGAAGAT<br>CGCAGCACGGTAACAGCGGCA<br>ACCGGCATGACCGTGACGCCT<br>GCCAGCACCTCGGTGGTGAAA<br>GGGCAGAGCACCACGCTGACC<br>GTGGCCTTCCAGCCGGAGGGC<br>GTAACCGACAAGAGCTTTCGT<br>GCGGTGTCTGCGGATAAAACA<br>AAAGCCACCGTGTCGGTCAGT |

| SEQ ID NO | Name | Sequence (5'→3') |
|---|---|---|
| | | GGTATGACCATCACCGTGAAC<br>GGCGTTGCTGCAGGCAAGGTC<br>AACATTCCGGTTGTATCCGGT<br>AATGGTGAGTTTGCTGCGGTT<br>GCAGAAATTACCGTCACCGCC<br>AGTTAATCCGGAGAGTCAGCG<br>ATG |

Section 4: Successive Sequencing Dephasing Correction 4.1. Signal Leading and Lagging One of the inevitable limiting factors for amplification-based sequencing-by-synthesis method is dephasing, i.e., the loss of synchronicity of extended molecules. This phenomenon is caused by unexpected addition of nucleotides (lead) or incomplete extension (lag), and will lead to an increase of noise and sequencing errors. In the ideal situation, namely, that dephasing doesn't exist, all nascent DNA molecules have the same extension length; but when allowing for the dephasing problem, the nascent DNA molecules may have different extension lengths. And the distribution of the extension lengths may get more and more dispersive as the sequencing reactions proceed.

4.2. Virtual Sequencer 4.2.1. Virtual Sequencer Based on MATLAB

To monitor the distribution of nascent DNA extension lengths in the sequencing reactions, a virtual sequencer program was developed by MATLAB for the simulation of all sequencing reactions. For a DNA sequence of length L, considered chemical reactions and their corresponding kinetic constants are given below:

TABLE 27

Chemical reactions and their corresponding kinetic constants in the virtual sequencer program

| Reaction | k | $k_{-1}$ |
|---|---|---|
| $Bst + DNA_{k-1} \Leftrightarrow Bst - DNA_{k-1}$ | 0.1 | 0.001 |
| $Bst - DNA_{k-1} + dN_k4P \Leftrightarrow Bst - DNA_{k-1} - dN_k4P$ | 0.1 | 0.001 |
| $Bst - DNA_{k-1} - dN_k4P \Leftrightarrow Bst - DNA_k + pFluorescein$ | 1 | 0 |
| $Phosphatase + pFluorescein \Leftrightarrow Phosphatase - pFluorescein$ | 1 | 0.01 |
| $Phosphatase - pFluorescein \Leftrightarrow Phosphatase + p + Fluorescein$ | 1 | 0 | where k=1, 2, . . . L, and

Bst denotes the Bst DNA polymerase, $DNA_{k-1}$ denotes the (k−1)-th position of the DNA to be sequenced, $dN_k4P$ denotes the terminal phosphate-labeled fluorogenic nucleotide which can pair with the k-th position of the DNA, pFluorescein denotes the phosphated fluorescein which is not fluorescent, Phosphatase denotes the alkaline phosphatase, p denotes the phosphate, Fluorescein denotes the unphosphated fluorescein which is fluorescent, $Bst-DNA_{k-1}$, $Bst-DNA_{k-1}$, $Bst-DNA_{k-1}-dN_k4P$, etc., denote the corresponding complexes.

Initial concentrations of species used in the simulation are listed in the table below:

TABLE 28

Initial concentrations of species in the virtual sequencer program

| Specie | Initial Concentration |
|---|---|
| Bst DNA Polymerase | 0.5 |
| Alkaline Phosphatase | 0.1 |
| Original DNA to be sequenced | 0.05 |
| phosphated fluorescein | 0 |
| phosphate | 0 |
| unphosphated fluorescein | 0 |

The virtual sequencer program reads the given DNA sequence and automatically generates a series of chemical reactions according to the table, which are passed to the SimBiology toolbox of MATLAB to generate the corresponding ordinary differential equations (ODEs). All chemical kinetics used in the ODEs are mass-action. The ODEs are solved by the 4-order Runge-Kutta method.

In the first sequencing cycle, the original value of DNA, is set to 0.05, and DNA (k>0) to 0. The final values of $DNA_k$ (k≥0) are set to be the original value of the next cycle. Concentrations of other species are reset to values listed in the table. By alternating the origin value of dN4P in every cycle, the flowgram of the sequencing process was simulated. The final values of Fluorescein are viewed as the signal of each cycle.

Figure 27A:
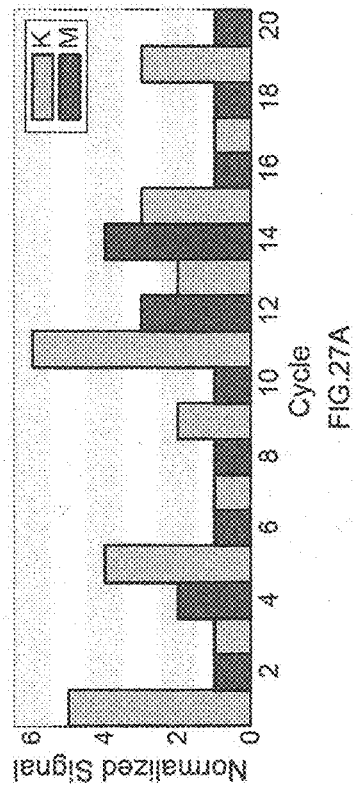
FIGS. 27A-F show simulated sequencing signal (left) and DNA concentration distribution in different positions (right). Color bar: DNA proportion.
Figure 27B:
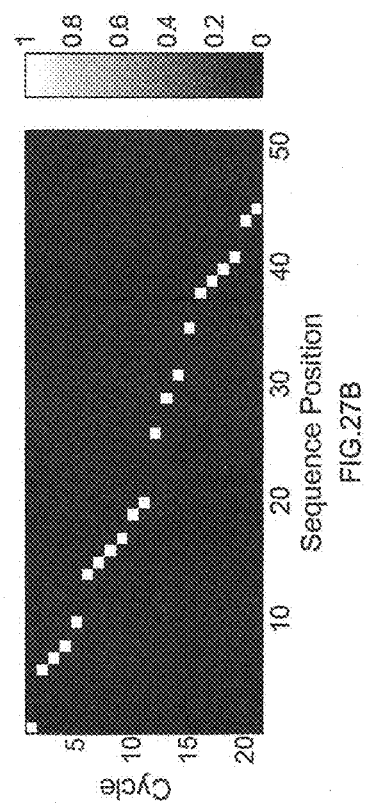

In a 2+2 sequencing simulation by the virtual sequencer program, if the concentrations of the main dN4P specie are sufficient and there exist no impurities in the modified nucleotides, the signals it gives out in every cycle are proportional to the length of each copolymer, and all nascent DNA molecules will have exactly the same length (FIGS. 27A-B). The sequence used in the simulation is L10115-301, and the base combination is M/K.

Figure 27C:
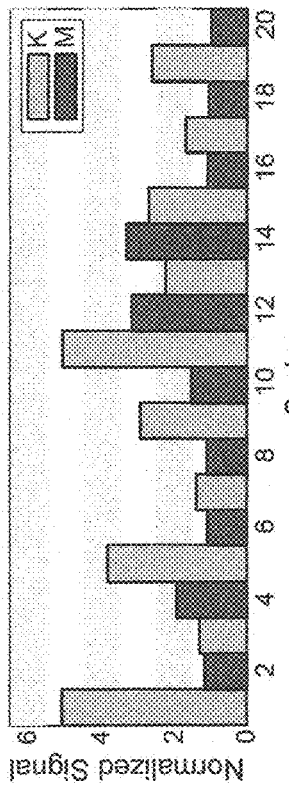
Figure 27D:
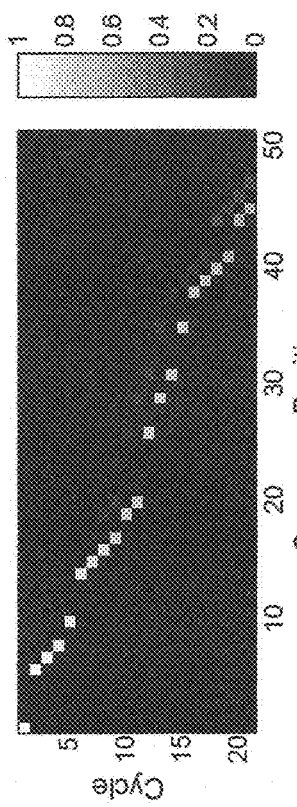
Figure 27E:
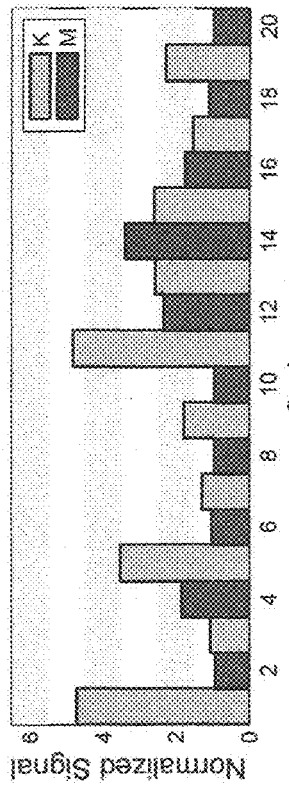
Figure 27F:
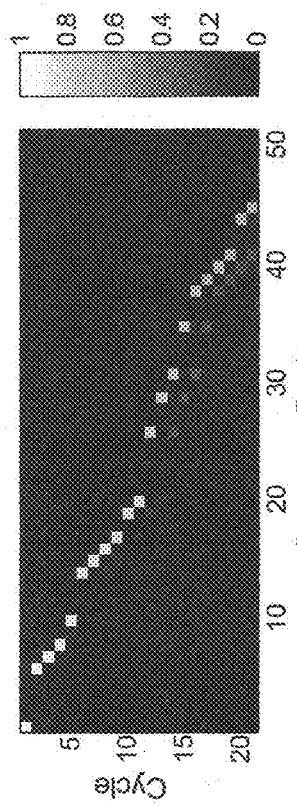

When there exist impurities in the modified nucleotides or the reaction time is insufficient, the dephasing phenomenon will occur and the sequencing signals are no longer proportional to the length of their corresponding copolymer length. By the virtual sequencer program, the influence of impurities and reaction time on sequencing signals was assessed, and the concentration distribution of nascent DNA molecules was monitored. When there exist impurities and the reaction time is sufficient, the leading effect is observed (FIGS. 27C-D). And when no impurities exist but the reaction time is insufficient, the lagging effect is observed (FIGS. 27E-F).

4.2.2. The One Pass, More Stop principle

Figure 28A:
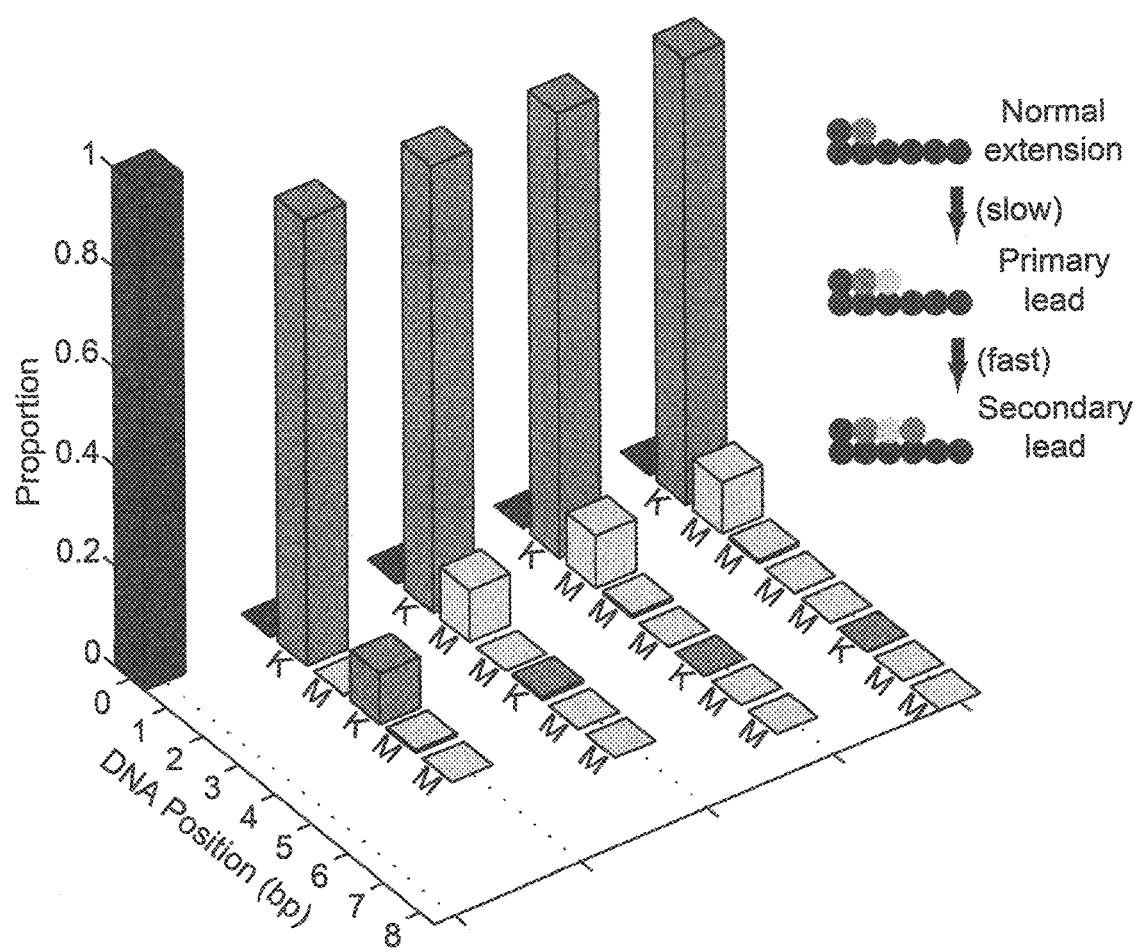
FIG. 28A shows the One Pass, More Stop principle.

In order to observe the impact of dephasing on the distribution of nascent DNA molecule extension lengths, the virtual sequencer program was used to simulate the sequencing reactions by ordinary differential equations (ODE). In the simulation, the molecule to be sequenced was set to $K(M)_n KMM$, the main nucleotide specie in the reaction solution to K (G and T), and impurities to M (A and C). Other parameters such as reaction time and kinetic parameters are set to estimated normal values. It was observed that, after the first nucleotide K is extended by the main specie, the successive M is partly extended by the impurities as expected, causing the lead effect. If n=1, then the K next to M will be almost all extended by the main nucleotide species. However, this secondary lead will quickly diminish if n>1 (FIG. 28A). This One Pass, More Stop property enables prediction of the DNA extension length distribution and development of the following correction algorithm (see below).

4.3. Dephasing Correction by Flux Matrix

Suppose in a 2+2 sequencing run, the parameters are defined as follows: N denotes the number of sequencing cycles; M denotes the number of copolymers of the molecule to be sequenced; his a column vector whose element $h_j$ denotes the length of the j-th copolymer; s is a column vector whose element denotes the sequencing signal of Cycle i; $D_{N \times M}$ denotes the distribution matrix, whose element $d_{ij}$ denotes the proportion of nascent DNA molecules with copolymers extended in the sequencing cycle; $T_{N \times M}$ denotes the flux matrix, whose element $t_{ij}$ denotes the proportion of nascent DNA molecules that extend out of (pass through) the j-th copolymer in the i-th sequencing cycle; λ denotes the lagging coefficient, i.e., the proportion of nascent DNA molecules with the same length and NOT extended by the main nucleotide species in a given cycle; ε denotes the leading coefficient, i.e., the proportion of nascent DNA molecules with the same length and extended by the impurity nucleotide species in a given cycle; and h' is a column vector where its element.

$$h'_j = \begin{cases} 1 & h_j > 1 \\ 0 & h_j \leq 1 \end{cases} \qquad (1)$$

Figure 28B:
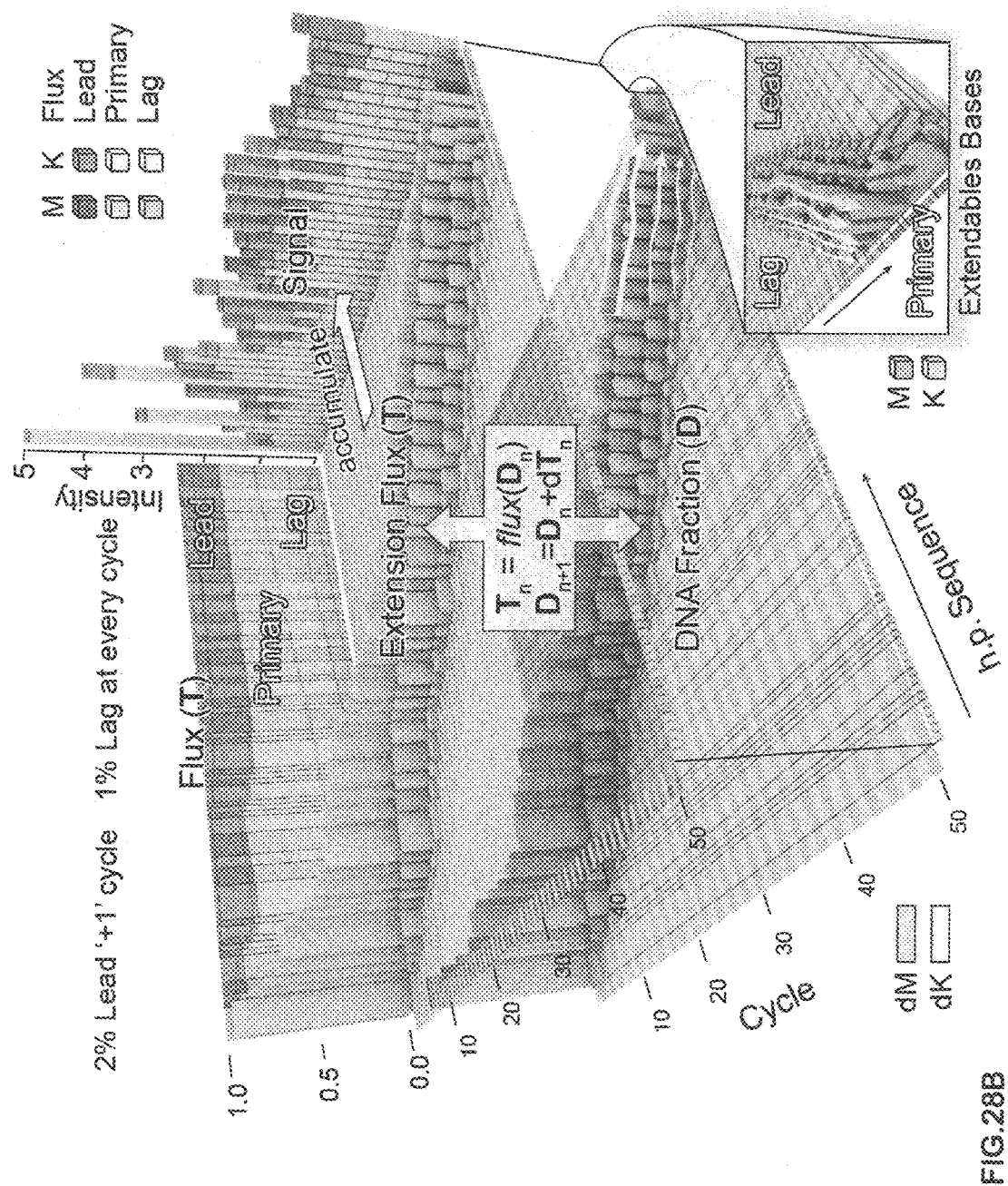
FIG. 28B demonstrates the distribution and flux matrix and their relationship. The lead ε and lag λ coefficients are set to 2% and 1%, respectively. The values of these two coefficients are relatively large in order to show an obvious effect of dephasing, but are not estimation of the experimental data.

As illustrated in FIGS. 27A-F, the dephasing phenomenon leads to signal aberrations and reduce the sequencing accuracy. An algorithm was developed to correct this aberrations caused by dephasing, which will be discussed below in detail. FIG. 28B gives a summary of key concepts and the outline of the correction algorithm. The lower and upper parts of FIG. 28B are the 3D demonstration of the distribution matrix $D_{N \times M}$ and the flux matrix $T_{N \times M}$, respectively. Each entry of D and T is represented as a cuboid, whose dimension along the Sequence Axis is subjected to its corresponding copolymer length. Matrix D and T can be computed in a mutual and iterative manner, and both have positive values in and near its diagonal and zeros otherwise. The accumulations of T along the Cycle axis are equivalent to 1, based on the truth that, in the end, all nascent DNA strands are extended over every copolymer. The accumulations of T along the Sequence axis are the measured dephased sequencing signals. Matrix D, T and its accumulations along the two axes can all be cataloged in three parts: primary, lead, and lag. The primary part is the diagonal of matrix D and T, representing nascent DNA strands with the right expected length. The lead and lag parts are the upper triangular and lower triangular parts of matrix D and T, representing nascent DNA strands with length greater than or less than expectation, respectively. As is shown in FIG. 28B in the first few sequencing cycles, the primary part dominates in matrix D, T and its accumulations, and contributes most part of the sequencing signals. However, as the sequencing cycle goes on, the primary part decreases while the lead and lag parts increase, indicating the signal aberrations.

4.3.1. The distribution and flux matrix

The following assumptions are made: 1) no nucleotides are misincorporated in the sequencing reactions, thus not a reason accounting for leading; 2) leading is caused by the impurity nucleotides leftover from the previous cycle; 3) at most one base of each molecule will be extended by the impurity nucleotides in one given cycle; 4) if the copolymer extended by the impurity nucleotides is of length 1, it will be further extended by the main nucleotides, which is called the secondary leading; 5) if the length of the copolymer extended by the impurity nucleotides is greater than 1, secondary leading will not occur; 6) the secondary leading strand will not be further extended by the impurity nucleotides. Assumption 3-6 are based on the fact that the impurity nucleotide species are in trace amount, and are consistent with the simulation result herein by the virtual sequencer program (the One Pass, More Stop principle).

According to the assumptions above, for a given N, M, h, λ and ε, D and T are calculated as follows:

$$D_{ki} = \begin{cases} 1 & i = k = 1 \\ 0 & k = 1, i > 1 \\ D_{k-1,i} - T_{k-1,i} & i = 1 \\ D_{k-1,i} - T_{k-1,i} + T_{k-1,i-1} & i > 1 \end{cases} \quad (2)$$

$$T_{ki} = \begin{cases} (1-\lambda)D_{k,i} & i = 1, \mod(k+i, 2) = 0 \\ 0 & i = 1, \mod(k+i, 2) = 1 \\ (1-\lambda)D_{k,i} + h'_{i-1}T_{k,i-1} & i > 1, \mod(k+i, 2) = 0 \\ \varepsilon(1-\lambda)D_{k,i-1} & i > 1, \mod(k+i, 2) = 1 \end{cases} \quad (3)$$

For example, consider the sequencing of sequence AAGTCTGTAGGAATCACT using combination M/K with 6 cycles, then $h=(2,2,1,3,1,2,2,1,3,1)^T$. Suppose the leading and lagging coefficients are both 0.05, then the matrix D and T are:

$$D = \begin{pmatrix} 1.0000 & 0 & 0 & 0 & 0 & 0 & 0 & 0 & 0 & 0 \\ 0.0500 & 0.9025 & 0.0475 & 0 & 0 & 0 & 0 & 0 & 0 & 0 \\ 0.0500 & 0.0451 & 0.8620 & 0 & 0.0429 & 0 & 0 & 0 & 0 & 0 \\ 0.0025 & 0.0903 & 0.0455 & 0.7780 & 0.0431 & 0.0387 & 0.0020 & 0 & 0 & 0 \\ 0.0025 & 0.0045 & 0.1269 & 0.0389 & 0.7495 & 0.0019 & 0.0739 & 0.0018 & 0 & 0 \\ 0.0001 & 0.0068 & 0.0065 & 0.1534 & 0.0435 & 0.6783 & 0.0393 & 0.0685 & 0 & 0.0035 \end{pmatrix}$$

$$T = \begin{pmatrix} 0.9500 & 0.0475 & 0 & 0 & 0 & 0 & 0 & 0 & 0 & 0 \\ 0 & 0.8574 & 0.0429 & 0.0429 & 0 & 0 & 0 & 0 & 0 & 0 \\ 0.0475 & 0.0024 & 0.8189 & 0.0409 & 0.0407 & 0.0020 & 0 & 0 & 0 & 0 \\ 0 & 0.0857 & 0.0043 & 0.7433 & 0.0370 & 0.0737 & 0.0018 & 0 & 0 & 0 \\ 0.0024 & 0.0001 & 0.1206 & 0.0060 & 0.7120 & 0.0356 & 0.0702 & 0.0035 & 0.0035 & 0 \\ 0 & 0.0064 & 0.0003 & 0.1461 & 0.0073 & 0.6517 & 0.0322 & 0.0651 & 0.0033 & 0.0033 \end{pmatrix}$$

Allowing for the fact that the incorporation rates and impurity content of different nucleotides are also different, different λ and ε are used for the two sequencing mixes.

Dephasing Correction Algorithm

The relationship between h and s is as follows:

$$s = T(h',\varepsilon,\lambda)h \quad (4)$$

Since dim(s)<dim(h), this linear equation is indeterminate, so the Moore-Penrose pseudo-inverse and an iteration algorithm are used to get the minimum norm solution (FIG. 29):

1.

$$\text{Let } h_1 \leftarrow \begin{cases} s_j, & 1 < j \leq N \\ 1, & N < j \leq M \end{cases}$$

2. Calculate matrix and T according to Formula (2) and (3).
3. Let $h_2 \leftarrow T^\dagger(h'_1,\varepsilon,\lambda)s$ where $T^\dagger$ is the pseudo-inverse of T.
4. Compare $[h_2]$ and $[h_1]$, where [ ] is the round operation. Return $h_2$ if they are equal. If not, move to Step 5.
5. Let $h_1 \leftarrow h_2$. Move to Step 2.

Figure 29:
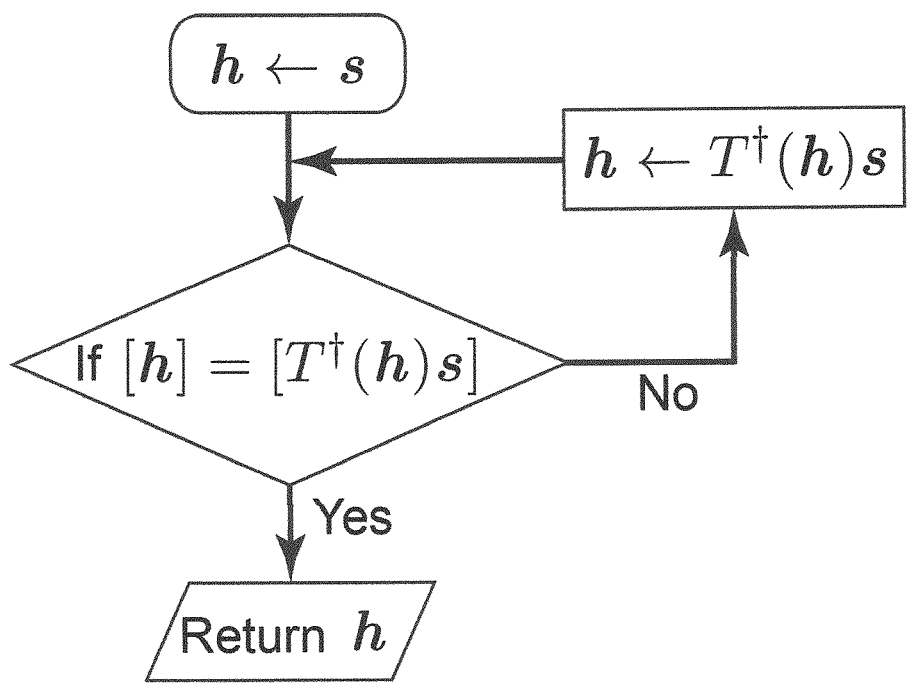
FIG. 29 shows a simplified flowchart of the correction algorithm.
Figure 30:
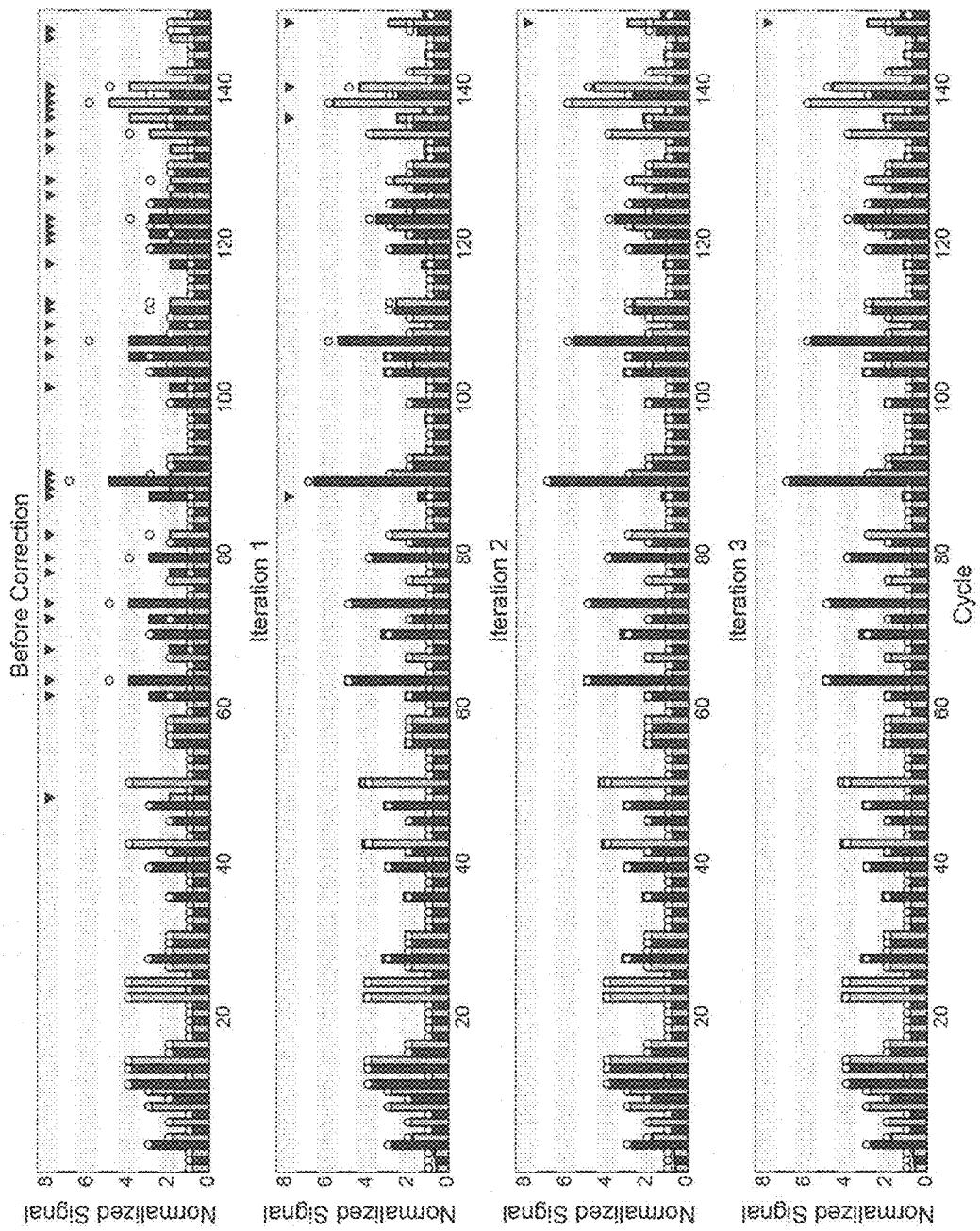
FIG. 30 shows an application of the correction algorithm.

FIG. 29 shows a simplified flowchart of the dephasing correction algorithm. Briefly, the algorithm adopts an iteration method to refine the sequencing signal until it converges. Typically, the iteration will stop in less than 5 cycles. One example of its application to real sequencing data is shown in FIG. 30. FIG. 30 is a demonstration of the refinement process during the iteration of the dephasing correction algorithm.

4.3.2. General solution to equation

The relationship between h and s is as follows:

$$s = T(h',\varepsilon,\lambda)h \quad (4)$$

Figure 31:
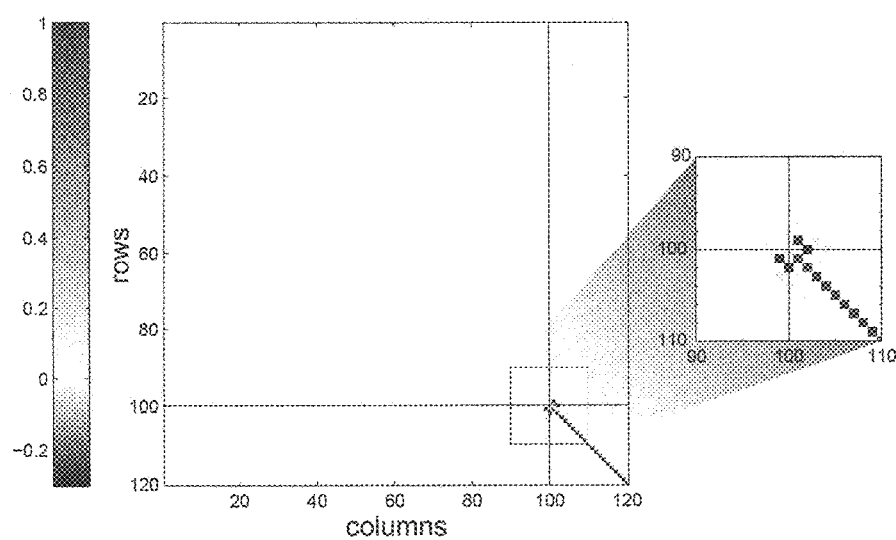
FIG. 31 shows a dephasing correction algorithm.

Since dim(s)<dim(h), this linear equation is indeterminate and there exist infinite number of solutions which all exactly satisfy the equation. And the general form of these solutions can be given below:

$$h = T^\dagger s + [1 - T^\dagger T]w = T^\dagger s + Rw \quad (5)$$

Where I is identity matrix and w is an arbitrary vector. In the dephasing correction algorithm, w is set to zero vector. The term $R = I - T^\dagger T$ is examined to see what effect it will has on h. The sequence is set to be L10115-301, base combination to M/K, lead coefficient to 0.007, lag coefficient to 0.005, sequencing cycle to 100, and found that entries in R between Row 1-99, Column 1-99 are so close to zero ($\sim 10^{-16}$) that they can be seen as calculation errors (FIG. 31, which shows the values of matrix $R = I - T^\dagger T$), thus h is de facto determinant except for the last element.

4.3.3. The robustness of dephasing correction algorithm—condition number

The Moore-Penrose pseudo-inverse matrix is used in the dephasing correction algorithm. For the flux matrix T, the condition number is defined as:

$$\text{cond}(T) = \|T\|\|T^\dagger\| \quad (6)$$

Figure 32:
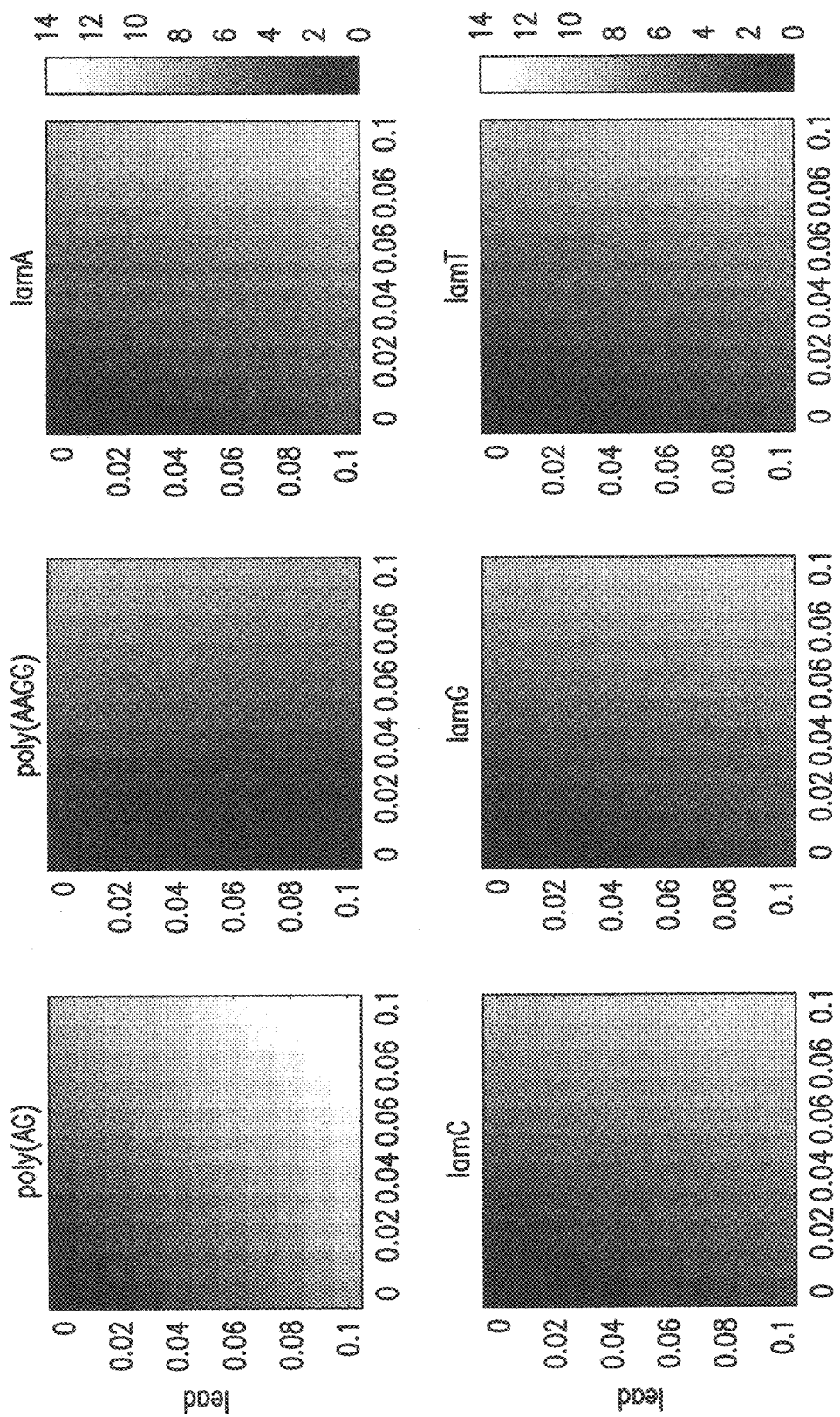
FIG. 32 shows the influence of dephasing coefficients on the condition number of T.

A large condition number implies that small errors in the entries of T can lead to huge errors in the entries of the solution. The influence of dephasing coefficients on the condition number of T was evaluated. Sequence adopted were poly(AG) (AGAGAG . . . ), poly(AAGG) (AAGGAAGG . . . ), L718-308, L4418-305, L9730-303, and L10115-301, and the base combination was M/K. The leading and lagging coefficients used for evaluation were 0, 0.01, 0.02, 0.03, 0.04, 0.05, 0.06, 0.07, 0.08, 0.09 and 0.1. For each sequence and dephasing coefficients, the flux matrix T according to formula (3) and its condition number according to formula (6) were calculated. FIG. 32 shows the logarithm of the condition number at different dephasing coefficients. In all the sequences except poly(AAGG), increased leading or lagging coefficient both leads to the increase of condition number, indicating the more the molecules dephased, the worse the correction would be. However, in sequence poly(AAGG), whose DPLs are all equal to 2, increased leading coefficient leads to the decrease of condition number. This implies that long DPLs (with length >2) have a significant retardant effect on dephasing.

4.3.4. Algorithm robustness

A) Impact of Dephasing Coefficient Deviation on Signal Correction

Figure 33A:
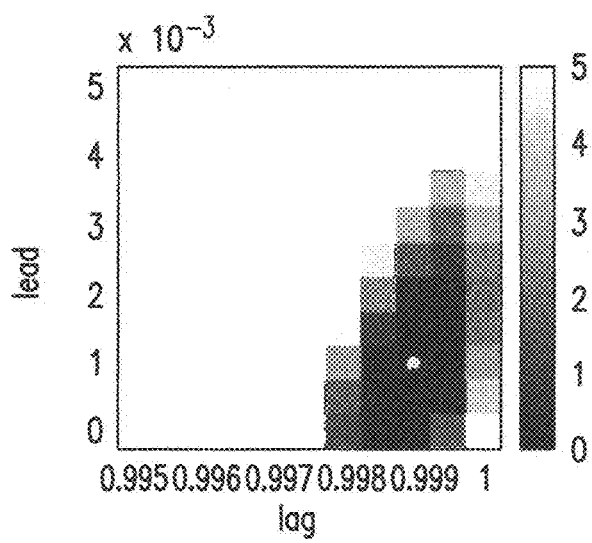
FIGS. 33A-C show the impact of dephasing coefficient deviation on signal correction.
Figure 33B:
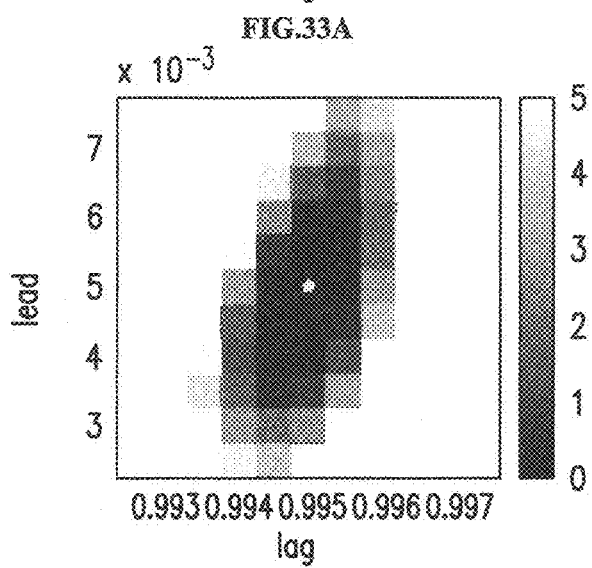
Figure 33C:
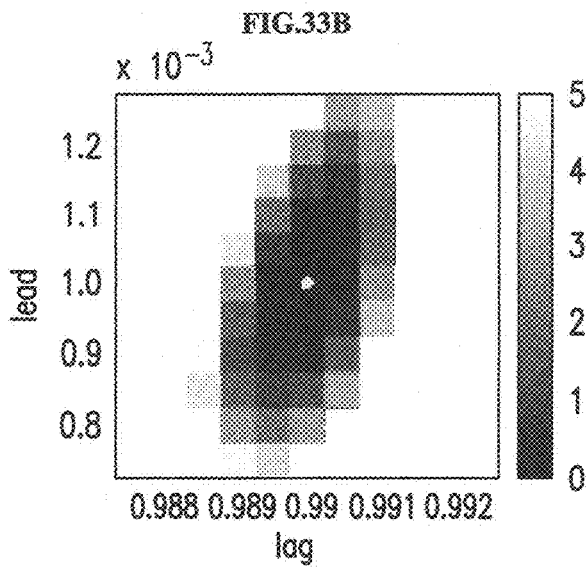
Figure 34A:
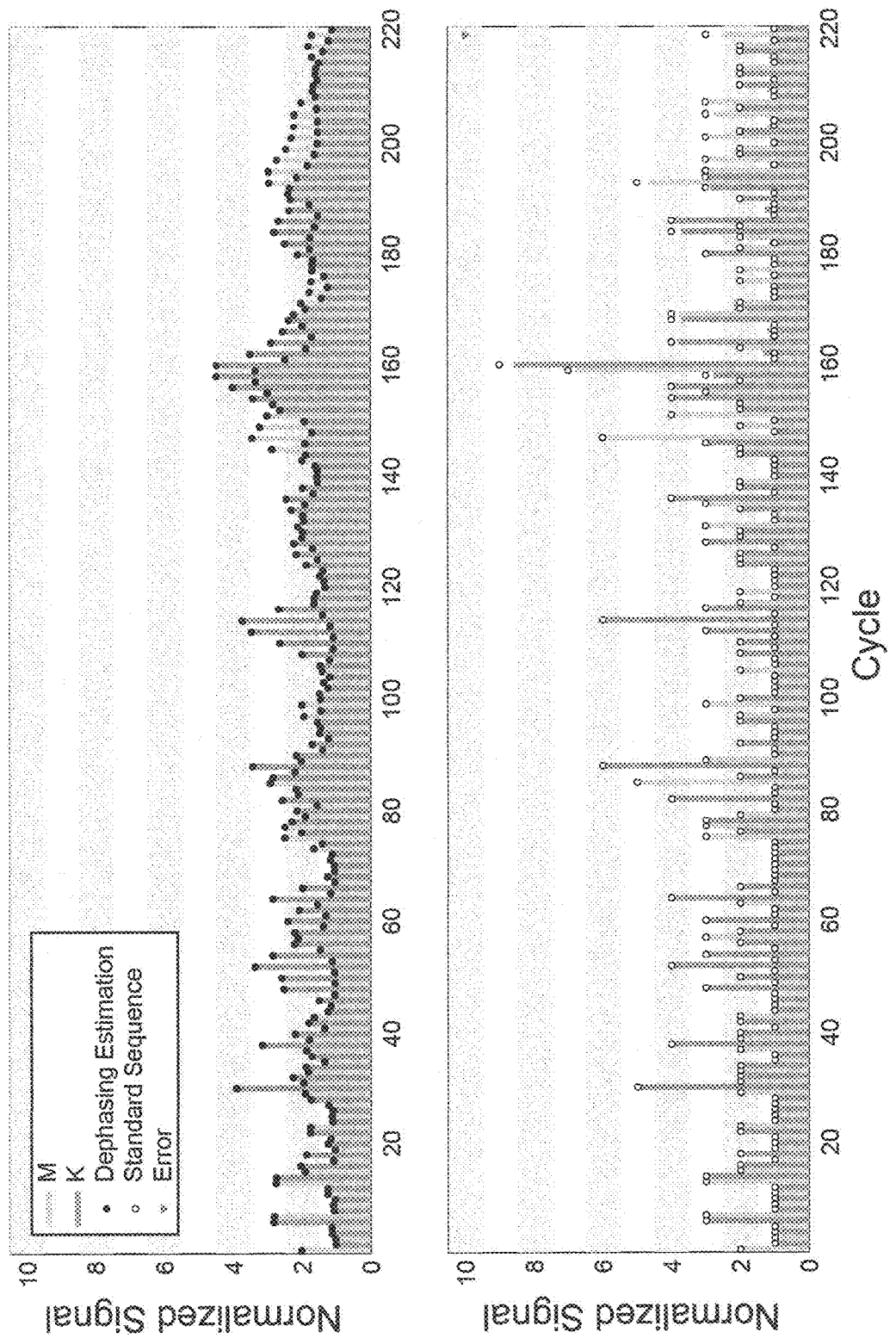
FIGS. 34A-C show that global white noise will reduce the accuracy of the corrected signal and make the latter cycles error-prone.
Figure 34B:
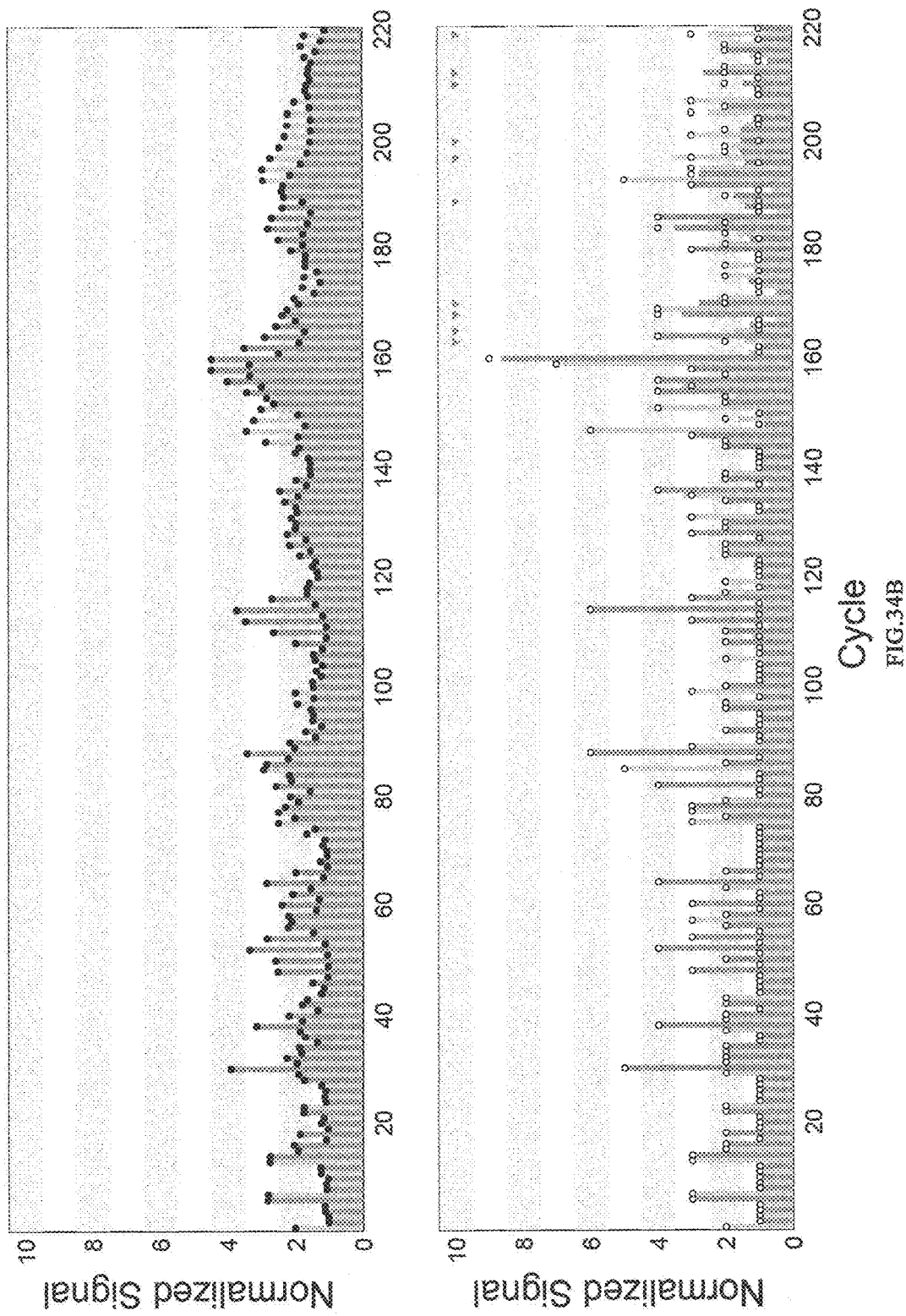
Figure 34C:
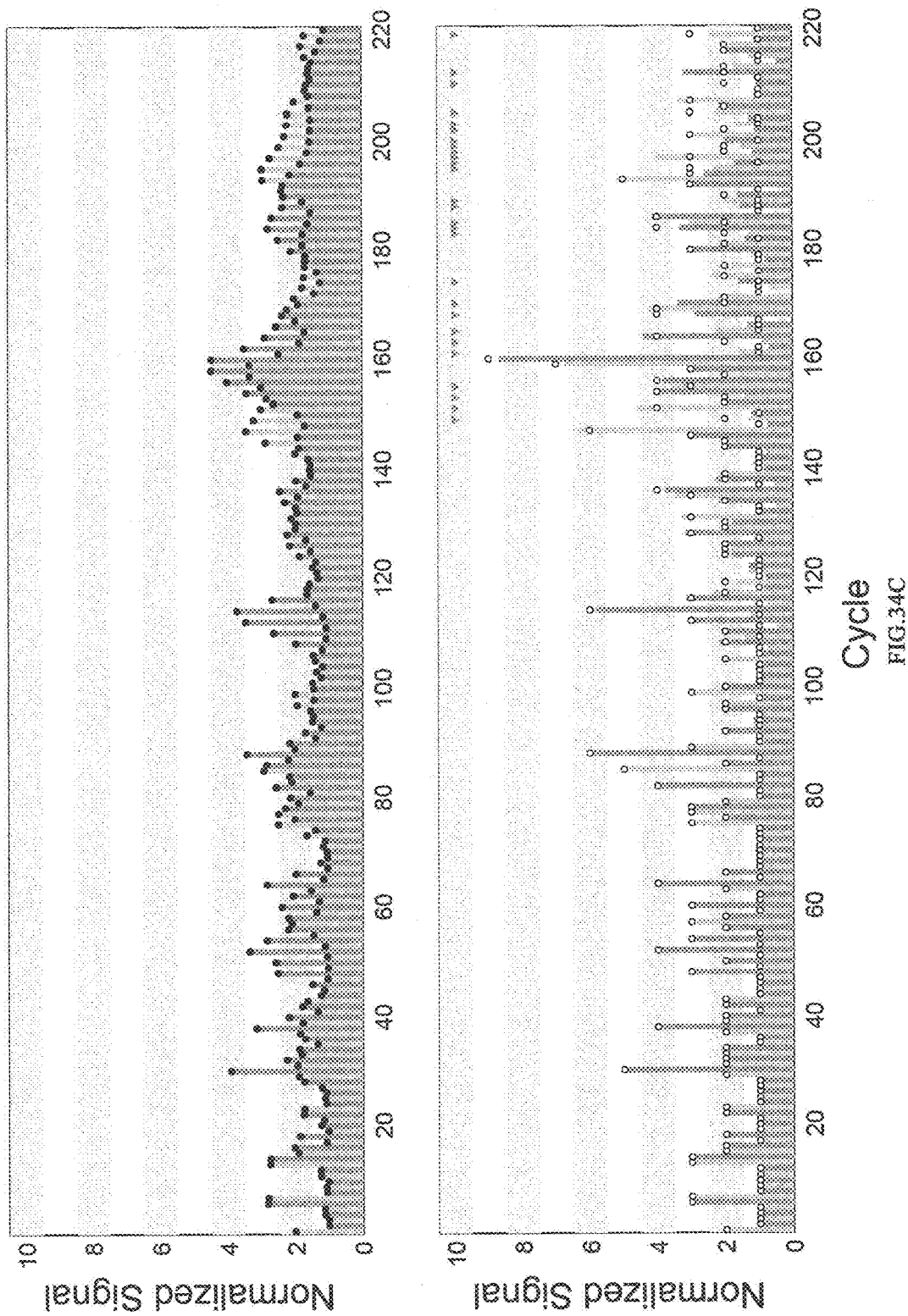

The dephasing coefficients are obtained through fitting signals of reference sequences and are used for correction of other unknown sequences. In ideal cases, the dephasing coefficients are identical for both reference and unknown sequences. However, slight differences inevitably exist between the two groups due to random reasons. Thus it is necessary to test how many errors it will produce in the dephasing correction if the coefficients are inaccurate. 100 DNA sequences with 370 bp were randomly generated, and their dephased signals in given dephasing coefficients were calculated and corrected using different but very close coefficients. The base combination is set to M/K, the sequencing cycle number is 150, and the tested given dephasing coefficients are 0.001, 0.005 and 0.010, respectively. Since the correction algorithm will produce errors in the last few cycles even with accurate dephasing coefficients, the difference of error numbers between using accurate and inaccurate dephasing coefficients is used to characterize the performance, whose average is illustrated in FIG. 33A-C, which show the impact of dephasing coefficient deviation on signal correction. The star in each panel dictates the position of the accurate coefficient, and the color bar is limited to range 0-5, so any error number greater than 5 is shown as deep red. The results show that the more the dephasing coefficients deviate, the more errors it will produce, and the tolerance to deviation of leading is relatively greater than that of lagging.

B) Tolerance to global noise

The sequencing signal noise may come from out-of-focus imaging, CCD imaging, fluid or instability or anomaly, etc. The impact of global white noise on dephasing correction was examined. A 2+2 sequencing run with 220 cycles was first simulated by the virtual sequencer. In the simulation, the sequence was set to L8703-1012, base combination was M/K, the reaction time was 130, and the concentration of the main specie and impurity were 2 and 0.002, respectively. All the signals in the simulation with white noise were added and corrected using the algorithms described above. When the standard variation $\sigma$ of the white noise was 0, the algorithm fitted the signal precisely (with correlation 0.9996) and there was only 1 error in the corrected signal (Cycle 219). However, when $\sigma$=0.01, the algorithm was also able to fit the signal well (with correlation 0.9994), but more errors occurred in the corrected signal (Cycle 1162 were error-free, and 10 error cycles from Cycle 163 to Cycle 220). And the corrected signal was even less precise when $\sigma$=0.02 (Cycle 1-148 were error-free, and 27 error cycles from Cycle 149 to Cycle 220). These results indicated that global white noise will reduce the accuracy of the corrected signal and make the latter cycles error-prone.

Figure 35:
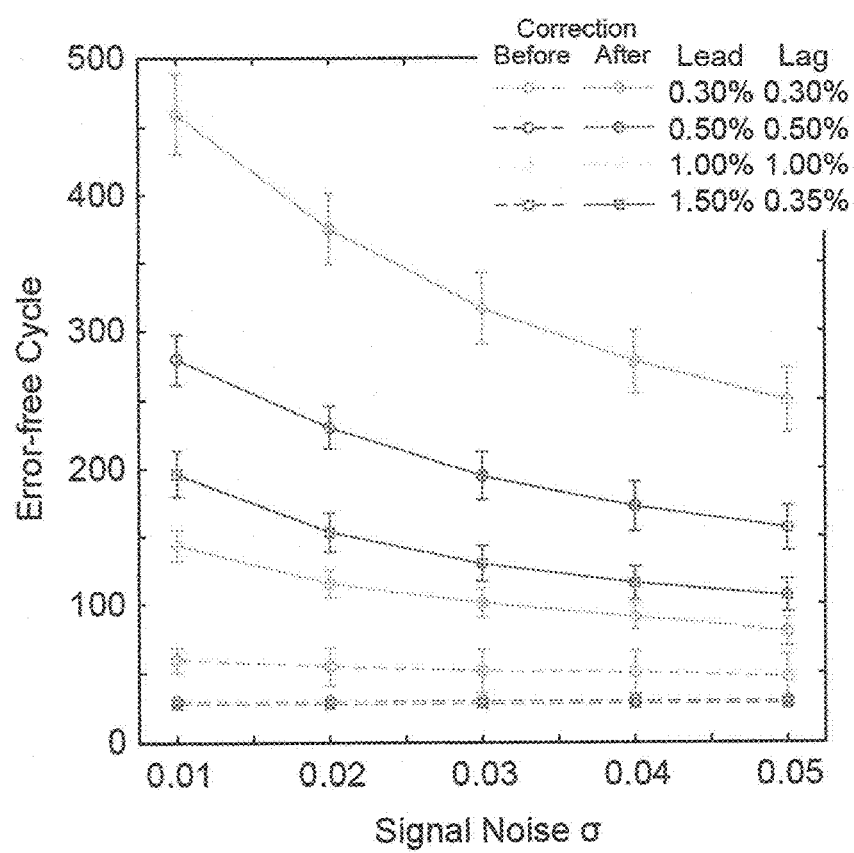
FIG. 35 shows the number of error-free cycles after dephasing correction under given dephasing coefficients and global white noise.

The number of error-free cycles after dephasing correction under given dephasing coefficients and global white noise was next examined. The dephased signal according to Formula (4) was calculated, white noise was added, and the signals were corrected using the algorithms described above. The sequence used in the simulation was 1am1, the base combination was M/K, the number of sequencing cycle was 500, and each condition (a given dephasing coefficient and standard variation of the white noise) was repeated for 100 times. The term number of error-free cycles was defined as $n_{ef}$ if the first error in the corrected signal occurs in Cycle ($n_{ef}$+1.) When the dephasing coefficient is as low as 0.30% and $\sigma$=0,01, only about 50 cycles are error free, but all errors are corrected after correction. As the dephasing coefficient or the noise increase, the number of error-free cycle after correction also decreases, but still at least 3 times than that before correction (FIG. 35, which shows the number of error-free cycles after dephasing correction under given dephasing coefficients and global white noise.). These results demonstrate the effectiveness of the correction algorithm in increasing the length of the read and the negative effect of noise on read length.

C) Tolerance to spike noise

Figure 36A:
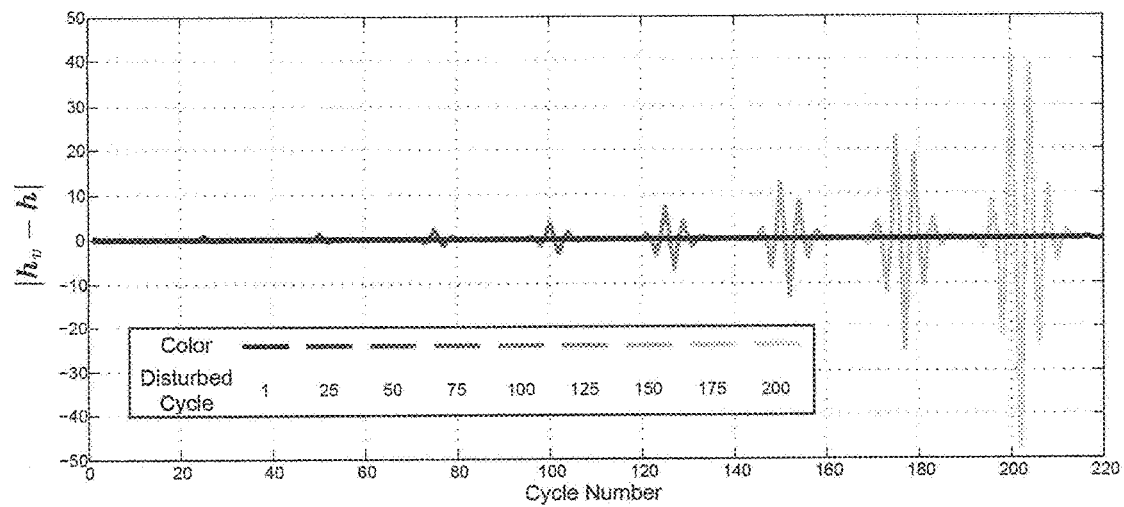
FIGS. 36A-B show the effect that a signal in a certain cycle was abnormal.

The effect that a signal in a certain cycle was abnormal was also examined. The dephased signal s according to Formula (4) was calculated and corrected to h. Then the signal was enhanced in a certain single cycle with given spike and got the varied signal $s_v$ and corrected $s_v$ to $h_v$. The sequence used in the simulation is L29732-497, base combination is M/K, the number of sequencing cycles is 220, the spike tested were 0.01, 0.1 and 0.5, the dephasing coefficients tested were 0.001, 0.005 and 0.01, and the cycles adding spike were Cycle 1, 25, 50, 75, 100, 125, 150, 175 and 200. In the case of dephasing coefficient 0.01 and spike 0.5 (FIG. 36A), the same spike causes more severe disturbance in latter cycles than that in former cycles. If the spike is added to Cycle 200, the maximum difference between $h_v$ and h can reach 47.5, despite a small spike of 0.5. In addition, adding a spike in a single cycle will cause aberration of $h_v$ in adjacent cycles. Similar phenomenon is observed in other conditions.

Figure 36B:
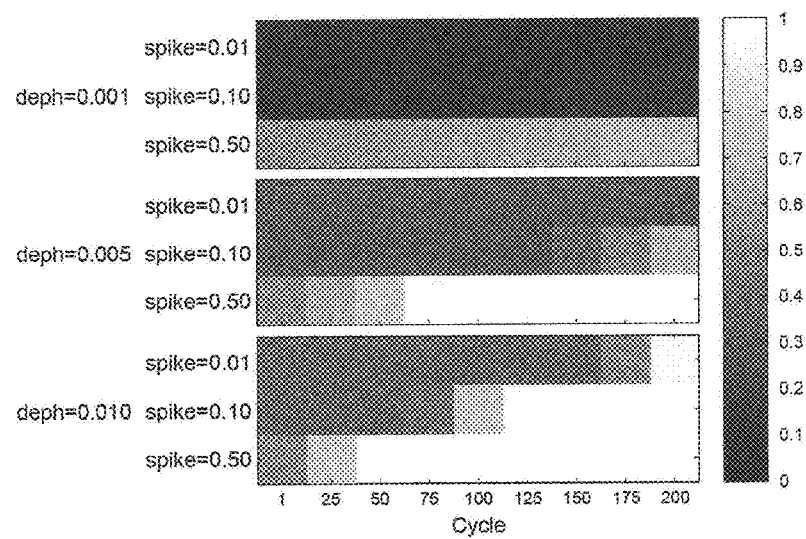

The heat map of the maximum of $|h_v-h|$ in each condition was plotted and the range of the color map was set to [0, 1] (FIG. 36B). The maximum of $|h_v-h|$ increases when either dephasing coefficients, the added spikes or the cycle number increases. These results indicated that as the nascent DNA lengths get more dispersed in the sequencing, the signal is less robust to noise as the abnormality of sequencing signal in one cycle will lead to deviation in more adjacent cycles of the corrected signal.

4.4. Dephasing Coefficients Determination (Fitting)

The leading and lagging coefficients can be estimated from the sequencing results of reference DNA molecules, i.e., molecules with known sequences.

For a given copolymer length array h, leading coefficient $\varepsilon$ and lagging coefficient $\lambda$, the sequencing signal will be:

$$s = T(h', \varepsilon, \lambda)h \qquad (4)$$

Let f be the array of raw fluorescent signals directly collected by the CCD of the sequencer, and $s^{(1)}$, $s^{(2)}$ be the parity split of s, i.e., $$s^{(1)} = \begin{cases} s_j & \text{if } j \text{ is odd} \\ 0 & \text{if } j \text{ is even} \end{cases} \qquad (7)$$

$$s^{(2)} = \begin{cases} s_j & \text{if } j \text{ is even} \\ 0 & \text{if } j \text{ is odd} \end{cases} \qquad (8)$$

And

-continued $$s^{*(1)} = \begin{cases} 1 & \text{if } j \text{ is odd} \\ 0 & \text{if } j \text{ is even} \end{cases} \quad (9)$$

$$s^{*(2)} = \begin{cases} 1 & \text{if } j \text{ is even} \\ 0 & \text{if } j \text{ is odd} \end{cases} \quad (10)$$

So the relationship between f and $s^{(1)}$, $s^{(2)}$ is:

$$f = a \cdot b^t(s^{(1)} + s^{(2)}) + cs^{*(1)} + ds^{*(2)} + \xi \quad (11)$$

where a, b, c, d and $\xi$ are the unit sequencing signal, the decay coefficient, the signal offset for the two sequencing mixes and the white noise term. And t is an array recording the cycle numbers, i.e., $t=[1, 2, \ldots, N]^T$.

So for any given h, $\varepsilon$ and $\lambda$, s can be calculated and a set of a, b, c and d can be found that best fit formula (5). The best $\varepsilon$ and $\lambda$ are then determined by the gradient descend strategy. The whole algorithm is:
1. Define $x = (\varepsilon, \lambda)$. Define function $F(x)$ as follows: calculate s according to h and x by Formula (4); find a*, b*, c* and d* that best fit Formula (11) using either trust region reflective or Levenberg-Marquardt algorithm; calculate $\hat{f} = a^* \cdot (b^*)^t(s^{(1)} + s^{(2)}) + c^*s^{*(1)} + d^*s^{*(2)}$ and use the Pearson correlation coefficient between f and $\hat{f}$ as the function value of $F(x)$.
2. Set the original value of $\varepsilon$ and $\lambda$ to $\varepsilon_0 = \lambda_0 = 0.001$ or any other reasonable value. Set step length and to arbitrary small positive numbers, say 0.01.
3. Consider the sequence $x^{(0)}, x^{(1)}, x^{(2)}, \ldots$ such that $$\begin{cases} x^{(0)} = (\varepsilon_0, \lambda_0) \\ x^{(n+1)} = x^{(n)} + \gamma_s \cdot \text{grad } F(x^{(n)}) \end{cases} \quad (12)$$

Where $$\text{grad } F(x^{(n)}) = \left( \frac{\partial F}{\partial x_1^{(n)}}, \frac{\partial F}{\partial x_2^{(n)}} \right) \approx \quad (13)$$

$$\left( \frac{F(x_1^{(n)} + \gamma_g, x_2^{(n)}) - F(x^{(n)})}{\gamma_g}, \frac{F(x_1^{(n)}, x_2^{(n)} + \gamma_g) - F(x^{(n)})}{\gamma_g} \right)$$

4. Stop iteration if $|F(xx^{(n+1)}) - F(x^{(n)})| < \in$, where $\in$ is an arbitrary small positive number, say $10^{-6}$.

If different dephasing coefficients are considered for each sequencing mix, then x is defined as $x = (\varepsilon_1, \varepsilon_2, \lambda_1, \lambda_2)$ instead, and the rest can be done in the same manner.

Figure 37A:
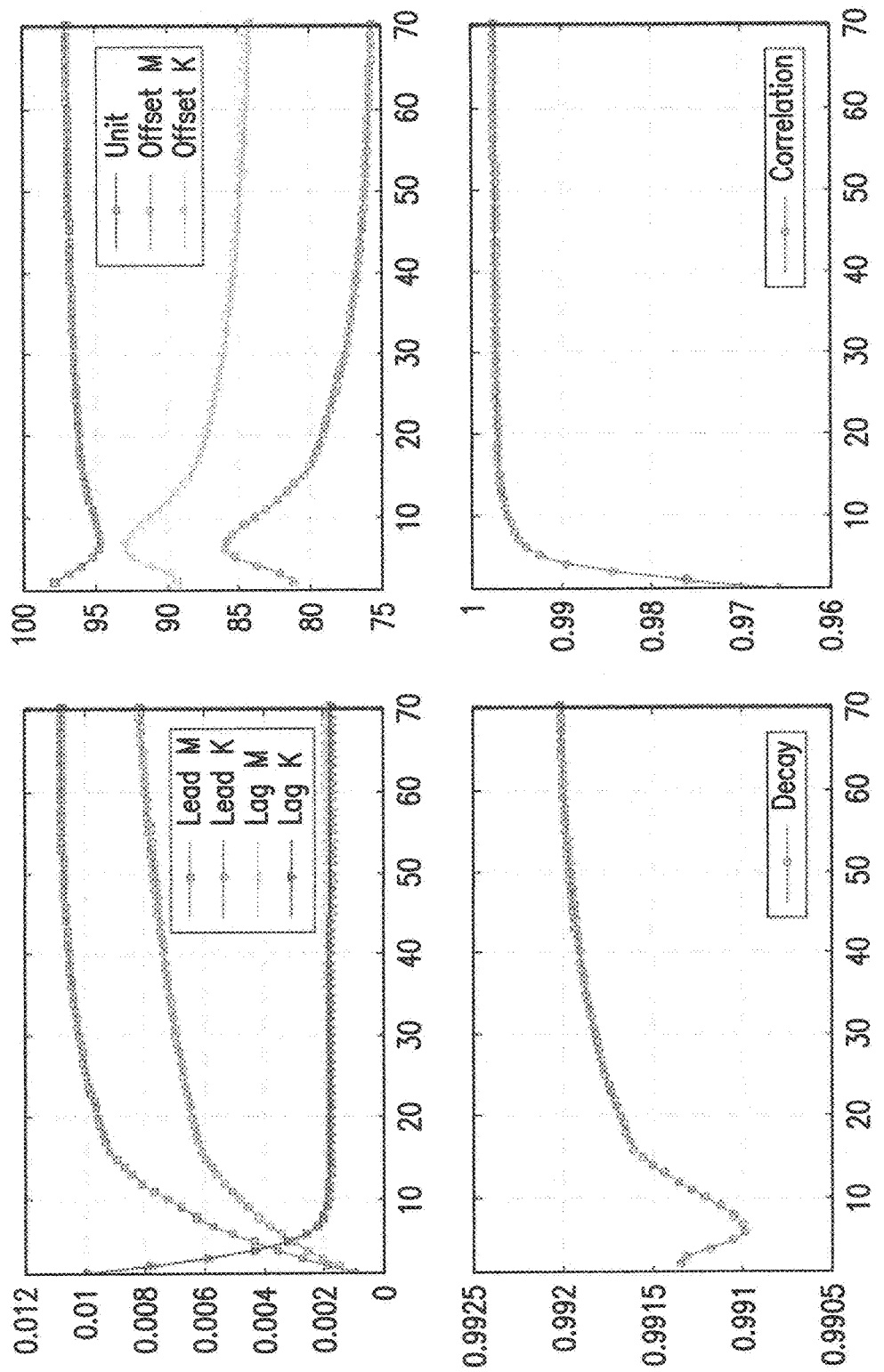
FIG. 37A shows the changing trajectories of each coefficient in the dephasing coefficient estimation algorithm.

4.4.1. Coefficient changing trajectory; Summary of dephasing coefficients; and Relationship between dephasing coefficients and sequencing reaction time Coefficient Changing Trajectory In one typical sequencing round, the fluorescent signal was fitted to the DNA sequence using the dephasing coefficient estimation algorithm, and the changing trajectories of each coefficient is depicted in FIG. 37A, which shows the changing trajectories of each coefficient in the dephasing coefficient estimation algorithm. X label: iteration times. All coefficients are convergent to constant values during the iteration, implying an accurate estimation of the coefficients.

Summary of Dephasing Coefficients

Figure 37B:
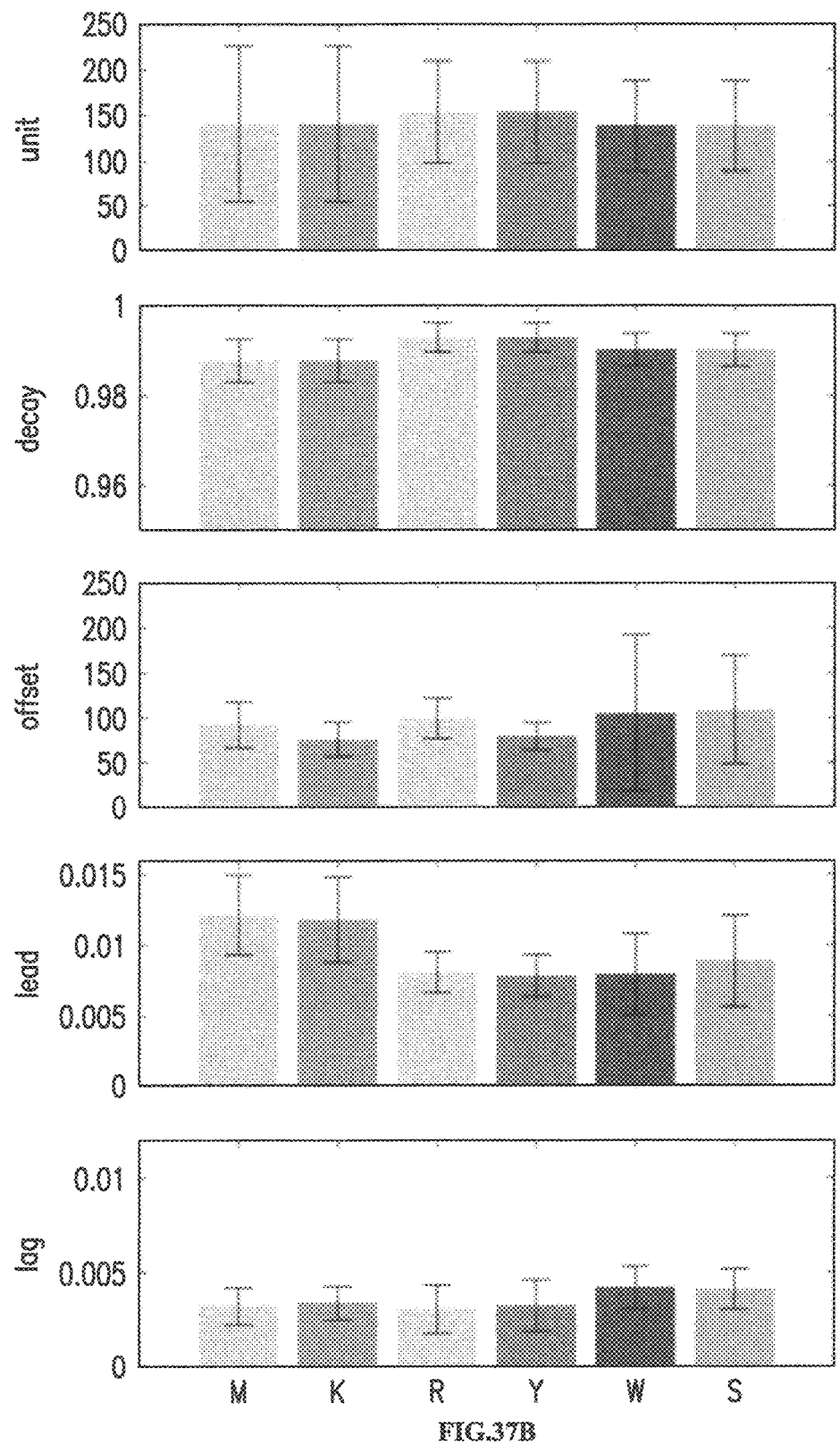
FIG. 37B summarizes dephasing coefficients in multiple sequencing rounds.

The dephasing coefficients in all sequencing rounds were counted and summarized in FIG. 37B (dephasing coefficients. Error bar: standard variance). The symbol a, b, c and d in Formula (11) are termed as unit, decay and two offsets.

Relationship between dephasing coefficients and sequencing reaction time

Figure 37C:
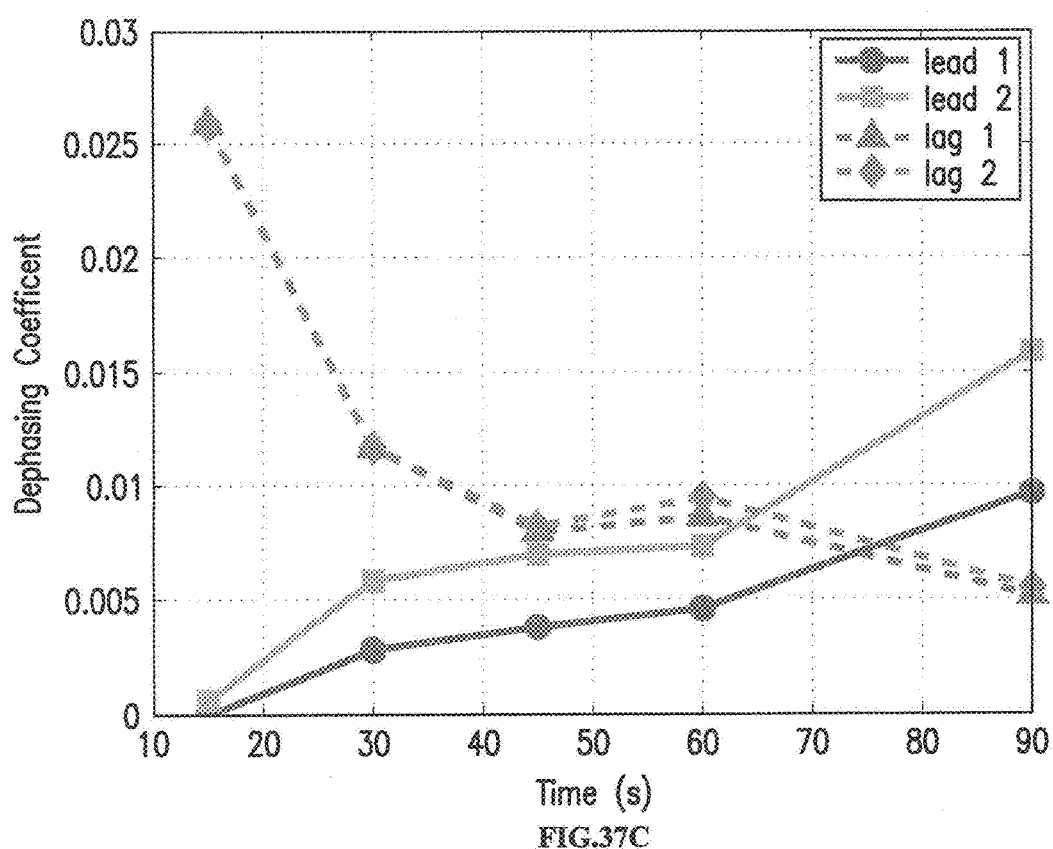
FIG. 37C shows the relationship between dephasing coefficients and sequencing reaction time.

To examine the relationship between dephasing coefficients and the sequencing reaction time, five 2+2 sequencing runs were performed successively in the same lane, increasing reaction time from 15s to 90s every run. The DNA template in the experiment is L4418-305, the base combinations are all M/K, and the numbers of sequencing cycle are all 40. The sequencing signals of each run was fitted using the algorithm described above, and found that increased reaction time leads to the increase of leading coefficient and the decrease of lagging coefficient. The final reaction time for the other sequencing experiments is adopted to be 60s, allowing for a trade-off of both leading and lagging coefficients. FIG. 37C shows the dephasing coefficients under different reaction times.

Section 5: Decoding 5.1. Characteristics of different sequencing flowgrams 5.1.1 Information entropy of DNA For a sufficiently long DNA molecule of length d, if the type of each base is independent and the probability of the occurrence of each type of base is equal, i.e., $$P(\text{position}=i, \text{base}=j) \equiv \frac{1}{4}, j \in \{A, C, G, T\}$$

Then the Shannon entropy of this DNA molecule is $$H_{DNA} = d \cdot \frac{1}{4} \log_2 4 = 2d \text{ bits}$$

5.1.2 Information Entropy of Pyrosequencing

In this example, the term "degenerated sequence of a DNA molecule" is used to describe the sequence which has the same order of nucleotide type but whose homopolymer lengths are all equal to 1. For example, the degenerated sequence of 'ATTCCCG' is 'ATCG'.

In this example, the term "dark cycle" is used to describe a reaction cycle in 1×4 sequencing of which the signal intensity is 0.

Consider a 1×4 sequencing process with flowgram (T, C, A, G, T, C, A, G, ...). Without loss of generality, suppose Cycle 1 is not a dark cycle and the nucleotide delivered is T. The type of second homopolymer would be either C, A or G, with equal probability of ⅓. If the second homopolymer is C, Cycle 2 would not be a dark cycle. If the second homopolymer is A, Cycle 2 is a dark cycle and Cycle 3 is not. If the second homopolymer is G, Cycle 2 and 3 are both dark cycle and Cycle 4 is not. So the probability distribution of the number of dark cycles between two non-dark cycles $N_{dark}$ is as follows:

| | $N_{dark}$ | | |
|---|---|---|---|
| | 0 | 1 | 2 |
| Probability | ⅓ | ⅓ | ⅓ |

So the expectation of n is $N_{dark}$ is $EN_{dark} = 0 \times \frac{1}{3} + 1 \times \frac{1}{3} + 2 \times \frac{1}{3} = 1$. Namely, the ratio of number of non-dark cycle and dark cycle is 1:1.

The probability of signal intensity x in a non-dark cycle is:

$$P_{1 \times 4}(x = i, i > 0) = \frac{3}{4^i}$$

The average signal intensity of a non-dark cycle (expectation) is:

$$L_{1\times4}^+ = \sum_{i=1}^{\infty} i \cdot \frac{3}{4^i} = \frac{4}{3}$$

Because the ratio of number of non-dark cycle and dark cycle is 1:1, the average signal intensity (expectation) of arbitrary 1×4 sequencing cycle is:

$$L_{1\times4} = (L_{1\times4}^+ + 0)/2 = \frac{2}{3}$$

The expected cycles for sequencing through a DNA molecule with length d is:

$$N_{1\times4} = \frac{d}{L_{1\times4}} = 1.5\,d$$

The Shannon entropy that a single signal of a 1×4 sequencing is:

$$H_{1\times4} = \frac{H_{DNA}}{N_{1\times4}} = \frac{4}{3}\ \text{bits}$$

Notice that if considering a single signal of a 1×4 sequencing without any prior knowledge of its previous cycle, the probability of signal intensity is:

$$P_{1\times4}(x = i) = \begin{cases} 1/2 & i = 0 \\ \dfrac{3}{2\cdot(4)^i} & i > 0 \end{cases}$$

The average signal intensity remains the same:

$$L'_{1\times4} = \frac{1}{2}\cdot 0 + \sum_{i=1}^{\infty} i \cdot \frac{3}{2\cdot(4)^i} = \frac{2}{3} = L_{1\times4}$$

But the Shannon entropy turns out to be:

$$H'_{1\times4} = -\frac{1}{2}\cdot\log_2\frac{1}{2} - \sum_{i=1}^{\infty}\left(\frac{3}{2\cdot(4)^i}\cdot\log_2\left(\frac{3}{2\cdot(4)^i}\right)\right) =$$

$$\frac{7}{3} - \frac{1}{2}\log_2 3 \approx 1.5409\ \text{bits} > H_{1\times4}$$

And:

$$H'_{1\times4} \times N_{1\times4} = 2.31d > H_{DNA}$$

This counterintuitive phenomenon is due to the fact that the signal intensities of each cycle in the same 1×4 sequencing run are not independent, thus their Shannon entropy cannot be simply summed up together.

5.1.3 Information entropy of ECC sequencing (monochromatic)

The probability of signal intensity x in 2+2 sequencing is:

$$P_{sm}(x = i) = \frac{1}{2^i}$$

So the average signal intensity of 2+2 sequencing is:

$$L_{sm} = \sum_{i=1}^{\infty} \frac{i}{2^i} = 2$$

The Shannon entropy of a single mono-color 2+2 sequencing signal is:

$$H_{sm} = \sum_{i=1}^{\infty} \frac{\log_2 2^i}{2^i} = 2\ \text{bits}$$

Therefore, one round of monochrome sequencing provides an amount of information $$2 \times \frac{d}{2} = d\ \text{bits}.$$

5.1.4 Information entropy of ECC sequencing (dichromatic)

The probability of signal intensity (x, y) in 2+2 sequencing is:

$$P_{sd}(x = i, y = j) = \frac{1}{2^{i+j}} \cdot \frac{C_{i+j}^i}{2^{i+j}} = \frac{C_{i+j}^i}{4^{i+j}}$$

The Shannon entropy of a single dual-color 2+2 sequencing signal is:

$$H_{sd} = -\sum_{\substack{i=0, j=0 \\ |i+j|>0}}^{\infty} \frac{C_{i+j}^i}{4^{i+j}} \cdot \log_2 \frac{C_{i+j}^i}{4^{i+j}} \approx 3.3731\ \text{bits}$$

Given the fact that the average signal intensity of successive sequencing is 2, it takes d/2 cycles to complete the sequencing. Therefore, one round of two-color sequencing provides an amount of information $$3.3731 \times \frac{d}{2} = 1.6865d\ \text{bits}.$$

Figure 57:
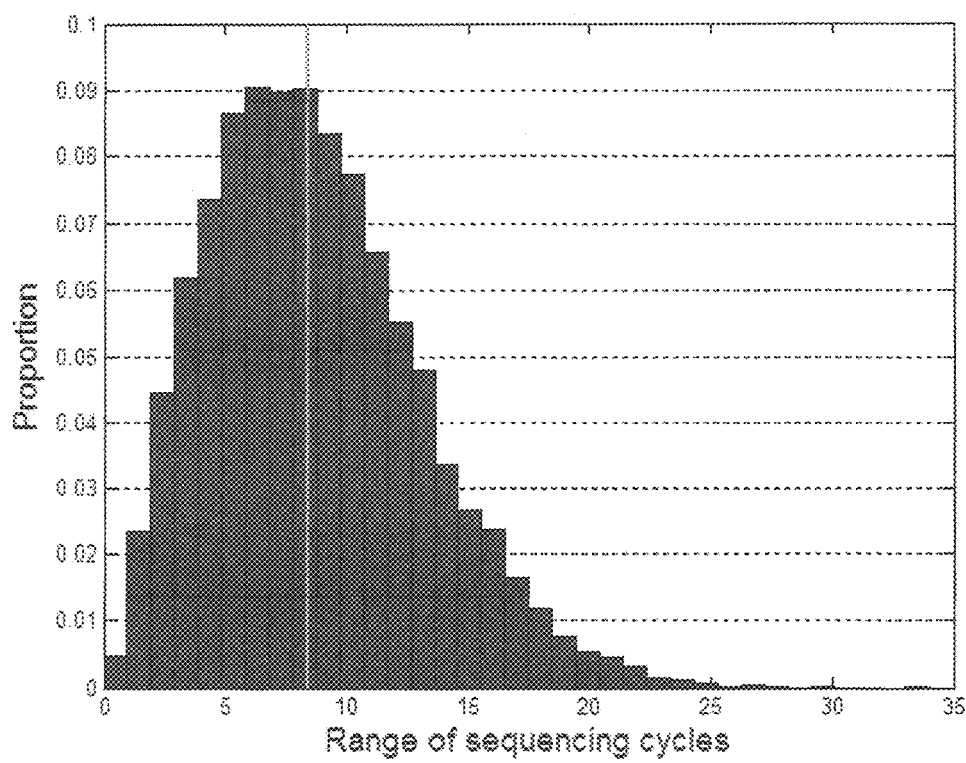
FIG. 57 shows the distribution of the range of cycles by the three base combinations, according to one aspect of the present disclosure.

5.1.5 Difference of Sequencing Reactions Required for the Three Rounds of ECC Sequencing It takes different number of cycles for different base combinations to sequence the same molecule. For example, for sequence 'ACACA', it takes 5 cycles to extend the whole molecule for R/Y, but only 1 cycle for M/K. 10000 different DNA sequences with length 100 bp were randomly generated and the sequencing cycles it takes by the three base combinations, M/K, R/Y and W/S, were calculated. FIG. 57 shows the distribution of the range of cycles by the three base combinations. The average of the range is 8.43, which is indicated by the red vertical line.

5.2 ECC decoding algorithm 5.2.1 Graph representation of signal

Let the homopolymer lengths of the DNA molecule to be sequenced is h, and the signal (after the dephasing correction) in the ECC sequencing be s=($s_1$, $s_2$, . . . , $s_n$). Suppose in Cycle i, the probability for $h_i$ given signal $s_i$ is $P(h_i|s_i)$. So the signals can be represented as a graph described below.

For each signal $s_i$ in s, represent it with $s_i$ nodes. For each node representing signal $s_i$, draw a directed edge from the j-th node to the (j+1)-th node, j=1, 2, ..., $s_i$. Draw a directed edge from the $s_i$-th node (the last node) representing signal $s_i$ to itself. Draw a directed edge from every node representing signal $s_i$ to the first node representing $s_{i+1}$.

Each node in the graph can be labeled 1 or 0 according to the nucleotide species delivered in this cycle.

Next the weight of a path in the graph representing the sequencing signals is defined. A path is defined as a series of nodes $v_1 v_2 \ldots v_K$, in which for every adjacent nodes $v_k$ and $v_{k+1}$, there is a directed edge from $v_k$ to $v_{k+1}$. It is allowed that $v_k$ and $v_{k+1}$ are the same node, and in this case they are the last node representing a signal of a certain cycle.

If in path $v_1 v_2 \ldots v_K$, $v_k v_{k+1} \ldots v_{k+t_i}$ are all the nodes representing signal $s_i$, then these nodes are all assigned with weight $P(t_i|s_i)$. The weight of the path $v_1 v_2 \ldots v_K$ is defined as the product of weights of all its nodes. For computation convenience, the weight of a node can also be assigned as the logarithm of the probability, and the weight of the path is adapted to the sum of all its nodes, respectively.

A path of the graph represents one possible DPLs from the sequencing result, as shown in FIG. 1. Specifically, the edge from the last node representing $s_i$ to itself represents the insertion, and the edge from node representing $s_i$ except for the last one to the first node representing $s_{i+1}$ represents the deletion.

For a DNA molecule, it is sequenced with base combination M/K, R/Y and W/S in order to obtain three signals. Each of the three signals can be represented as a graph as described above. Suppose $v_1^{(1)} v_2^{(1)} \ldots v_k^{(1)}$, $v_1^{(2)} v_2^{(2)} \ldots v_k^{(2)}$, and $v_1^{(3)} v_2^{(3)} \ldots v_K^{(3)}$ are paths from the three graphs respectively and have the same length K: if the parity check of $(v_k^{(1)}, v_k^{(2)}, v_K^{(3)})$ is true for all k=1, 2, ..., K, then these three paths are called a common path for the three graphs. And it is obvious that the decoding problem is actually to find the common path for the three graphs with the maximal weight (maximum common path, MCP).

5.2.2 ECC Decoding by Dynamic Programming

Terms in this Section:

Codeword space and node: A 3D discrete space in which element index [i,j,k] (I, j, k∈N), called a Node, represents the codeword comprise i-th bit of round 1, j-th bit of round 2, and k-th bit of round 3. Codeword space, in compare with BS(degenerate sequence), records every possible codeword alignment in an intuitive way.

Jump: a one-way link between bit to bit.

Connection: a directional link between node to node. A Connection comprises three jumps on different rounds.

Parity of node: is the xor value of three bits of the node.

Preparation of Necessary Variables

Preprocess the binary string (degenerate nucleotide sequence) into query tables, assuming the max length of three binary strings is N.

BS (binary string), a 3*N Boolean matrix, is the binary version of sequencing data. Value 0 (or 1) stands for a degenerate base. For example:

[0,0,1,1,1,0,0,0,1,0,1,1,1,0,0,1,0,0,1,0,0;
0,1,1,1,1,0,0,0,0,1,1,0,0,1,0,1,1,1,1,0,1;
1,0,1,1,0,1,1,1,1,0,0,0,1,0,0,0,1,0,1,1,0;]

CNS (cycle number sequence), a 3*N integer matrix, record the cycle number in which the binary bit (degenerate base) is read out.

[1,1,2,2,2,3,3,3,4,5,6,6,6,7,7,8,9,9,10,11,11;
1,2,2,2,2,3,3,3,3,4,4,5,5,6,7,8,8,8,8,9,10;
1,2,3,3,4,5,5,5,5,6,6,6,7,8,8,8,9,10,11,11,12;]

DPL (degenerated polymer length), a 3*N integer matrix, recorded the DPL of the read out cycle

[2,2,3,3,3,3,3,3,1,1,3,3,3,2,2,1,2,2,1,2,2;
1,4,4,4,4,4,4,4,4,2,2,2,2,1,1,4,4,4,4,1,1;
1,1,2,2, 1,4,4,4,4,3,3,3, 1,3,3,3, 1,1,2,2, 1;]

These tables allow easy query of cycle and DPL information of a bit. Different cycle number indicates two different bit are from different cycles. DPL is an input for score function of dynamic programming. For example, cycle number of 11th bit of round 1 is CNS (1,11)=6, and the DPL (monomers in this cycle) is DPL (1,11)=3.

Initialize alignment variables.

SCORE=numeric matrix, size N*N*N, default NaN

CONNECTION=node matrix, size N*N*N

ROUTABLE=Boolean matrix, size N*N*N, default False, except Routable(1,1,1)=True Query ROUTABLE(node) is True means this node has connections back to node(1,1,1).

STEP=3-element tuple matrix, size N*N*N, default (0,0, 0), except Step(1,1,1)=(1,1,1)

The 3-element tuple of STEP(node) record the number of already-counted bits in this cycle, of the three round of sequencing. STEP value increase by 1 per connection within cycle and reset to 1 in new cycle. When jump cross cycle, STEP value is taken as corrected DPL value.

| Pseudocode of the alignment process |
| --- |
| # construction of SCORE and CONNECTION matrix
FOR L in [1, 2, 3, ..., N]
 \| FOR each Node in all nodes of Layer L
 \| \| # Node traversing has a specific order. See supplement illustration.
 \| \| # Variable Node = (i, j, k)
 \| \| IF parity(Node) == 1 THEN
 \| \| \| ## Finding all routable parent nodes to Node
 \| \| \| FOR R in [1, 2, 3]
 \| \| \| \| list_jump_index(R) <- find all possible jumps to bit R of Node
 \| \| \| \| # Detailed rules see supplement illustration
 \| \| \| ENDFOR
 \| \| \| FOR ii in list_jump_index(1)
 \| \| \| \| FOR jj in list_jump_index(2)
 \| \| \| \| \| FOR kk in list_jump_index(3)
 \| \| \| \| \| \| PNode <- (ii, jj, kk)
 \| \| \| \| \| \| IF ( ROUTABLE(PNode) == 1) and ( PNode is not Node ) THEN
 \| \| \| \| \| \| \| append PNode to list_PNode
 \| \| \| \| \| \| ENDIF
 \| \| \| \| \| ENDFOR
 \| \| \| \| ENDFOR |

| Pseudocode of the alignment process |
| --- |
| ``` 
| | | ENDFOR
| | |
| | | # Traversing all possible parent nodes to filter the local optimal one.
| | | IF list_PNode is not empty THEN
| | | | Routable(Node) <- True
| | | | FOR each PNode in list_PNode
| | | | | jump_score <- [0, 0, 0]
| | | | | FOR R in [1, 2, 3]
| | | | | | IF CNS(R,PNode(R)) == CNS(R,Node(R)) THEN
| | | | | | | jump_score(R) <- 0
| | | | | | Else
| | | | | | | DPL_cor <- STEP(PNode)(R)
| | | | | | | jump_score(R) <- log( Probability(DPL_cor|DPL_obs) )
| | | | | | ENDIF
| | | | | ENDFOR
| | | | | list_connection_score(PNODE) <- sum(jump_score) + Score(PNODE)
| | | | ENDFOR
| | | | PNode = PNode with max score in list_connection_score
| | | | Score(Node) <- max score
| | | | Connect(Node) <- PNode
| | | | # give value to STEP(Node)
| | | | FOR R in [1, 2, 3]
| | | | | IF CNS(PNode(R)) == CNS(Node(R)) Then
| | | | | | STEP(Node)(R) <- STEP(PNode with max score) + 1
| | | | | ELSE
| | | | | | STEP(Node)(R) <- 1
| | | | | ENDIF
| | | | ENDFOR
| | | ENDIF
| | ENDIF
| ENDFOR
ENDFOR
# Trace back the optimal path from SCORE and CONNECTION
Node <- node with max score on L-th layer
WHILE Node is not [1, 1, 1] THEM
| append Node into Path
| Node <- CONNECTION(Node)
ENDWHILE
append (1, 1, 1) into Path
Path <- reverse Path
``` |

Parity(node) checks the parity of node. The binary value of node(i, j, k) are taken from BS(1,i), BS(2,j), BS(3,k). Calculation the xor of the three bits.

Figure 58:
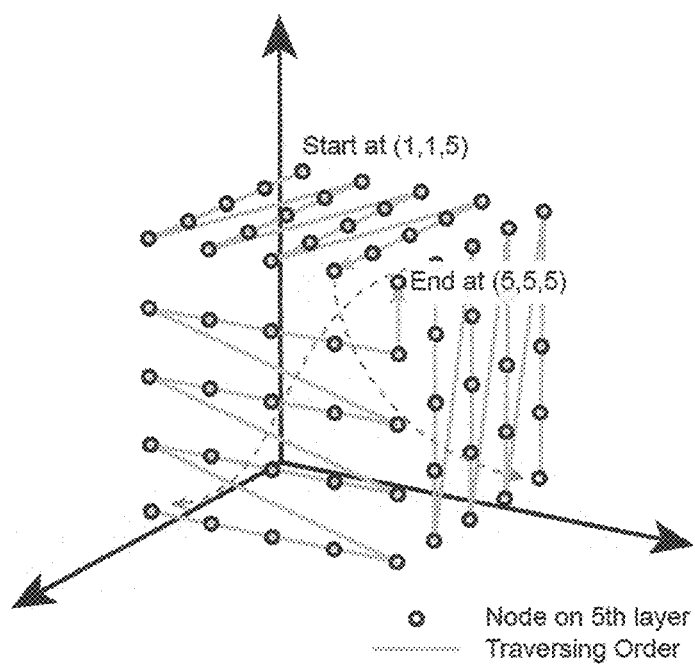
FIG. 58 shows an example of layer and node traversing order for score matrix construction.

Layers and traversing. L-th Layer of codeword space contains all nodes within box [L, L, L] and not in box [L−1, L−1, L−1]. Take the 5th layer as an example. There are 61 nodes on this layer. Traversing order must make sure that each node (indexed [i, j, k]) can be connect from a traversed node (indexed [ii,jj,kk], jj<=j, and kk<=k). FIG. 58 shows one possible traversing order—example of layer and node traversing order for score matrix construction.

5.2.3 A hidden Markov model of ECC decoding

Analog to its application to sequence alignment, the hidden markov model can also be applied to the signal decoding problem. Three symbols were introduced to describe the states: match (m), star (*) and gap (−). A signal with intensity a is represented as a matches. If the ideal signal intensity is b and b>a, then (b−a) stars are added right after the a matches. And if b<a, then (a−b) gaps are added in the two orthogonal position of the last matches representing the signal. For example, the ideal DPLs for sequence TGAACTTTAGCCACGGAGTA in the three base combinations are:

M/K: 0, 2, 3, 3, 1, 1, 4, 2, 1, 2, 1;
R/Y: 0, 1, 3, 4, 2, 2, 1, 1, 4, 1, 1;
W/S: 1, 1, 2, 1, 4, 3, 1, 3, 1, 1, 2.

And the measured DPLs in the experiment are: (bolded and underlined numbers indicate errors)

M/K: 0, 2, 3, 3, 1, 1, 3, 2, 1, 2, 1;
R/Y: 0, 1, 4, 4, 2, 2, 1, 1, 4, 1, 1;
W/S: 1, 1, 2, 1, 4, 3, 1, 3, 1, 1, 2.

The decoding-corrected signals using the representation method described above are:

M/K: mmmm-mmmmmmmmm*mmmmmm
R/Y: mmmmmmmmmmmmmmmmmmmmm
W/S: mmmm-mmmmmmmmmmmmmmmm It is obvious that the alignment of signal M/K, R/Y and W/S can be viewed as the transition process of the following aligned states: (mmm), (mmm), (mmm), (mmm), (-m-), (mmm), (mmm), (mmm), (mmm), (mmm), (mmm), (mmm), (mmm), (mmm), (*mm), (mmm), (mmm), (mmm), (mmm), (mmm), (mmm). This inspires us to use the hidden Markov model to describe the signal alignment.

Figure 59:
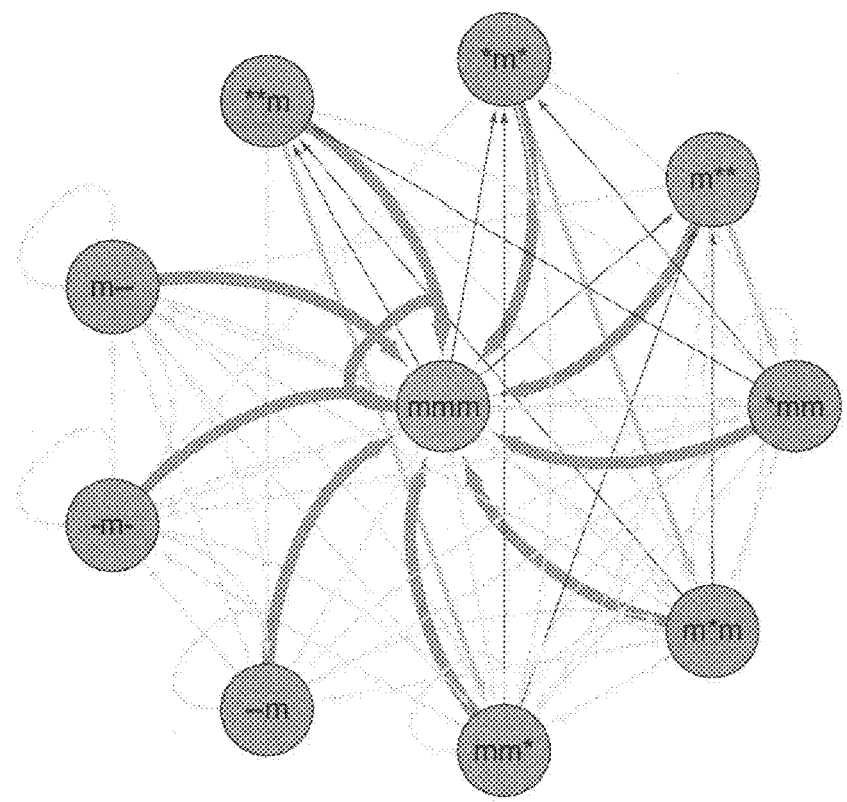
FIG. 59 shows the state transition network of the hidden Markov model of ECC decoding, according to one aspect of the present disclosure.

In general, the overall hidden states of the model are: (mmm), (m--), (-m-), (--m), (*mm), (m*m), (mm*), (m**), (*m*), and (m). Each of the states except for (m--), (-m-), and (--m) will emit a nucleotide, whose type is determined by the corresponding sequencing signal types. States (m--), (-m-), and (--m) will not emit any nucleotide. 1 million DNA reads were simulated to count the probability of state transition (FIG. 59), and the Vertebi algorithm of this hidden Markov model would be an alternative implementation of the ECC decoding algorithm. FIG. 59** shows the state transition network of the hidden Markov model of ECC decoding. Width of the edges represents the magnitude of transition probability.

5.3 Other ECC Decoding Results

Figure 61:
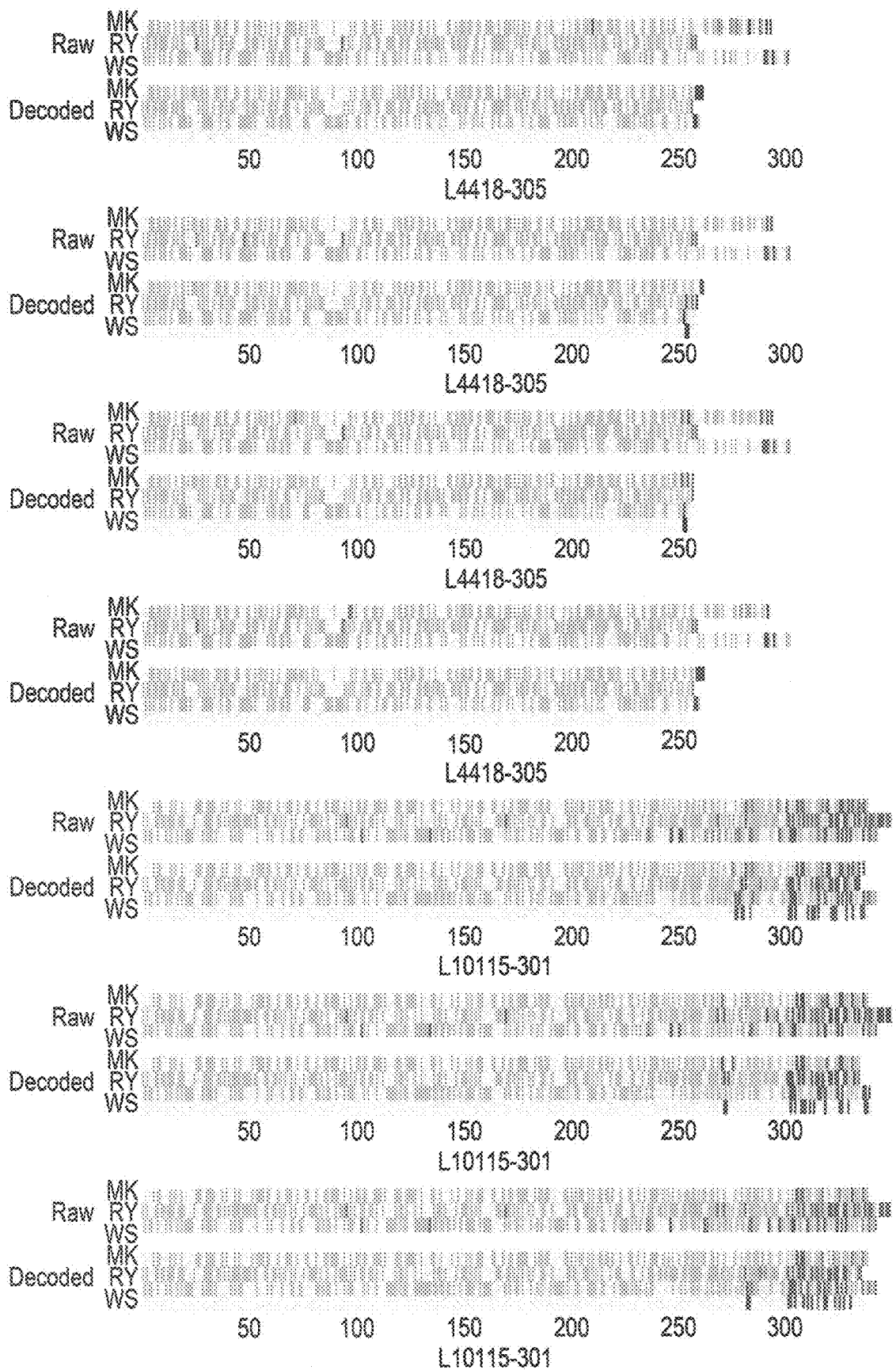
FIG. 61 shows exemplary decoding results.
Figure 61:
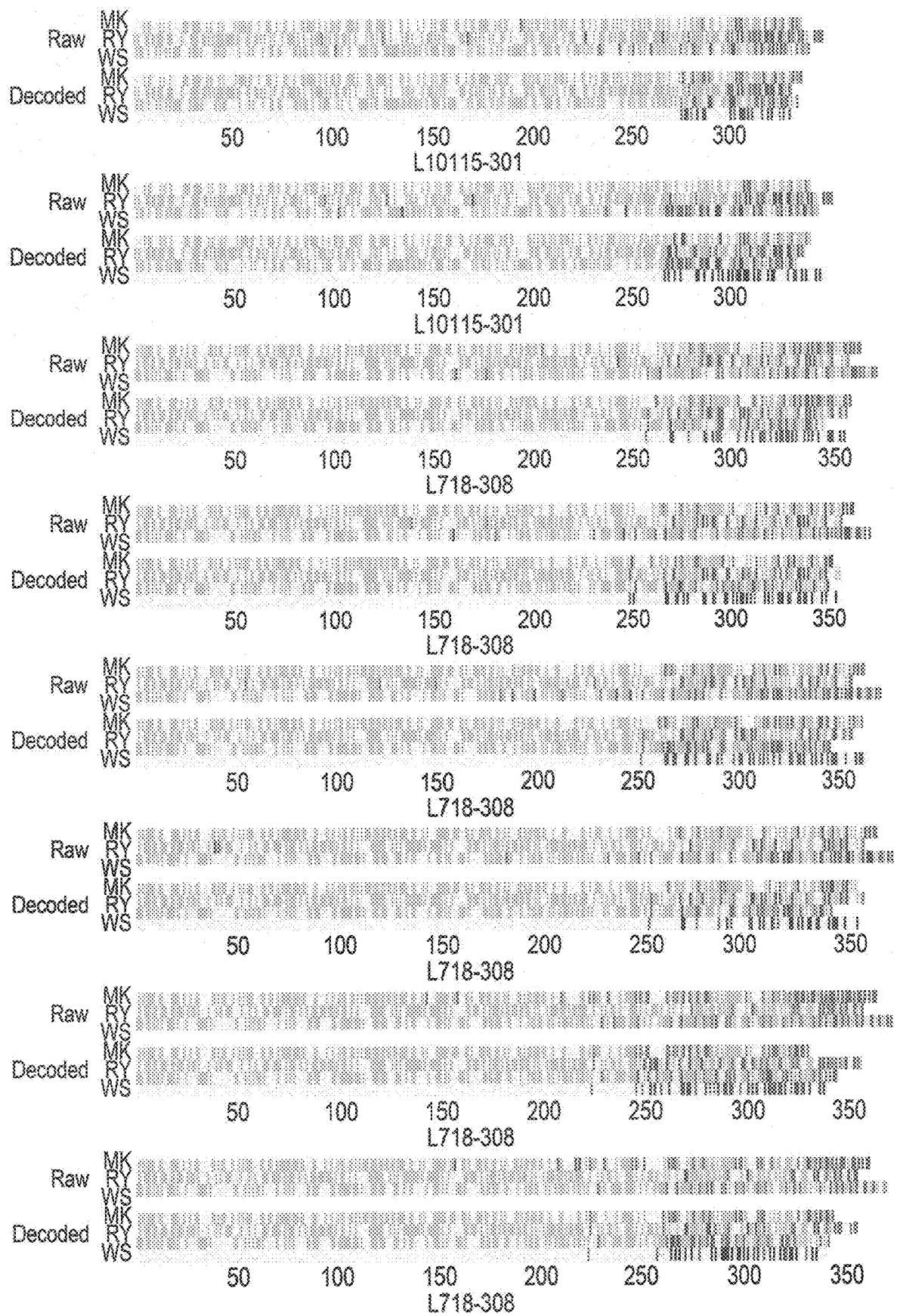

Exemplary decoding results are shown in FIG. 61.

5.4 Simulation of Decoding Under Different Raw Accuracies

To further investigate the capability of ECC decoding in enhancing accuracy, decoding under five different levels of raw accuracies, each with 10000 DNA sequences, were simulated. Two parameters γ and δ were used to generate the probability matrix P, whose entry $P_{ij}$ denotes the probability of a DPL with length i to be sequenced as length following the steps below:

1. For each entry $P_{ij}$ in P, let $$\sigma = \frac{1}{\sqrt{2\pi}} \cdot \frac{1}{\gamma - \left(\frac{i+j}{2} - 1\right)\delta};$$

2. Let $N(x;\mu,\sigma^2)$ be the probability density function of normal distribution, i.e., $$N(x;\mu, \sigma^2) = \frac{1}{\sqrt{2\pi}} \cdot e^{-\frac{(x-\mu)^2}{2\sigma^2}}, \text{ then } P_{ij} = N\left(\frac{|i-j|}{\sqrt{2}};0, \sigma^2\right);$$

3. Normalize P such that the sum of each row all equals one.

In the simulation, γ is set to 1.6, 1.7, 1.8, 2.0 and 2.1, respectively, and δ is set to 0.1. The overall raw accuracies under these parameter settings are 97.42%, 98.34%, 98.97%, 99.64% and 99.80%, respectively. Using the same 10000 random 400 bp DNA sequences, their theoretical DPLs were calculated, randomly modified to new values according to the generated probability matrix P, and rectified using the decoding algorithm. The score function used in the decoding algorithm is subjected to their respective probability matrix P. If two of three successive DPLs of a DNA sequence are modified by the decoding algorithm, this DNA sequence is discarded due to high possibility of error decoding. The accuracy of sequencing is defined as follows: if a DPL with length i is sequenced (or decoded) as length l, then the accuracy of these i bases in this DPL is $$\frac{|i-j|}{i}.$$

Figure 60:
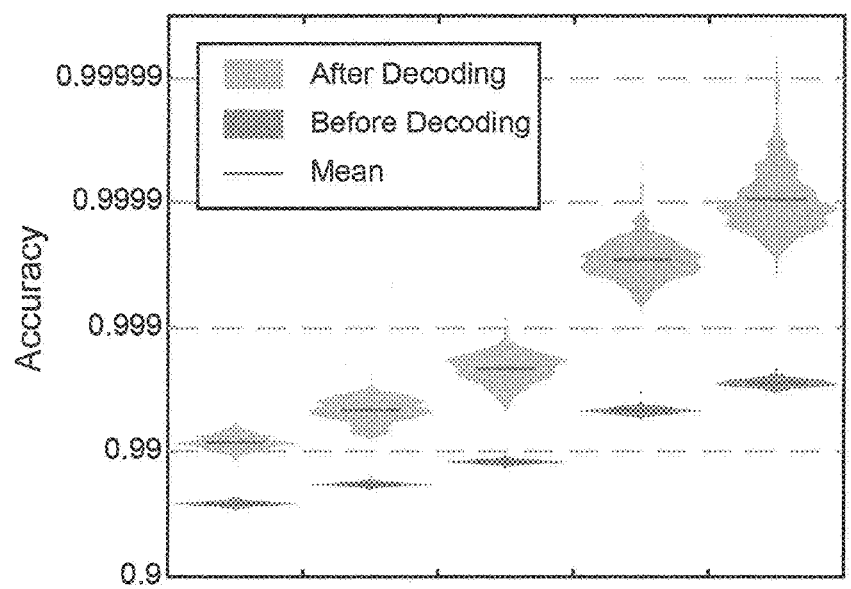
FIG. 60 shows simulated distribution of accuracy before and after decoding, according to one aspect of the present disclosure.

The distribution of accuracies of the first 300 bp of the DNA sequences were calculated before and after decoding, and a significant accuracy shift after decoding (FIG. 60) was found, indicating the power of the decoding algorithm. FIG. 60 shows simulated distribution of accuracy before and after decoding.

Example 12: A Method of Correcting Sequencing Errors

Construction of Transformation Matrix

In this example, the 2+2 sequencing method is used to form the combination of M/K. For odd number round, A or C should be added, and for even number round, G or T should be added. When the sequence of the DNA to be tested is CCTGTATGACCGTATTCCGGGTCCTGTCGGTA (SEQ ID NO: 40), the obtained ideal signal will be h=(2, 3, 1, 2, 3, 2, 1, 2, 2, 4, 2, 3, 1, 3 and 1).

For the sake of simplicity, suppose the lead coefficients as well as the lag coefficients of M and K are the same in the calculation. For example, when the lead coefficient is 0.02, the lag coefficient is 0.01, and a total of 10 sequencing reactions have been conducted, then the transformation matrix constructed with the above-mentioned method is:

$$\begin{pmatrix}
0.9900 & 0.0198 & 0 & 0 & 0 & 0 & 0 & 0 & 0 & 0 & 0 & 0 & 0 & 0 & 0 \\
0 & 0.9605 & 0.0192 & 0.0192 & 0 & 0 & 0 & 0 & 0 & 0 & 0 & 0 & 0 & 0 & 0 \\
0.0099 & 0.0002 & 0.9515 & 0.0190 & 0.0190 & 0.0004 & 0 & 0 & 0 & 0 & 0 & 0 & 0 & 0 & 0 \\
0 & 0.0192 & 0.0004 & 0.9235 & 0.0185 & 0.0185 & 0.0004 & 0.0004 & 0 & 0 & 0 & 0 & 0 & 0 & 0 \\
0.0001 & 0 & 0.0283 & 0.0006 & 0.9150 & 0.0183 & 0.0183 & 0.0004 & 0.0004 & 0 & 0 & 0 & 0 & 0 & 0 \\
0 & 0.0003 & 0 & 0.6367 & 0.0007 & 0.9062 & 0.0181 & 0.0359 & 0.0004 & 0.0004 & 0 & 0 & 0 & 0 & 0 \\
0 & 0 & 0.0006 & 0 & 0.0454 & 0.0009 & 0.8975 & 0.0180 & 0.0355 & 0.0007 & 0.0004 & 0 & 0 & 0 & 0 \\
0 & 0 & 0 & 0.0009 & 0 & 0.0538 & 0.0011 & 0.8720 & 0.0174 & 0.0348 & 0.0007 & 0.0003 & 0 & 0 & 0 \\
0 & 0 & 0 & 0 & 0.0014 & 0 & 0.0621 & 0.0012 & 0.8642 & 0.0173 & 0.0345 & 0.0007 & 0.0003 & 0 & 0 \\
0 & 0 & 0 & 0 & 0 & 0.0019 & 0 & 0.0690 & 0.0014 & 0.8560 & 0.0171 & 0.0341 & 0.0007 & 0.0010 & 0
\end{pmatrix}$$

For the sake of calculation accuracy, suppose the lead coefficients as well as the lag coefficients of M and K are different in the calculation. For example, when the lead coefficient and the lag coefficient of M are respectively 0.02 and 0.01, those of K are respectively 0.01 and 0.02, and a total of 10 sequencing reactions have been conducted, then the transformation matrix constructed with the above-mentioned method is:

$$\begin{pmatrix} 0.9900 & 0.0198 & 0 & 0 & 0 & 0 & 0 & 0 & 0 & 0 & 0 & 0 & 0 & 0 & 0 \\ 0 & 0.9508 & 0.0995 & 0.0095 & 0 & 0 & 0 & 0 & 0 & 0 & 0 & 0 & 0 & 0 & 0 \\ 0.0099 & 0.0002 & 0.9515 & 0.0190 & 0.0094 & 0.0002 & 0 & 0 & 0 & 0 & 0 & 0 & 0 & 0 & 0 \\ 0 & 0.0285 & 0.0003 & 0.9141 & 0.0091 & 0.0000 & 0.0001 & 0.0001 & 0 & 0 & 0 & 0 & 0 & 0 & 0 \\ 0.0001 & 0 & 0.0377 & 0.0008 & 0.9148 & 0.0183 & 0.0090 & 0.0002 & 0.0001 & 0 & 0 & 0 & 0 & 0 & 0 \\ 0 & 0.0007 & 0 & 0.0545 & 0.0005 & 0.8877 & 0.0089 & 0.0176 & 0.0001 & 0.0001 & 0 & 0 & 0 & 0 & 0 \\ 0 & 0 & 0.0010 & 0 & 0.0633 & 0.0013 & 0.8883 & 0.0178 & 0.0175 & 0.0003 & 0.0001 & 0 & 0 & 0 & 0 \\ 0 & 0 & 0 & 0.0021 & 0 & 0.0791 & 0.0008 & 0.8541 & 0.0085 & 0.0169 & 0.0002 & 0.0001 & 0 & 0 & 0 \\ 0 & 0 & 0 & 0 & 0.0027 & 0.0001 & 0.0876 & 0.0018 & 0.8548 & 0.0171 & 0.0169 & 0.0003 & 0.0001 & 0 & 0 \\ 0 & 0 & 0 & 0.0001 & 0 & 0.0042 & 0 & 0.1013 & 0.0010 & 0.8297 & 0.0083 & 0.0164 & 0.0002 & 0.0002 & 0 \end{pmatrix}$$

If the 2+2 bi-color sequencing method is used, then the calculation method of the transformation matrix will not be changed. The difference is just from the application way in the parameter estimation and signal correction.

Parameter Estimation for the Monochrome 2+2 Sequencing

In this example, the primary monochrome 2+2 sequencing method is used to form the nucleotide combination of M/K. For odd number round, A or C should be added, and for even number round, G or T should be added. The tested sequence is as below:

(SEQ ID NO: 41)
AAGAGCTGGACAGCGATACCTGGCAGGCGGAGCTGCATATCGAAGTTTTC

CTGCCTGCTCAGGTGCCGGATTCAGAGCTGGATGCGTGGATGGAGTCCCG

GATTTATCCGGTGATGAGCGATATCCCGGCACTGTCAGATTTGATCACCA

GTATGGTGGCCAGCGGCTATGACTACCGGCGCGACGATGATGCGGGCTTG

TGGAGTTCAGCCGATCTGACTTATGTCATTACCTATGAAATGTGAGGACG

CTATGCCTGTACCAAATCCTACAATGCCGGTGAAAGGTGCCGGGACCACC

CTGTGGGTTTATAAGGGGAGCGGTGACCCTTACGCGAATCCGCTTTCAGA

CGTTGACTGGTCGCGTCTGGCAAAAGTTAAAGACCTGACGCCCGGCGAAC

TGACCGCTGAGTCCTATGACGACAG

Figure 43:
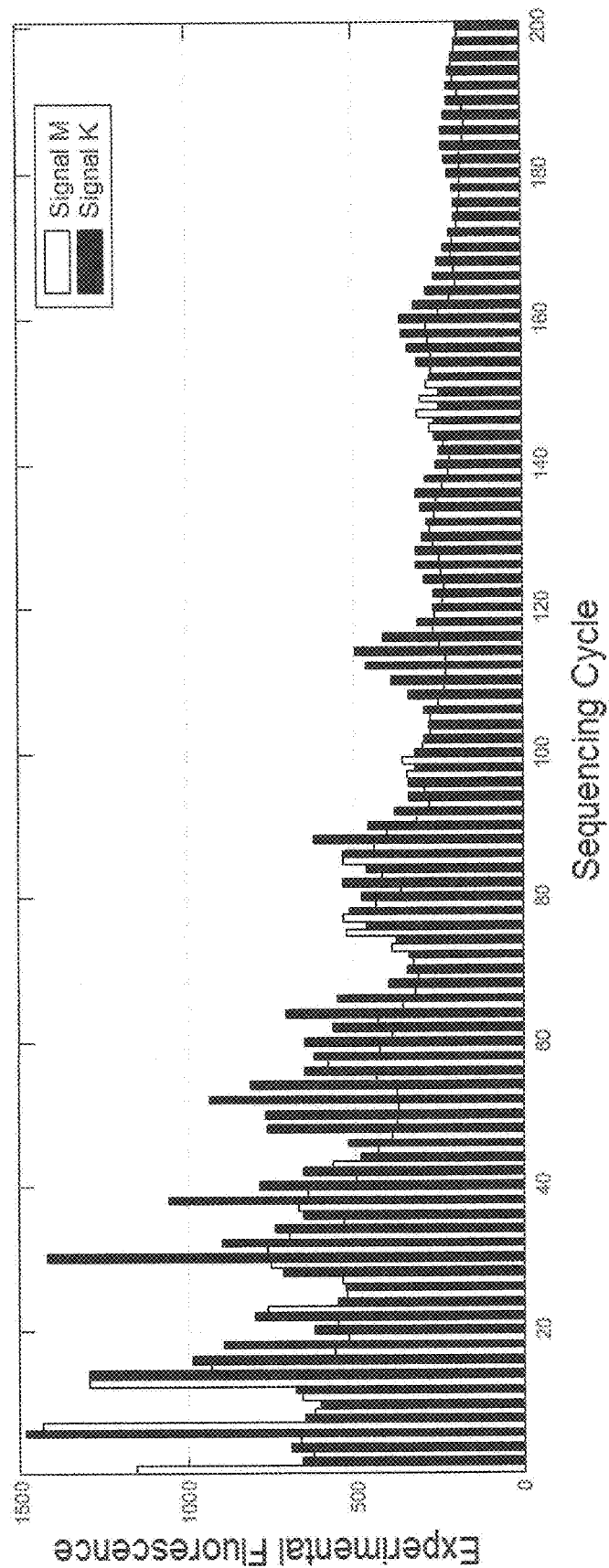
FIG. 43 shows the monochrome 2+2 original sequencing signal.

A total of 200 sequencing reactions have been conducted, and the obtained actual original sequencing signal is as shown in FIG. 43. It can be seen that: the value range of the original sequencing signal is about 100 to 1500, showing an overall down trend. Approximately from the 80$^{th}$ sequencing reaction, the signals fluctuate alternately, so it is impossible to read the sequence information directly. The ideal signal may be deduced as h=(2, 1, 1, 1, 1, 3, 3, 1, 1, 1, 1, 1, 3, 3, 2, 2, 1, 2, 1, 1, 1, 2, 2, 1, 1, 1, 1, 1, 2, 5, 2, 2, 2, 2, 1, 1, 2, 4, 2, 2, 1, 2, 2, 1, 1, 1, 1, 3, 1, 2, 1, 4, 1, 3, 1, 2, 3, 2, 1, 3, 1, 1, 2, 4, 1, 2, 1, 1, 1, 1, 1, 1, 1, 3, 2, 3, 3, 2, 1, 1, 4, 1, 1, 5, 2, 1, 6, 3, 1, 1, 2, 1, 1, 1, 2, 2, 1, 3, 2, 1, 1, 1, 1, 2, 1, 1, 2, 1, 2, 1, 3, 1, 6, 1, 3, 2, 1, 2, 1, 1, 1, 2, 2, 2, 1, 3, 2, 2, 3, 1, 1, 2, 3, 4, 1, 2, 2, 1, 1, 1, 2, 2, 3, 6, 1, 2, 1, 4, 2, 2, 4, 3, 4, 2, 3, 7, 9, 1, 1, 2, 4, 1, 1, 1, 4, 4, 2, 2, 1, 1, 1, 2, 1, 2, 1, 1, 3, 2, 1, 2, 4, 2, 4, 1, 1, 1, 2, 1, 3, 5, 3, 3, 1, 3, 2, 2, 1, 3, 2, 1, 1, 3, 2, 3, 1, 1, 2, 1, 2, 2, 1, 1, 2, 2, 1, 3, 1) using the above-mentioned parameter estimation method, based on the sequence and sequencing method of the DNA molecules to be tested. Estimate relevant parameters in this sequencing with the above-mentioned parameter estimation method. When constructing the transformation matrix, suppose the lead and lag coefficients of M and K are different, for the sake of accurate calculation. Set t as the times of sequencing reaction. Construct the transformation function $\varphi(s) = \varphi_a \varphi_b \varphi_s + \varphi_c$, wherein:

1. $\varphi_a(t) = a$, where, a is called as the unit signal;
2. $\varphi_b(t) = bt$, where, b is called as the attenuation coefficient;
3.

$$\varphi_c(t) = \begin{cases} d & t \text{ is odd number} \\ e & t \text{ is even number} \end{cases},$$

d and e are the overall offset of M and K, respectively;

4. $\varphi_s(t) = s$, where, s refers to the dephasing signal.

Figure 44:
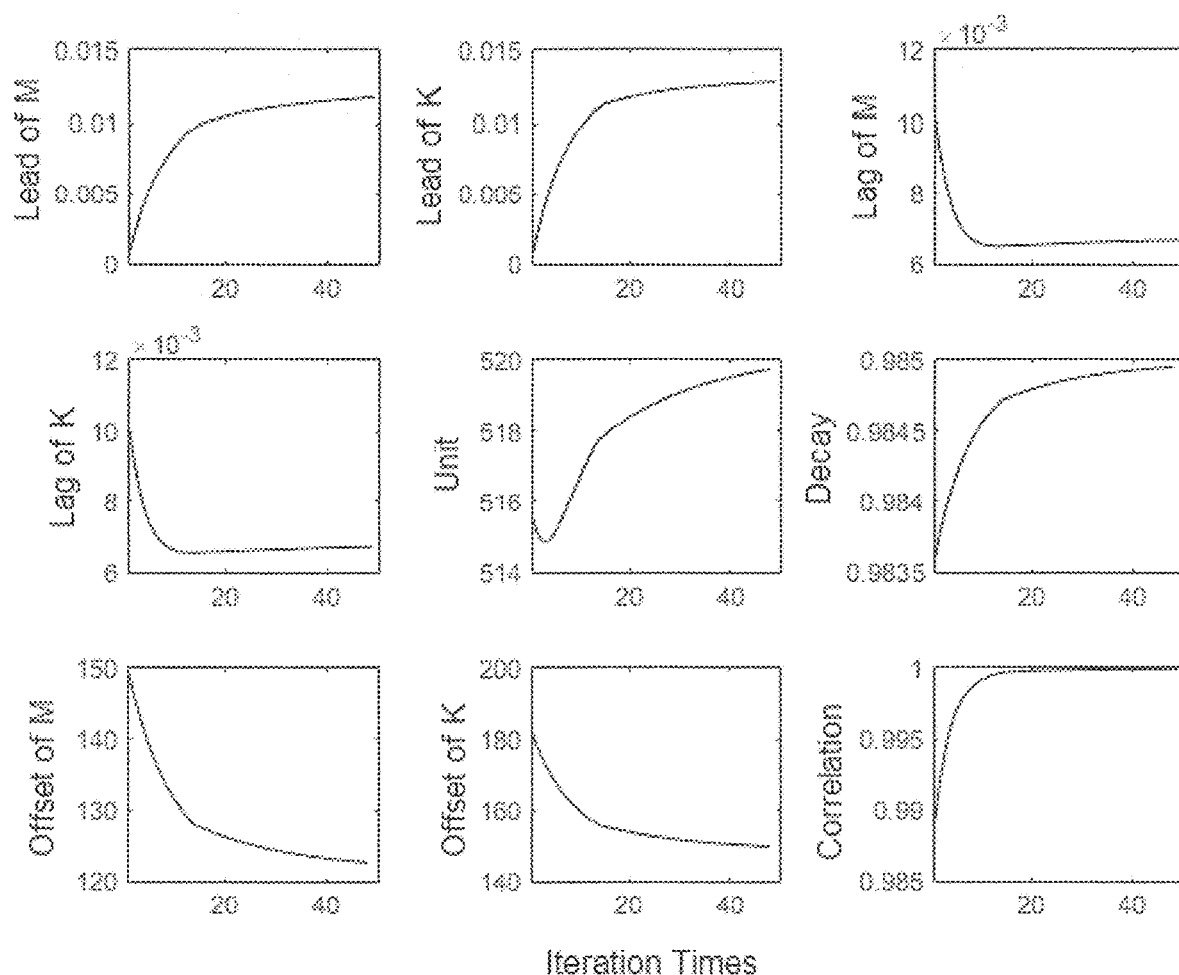
FIG. 44 shows the variation trend of all parameters in the process of parameter estimation for monochrome 2+2 original sequencing signal.

In the parameter estimation, the correlation coefficient used is Pearson correlation coefficient and the optimization method used is the gradient descent method. After 48 rounds of iteration calculation, the gradient descent met the convergence conditions, and the obtained lead coefficient of M is 0.0117, and its lag coefficient is 0.0067. The lead coefficient of K is 0.0128, and its lag coefficient is 0.0067. The unit signal is 519.7, the attenuation coefficient is 0.9849, the overall offset of M is 122.7, the overall offset of K is 150.1 and the correlation coefficient is 0.999961. The variation trend of all the parameters in the process of iteration calculation is shown in FIG. 44.

Signal Correction of Monochrome 2+2 Sequencing

Figure 45:
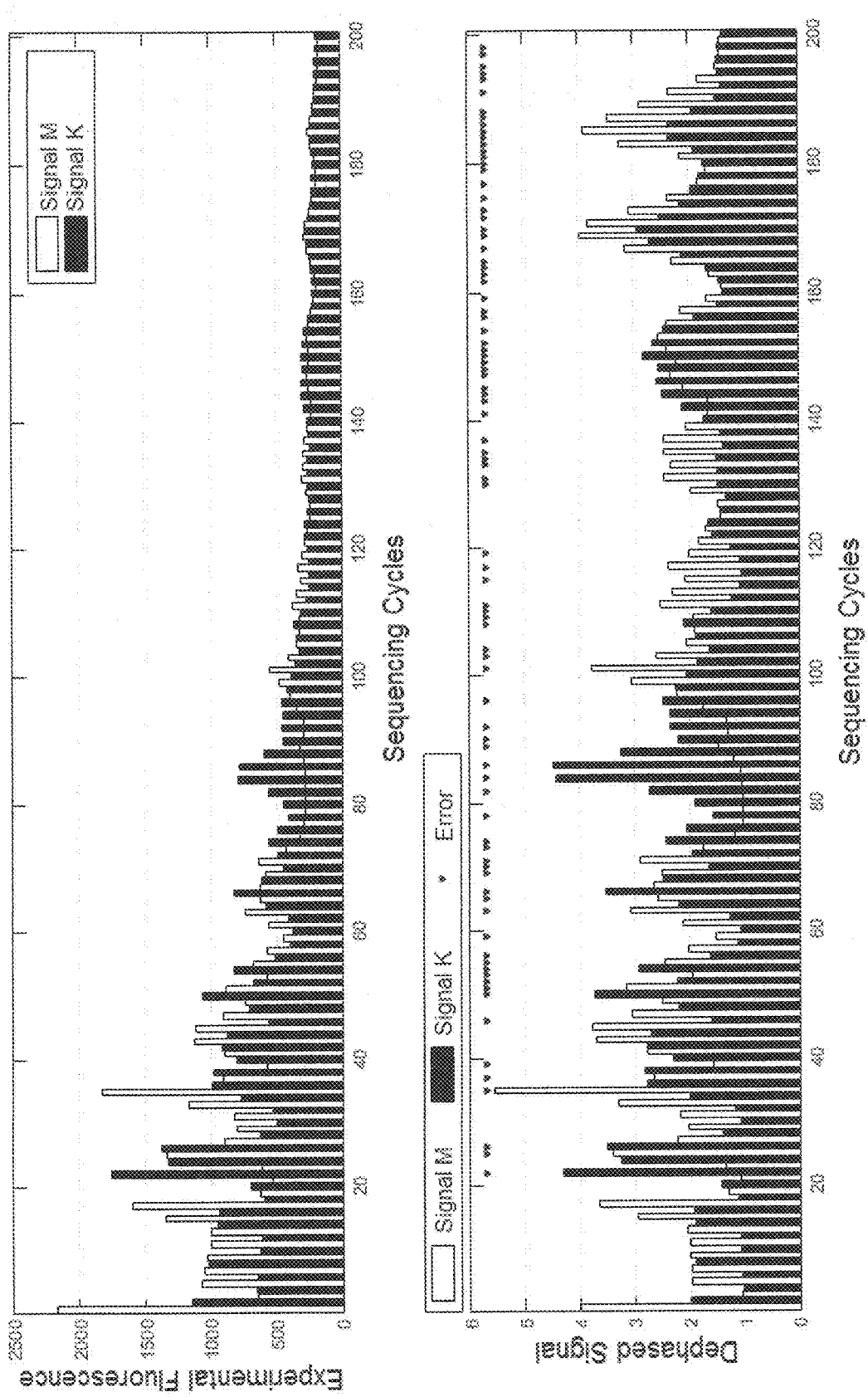
FIG. 45 shows the original signal and dephasing signal for the monochrome 2+2 sequencing.

In this example, the primary monochrome 2+2 sequencing test is used: the tested sequence is unknown. Its actual original sequencing signal f, and the dephasing signal obtained through the transformation of the inverse function of the transformation function $\varphi(s)$ in Application Example 1 and relevant parameters are as shown in FIG. 45 (the inverted triangle indicates that the intensity of the signal in this position does not match with the ideal signal).

Figure 46:
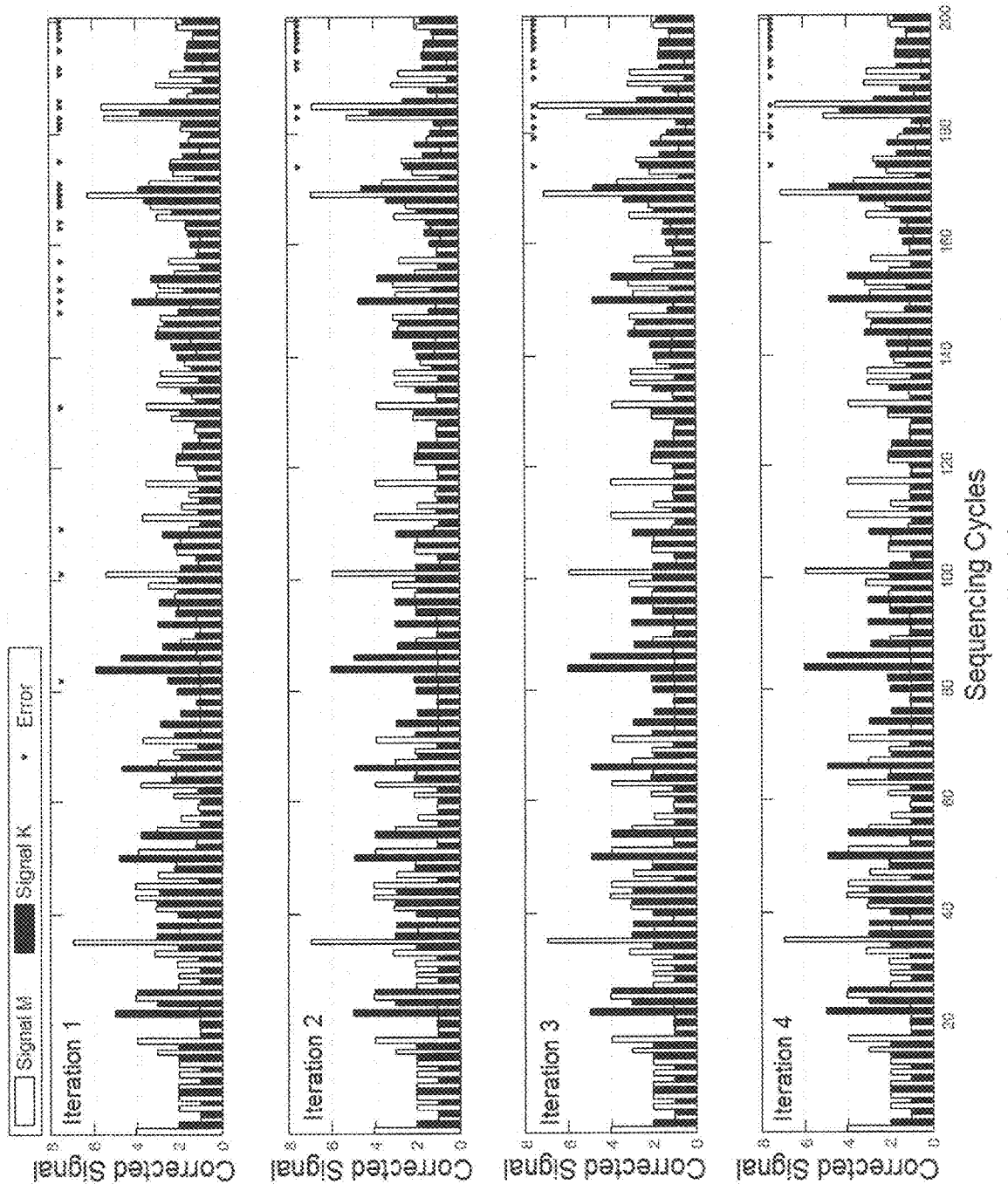
FIG. 46 shows the iteration steps in the signal correction for monochrome 2+2 sequencing signal.

It can be seen that: among the dephasing signals obtained through the transformation of the inverse function of the transformation function $\varphi(s)$, the signals in many positions still do not match with the ideal signal. A total of 4 iterations have been conducted via the above-mentioned steps for signal correction, and the first-order dephasing signal $s_1$, the second-order dephasing signal $s_2$, the third-order dephasing signal $s_3$ and the fourth-order dephasing signal $s_4$ are respectively obtained. After rounding off, all signal values of $s_3$ and $s_4$ are equal to each other, thus the iteration is stopped, and $s_4$ is output as the correction result. The four orders of dephasing signals are as shown in FIG. 46, in which, the inverted triangle indicates that the intensity of the signal in this position does not match with the ideal signal. It can be seen that the inverted triangle signals gradually become less with the going-on of iteration, which indicates the accuracy is getting higher and higher. In the final correct results, the signals from the first 173 sequencing reactions are all completely corrected. The correction error does not appear till 174$^{th}$ sequencing reaction.

Parameter Estimation for the Bi-Color 2+2 Sequencing

In this example, the primary bi-color 2+2 sequencing test is used: the nucleotide combination is M/K, of which, A and G are marked with fluorescence groups in the same color, and C and T are marked with fluorescence groups in the same color as well. The tested sequence is:

(SEQ ID NO: 41)
AAGAGCTGGACAGCGATACCTGGCAGGCGGAGCTGCATATCGAAGTTTTC

CTGCCTGCTCAGGTGCCGGATTCAGAGCTGGATGCGTGGATGGAGTCCCG

GATTTATCCGGTGATGAGCGATATCCCGGCACTGTCAGATTTGATCACCA

GTATGGTGGCCAGCGGCTATGACTACCGGCGCGACGATGATGCGGGCTTG

TGGAGTTCAGCCGATCTGACTTATGTCATTACCTATGAAATGTGAGGACG

CTATGCCTGTACCAAATCCTACAATGCCGGTGAAAGGTGCCGGGACCACC

CTGTGGGTTTATAAGGGGAGCGGTGACCCTTACGCGAATCCGCTTTCAGA

CGTTGACTGGTCGCGTCTGGCAAAAGTTAAAGACCTGACGCCCGGCGAAC

TGACCGCTGAGTCCTATGACGACAG

Figure 47:
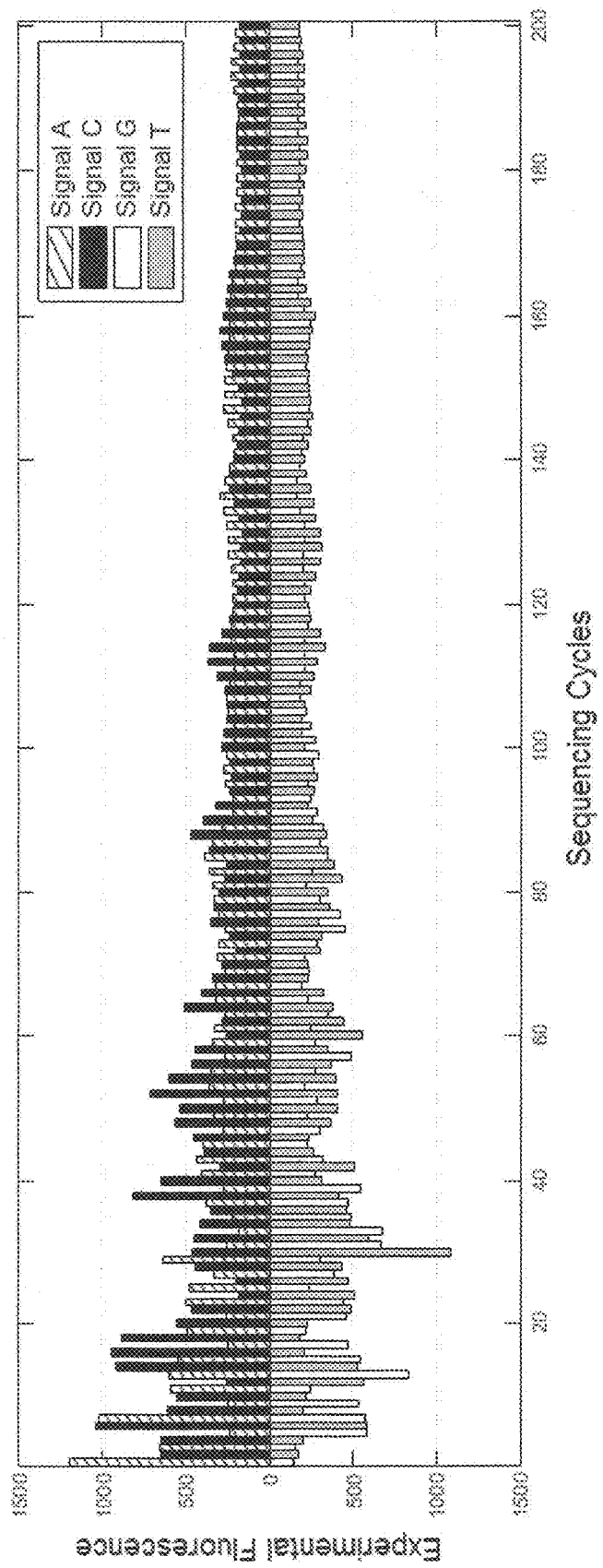
FIG. 47 shows the original signal for the primary bi-color 2+2-color sequencing.

A total of 200 sequencing reactions have been conducted, and the obtained actual original sequencing signal is as shown in FIG. 47.

It can be seen that: the value range of the original sequencing signal is about 100 to 1200, showing an overall down trend. Approximately from the 80$^{th}$ sequencing reaction, the signals fluctuate alternately, so it is impossible to read the sequence information directly. As the bi-color sequencing method is employed, the numbers of ideal signal, dephasing signal and original sequencing signal are respectively 2, and they respectively correspond to the fluorescence groups marked for A and G, as well as the fluorescence groups marked for C and T.

With the above-mentioned parameter estimation method, based on the sequence and sequencing method of the DNA molecules to be tested, the ideal signal of the fluorescence groups marked for A and G may be deduced as: $h_1$=(2, 1, 1, 1, 0, 2, 2, 1, 0, 1, 1, 1, 0, 1, 2, 1, 2, 0, 2, 1, 1, 0, 1, 1, 0, 1, 0, 0, 1, 2, 1, 0, 1, 0, 1, 0, 0, 1, 3, 0, 2, 1, 0, 1, 1, 1, 1, 0, 2, 1, 1, 0, 3, 1, 2, 1, 1, 0, 2, 1, 0, 1, 0, 0, 3, 1, 1, 1, 0, 1, 1, 0, 1, 0, 0, 2, 1, 1, 1, 1, 1, 1, 0, 2, 1, 1, 4, 1, 1, 0, 2, 0, 0, 1, 1, 1, 0, 1, 2, 0, 1, 0, 1, 1, 1, 1, 1, 1, 0, 3, 0, 3, 1, 1, 1, 1, 0, 1, 1, 0, 0, 1, 1, 0, 1, 1, 1, 0, 1, 0, 1, 1, 3, 2, 1, 2, 1, 1, 0, 0, 1, 1, 0, 1, 4, 0, 0, 0, 3, 1, 0, 3, 3, 3, 0, 3, 2, 4, 1, 0, 2, 4, 1, 1, 0, 3, 1, 0, 1, 1, 0, 1, 2, 0, 0, 1, 0, 0, 1, 1, 1, 2, 1, 2, 0, 1, 0, 1, 0, 2, 4, 1, 3, 1, 1, 1, 1, 1). And the ideal signal of the fluorescence groups marked for C and T is: $h_2$=(0, 0, 0, 0, 1, 1, 1, 0, 1, 0, 0, 1, 2, 1, 1, 0, 1, 0, 0, 0, 1, 1, 1, 1, 0, 1, 1, 0, 0, 4, 2, 1, 2, 1, 1, 1, 1, 1, 2, 0, 0, 2, 1, 0, 0, 0, 1, 1, 0, 1, 1, 1, 0, 1, 0, 1, 3, 0, 0, 3, 0, 1, 2, 1, 0, 1, 0, 0, 1, 0, 0, 1, 0, 1, 3, 0, 2, 2, 1, 0, 0, 3, 0, 1, 3, 1, 0, 2, 2, 0, 1, 0, 1, 1, 0, 1, 1, 1, 2, 0, 1, 0, 1, 0, 1, 0, 0, 1, 0, 1, 1, 0, 1, 3, 0, 2, 1, 0, 2, 0, 0, 1, 1, 1, 1, 2, 0, 2, 1, 2, 2, 1, 0, 1, 0, 2, 0, 0, 1, 0, 1, 1, 0, 1, 2, 2, 2, 1, 2, 1, 1, 1, 2, 1, 0, 1, 2, 0, 5, 5, 0, 1, 0, 0, 0, 0, 1, 1, 3, 2, 1, 0, 1, 0, 0, 1, 2, 0, 1, 3, 1, 0, 1, 2, 1, 2, 1, 0, 1, 1, 1, 1, 1, 2, 0, 0, 2, 1, 1, 0).

Estimate relevant parameters in this sequencing with the above-mentioned parameter estimation method. When constructing the transformation matrix, suppose the lead and lag coefficients of M and K are different, for the sake of accurate calculation. For a certain transformation matrix T constructed based on some given dephasing coefficient, suppose the dephasing signal of the fluorescence groups marked for A and G is $s_1$=$Th_1$, and the dephasing signal of the fluorescence groups marked for C and T is $s_2$=$Th_2$. Set t as the times of sequencing reaction. Construct the transformation function $\varphi1(s)=\varphi_{a1}\varphi_b\varphi_s+\varphi_{c1}$ 和 $\varphi2(s)=\varphi_{a2}\varphi_b\varphi_s+\varphi_{c2}$ respectively for the fluorescence groups marked for A and G and those marked for C and T, wherein 1. $\varphi_{a1}(t)$=a1, $\varphi_{a2}(t)$=a2, where, $a_1$ and $a_2$ are respectively the unit signals released by the fluorescence groups marked for A and G and those marked for C and T;
2. $\varphi_b(t)=b^t$, where, b is called as the attenuation coefficient;
3.

$$\varphi_{c1}(t) = \begin{cases} d_1 & t \text{ is odd number} \\ e_1 & t \text{ is even number} \end{cases}, \varphi_{c2}(t) = \begin{cases} d_2 & t \text{ is odd number} \\ e_2 & t \text{ is even number} \end{cases},$$

wherein $d_1$, $e_1$, $d_2$ and $e_2$ respectively refer to the overall offset of A, G, C and T;

4. $\varphi_s(t)$=s, where, s refers to the dephasing signal.

Figure 48:
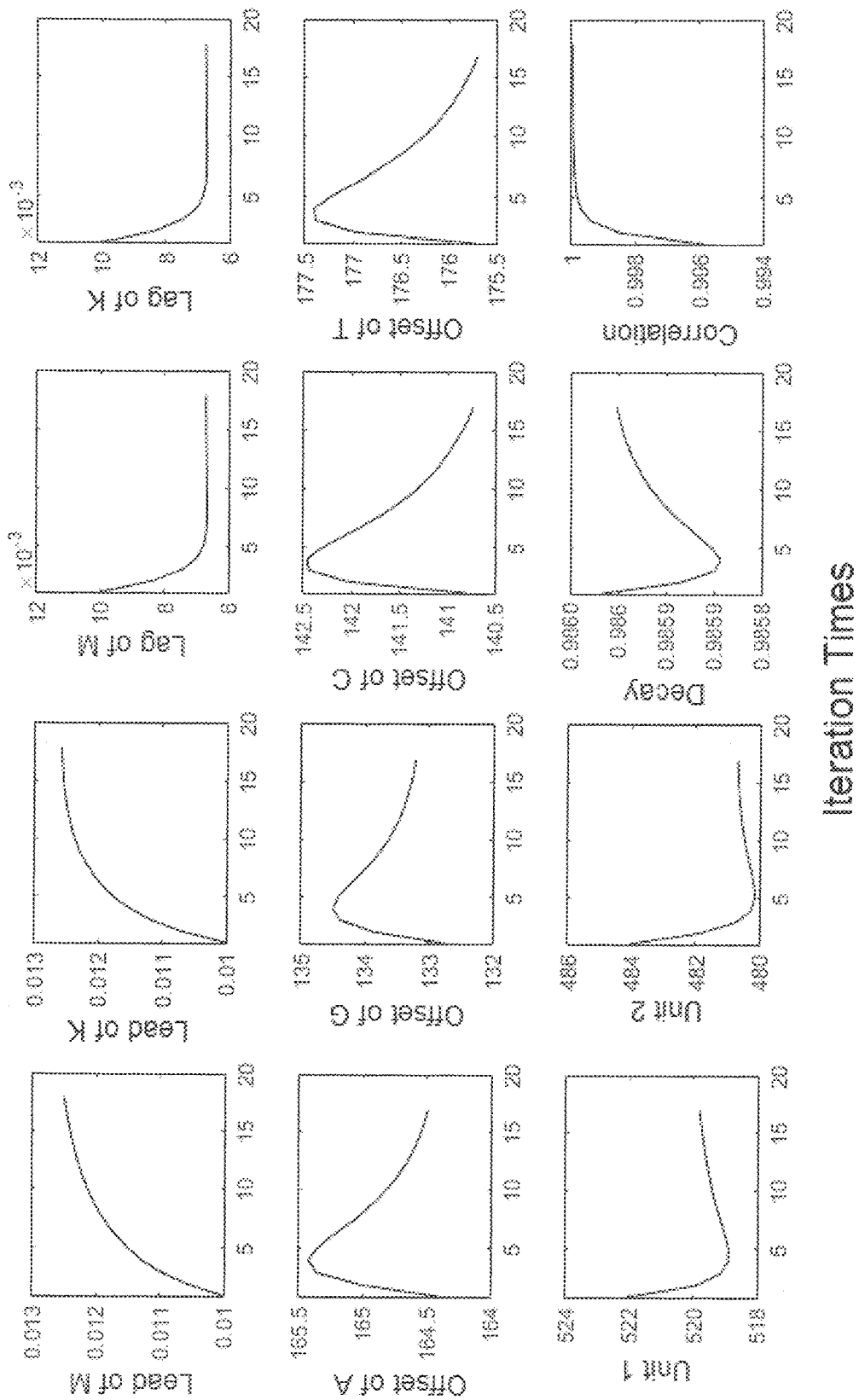
FIG. 48 shows the variation trend of all parameters in the process of parameter estimation for bi-color 2+2 sequencing.

In the parameter estimation, the correlation coefficient used is Pearson correlation coefficient and the optimization method used is the gradient descent method. After 17 rounds of iteration calculation, the gradient descent met the convergence conditions, and the obtained lead coefficient of M is 0.0125, and its lag coefficient is 0.0067. The lead coefficient of K is 0.0126, and its lag coefficient is 0.0068. The unit signals released by the fluorescence groups marked for A and G and those marked for C and T are respectively 519.8 and 480.7, the attenuation coefficient is 0.9860, the overall offset of A is 164.5, and that of G is 133.2. The overall offset of C is 140.7 and that of T is 175.7. The correlation coefficient is 0.999964. The variation trend of all the parameters in the process of iteration calculation is shown in FIG. 48.

Signal Correction of Bi-Color 2+2 Sequencing

Figure 49:
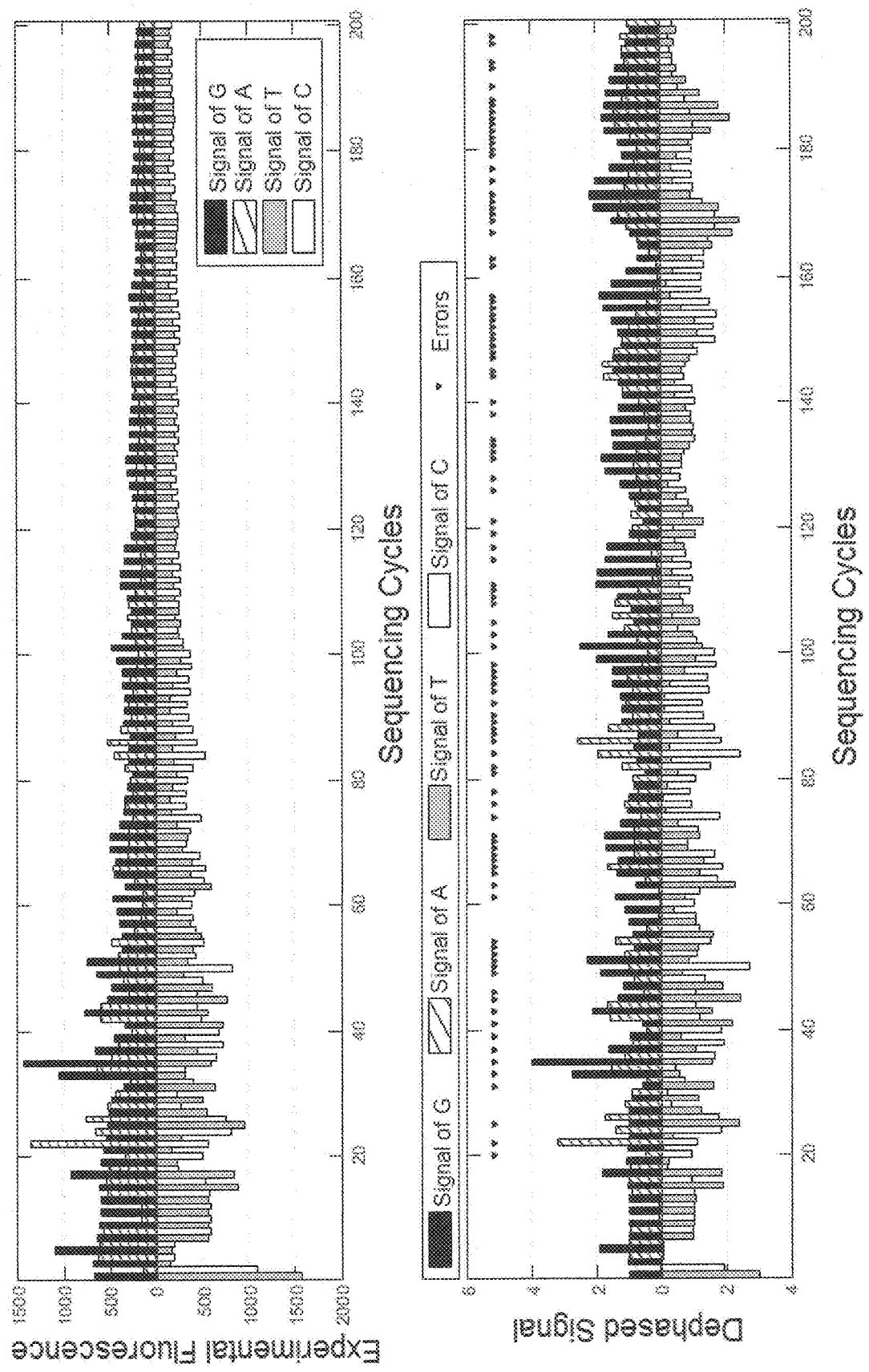
FIG. 49 shows the original signal and dephasing signal for the primary bi-color 2+2 sequencing.

Primary bi-color 2+2 sequencing test: G and T are added for odd number rounds and A and C are added for even number rounds, of which, A and G are marked with fluorescence groups in the same color. C and T are marked with fluorescence groups in the same color which is different from the color for A and G. The tested sequence is unknown. The actual original sequencing signal f obtained in this sequencing, and the dephasing signal obtained through the transformation of the inverse function of the transformation functions $\varphi1(s)$ and $\varphi2(s)$ in Application Example 4 and relevant parameters are as shown in FIG. 49. As the bi-color sequencing method is employed, the numbers of ideal signal, dephasing signal and original sequencing signal are respectively 2, and they respectively correspond to the fluorescence groups marked for A and G, as well as the fluorescence groups marked for C and T. It can be seen there are a lot of inverted triangle signals in FIG. 49, which indicates that among the dephasing signal (or the phase mismatch) s, the signals in many positions still do not match with the ideal signal.

Figure 50:
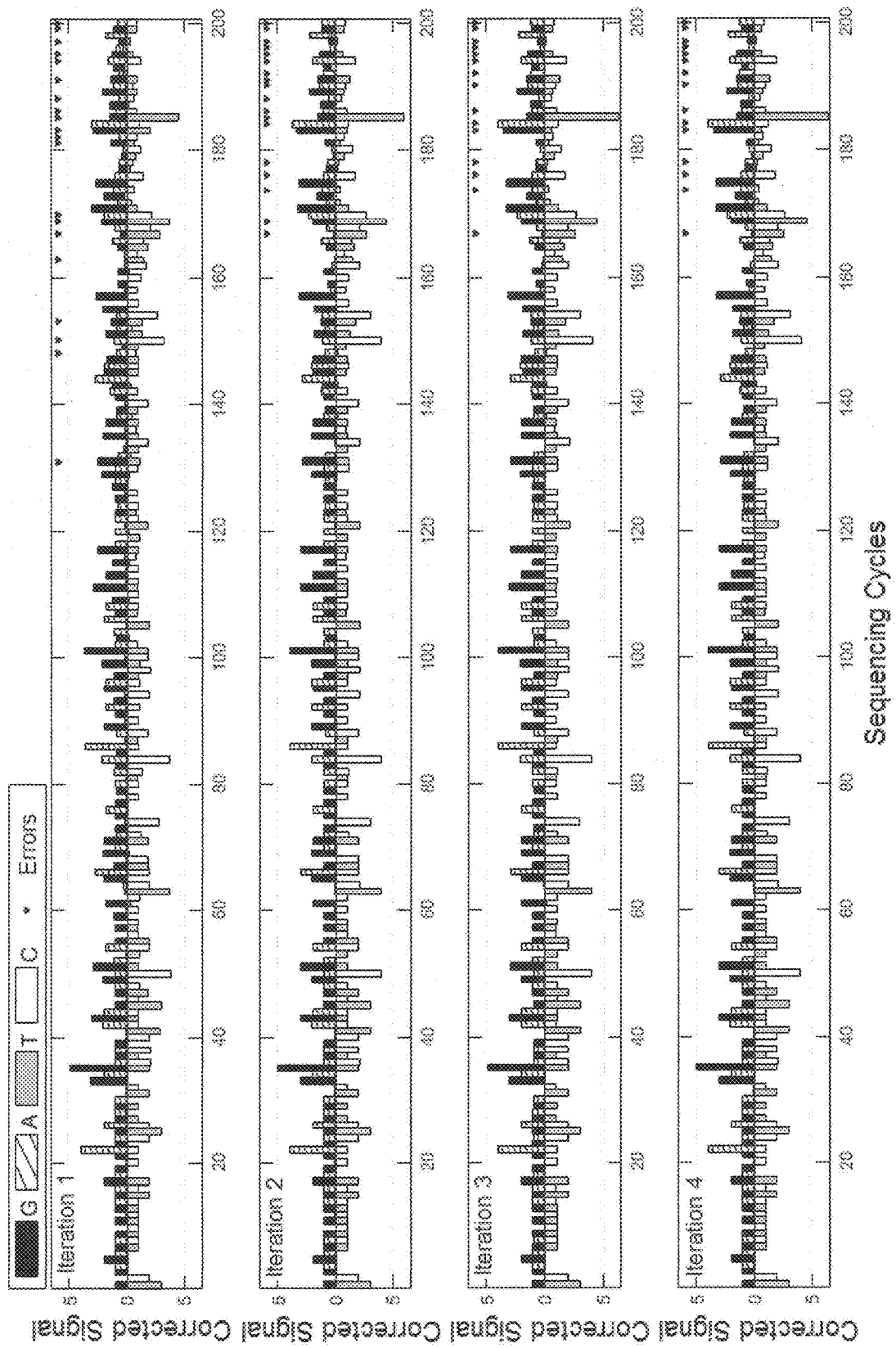
FIG. 50 shows the iteration steps in the signal correction for bi-color 2+2 sequencing.

A total of 4 iterations have been conducted via the above-mentioned steps for signal correction, and the first-order dephasing signal $s_1$, the second-order dephasing signal $s_2$, the third-order dephasing signal $s_3$ and the fourth-order dephasing signal $s_4$ are respectively obtained. After rounding off, all signal values of $s_3$ and $s_4$ are equal to each other, thus the iteration is stopped, and $s_4$ is output as the correction result. The four orders of dephasing signals are as shown in FIG. 50, in which, the inverted triangle indicates that the intensity of the signal in this position does not match with the ideal signal. It can be seen that the inverted triangle signals gradually become less with the going-on of iteration, which indicates the accuracy is getting higher and higher. In the final correct results, the signals from the first 166 sequencing reactions are all completely corrected. The correction error does not appear till 167$^{th}$ sequencing reaction.

Comprehensive Performance Obtained Through a Lot of Sequences

To comprehensively assess the accuracy of the present disclosure to read the sequence information from the original sequencing signal, five times of monochrome 2+2 sequencing tests have been respectively conducted. In one aspect, 500 times of sequencing reactions are performed for each sequencing reaction. In each sequencing test, some of the tested DNAs are used as the reference, and their sequences and original sequence signals are used in the parameter estimation; and the other tested DNAs are used as the sequencing samples. Two methods will be employed for the signal correction: one method is to use the parameters estimated on the basis of reference DNA to conduct the signal correction; and the other method is to simply suppose there is a simple proportional relation between the original signal and the ideal signal, based on which, deduce the DNA sequence information.

Figure 51:
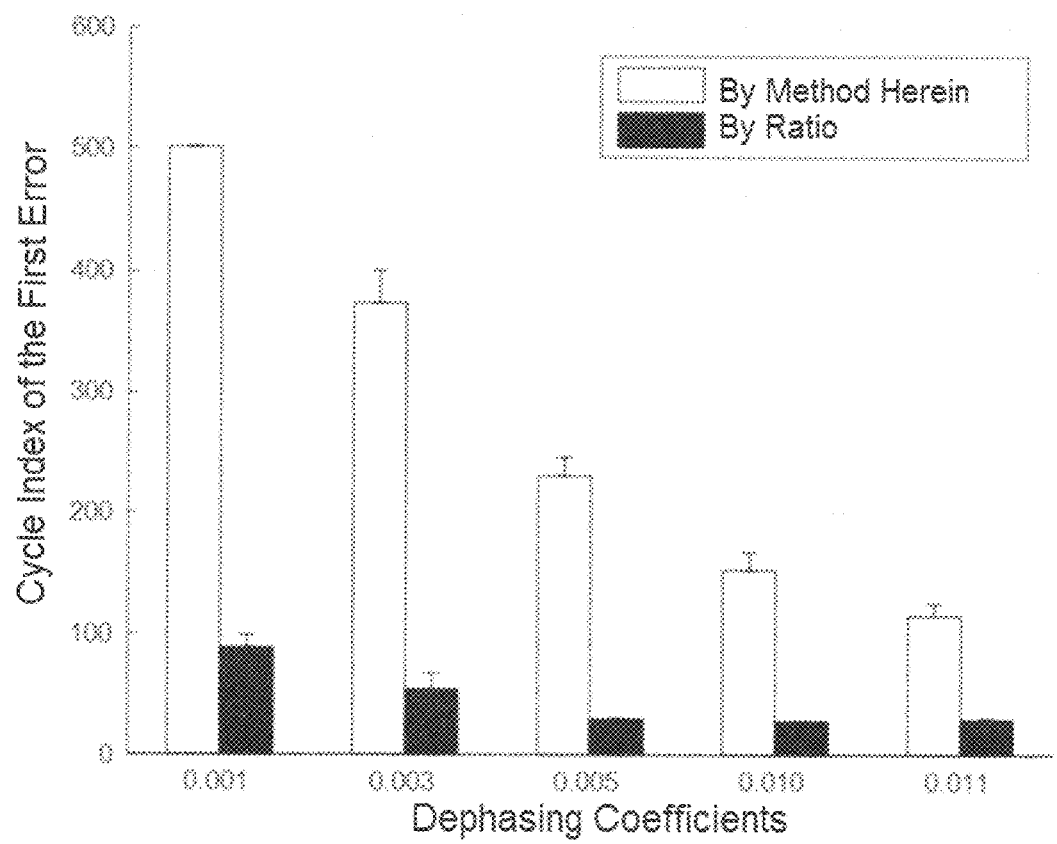
FIG. 51 shows the statistical results of signal correction for multiple monochrome 2+2 sequencing.

In the five sequencing tests, the dephasing coefficients estimated using the original sequencing signal of the reference DNA are respectively 0.001, 0.003, 0.005, 0.010, and 0.011 (during the parameter estimation, the lead and lag coefficient were set to be equal). For signal correction, respectively record the numbers (i.e. the length of the completely-correct correction signal) of the first sequencing reaction in which the intensity of the signal obtained with the two methods does not match with the intensity of the ideal signal, and plot a histogram (as shown in FIG. 51, the error bar refers to the standard deviation). It can be seen that when the dephasing coefficient is 0.001, the correction error occurs in the correction signal obtained by calculation according to the simple proportional relation, within less than 100 sequencing reactions, while the method described in the present disclosure has the completely correct correction results. With the increasing of the dephasing coefficient, the accuracies of both methods have decreased. However, in one aspect, in the correction results obtained herein, the length of the completely-correct correction signal is still 3 to 5 times of the value calculated based on the simple proportional relation, which reflects the significant advantages of the present disclosure in improving the accuracy of reading DNA sequence from the original sequencing signal and the effective read length.

Example 13: Error-Correction Code Fluorogenic DNA Sequencing

Figure 23:
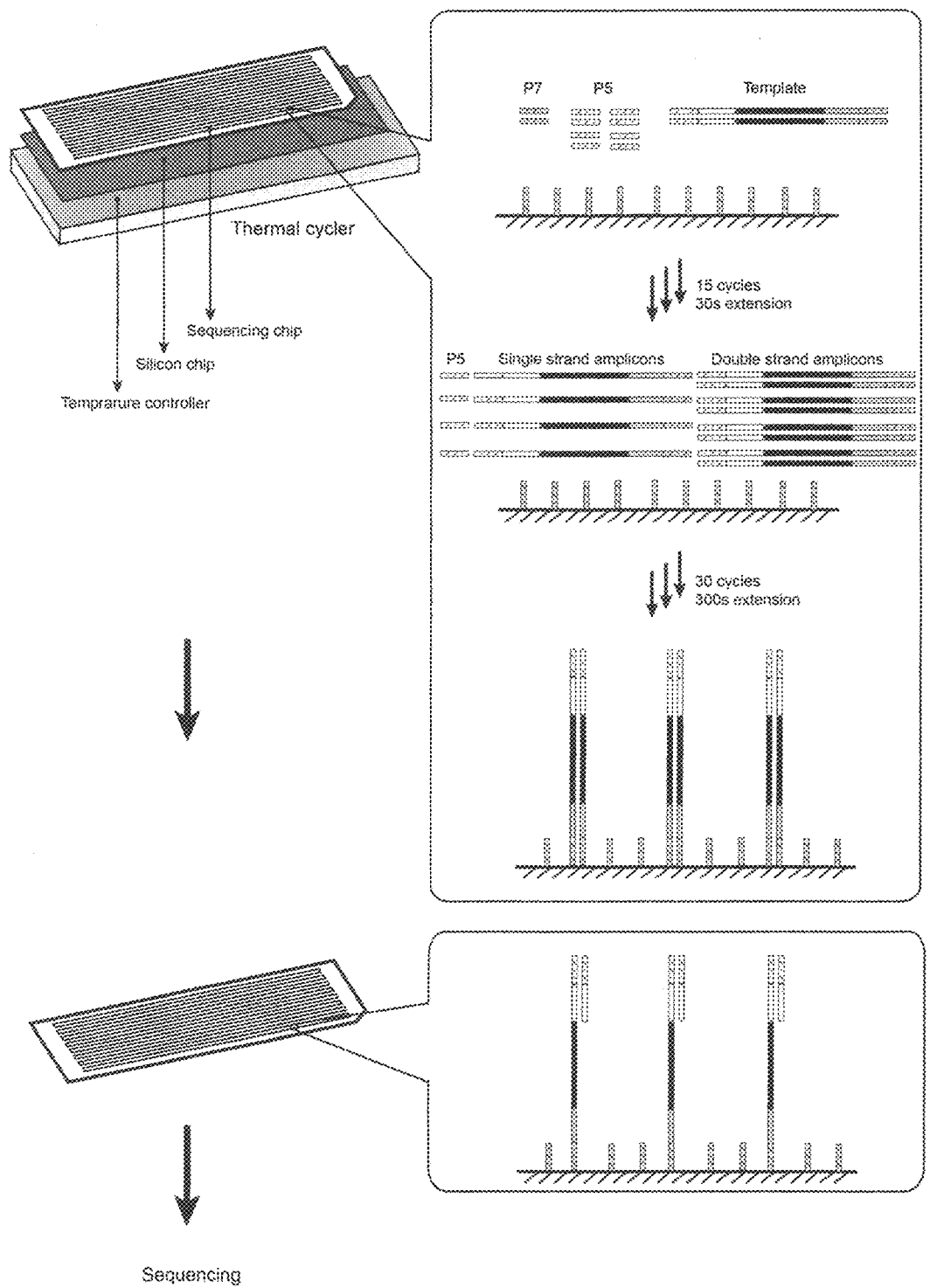
FIG. 23 shows solid phase PCR process.

The Principle of Degenerated-Base Fluorogenic Sequencing:

In this example, a family of fluorogenic sequencing substrates (using Tokyo Green (TG), a high-performance fluorophore) were developed to terminally label tetra-phosphate nucleotides (dN4P or dN, see FIG. 52A, and FIGS. 5A-5C). TG offers higher fluorescence quantum yield (0.82 at 490 nm), higher absorption coefficient, higher on-off ratio, and better photo-stability than previously reported fluorogenic dyes. During the fluorogenic sequencing-by-synthesis (SBS) process, the single-strand DNA templates were grafted onto the surface of a glass flow-cell using solid-phase PCR (FIG. 23). Each template was then annealed with sequencing primer with its 3'-end serving as the starting point for SBS reactions. In each cycle of the sequencing, a reaction mix (Bst polymerase, alkaline phosphatase, and fluorogenic nucleotides) was brought to react with those immobilized primed DNA templates. When the polymerase incorporates a correct nucleotide onto the primer terminus, a non-fluorescent "dark" state dye-triphosphate will be released simultaneously, and then immediately switched to a highly-fluorescent "bright" state through dephosphorylation. This fluorogenic SBS reaction produces native DNA duplex, leaving the 3'-end of the synthesized strand unterminated (still extendable, ready-to-extend). The substrates that can form correct Watson-Crick pairs at the primer terminus will continuously extend until the first mismatch encounters.

Figure 52A:
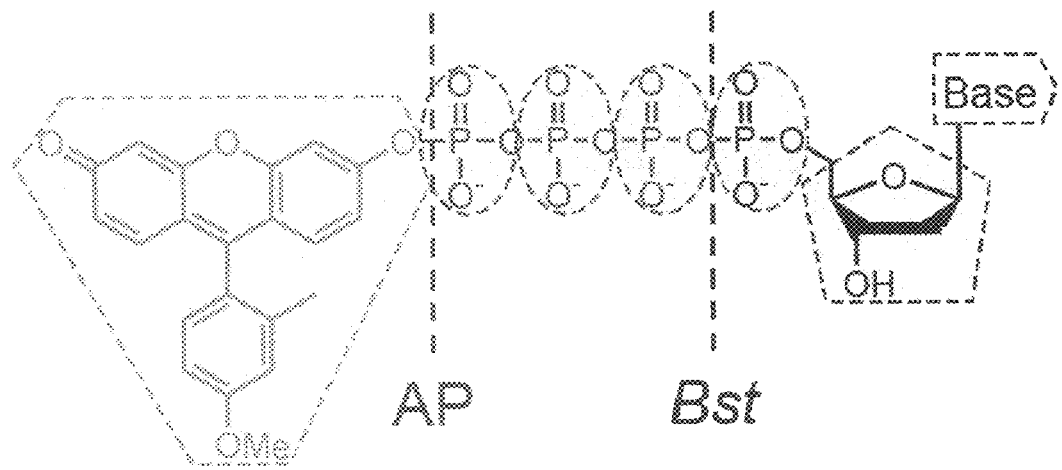
FIGS. 52A-C show the principle of degenerated-base fluorogenic sequencing, according to one aspect of the present disclosure.
Figure 52B:
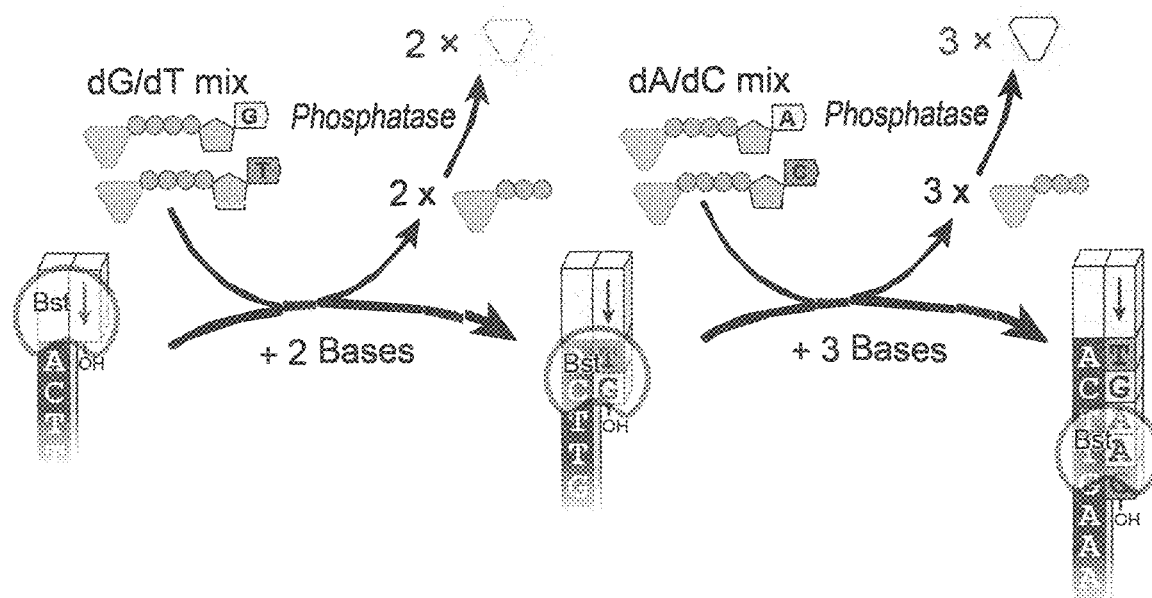
Figure 52C:
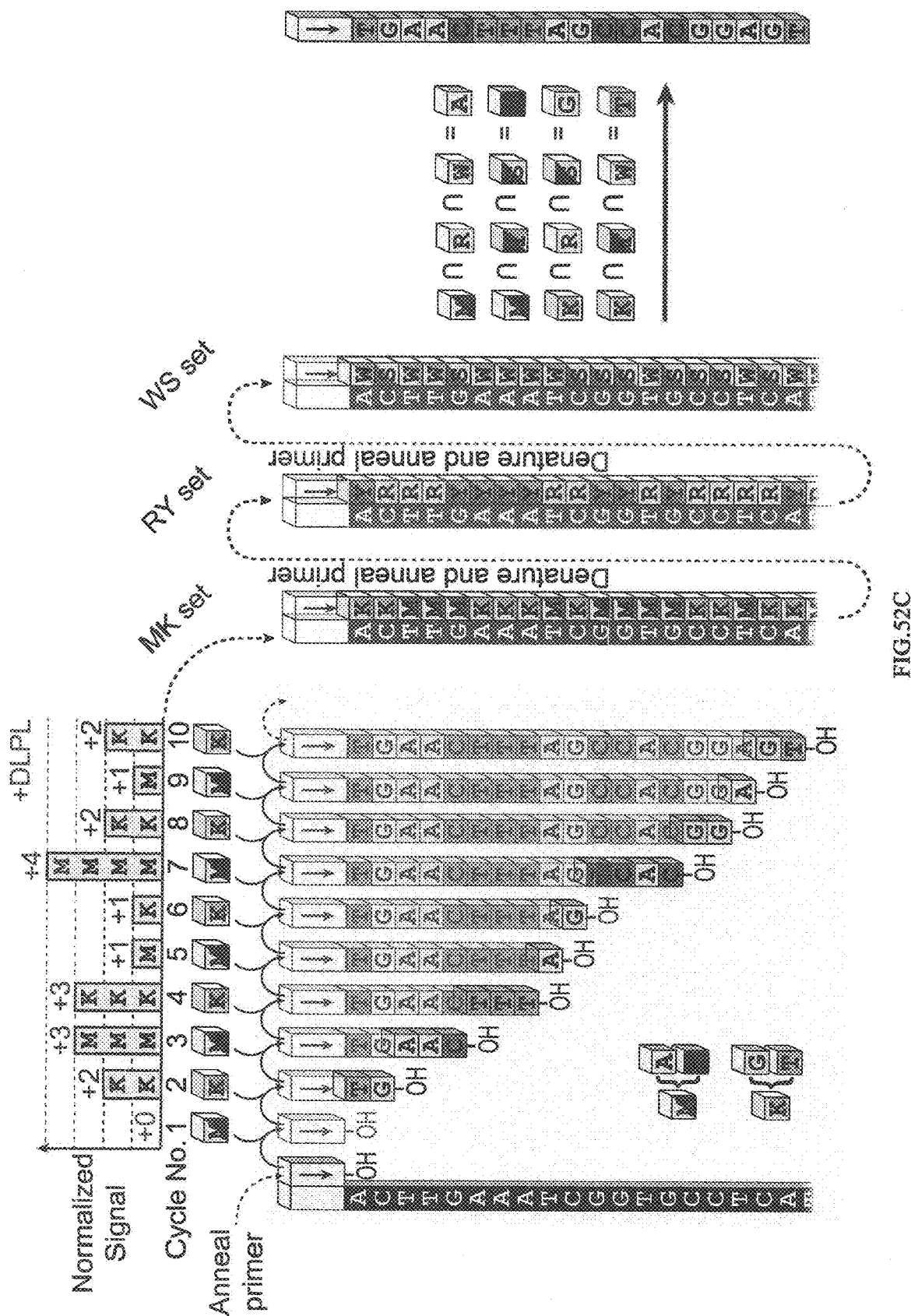

This feature has been utilized to sequence 30-40 bases through a single-base flowgram, in which one of the four substrates was introduced into the reaction in each cycle. In this example, a dual-base flowgram was used. For example, in the first cycle of the sequencing (FIG. 52B, K(dG & dT) reaction mix is brought to primed DNA template with the starting sequence ACTTGAAA. DNA polymerase will incorporate one dT and one dG to pair the first two bases AC and yield two fluorophores, then stop upon the third base T because of mismatch. In the following M cycle, two dA and one dC are paired with the next three bases TTG and yield three fluorophores. Conjugated mixes M and K are alternately introduced to react with the primed DNA template (FIG. 52C). The amount of fluorophores produced in each cycle is equivalent to the number of extended bases.

Fluorescence signal is measured upon the completion of polymerase elongation. Normalized fluorescence signal, representing the number, not the actual composition and sequence, of bases extended in each cycle, is named degenerated polymer length (DPL). In FIG. 52C, the DPL array (0, 2, 3, 3, 1, . . . ) can be transformed to a degenerate sequence (KKMMMKKKM . . . ), where M=A or C, K=G or T. Besides this M-K dual-base flowgram, there are two additional dual-base flowgrams R (A,G)-Y (C,T) and W (A,T)-S (C,G), through which the same template can be expressed as different degenerate sequences (YRRRYYYYRRYY . . . ) and (WSWWSWWWW . . . ). To acquire these three orthogonal degenerate sequences, a reset operation is needed between sequencing rounds to denature the nascent strand and reanneal the sequencing primer. Each actual base can be deduced from three sequences by calculating the intersection of degenerate bases. This sequencing method is named Error-Correcting Code (ECC) sequencing, through which sequencing errors can be detected and rectified.

Degenerated Base-Calling

Figure 53A:
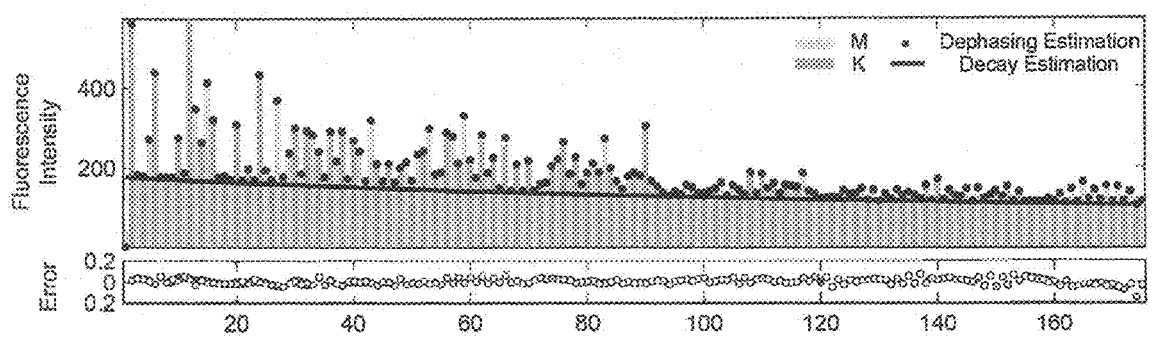
FIGS. 53A-E show the results of degenerated base-calling, according to one aspect of the present disclosure.
Figure 53B:
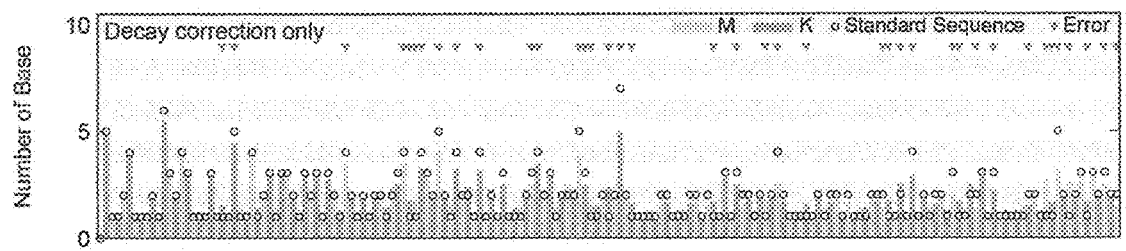

In this example, a lab-prototype was built to perform fluorogenic sequencing using dual-base flowgrams. Similar to other SBS sequencing approaches, the fluorescence intensity decay is inevitable. This decay, mainly due to the reaction imperfection and the loss of template or primer, has caused severe challenges in base-calling (FIG. 53A). In a typical fluorogenic degenerated sequencing run, the fluorescence intensity decline could be normalized by an exponential decay function with about 1% of signal drop between reaction cycles. Normalized fluorescence signal in each cycle should have been rounded into DPL (FIG. 53B). However, the correspondence between intensity and DPL could only be preserved in about first 30 cycles, after which dephasing could not be neglected, that is, the signal of each cycle became significantly affected by the neighboring cycles.

Dephasing, the asynchronization of primer ensemble, has two major components, the "lag" and the "lead." The lagging strands are majorly caused by incomplete extension, while in dual-base sequencing the leading strands are majorly attributed to unexpected extension caused by contaminating bases. In a given cycle the fluorescence signal, contributed from the asynchronized primer ensemble, is different from the corresponding DPL. The accumulation of dephasing will gradually reduce the correlation between the sequencing signals and DPL array.

Figure 53C:
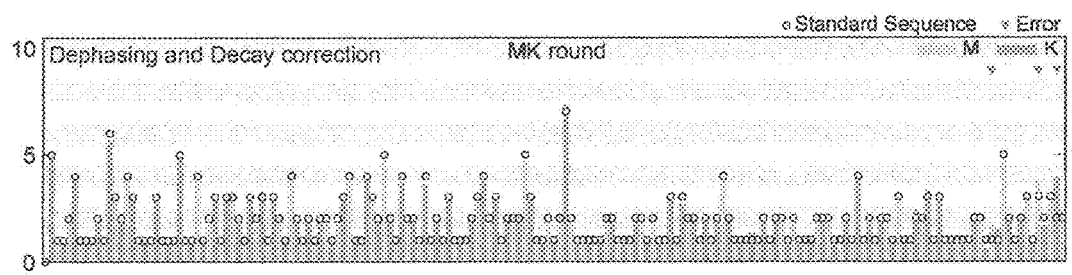
Figure 53D:
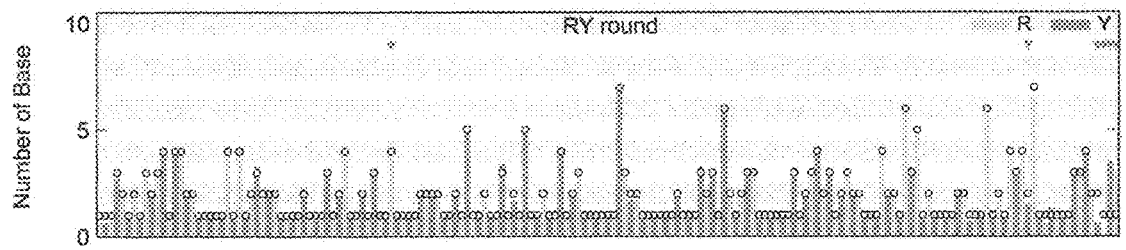
Figure 53E:
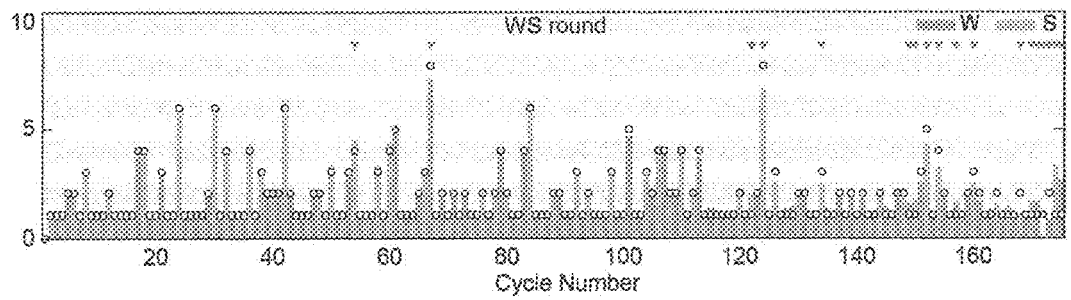

Nevertheless, it was demonstrated that the accumulation effect of signal dephasing and decay could be well estimated according to the first-order reaction manner, with residues between estimated and measured value less than 0.2. Furthermore, a sequence-independent iterative dephasing rectification algorithm was developed to deduce the DPL array of each sequencing round. With dephasing rectification, the low-error span of DPL array length can be significantly extended from the first 50 cycles (ca. 100 nt) to more than 150 cycles (ca. 300 nt), beyond which the crowded errors could not be correctly rectified with dephasing algorithm (FIG. 53C). For the same template, such rectification method can also be applied to the other two orthogonal degenerate sequences using RY and WS flowgrams (FIGS. 53D-E). Each of the three degenerate sequences harbors infrequent errors (<1%) that are unlikely to locate on the same base position. Information Communication Model for ECC Sequencing From the perspective of information theory, the information redundancy in dual-base sequencing was analyzed. In one aspect, a DPL array acquired from one dual-base sequencing round cannot provide an explicit DNA sequence. When there is no sequencing error, the information entropy of an L-nt long random DNA sequence is 2 L bits, while that of its DPL array is only L bits. The orthogonal nature guarantees that the mutual information entropy of two DPL arrays acquired from different flowgrams is 0 bit, and the joint information entropy is 2 L bits. Therefore, two degenerate sequences provide both sufficient and necessary information of an explicit DNA sequence (L+L−0=2 L). The explicit DNA sequence can be deduced by taking the intersection of the degenerated bases in two DPL arrays from different flowgrams. For example, if a base in the MK DPL array is sequenced as M(A/C), and in the RY DPL array as R(A/G), then it can be deduced as base A ({A, C}∩{A, G}={A}).

However, due to experimental sequencing errors, the entropy of DPL array (denoted as l) is lower than L bits. Two of such error-containing DPL arrays providing insufficient joint information to deduce the DNA sequence (l+l−0<2 L). With our current experimental error rate, an extra DPL array is introduced to provide the mutual/redundant information (2 L<3l<3 L), which can be used to both detect errors and deduce the explicit sequence.

An information communication model was also established, and the model contains an encoder, a decoder and a communication channel, to depict the dual-base sequencing with intrinsic characteristic of error detection and correction (FIG. 54A). Three orthogonal dual-base flowgrams encode a DNA sequence, the information source, into three original DPL arrays (n). The DPL distribution in human, yeast and *E. coli* genomes was analyzed and it was found that they are close to P(n)=½ⁿ, the theoretical distribution of DPL from a random DNA sequence. From FIG. 54B, it was also found that only 0.39% of DPL is greater than 8.0.

The sequencing reaction is regarded as the communication channel, through which sequencing errors are inevitably introduced into the received message. For instance, in Cycle 3 of the R-Y round, original DPL n=3 is mistakenly measured as m=4 (a 3-to-4 insertion error, FIG. 54A. The concordance of original and measured DPLs was analyzed in the 42 rounds of dual-base sequencing data. 5503 out of 5609 (98.1%) original DPL (n<9) are faithfully transmitted (FIG. 54C).

The measured DPL array were rewritten into degenerate base sequences by defining a codeword as the 3-tuple of degenerated bases in the same position from degenerate base sequence in the order of MK, RY and WS. In the case of FIG. 54A, the first few codewords are (KYW), (KRS), (MRW), etc. Such codeword can be further compiled into a binary format. M, R and W were assigned as logical 1, and K, Y and S as logical 0. Each degenerate sequence in any single flowgram became a bit string (BS). The parity of a codeword is defined as the result of XOR (exclusive or) operation of its three bits (FIG. 54D). The degenerated bases in a codeword have only one common base if and only if the parity is logical 1, and this common base is regarded as the decoding result. Specifically, 111 (MRW) is decoded as a base A, 100 (MYS) as a C, 010 (KRS) as a G, 001 (KYW) as a T. These four legitimate codewords have Hamming distances of 2 in between. On the other hand, the rest four illegitimate codewords with parity logical 0 (no common base) indicate sequencing errors. As the case in FIG. 54A, the DNA sequence was decoded from the BS and a 3-to-4 error at the fifth codeword (MRS/110) was caught by decoder through parity check. Conventionally, memoryless codewords with hamming distance 2 are only error-detectable but not correctable. However, it was discovered that dual-base sequencing results in BS format are not memoryless but context dependent, providing extra information for error correction besides error detection.

Sequence Decoding Using Dynamic Programming

The error correction decoding was performed through an algorithm based on dynamic programming. Dual-base sequencing errors, mistakenly measured DPLs, can be easily identified in the codeword list by parity check. These unique errors are only bit insertions or deletions, but not bit alterations, in a BS. When an error is found, it is possible to be rectified by changing the corresponding DPLs based on BS context. Errors must be rectified sequentially from the first error, because the changes of DPL, corresponding to B S-shift operations, will affect the downstream codewords.

Figure 55A:
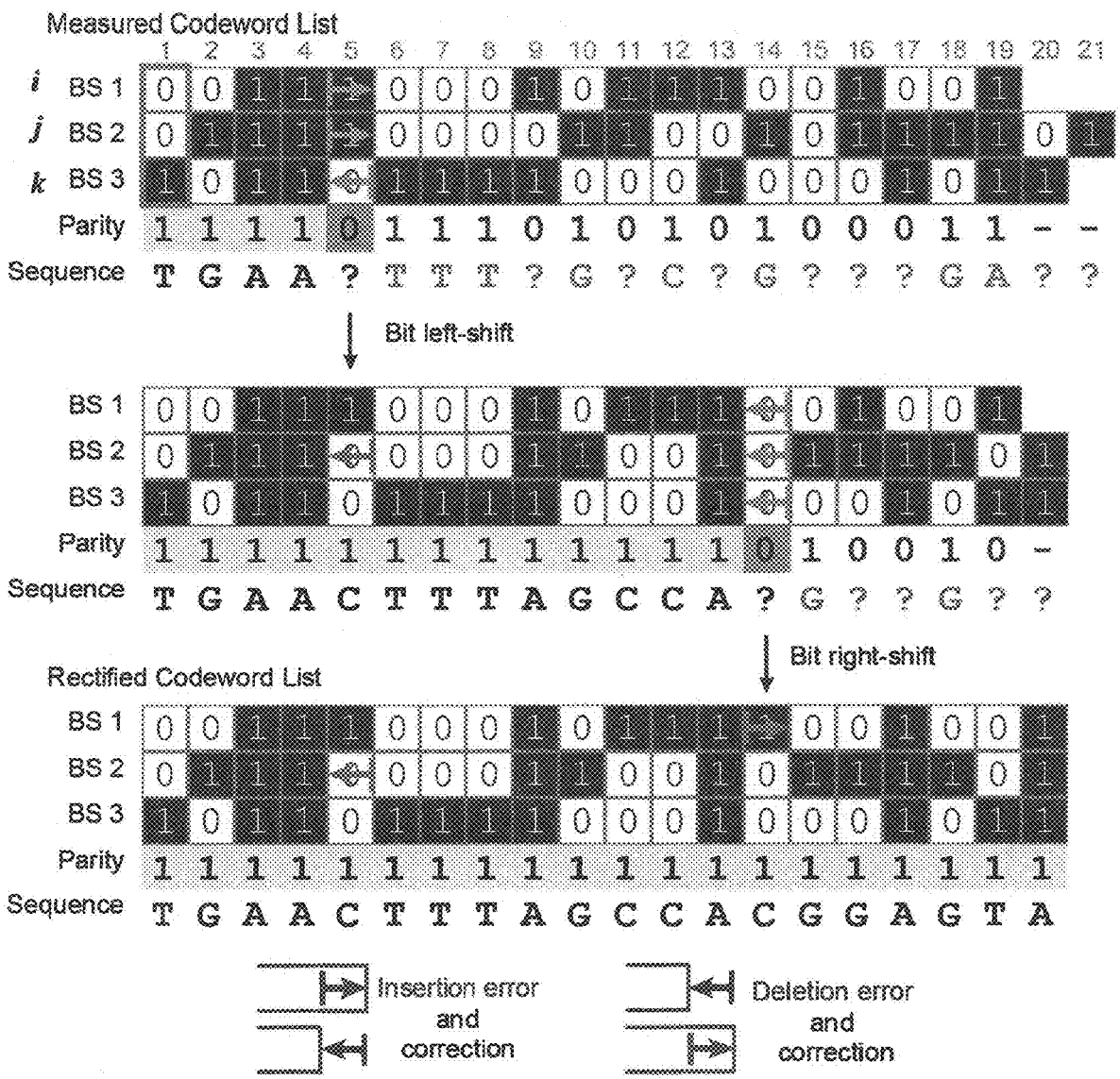
FIGS. 55A-C show the results of sequence decoding using dynamic programming, according to one aspect of the present disclosure.
Figure 55B:
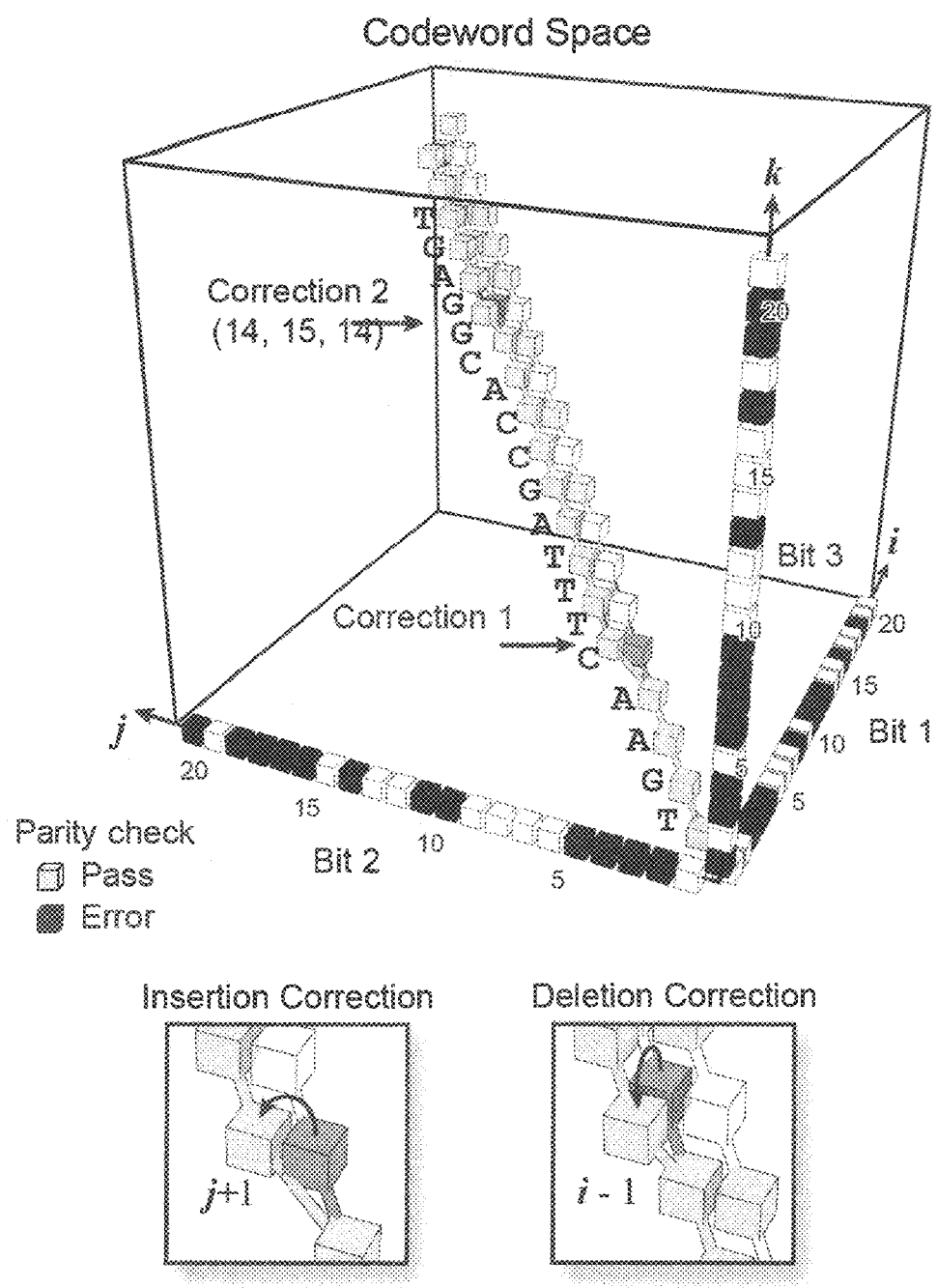

A typical example is shown in FIG. 55A. The first illegitimate codeword is detected at Codeword 5, and there are three possible error sources: (1) insertion error in Cycle 2 of M-K Round, original DPL (n=2) is erroneously measured as 3; (2) insertion error in Cycle 2 of R-Y Round, original DPL (n=3) is measured as 4; and (3) deletion error in Cycle 3 of W-S Round, original DPL (n=3) is measured as 2. Insertion error in Cycle 2 of R-Y Round is corrected by left-shifting BS2 since the 6th bit. With this shift operation, many following illegitimate codewords pass parity check concomitantly. Then a second error is detected at Base 14. This deletion error, together with the rest illegitimate codewords, is rectified by right-shifting BS1 since the 14th bit. In this case, nine codeword illegitimacies are legitimized by only two correction operations, resulting in an error-free decoded DNA sequence.

In fact, there are numerous possible operation combinations to decode the sequence. Moreover, the number of combinations increases exponentially with the read length, making it practically impossible to obtain the optimal sequence by enumerating all possible combinations.

Figure 55C:
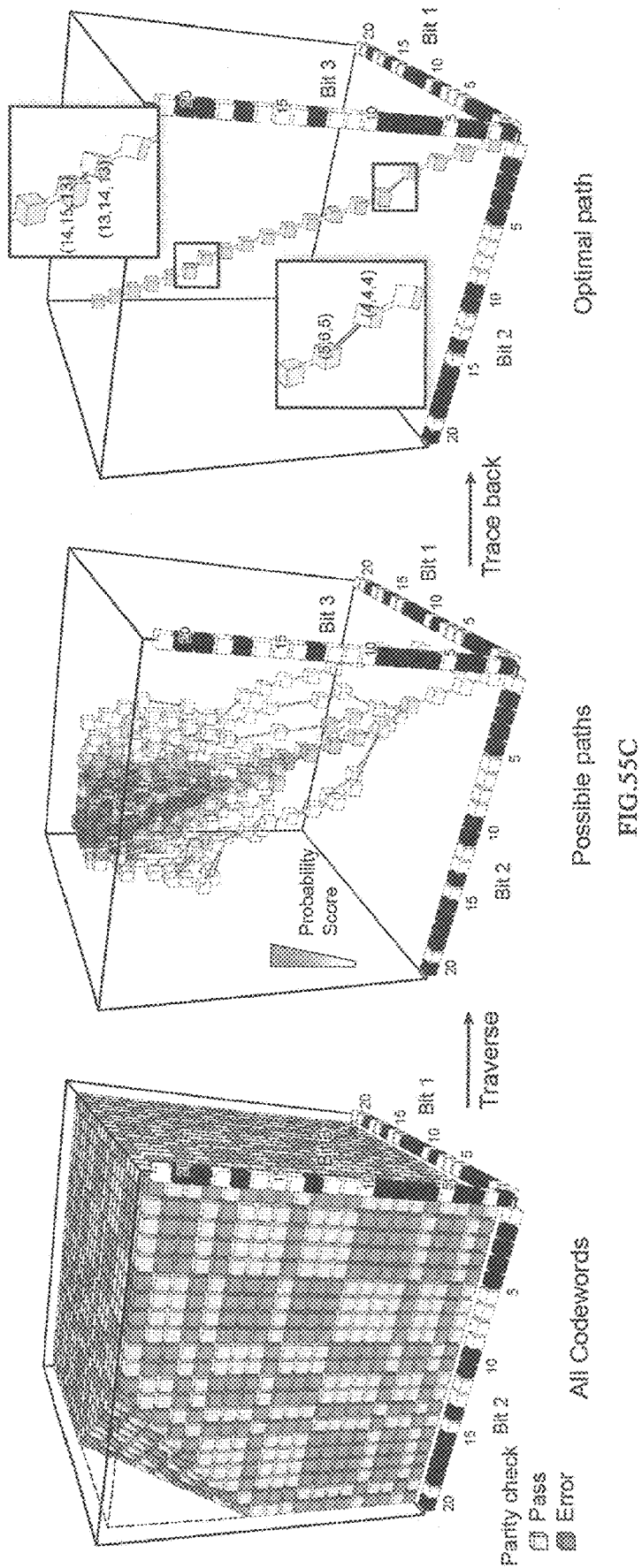

Therefore, dynamic programming was utilized to determine the global optimal decoded sequence. A codeword space was constructed as a 3-dimensional matrix with the three BSs as its axis. Each node (i, j, k) represents the codeword consisting of the i-th bit of BS1, the j-th bit of BS2 and the k-th bit of BS3, and it can be classified as or separated into two categories, Pass or Error, according to the parity checking (FIG. 55C). Any path starting from the node (1, 1, 1) and only passing through the Pass nodes represents a possible decoded DNA sequence. The probability of a given path in the codeword space can be calculated by the Bayesian formula. The prior probability of the occurrence of DPL with length n is $½^n$ (FIG. 54B), and the probability of DPL with length n to be sequenced as length m P(m|n) can be obtained from reference sequences and compare the data to theoretical values (FIG. 54C). Then for Round r (r is MK, RY, or WS), the posterior probability $P_r(n_i|m_i)$ that its i-th measured DPL of length $m_i$ is produced from a DPL of length $n_i$ can be give below:

$$P_r(n_i | m_i) = \frac{P(m_i | n_i)/2^{n_i}}{\sum_{k=1}^{\infty} P(m_i | k)/2^k}, r \in \{MK, RY, WS\}.$$

The probability $P_r$ that a measured DPL array is produced from a certain DNA is the cumulative product of $P_r(n_i|m_i)$. Under the hypothesis that the three rounds of ECC sequencing are independent to each other, the probability of a given path is $$P_{Path} = P_{MK} \cdot P_{RY} \cdot P_{WS}.$$

The probability of every path in the codeword space can be calculated in the same way (FIG. 55C). A dynamic programming approach is adopted to obtain the path with the maximum probability.

Decoding Upheaves ECC Sequencing Accuracy

Figure 56A:
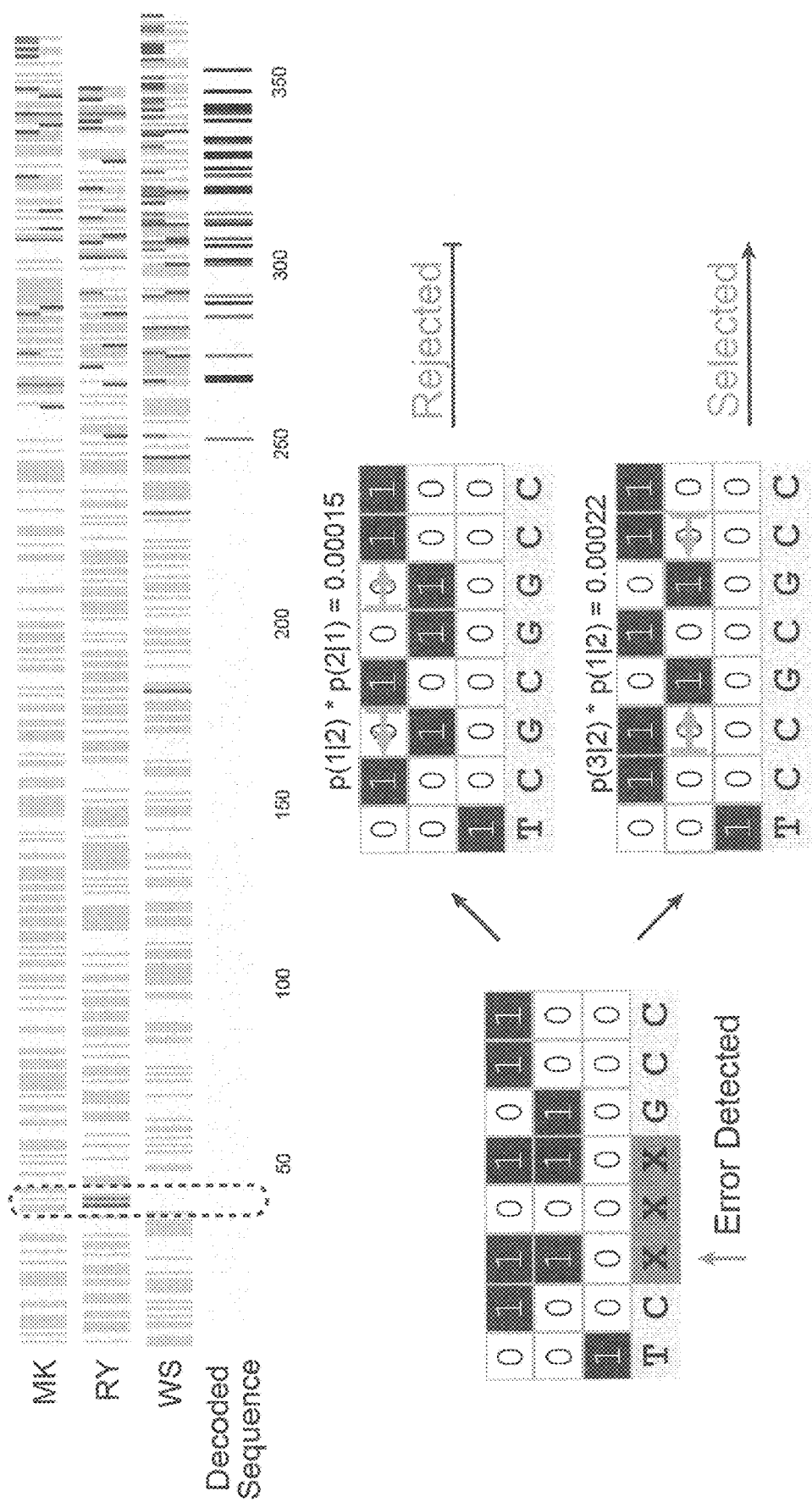
FIGS. 56A-C show that decoding upheaves ECC sequencing accuracy, according to one aspect of the present disclosure.
Figure 56B:
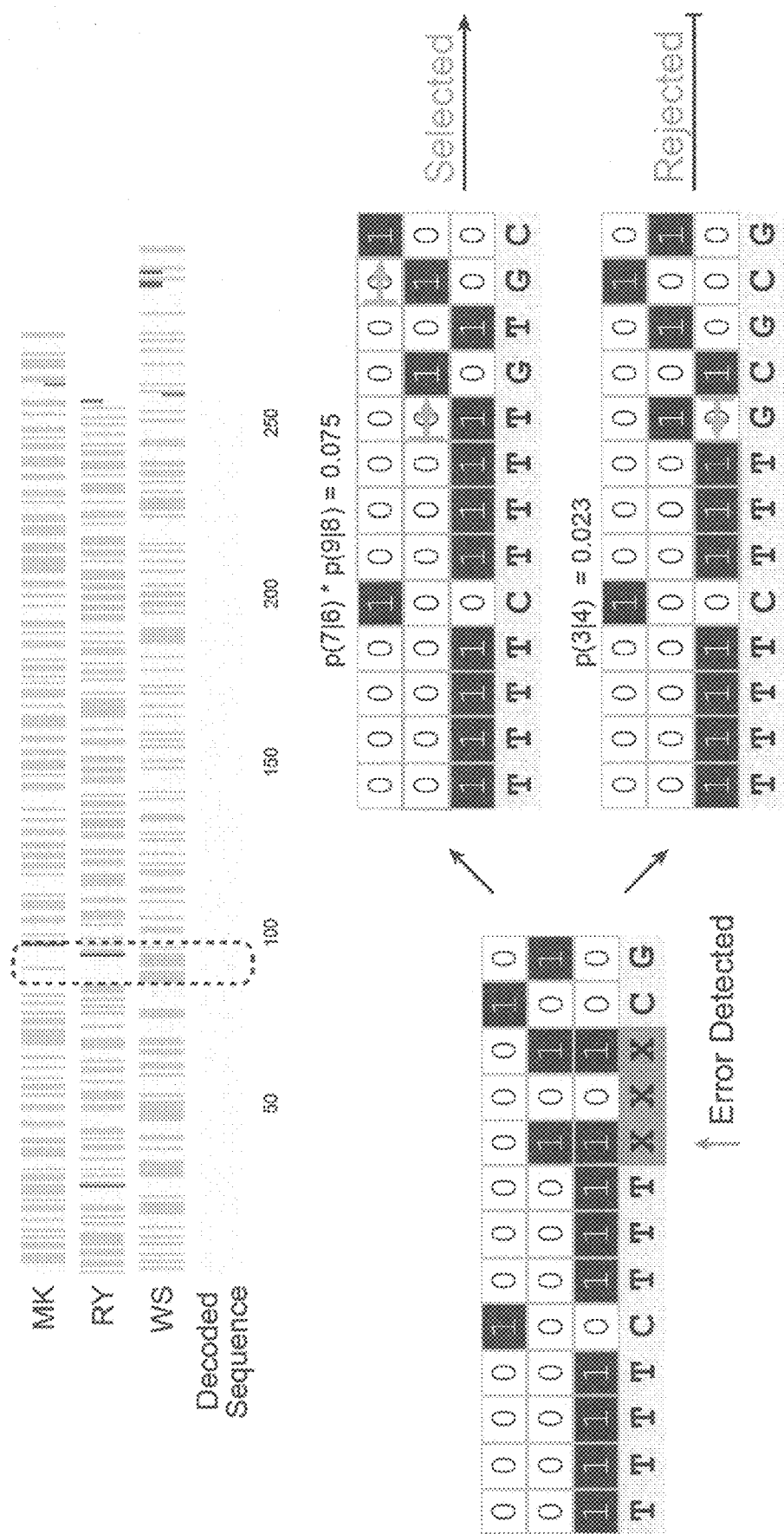
Figures 56C, 56D:
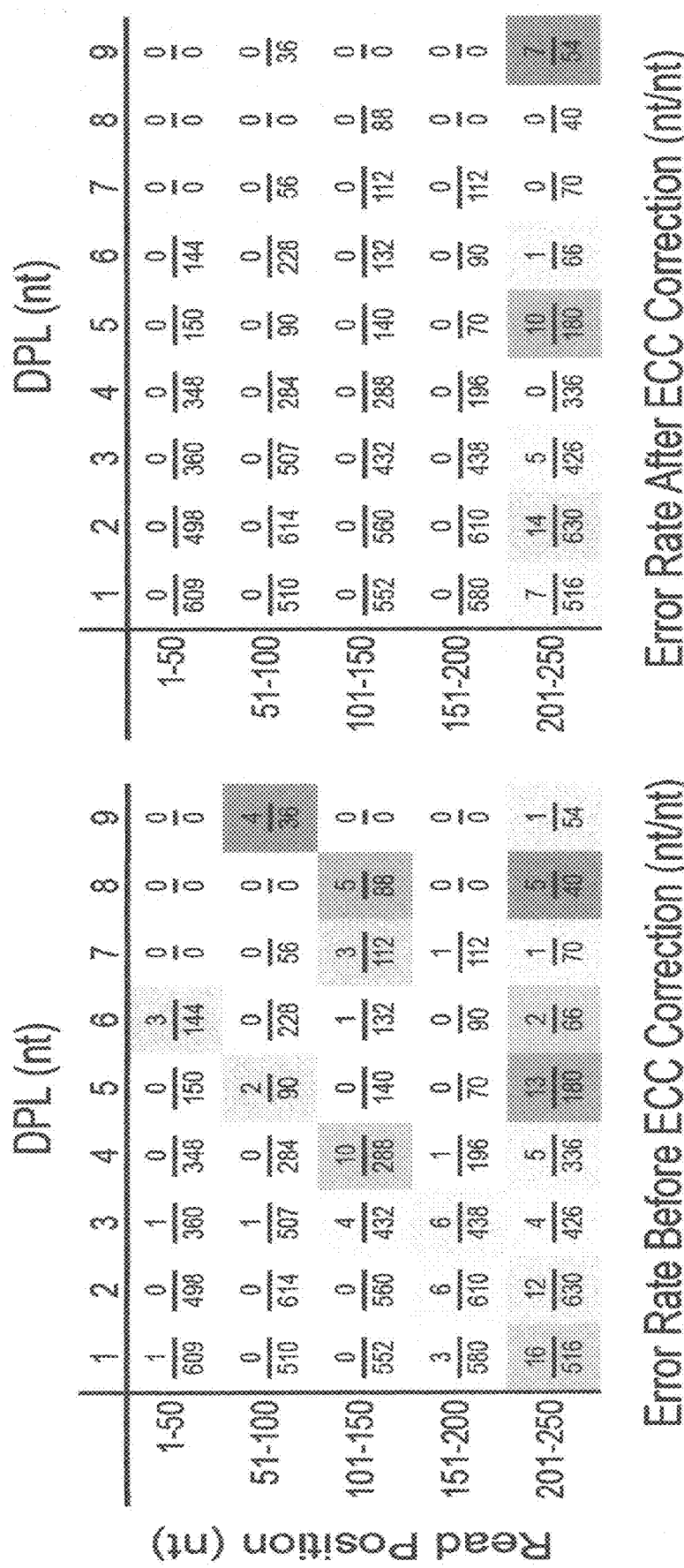
FIG. 56D shows the error frequencies of different DPLs along the sequencing read analyzed every 50 nt after ECC correction.

ECC decoding can efficiently rectify errors for long sequencing reads. 14 long-length three-round ECC experiments were performed to sequence 3 different templates from lambda phage. Before ECC decoding, there are minor errors occasionally in the sequencing signals. After decoding, these errors are completely eliminated before 200 bp, and also significantly reduced in 200-250 bp (FIGS. 56A-C). For example in FIG. 56A, although the first sequencing error occurs in Base 39 of Round RY, it was successfully corrected after ECC decoding along with other several sequencing errors in Round WS. The first error after ECC decoding was put off beyond 270 bp.

ECC decoding algorithm has the power to accurately identify complex error forms. Compared to scattered sequencing errors, neighboring errors in the same or different rounds are more challenging to correct since more and exquisite correction operations are required in the decoding algorithm. When parity check failed between the three-round sequencing signals, the algorithm will calculate the probabilities of different operations.

In one case, two sequencing errors occurred within 3 cycles in round RY (1base deletion in cycle 22 and 1 base insertion at cycle 24). At least two alternative correction approaches, each of which contains two correction operations, can fix these errors (FIG. 56B). The first approach operates an 1-to-2 insertion correction and a 2-to-1 deletion correction (p(2|1)*p(1|2)=0.00015, while the second approach contains an 1-to-2 insertion correction and a 3-to-2 deletion correction (p(2|1)*p(3|2)=0.00022. Therefore, the second approach is preferred because of the higher probability.

In another case, two neighboring long DPL sequencing errors occurred in round MK and RY, respectively. Apparently, left shift of one base in round WS can also restore the parity legitimacy (FIG. 56C). However, since long DPLs are more error-prone, the algorithm prefers correcting two longer DPLs rather than a shorter one through comparing the probabilities of different approaches.

Fluorogenic degenerate sequencing has intrinsically high accuracy. The error frequencies of different DPL along the sequencing read were analyzed every 50 nt (FIG. 56D). Without ECC correction, 106 errors in 11062 bases were found. These errors are more likely to happen on longer DPLs and on posterior positions, similar to other sequencing methods. See Forgetta et al. (2013) *Journal of Biomolecular Techniques*, 24(1), 3949; and Loman et al. (2012) *Nature Biotechnology*, 30(5), 4349. The raw accuracy is 99.82% in the first 100 nt, and 99.45% in the first 200 nt. With 99% accuracy cut-off, the read length of more than 250 nt can be achieved.

ECC decoding eliminates the majority of sequencing errors. The high raw accuracy of fluorogenic degenerate sequencing approach provides a foundation for ECC correction to completely eliminate all errors in the first 200 nt, including the errors in DPL up to 9 nt, with the estimated the upper boundary error rate as low as 0.034%. In addition, ECC decoding effectively reduced the cumulative error rate of 250 nt, from 0.96% to 0.33%.

SEQUENCE LISTING

<160> NUMBER OF SEQ ID NOS: 41

<210> SEQ ID NO 1
<211> LENGTH: 15
<212> TYPE: DNA
<213> ORGANISM: Artificial Sequences
<220> FEATURE:
<223> OTHER INFORMATION: Synthetic

<400> SEQUENCE: 1
aactttggat tgcct                                                    15

<210> SEQ ID NO 2
<211> LENGTH: 20

```
<212> TYPE: DNA
<213> ORGANISM: Artificial Sequences
<220> FEATURE:
<223> OTHER INFORMATION: Synthetic

<400> SEQUENCE: 2
tgaactttag ccacggagta                                                    20

<210> SEQ ID NO 3
<211> LENGTH: 31
<212> TYPE: DNA
<213> ORGANISM: Artificial Sequences
<220> FEATURE:
<223> OTHER INFORMATION: Synthetic

<400> SEQUENCE: 3
tttttttttt caagcagaag acggcatacg a                                       31

<210> SEQ ID NO 4
<211> LENGTH: 20
<212> TYPE: DNA
<213> ORGANISM: Artificial Sequences
<220> FEATURE:
<223> OTHER INFORMATION: Synthetic

<400> SEQUENCE: 4
aatgatacgg cgaccaccga                                                    20

<210> SEQ ID NO 5
<211> LENGTH: 21
<212> TYPE: DNA
<213> ORGANISM: Artificial Sequences
<220> FEATURE:
<223> OTHER INFORMATION: Synthetic

<400> SEQUENCE: 5
caagcagaag acggcatacg a                                                  21

<210> SEQ ID NO 6
<211> LENGTH: 58
<212> TYPE: DNA
<213> ORGANISM: Artificial Sequences
<220> FEATURE:
<223> OTHER INFORMATION: Synthetic

<400> SEQUENCE: 6
aatgatacgg cgaccaccga gatctacact ctttccctac acgacgctct tccgatct          58

<210> SEQ ID NO 7
<211> LENGTH: 21
<212> TYPE: DNA
<213> ORGANISM: Artificial Sequences
<220> FEATURE:
<223> OTHER INFORMATION: Synthetic

<400> SEQUENCE: 7
tcgtatgccg tcttctgctt g                                                  21

<210> SEQ ID NO 8
<211> LENGTH: 35
<212> TYPE: DNA
<213> ORGANISM: Artificial Sequences
<220> FEATURE:
<223> OTHER INFORMATION: Synthetic

<400> SEQUENCE: 8
```
ttacactctt tccctacacg acgtctcttcc gatct          35

<210> SEQ ID NO 9
<211> LENGTH: 55
<212> TYPE: DNA
<213> ORGANISM: Artificial Sequences
<220> FEATURE:
<223> OTHER INFORMATION: Synthetic

<400> SEQUENCE: 9
acactctttc cctacacgac gctcttccga tctgtgttcg acggtgagct gagtt          55

<210> SEQ ID NO 10
<211> LENGTH: 54
<212> TYPE: DNA
<213> ORGANISM: Artificial Sequences
<220> FEATURE:
<223> OTHER INFORMATION: Synthetic

<400> SEQUENCE: 10
gtgactggag ttcagacgtg tgctcttccg atctcaagcc ctgccgcttt ctgc          54

<210> SEQ ID NO 11
<211> LENGTH: 55
<212> TYPE: DNA
<213> ORGANISM: Artificial Sequences
<220> FEATURE:
<223> OTHER INFORMATION: Synthetic

<400> SEQUENCE: 11
acactctttc cctacacgac gctcttccga tctgtgacag cagagctgcg taatc          55

<210> SEQ ID NO 12
<211> LENGTH: 54
<212> TYPE: DNA
<213> ORGANISM: Artificial Sequences
<220> FEATURE:
<223> OTHER INFORMATION: Synthetic

<400> SEQUENCE: 12
gtgactggag ttcagacgtg tcatgcgatc atatgagtac ggctgcagcg cccg          54

<210> SEQ ID NO 13
<211> LENGTH: 57
<212> TYPE: DNA
<213> ORGANISM: Artificial Sequences
<220> FEATURE:
<223> OTHER INFORMATION: Synthetic

<400> SEQUENCE: 13
acactctttc cctacacgac gctcttccga tcttatcgaa cagtcaggtt aacaggc          57

<210> SEQ ID NO 14
<211> LENGTH: 54
<212> TYPE: DNA
<213> ORGANISM: Artificial Sequences
<220> FEATURE:
<223> OTHER INFORMATION: Synthetic

<400> SEQUENCE: 14
gtgactggag ttcagacgtg tcatgcgatc atatcaacca gataagggtg ttgc          54

<210> SEQ ID NO 15
<211> LENGTH: 53
<212> TYPE: DNA
<213> ORGANISM: Artificial Sequences

```
<220> FEATURE:
<223> OTHER INFORMATION: Synthetic

<400> SEQUENCE: 15
acactctttc cctacacgac gctcttccga tctactccgc tgaagtggtg gaa          53

<210> SEQ ID NO 16
<211> LENGTH: 54
<212> TYPE: DNA
<213> ORGANISM: Artificial Sequences
<220> FEATURE:
<223> OTHER INFORMATION: Synthetic

<400> SEQUENCE: 16
gtgactggag ttcagacgtg tcatgcgatc atatttatgc tctataaagt aggc         54

<210> SEQ ID NO 17
<211> LENGTH: 53
<212> TYPE: DNA
<213> ORGANISM: Artificial Sequences
<220> FEATURE:
<223> OTHER INFORMATION: Synthetic

<400> SEQUENCE: 17
acactctttc cctacacgac gctcttccga tctcactcac aacaatgagt ggc          53

<210> SEQ ID NO 18
<211> LENGTH: 54
<212> TYPE: DNA
<213> ORGANISM: Artificial Sequences
<220> FEATURE:
<223> OTHER INFORMATION: Synthetic

<400> SEQUENCE: 18
gtgactggag ttcagacgtg tcatgcgatc atatcacgga atgcattttt ctgg         54

<210> SEQ ID NO 19
<211> LENGTH: 53
<212> TYPE: DNA
<213> ORGANISM: Artificial Sequences
<220> FEATURE:
<223> OTHER INFORMATION: Synthetic

<400> SEQUENCE: 19
acactctttc cctacacgac gctcttccga tctgcctaaa gtaataaaac cga          53

<210> SEQ ID NO 20
<211> LENGTH: 54
<212> TYPE: DNA
<213> ORGANISM: Artificial Sequences
<220> FEATURE:
<223> OTHER INFORMATION: Synthetic

<400> SEQUENCE: 20
gtgactggag ttcagacgtg tcatgcgatc atatggcata atgcaatacg tgta         54

<210> SEQ ID NO 21
<211> LENGTH: 53
<212> TYPE: DNA
<213> ORGANISM: Artificial Sequences
<220> FEATURE:
<223> OTHER INFORMATION: Synthetic

<400> SEQUENCE: 21
acactctttc cctacacgac gctcttccga tctaagagct ggacagcgat acc          53
```

<210> SEQ ID NO 22
<211> LENGTH: 54
<212> TYPE: DNA
<213> ORGANISM: Artificial Sequences
<220> FEATURE:
<223> OTHER INFORMATION: Synthetic

<400> SEQUENCE: 22
gtgactggag ttcagacgtg tgctcttccg atctcatcgc tgactctccg gatt           54

<210> SEQ ID NO 23
<211> LENGTH: 57
<212> TYPE: DNA
<213> ORGANISM: Artificial Sequences
<220> FEATURE:
<223> OTHER INFORMATION: Synthetic

<400> SEQUENCE: 23
acactctttc cctacacgac gctcttccga tcttatcgaa cagtcaggtt aacaggc        57

<210> SEQ ID NO 24
<211> LENGTH: 54
<212> TYPE: DNA
<213> ORGANISM: Artificial Sequences
<220> FEATURE:
<223> OTHER INFORMATION: Synthetic

<400> SEQUENCE: 24
gtgactggag ttcagacgtg tgctcttccg atcttcgctg cccatcgcat tcat           54

<210> SEQ ID NO 25
<211> LENGTH: 55
<212> TYPE: DNA
<213> ORGANISM: Artificial Sequences
<220> FEATURE:
<223> OTHER INFORMATION: Synthetic

<400> SEQUENCE: 25
acactctttc cctacacgac gctcttccga tctgtgttcg acggtgagct gagtt          55

<210> SEQ ID NO 26
<211> LENGTH: 54
<212> TYPE: DNA
<213> ORGANISM: Artificial Sequences
<220> FEATURE:
<223> OTHER INFORMATION: Synthetic

<400> SEQUENCE: 26
gtgactggag ttcagacgtg tgctcttccg atctgctgaa aaacaggctg agca           54

<210> SEQ ID NO 27
<211> LENGTH: 51
<212> TYPE: DNA
<213> ORGANISM: Artificial Sequences
<220> FEATURE:
<223> OTHER INFORMATION: Synthetic

<400> SEQUENCE: 27
caagcagaag acggcatacg agatactgac gtgactggag ttcagacgtg t              51

<210> SEQ ID NO 28
<211> LENGTH: 45
<212> TYPE: DNA
<213> ORGANISM: Artificial Sequences
<220> FEATURE:
<223> OTHER INFORMATION: Synthetic

```
<400> SEQUENCE: 28
aatgatacgg cgaccaccga gatctacact ctttccctac acgac          45

<210> SEQ ID NO 29
<211> LENGTH: 201
<212> TYPE: DNA
<213> ORGANISM: Artificial Sequences
<220> FEATURE:
<223> OTHER INFORMATION: Synthetic

<400> SEQUENCE: 29
gtgttcgacg gtgagctgag ttttgccctg aaactggcgc gtgagatggg gcgacccgac     60
tggcgtgcca tgcttgccgg gatgtcatcc acggagtatg ccgactggca ccgcttttac    120
agtacccatt attttcatga tgttctgctg gatatgcact tttccgggct gacgtacacc    180
gtgctcagcc tgttttttcag c                                             201

<210> SEQ ID NO 30
<211> LENGTH: 193
<212> TYPE: DNA
<213> ORGANISM: Artificial Sequences
<220> FEATURE:
<223> OTHER INFORMATION: Synthetic

<400> SEQUENCE: 30
tatcgaacag tcaggttaac aggctgcggc attttgtccg cgccgggctt cgctcactgt     60
tcaggccgga gccacagacc gccgttgaat gggcggatgc taattactat ctcccgaaag    120
aatccgcata ccaggaaggg cgctgggaaa cactgcccct tcagcgggcc atcatgaatg    180
cgatgggcag cga                                                       193

<210> SEQ ID NO 31
<211> LENGTH: 308
<212> TYPE: DNA
<213> ORGANISM: Artificial Sequences
<220> FEATURE:
<223> OTHER INFORMATION: Synthetic

<400> SEQUENCE: 31
tatcgaacag tcaggttaac aggctgcggc attttgtccg cgccgggctt cgctcactgt     60
tcaggccgga gccacagacc gccgttgaat gggcggatgc taattactat ctcccgaaag    120
aatccgcata ccaggaaggg cgctgggaaa cactgcccct tcagcgggcc atcatgaatg    180
cgatgggcag cgactacatc cgtgaggtga atgtggtgaa gtctgcccgt gtcggttatt    240
ccaaaatgct gctgggtgtt tatgcctact ttatagagca taagcagcgc aacacccta    300 tctggttg                                                             308

<210> SEQ ID NO 32
<211> LENGTH: 305
<212> TYPE: DNA
<213> ORGANISM: Artificial Sequences
<220> FEATURE:
<223> OTHER INFORMATION: Synthetic

<400> SEQUENCE: 32
gtgacagcag agctgcgtaa tctcccgcat attgccagca tggcctttaa tgagccgctg     60
atgcttgaac ccgcctatgc gcgggttttc ttttgtgcgc ttgcaggcca gcttgggatc    120
agcagcctga cggatgcggt gtccggcgac agcctgactg cccaggaggc actcgcgacg    180
```

```
ctggcattat ccggtgatga tgacggacca cgacaggccc gcagttatca ggtcatgaac    240
ggcatcgccg tgctgccggt gtccggcacg ctggtcagcc ggacgcgggc gctgcagccg    300
tactc                                                                305
```

<210> SEQ ID NO 33
<211> LENGTH: 303
<212> TYPE: DNA
<213> ORGANISM: Artificial Sequences
<220> FEATURE:
<223> OTHER INFORMATION: Synthetic

<400> SEQUENCE: 33

```
catttgaaca taacggtgtg accgtcacgc tttctgaact gtcagccctg cagcgcattg    60
agcatctcgc cctgatgaaa cggcaggcag aacaggcgga gtcagacagc aaccggaagt   120
ttactgtgga agacgccatc agaaccggcg cgtttctggt ggcgatgtcc ctgtggcata   180
accatccgca agacgcag atgccgtcca tgaatgaagc cgttaaacag attgagcagg    240
aagtgcttac cacctggccc acggaggcaa tttctcatgc tgaaaacgtg gtgtaccggc   300
tgt                                                                303
```

<210> SEQ ID NO 34
<211> LENGTH: 301
<212> TYPE: DNA
<213> ORGANISM: Artificial Sequences
<220> FEATURE:
<223> OTHER INFORMATION: Synthetic

<400> SEQUENCE: 34

```
gtgttcgacg gtgagctgag ttttgccctg aaactggcgc gtgagatggg gcgacccgac    60
tggcgtgcca tgcttgccgg gatgtcatcc acggagtatg ccgactggca ccgcttttac   120
agtacccatt attttcatga tgttctgctg gatatgcact tttccgggct gacgtacacc   180
gtgctcagcc tgttttttcag cgatccggat atgcatccgc tggatttcag tctgctgaac   240
cggcgcgagg ctgacgaaga gcctgaagat gatgtgctga tgcagaaagc ggcagggctt   300
g                                                                  301
```

<210> SEQ ID NO 35
<211> LENGTH: 497
<212> TYPE: DNA
<213> ORGANISM: Artificial Sequences
<220> FEATURE:
<223> OTHER INFORMATION: Synthetic

<400> SEQUENCE: 35

```
tactcaaccc gatgtttgag tacggtcatc atctgacact acagactctg gcatcgctgt    60
gaagacgacg cgaaattcag catttcaca agcgttatct tttacaaaac cgatctcact   120
ctcctttgat gcaatgcca gcgtcagaca tcatatgcag atactcacct gcatcctgaa   180
cccattgacc tccaaccccg taatagcgat gcgtaatgat gtcgatagtt actaacgggt   240
cttgttcgat taactgccgc agaaactctt ccaggtcacc agtgcagtgc ttgataacag   300
gagtcttccc aggatggcga acaacaagaa actggtttcc gtcttcacgg acttcgttgc   360
tttccagttt agcaatacgc ttactcccat ccgagataac accttcgtaa tactcacgct   420
gctcgttgag ttttgatttt gctgtttcaa gctcaacacg cagtttccct actgttagcg   480
caatatcctc gttctcc                                                 497
```

<210> SEQ ID NO 36
<211> LENGTH: 500
<212> TYPE: DNA
<213> ORGANISM: Artificial Sequences
<220> FEATURE:
<223> OTHER INFORMATION: Synthetic

<400> SEQUENCE: 36

```
actccgctga agtggtggaa accgcattct gtactttcgt gctgtcgcgg atcgcaggtg      60
aaattgccag tattctcgac gggctccccc tgtcggtgca gcggcgtttt ccggaactgg     120
aaaaccgaca tgttgatttc ctgaaacggg atatcatcaa agccatgaac aaagcagccg     180
cgctggatga actgataccg gggttgctga gtgaatatat cgaacagtca ggttaacagg     240
ctgcggcatt ttgtccgcgc cgggcttcgc tcactgttca ggccggagcc acagaccgcc     300
gttgaatggg cggatgctaa ttactatctc ccgaaagaat ccgcatacca ggaagggcgc     360
tgggaaacac tgcccttca gcgggccatc atgaatgcga tgggcagcga ctacatccgt     420
gaggtgaatg tggtgaagtc tgcccgtgtc ggttattcca aaatgctgct gggtgtttat     480
gcctacttta tagagcataa                                                  500
```

<210> SEQ ID NO 37
<211> LENGTH: 500
<212> TYPE: DNA
<213> ORGANISM: Artificial Sequences
<220> FEATURE:
<223> OTHER INFORMATION: Synthetic

<400> SEQUENCE: 37

```
cactcacaac aatgagtggc agatatagcc tggtggttca ggcggcgcat ttttattgct      60
gtgttgcgct gtaattcttc tatttctgat gctgaatcaa tgatgtctgc catctttcat     120
taatccctga actgttggtt aatacgcttg agggtgaatg cgaataataa aaaggagcc     180
tgtagctccc tgatgatttt gcttttcatg ttcatcgttc cttaaagacg ccgtttaaca     240
tgccgattgc caggcttaaa tgagtcggtg tgaatcccat cagcgttacc gtttcgcggt     300
gcttcttcag tacgctacgg caaatgtcat cgacgttttt atccggaaac tgctgtctgg     360
ctttttttga tttcagaatt agcctgacgg gcaatgctgc gaagggcgtt ttcctgctga     420
ggtgtcattg aacaagtccc atgtcggcaa gcataagcac acagaatatg aagcccgctg     480
ccagaaaaat gcattccgtg                                                  500
```

<210> SEQ ID NO 38
<211> LENGTH: 500
<212> TYPE: DNA
<213> ORGANISM: Artificial Sequences
<220> FEATURE:
<223> OTHER INFORMATION: Synthetic

<400> SEQUENCE: 38

```
gcctaaagta ataaaaccga gcaatccatt tacgaatgtt tgctgggttt ctgttttaac      60
aacattttct gcgccgccac aaattttggc tgcatcgaca gttttcttct gcccaattcc     120
agaaacgaag aaatgatggg tgatggtttc ctttggtgct actgctgccg gtttgttttg     180
aacagtaaac gtctgttgag cacatcctgt aataagcagg gccagcgcag tagcgagtag     240
catttttttc atggtgttat tcccgatgct ttttgaagtt cgcagaatcg tatgtgtaga     300
aaattaaaca aaccctaaac aatgagttga aatttcatat tgttaatatt tattaatgta     360
tgtcaggtgc gatgaatcgt cattgtattc ccggattaac tatgtccaca gccctgacgg     420
```

```
ggaacttctc tgcgggagtg tccgggaata attaaaacga tgcacacagg gtttagcgcg    480
tacacgtatt gcattatgcc                                                500
```

<210> SEQ ID NO 39
<211> LENGTH: 1011
<212> TYPE: DNA
<213> ORGANISM: Artificial Sequences
<220> FEATURE:
<223> OTHER INFORMATION: Synthetic

<400> SEQUENCE: 39

```
aagagctgga cagcgatacc tggcaggcgg agctgcatat cgaagttttc ctgcctgctc     60
aggtgccgga ttcagagctg gatgcgtgga tggagtcccg gatttatccg gtgatgagcg    120
atatcccggc actgtcagat ttgatcacca gtatggtggc cagcggctat gactaccggc    180
gcgacgatga tgcgggcttg tggagttcag ccgatctgac ttatgtcatt acctatgaaa    240
tgtgaggacg ctatgcctgt accaaatcct acaatgccgg tgaaaggtgc cgggaccacc    300
ctgtgggttt ataaggggag cggtgaccct tacgcgaatc cgctttcaga cgttgactgg    360
tcgcgtctgg caaaagttaa agacctgacg cccggcgaac tgaccgctga gtcctatgac    420
gacagctatc tcgatgatga agatgcagac tggactgcga ccgggcaggg gcagaaatct    480
gccggagata ccagcttcac gctggcgtgg atgcccggag agcaggggca gcaggcgctg    540
ctggcgtggt ttaatgaagg cgatacccgt gcctataaaa tccgcttccc gaacggcacg    600
gtcgatgtgt ccgtggctg ggtcagcagt atcggtaagg cggtgacggc gaaggaagtg    660
atcacccgca cggtgaaagt caccaatgtg gacgtccgt cgatggcaga agatcgcagc    720
acggtaacag cggcaaccgg catgaccgtg acgcctgcca gcacctcggt ggtgaaaggg    780
cagagcacca cgctgaccgt ggccttccag ccggagggcg taaccgacaa gagctttcgt    840
gcggtgtctg cggataaaac aaaagccacc gtgtcggtca gtggtatgac catcaccgtg    900
aacggcgttg ctgcaggcaa ggtcaacatt ccggttgtat ccggtaatgg tgagtttgct    960
gcggttgcag aaattaccgt caccgccagt taatccggag agtcagcgat g           1011
```

<210> SEQ ID NO 40
<211> LENGTH: 32
<212> TYPE: DNA
<213> ORGANISM: Artificial Sequences
<220> FEATURE:
<223> OTHER INFORMATION: Synthetic

<400> SEQUENCE: 40

```
cctgtatgac cgtattccgg gtcctgtcgg ta                                   32
```

<210> SEQ ID NO 41
<211> LENGTH: 425
<212> TYPE: DNA
<213> ORGANISM: Artificial Sequences
<220> FEATURE:
<223> OTHER INFORMATION: Synthetic

<400> SEQUENCE: 41

```
aagagctgga cagcgatacc tggcaggcgg agctgcatat cgaagttttc ctgcctgctc     60
aggtgccgga ttcagagctg gatgcgtgga tggagtcccg gatttatccg gtgatgagcg    120
atatcccggc actgtcagat ttgatcacca gtatggtggc cagcggctat gactaccggc    180
gcgacgatga tgcgggcttg tggagttcag ccgatctgac ttatgtcatt acctatgaaa    240
tgtgaggacg ctatgcctgt accaaatcct acaatgccgg tgaaaggtgc cgggaccacc    300
```

```
ctgtgggttt ataaggggag cggtgaccct tacgcgaatc cgctttcaga cgttgactgg    360
tcgcgtctgg caaaagttaa agacctgacg cccggcgaac tgaccgctga gtcctatgac    420
gacag                                                                425
```

The invention claimed is:

1. A kit or system for obtaining sequence information of a polynucleotide, said kit or system comprising:
   a) a first sequencing reagent comprising at least two different nucleotide monomer/first label conjugates that are substantially non-fluorescent until after incorporation of said nucleotide monomer into a polynucleotide based on complementarity to a target polynucleotide; and
   b) a second sequencing reagent comprising one or more nucleotide monomers/second label conjugate(s) that is or are substantially non-fluorescent until after incorporation of said nucleotide monomer(s) into a polynucleotide based on complementarity to said target polynucleotide, at least one of said one or more nucleotide monomers being different from said nucleotide monomers present in said first sequencing reagent, and
   c) a detector for detecting fluorescence emission resulting from said first label and second label after incorporation of said nucleotide monomers into said polynucleotide, and
   which kit or system is configured to obtain a read length of about 200 or more base pairs and a code accuracy rate of at least 95%.

2. The kit or system of claim 1, which further comprises a first polynucleotide replicating catalyst and/or a second polynucleotide replicating catalyst.

3. The kit or system of claim 1, wherein the first and/or second label is conjugated to a terminal phosphate group of the nucleotide monomer.

4. The kit or system of claim 3, which further comprises an activating enzyme for releasing the first and/or second label(s) from the terminal phosphate group of the nucleotide monomer.

5. The kit or system of claim 1, which further comprises a solid surface upon which a target polynucleotide is configured to be immobilized.

6. The kit or system of claim 5, wherein the solid surface is a part of a microreactor.

7. The kit or system of claim 1, which further comprises means for obtaining sequence information for at least a portion of a target polynucleotide based on the fluorescence emission resulting from the first label and second label after incorporation of the nucleotide monomers into the polynucleotide.

8. The kit or system of claim 7, wherein the means comprises a computer readable medium containing executable instructions that when executed obtaining sequence information for at least a portion of a target polynucleotide based on the fluorescence emission resulting from the first label and second label after incorporation of the nucleotide monomers into the polynucleotide.

9. The kit or system of claim 1, which further comprises means for comparing multiple sequences to obtain a non-degenerate sequence and/or to reduce or eliminate sequence error(s) in the non-degenerate sequence.

10. The kit or system of claim 9, wherein the means comprises a computer readable medium containing executable instructions that when executed comparing multiple sequences to obtain a non-degenerate sequence and/or to reduce or eliminate sequence error(s) in the non-degenerate sequence.

11. The kit or system of claim 1, which is configured to obtain a read length of about 250, about 350, about 400, about 500, about 800, or about 2400 base pairs.

12. The kit or system of claim 11, which is configured to obtain a code accuracy rate of at least 99%.

* * * * *